(12) United States Patent
Miske et al.

(10) Patent No.: US 12,174,186 B2
(45) Date of Patent: Dec. 24, 2024

(54) METHOD AND REAGENTS FOR THE DETECTION OF AN AUTOANTIBODY

(71) Applicant: EUROIMMUN Medizinische Labordiagnostika AG, Luebeck (DE)

(72) Inventors: Ramona Miske, Luebeck (DE); Christiane Radzimski, Luebeck (DE); Kathrin Margalene Borowski, Luebeck (DE); Yvonne Denno, Luebeck (DE)

(73) Assignee: EUROIMMUN Medizinische Labordiagnostika AG, Luebeck (DE)

( * ) Notice: Subject to any disclaimer, the term of this patent is extended or adjusted under 35 U.S.C. 154(b) by 75 days.

(21) Appl. No.: 17/656,563

(22) Filed: Mar. 25, 2022

(65) Prior Publication Data

US 2022/0308053 A1 Sep. 29, 2022

(30) Foreign Application Priority Data

Mar. 29, 2021 (EP) .................................... 21165446

(51) Int. Cl.
*G01N 33/564* (2006.01)
*G01N 33/543* (2006.01)
*G01N 33/574* (2006.01)

(52) U.S. Cl.
CPC ..... *G01N 33/564* (2013.01); *G01N 33/54366* (2013.01); *G01N 33/57488* (2013.01); *G01N 2800/28* (2013.01)

(58) Field of Classification Search
CPC ........... G01N 33/564; G01N 33/54366; G01N 33/57488; G01N 2800/28; G01N 33/6854; G01N 33/558; G01N 33/574; C07K 16/28
See application file for complete search history.

(56) References Cited

U.S. PATENT DOCUMENTS 7,396,654 B2 * 7/2008 Hayes ................... C12Q 1/6883
435/7.1
2004/0229217 A1 11/2004 Weihe et al.

FOREIGN PATENT DOCUMENTS

WO           02/08384       1/2002
WO    WO2011160096 A2 *    6/2011

OTHER PUBLICATIONS

Bellocchio et al., "Uptake of Glutamate into Synaptic Vesicles by an Inorganic Phosphate Transporter", Science, vol. 289, Aug. 11, 2000, pp. 957-960.
Chen et al., "Genetic Mouse Models of Schizophrenia: From Hypothesis-Based to Susceptibility Gene-Based Models", Biological Psychiatry, vol. 59, 2006, pp. 1180-1188.
Eric Lancaster, "The Diagnosis and Treatment of Autoimmune Encephalitis", J. Clin. Neurol., vol. 12, No. 1, 2016, pp. 1-13.
Fremeau et al., "The Expression of Vesicular Glutamate Transporters Defines Two Classes of Excitatory Synapse", Neuron, vol. 31, Aug. 2, 2001, pp. 247-260.
Fremeau et al., "The identification of vesicular glutamate transporter 3 suggests novel modes of signaling by glutamate", PNAS, vol. 99, No. 22, Oct. 29, 2002, pp. 14488-14493.
Gras et al., "A Third Vesicular Glutamate Transporter Expressed by Cholinergic and Serotoninergic Neurons", The Journal of Neuroscience, vol. 22, No. 13, Jul. 1, 2002, pp. 5442-5451.
Herzog et al., "The Existence of a Second Vesicular Glutamate Transporter Specifies Subpopulations of Glutamatergic Neurons", The Journal of Neuroscience, vol. 21, 2001, pp. 1-6.
Kaneko et al., "Immunohistochemical Localization of Candidates for Vesicular Glutamate Transporters in the Rat Brain", The Journal of Comparative Neurology, vol. 444, 2002, pp. 39-62.
Kashani et al., "Loss of VGLUT1 and VGLUT2 in the prefrontal cortex is correlated with cognitive decline in Alzheimer disease", Neurobiology of Aging, vol. 29, 2008, pp. 1619-1630.
Lee et al., "The Laboratory Diagnosis of Autoimmune Encephalitis", Journal of Epilepsy Research, vol. 6, No. 2, 2016, pp. 45-52.
Leo et al., "Impairment of VGLUT2 but not VGLUT1 signaling reduces neuropathy-induced hypersensitivity", European Journal of Pain, Dec. 29, 2008, pp. 1-10.
Li et al., "Ion transport and regulation in a synaptic vesicle glutamate transporter", HHS public Access, Science, 2020, pp. 1-11.
Li et al., "VGLUT2 Trafficking Is Differentially Regulated by Adaptor Proteins AP-1 and AP-3", Frontiers in Cellular Neuroscience, vol. 11, Art. 324, Oct. 26, 2017, pp. 1-20.
Mackenzie et al., "Restricted Cortical and Amygdaloid Removal of Vesicular Glutamate Transporter 2 in Preadolescent Mice Impacts Dopaminergic Activity and Neuronal Circuitry of Higher Brain Function", The Journal of Neuroscience, vol. 29, No. 7, Feb. 18, 2009, pp. 2238-2251.
Nestler et al., "Neurobiology of Depression", Neuron, vol. 34, Mar. 28, 2002, pp. 13-25.
Schallier et al., "vGLUT2 heterozygous mice show more susceptibility to clonic seizures induced by pentylenetetrazol", Neurochemistry International, vol. 55, 2009, pp. 41-44.
Takamori et al. "Identification of a vesicular glutamate transporter that defines a glutamatergic phenotype in neurons", Nature, vol. 407, Sep. 14, 2000, pp. 189-194.
Wootz et al. "Reduced VGLUT2 expression increases motor neuron viability in Sod1$^{G93A}$ mice", Neurobiology of Disease, vol. 37, 2010, pp. 58-66.
Edited by K. Michael Pollard, "Detection of Autoantibodies", Autoantibodies and Autoimmunity, Molecular Mechanisms in Health Disease, Wiley-VCH, (2006) published Nov. 25, 2005, pp. 159-164.

(Continued)

*Primary Examiner* — Changhwa J Cheu

(74) *Attorney, Agent, or Firm* — Grüneberg and Myers PLLC

(57) ABSTRACT

A method involves detecting in a sample an autoantibody binding specifically to a mammalian VGLUT. An autoantibody binding specifically to a mammalian VGLUT and a diagnostically useful carrier with a solid phase with an immobilized polypeptide containing a mammalian VGLUT or a variant thereof, are useful. The autoantibody can be used for diagnosing a neurological autoimmune disease or a cancer.

8 Claims, 19 Drawing Sheets

Specification includes a Sequence Listing.

(56) References Cited

OTHER PUBLICATIONS

Zane, H.D., Immunology: Theoretical & Practical Concepts in Laboratory Medicine, W.B. Saunders Company, Philadelphia, Jan. 9, 2001, pp. 149 and 185.

* cited by examiner

```
VGLUT2 520-564      HEDELDEEETGDITQNYINYGTTKSYGATTQANGGWPSGWEKKEEF
VGLUT2/1 Mut1 518-564  FIGHDQLAGSDDSITQNYINYGTTKSYGATTQANGGWPSGWEKKEEF
VGLUT2 Mut2 520-570  HEDELDEEETGDITQNYINYGTTKSYGATTQANGGWPSGWPRPPPPVRDYVQ
VGLUT2/1 Mut3 520-564  HEDELDEEETGDEMEDEAEPPGAPPAPPSYGATHSTFQPEKKEEF
VGLUT1 491-560      ...GMDQLAGSDDSEMEDEAEPPGAPPAPPSYGATHSTFQPPRPPPPVRDY
```

Fig. 11A

SEQUENCE LISTING

<160> NUMBER OF SEQ ID NOS: 103

<210> SEQ ID NO 1
<211> LENGTH: 582
<212> TYPE: PRT
<213> ORGANISM: Homo sapiens

<400> SEQUENCE: 1

```
Met Glu Ser Val Lys Gln Arg Ile Leu Ala Pro Gly Lys Glu Gly Leu
1               5                   10                  15

Lys Asn Phe Ala Gly Lys Ser Leu Gly Gln Ile Tyr Arg Val Leu Glu
            20                  25                  30

Lys Lys Gln Asp Thr Gly Glu Thr Ile Glu Leu Thr Glu Asp Gly Lys
        35                  40                  45

Pro Leu Glu Val Pro Glu Arg Lys Ala Pro Leu Cys Asp Cys Thr Cys
    50                  55                  60

Phe Gly Leu Pro Arg Arg Tyr Ile Ile Ala Ile Met Ser Gly Leu Gly
65                  70                  75                  80

Phe Cys Ile Ser Phe Gly Ile Arg Cys Asn Leu Gly Val Ala Ile Val
                85                  90                  95

Asp Met Val Asn Asn Ser Thr Ile His Arg Gly Gly Lys Val Ile Lys
            100                 105                 110

Glu Lys Ala Lys Phe Asn Trp Asp Pro Glu Thr Val Gly Met Ile His
        115                 120                 125

Gly Ser Phe Phe Trp Gly Tyr Ile Ile Thr Gln Ile Pro Gly Gly Tyr
    130                 135                 140

Ile Ala Ser Arg Leu Ala Ala Asn Arg Val Phe Gly Ala Ala Ile Leu
145                 150                 155                 160

Leu Thr Ser Thr Leu Asn Met Leu Ile Pro Ser Ala Ala Arg Val His
                165                 170                 175

Tyr Gly Cys Val Ile Phe Val Arg Ile Leu Gln Gly Leu Val Glu Gly
            180                 185                 190

Val Thr Tyr Pro Ala Cys His Gly Ile Trp Ser Lys Trp Ala Pro Pro
        195                 200                 205
```

```
Leu Glu Arg Ser Arg Leu Ala Thr Thr Ser Phe Cys Gly Ser Tyr Ala
    210                 215                 220

Gly Ala Val Ile Ala Met Pro Leu Ala Gly Ile Leu Val Gln Tyr Thr
225                 230                 235                 240

Gly Trp Ser Ser Val Phe Tyr Val Tyr Gly Ser Phe Gly Met Val Trp
                245                 250                 255

Tyr Met Phe Trp Leu Leu Val Ser Tyr Glu Ser Pro Ala Lys His Pro
            260                 265                 270

Thr Ile Thr Asp Glu Glu Arg Arg Tyr Ile Glu Glu Ser Ile Gly Glu
        275                 280                 285

Ser Ala Asn Leu Leu Gly Ala Met Glu Lys Phe Lys Thr Pro Trp Arg
290                 295                 300

Lys Phe Phe Thr Ser Met Pro Val Tyr Ala Ile Val Ala Asn Phe
305                 310                 315                 320

Cys Arg Ser Trp Thr Phe Tyr Leu Leu Leu Ile Ser Gln Pro Ala Tyr
                325                 330                 335

Phe Glu Glu Val Phe Gly Phe Glu Ile Ser Lys Val Gly Met Leu Ser
            340                 345                 350

Ala Val Pro His Leu Val Met Thr Ile Ile Val Pro Ile Gly Gly Gln
        355                 360                 365

Ile Ala Asp Phe Leu Arg Ser Lys Gln Ile Leu Ser Thr Thr Thr Val
370                 375                 380

Arg Lys Ile Met Asn Cys Gly Gly Phe Gly Met Glu Ala Thr Leu Leu
385                 390                 395                 400

Leu Val Val Gly Tyr Ser His Thr Arg Gly Val Ala Ile Ser Phe Leu
                405                 410                 415

Val Leu Ala Val Gly Phe Ser Gly Phe Ala Ile Ser Gly Phe Asn Val
            420                 425                 430

Asn His Leu Asp Ile Ala Pro Arg Tyr Ala Ser Ile Leu Met Gly Ile
        435                 440                 445

Ser Asn Gly Val Gly Thr Leu Ser Gly Met Val Cys Pro Ile Ile Val
450                 455                 460

Gly Ala Met Thr Lys Asn Lys Ser Arg Glu Glu Trp Gln Tyr Val Phe
465                 470                 475                 480

Leu Ile Ala Ala Leu Val His Tyr Gly Gly Val Ile Phe Tyr Ala Ile
                485                 490                 495

Phe Ala Ser Gly Glu Lys Gln Pro Trp Ala Asp Pro Glu Glu Thr Ser
            500                 505                 510

Glu Glu Lys Cys Gly Phe Ile His Glu Asp Glu Leu Asp Glu Glu Thr
        515                 520                 525

Gly Asp Ile Thr Gln Asn Tyr Ile Asn Tyr Gly Thr Thr Lys Ser Tyr
530                 535                 540

Gly Ala Thr Thr Gln Ala Asn Gly Gly Trp Pro Ser Gly Trp Glu Lys
545                 550                 555                 560

Lys Glu Glu Phe Val Gln Gly Glu Val Gln Asp Ser His Ser Tyr Lys
                565                 570                 575

Asp Arg Val Asp Tyr Ser
            580

<210> SEQ ID NO 2
<211> LENGTH: 895
<212> TYPE: DNA
<213> ORGANISM: Artificial Sequence
<220> FEATURE:
```

<223> OTHER INFORMATION: VGLUT2, gene synthesis fragment 1, coding
       aa1-293

<400> SEQUENCE: 2

```
ggtctcgcat ggaatccgta aaacaaagga ttttggcacc tggcaaagaa gggctgaaga    60
actttgccgg taagtcactc ggccagattt accgagtgct ggagaagaag caggacactg   120
gagaaaccat cgagcttaca gaggatggga aaccgttgga ggtgcccgaa aggaaggccc   180
cactgtgtga ttgcacctgt ttcggtctgc ctcggcggta tattatagcg atcatgtctg   240
gactgggctt ttgcatatcc tttgggatca gatgcaatct cggggttgcc atagtggaca   300
tggtgaacaa ctccaccatc cacagaggag gcaaagtcat aaaagagaaa gctaagttca   360
actgggatcc tgaaacagtg gcatgatcc acggttcttt cttctgggga tacatcatca    420
cccagatacc cggcggctac atcgctagtc gcttggccgc aaatcgggtt tcggggctg    480
ccatcctgct tactagcacc ctcaatatgc tcattcctag cgctgccaga gtccactatg    540
gctgcgtcat tttcgtcagg atactgcagg gcttggtgga gggtgtgacg tatcccgcat    600
gtcatggcat ttggagcaaa tgggctccac ctttggagag gagcaggctg ccacaaccca    660
gcttctgtgg atcctatgca ggcgccgtga ttgctatgcc cctggctggt attctcgtcc    720
agtacactgg gtggtcctct gtcttttacg tgtatggcag ctttgggatg gtctggtaca    780
tgttctggct gcttgtgagc tacgaaagtc agccaagca tccgaccatt acggatgaag    840
agcgtcggta cattgaggag tctattggcg aatctgccaa tctgttggcg agacc        895
```

<210> SEQ ID NO 3
<211> LENGTH: 891
<212> TYPE: DNA
<213> ORGANISM: Artificial Sequence
<220> FEATURE:
<223> OTHER INFORMATION: VGLUT2, gene synthesis fragment 2, coding
       aa294-582

<400> SEQUENCE: 3

```
ggtctccttg ggagctatgg agaagtttaa gactccatgg cgcaaattct tcacaagcat    60
gcccgtatat gcaatcatcg ttgccaattt ctgcagatcc tggaccttt atctgctgtt    120
gatttctcaa cccgcgtatt tgaggaggt gtttgggttc gaaatcagca aggtgggaat    180
gctttcagca gttccacacc tggtgatgac aatcatcgta cccataggag gcaaattgc    240
tgactttctg cgcagtaaac agatcctgag taccacaact gtccgaaaga ttatgaactg    300
tggaggattc ggcatggaag ccaccctcct gcttgtggtt ggctatagcc ataccagagg    360
tgtcgccatc tcatttctgg ttctggcggt aggtttcagt ggatttgcca tctccggttt    420
caatgttaac cacctcgaca tcgcaccccg ttatgctagc attctgatgg catcagcaa    480
tggcgtgggc acactcagcg aatggtatg cccaattatc gtaggcgcca tgactaagaa    540
caaatcacgc gaagagtggc agtacgtgtt tctgattgca gcactggtgc attatggtgg    600
ggtcatttc tacgcgatct ttgcttcagg ggaaaagcaa ccgtgggcag atcctgaaga    660
gactagtgag gagaagtgcg gtttcatcca tgaggacgaa ctggacgagg aaacaggaga    720
cataacacag aactacatca actatggaac gacgaaatcc tacggggcca ccactcaggc    780
caatggaggc tggccttctg gtgggaaaa gaaggaggaa tttgtgcaag ggaggtgca    840
ggattcccac tcctataagg accgagttga ttattcataa tcgacgagac c            891
```

<210> SEQ ID NO 4
<211> LENGTH: 881

```
<212> TYPE: DNA
<213> ORGANISM: Artificial Sequence
<220> FEATURE:
<223> OTHER INFORMATION: VGLUT2, gene synthesis fragment 1, BsaI

<400> SEQUENCE: 4
catggaatcc gtaaaacaaa ggattttggc acctggcaaa gaagggctga agaactttgc      60
cggtaagtca ctcggccaga tttaccgagt gctggagaag aagcaggaca ctggagaaac     120
catcgagctt acagaggatg gaaaccgttg gaggtgccc gaaaggaagg ccccactgtg      180
tgattgcacc tgtttcggtc tgcctcggcg gtatattata gcgatcatgt ctggactggg     240
cttttgcata tcctttggga tcagatgcaa tctcggggtt gccatagtgg acatggtgaa     300
caactccacc atccacagag gaggcaaagt cataaaagag aaagctaagt caactgggga    360
tcctgaaaca gtgggcatga tccacggttc tttcttctgg ggatacatca tcacccagat    420
acccggcggc tacatcgcta gtcgcttggc cgcaaatcgg gttttcgggg ctgccatcct    480
gcttactagc accctcaata tgctcattcc tagcgctgcc agagtccact atggctgcgt    540
cattttcgtc aggatactgc agggcttggt ggagggtgtg acgtatcccg catgtcatgg    600
catttggagc aaatgggctc cacctttgga gaggagcagg ctggccacaa ccagcttctg    660
tggatcctat gcaggcgccg tgattgctat gcccctggct ggtattctcg tccagtacac    720
tgggtggtcc tctgtctttt acgtgtatgg cagctttggg atggtctggt acatgttctg    780
gctgcttgtg agctacgaaa gtccagccaa gcatccgacc attacggatg aagagcgtcg    840
gtacattgag gagtctattg gcgaatctgc caatctgttg g                         881

<210> SEQ ID NO 5
<211> LENGTH: 877
<212> TYPE: DNA
<213> ORGANISM: Artificial Sequence
<220> FEATURE:
<223> OTHER INFORMATION: VGLUT2, gene synthesis fragment 2, BsaI

<400> SEQUENCE: 5
ttgggagcta tggagaagtt taagactcca tggcgcaaat tcttcacaag catgcccgta      60
tatgcaatca tcgttgccaa tttctgcaga tcctggacct tttatctgct gttgatttct     120
caacccgcgt attttgagga ggtgtttggg ttcgaaatca gcaaggtggg aatgctttca    180
gcagttccac acctggtgat gacaatcatc gtacccatag gagggcaaat tgctgacttt    240
ctgcgcagta acagatcct gagtaccaca actgtccgaa agattatgaa ctgtggagga     300
ttcggcatga agccaccct cctgcttgtg gttggctata gccataccag aggtgtcgcc     360
atctcatttc tggttctggc ggtaggtttc agtggatttg ccatctccgg tttcaatgtt    420
aaccacctcg acatcgcacc ccgttatgct agcattctga tgggcatcag caatggcgtg    480
ggcacactca gcggaatggt atgcccaatt atcgtaggcg ccatgactaa gaacaaatca    540
cgcgaagagt ggcagtacgt gttctctgatt gcagcactgg tgcattatgg tggggtcatt    600
ttctacgcga tctttgcttc aggggaaaag caaccgtggg cagatcctga agagactagt    660
gaggagaagt gcggtttcat ccatgaggac gaactggacg aggaaacagg agacataaca    720
cagaactaca tcaactatgg aacgacgaaa tcctacgggg ccaccactca ggccaatgga    780
ggctggcctt ctgggtggga aaagaaggag gaatttgtgc aaggggaggt gcaggattcc    840
cactcctata aggaccgagt tgattattca taatcga                              877

<210> SEQ ID NO 6
```

```
<211> LENGTH: 28
<212> TYPE: DNA
<213> ORGANISM: Artificial Sequence
<220> FEATURE:
<223> OTHER INFORMATION: sense VGLUT2

<400> SEQUENCE: 6
ataggtctcc ttgggagcta tggagaag                                         28

<210> SEQ ID NO 7
<211> LENGTH: 42
<212> TYPE: DNA
<213> ORGANISM: Artificial Sequence
<220> FEATURE:
<223> OTHER INFORMATION: asense VGLUT2

<400> SEQUENCE: 7
tatggtctcg tcgagtgaat aatcaactcg gtccttatag ct                         42

<210> SEQ ID NO 8
<211> LENGTH: 895
<212> TYPE: DNA
<213> ORGANISM: Artificial Sequence
<220> FEATURE:
<223> OTHER INFORMATION: VGLUT2-PCR-fragment without Stop-Codon

<400> SEQUENCE: 8
ataggtctcc ttgggagcta tggagaagtt taagactcca tggcgcaaat tcttcacaag      60
catgcccgta tatgcaatca tcgttgccaa tttctgcaga tcctggacct tttatctgct     120
gttgatttct caacccgcgt attttgagga ggtgtttggg ttcgaaatca gcaaggtggg     180
aatgctttca gcagttccac acctggtgat gacaatcatc gtacccatag agggcaaat      240 tgctgacttt ctgcgcagta aacagatcct gagtaccaca actgtccgaa agattatgaa     300
ctgtggagga ttcggcatgg aagccaccct cctgcttgtg gttggctata gccataccag     360
aggtgtcgcc atctcatttc tggttctggc ggtaggtttc agtggatttg ccatctccgg     420
tttcaatgtt aaccacctcg acatcgcacc ccgttatgct agcattctga tgggcatcag     480
caatggcgtg gcacactca gcggaatggt atgcccaatt atcgtaggcg ccatgactaa      540
gaacaaatca cgcgaagagt ggcagtacgt gtttctgatt gcagcactgg tgcattatgg     600
tggggtcatt ttctacgcga tctttgcttc aggggaaaag caaccgtggg cagatcctga     660
agagactagt gaggagaagt gcggtttcat ccatgaggac gaactggacg aggaaacagg     720
agacataaca cagaactaca tcaactatgg aacgacgaaa tcctacgggg ccaccactca     780
ggccaatgga ggctggcctt ctgggtggga aaagaaggag gaatttgtgc aaggggaggt     840
gcaggattcc cacagctata aggaccgagt tgattattca ctcgacgaga ccata          895

<210> SEQ ID NO 9
<211> LENGTH: 7362
<212> TYPE: DNA
<213> ORGANISM: Artificial Sequence
<220> FEATURE:
<223> OTHER INFORMATION: pTriEx-1-VGLUT2 [human]

<400> SEQUENCE: 9
ggagtcgctg cgacgctgcc ttcgccccgt gccccgctcc gccgccgcct cgcgccgccc      60
gccccggctc tgactgaccg cgttactccc acaggtgagc gggcgggacg gcccttctcc     120
ttcgggctgt aattagcgct tggtttaatg acggcttgtt tcttttctgt ggctgcgtga     180
aagccttgag gggctccggg agggcccttt gtgcgggggg agcggctcgg ggctgtccgc     240
```

```
gggggacgg ctgccttcgg gggggacggg gcagggcggg gttcggcttc tggcgtgtga        300
ccggcggctc tagagcctct gctaaccatg ttcatgcctt cttctttttc ctacagctcc        360
tgggcaacgt gctggttatt gtgctgtctc atcattttgg caaagaattg gatcggaccg        420
aaattaatac gactcactat aggggaattg tgagcggata acaattcccc ggagttaatc        480
cgggaccttt aattcaaccc aacacaatat attatagtta ataagaatt attatcaaat         540 catttgtata ttaattaaaa tactatactg taaattacat tttatttaca atcaaaggag        600 ataccatg gaatccgtaa acaaaggat tttggcacct ggcaaagaag ggctgaagaa           660 cttgccggt aagtcactcg gccagattta ccgagtgctg gagaagaagc aggacactgg         720
agaaaccatc gagcttacag aggatgggaa accgttggag gtgcccgaaa ggaaggcccc       780
actgtgtgat tgcacctgtt tcggtctgcc tcggcggtat attatagcga tcatgtctgg       840
actgggcttt tgcatatcct ttgggatcag atgcaatctc ggggttgcca tagtggacat      900
ggtgaacaac tccaccatcc acagaggagg caaagtcata aaagagaaag ctaagttcaa      960
ctgggatcct gaaacagtgg gcatgatcca cggttctttc ttctggggat acatcatcac      1020 ccagatacccc ggcggctaca tcgctagtcg cttggccgca aatcgggttt cggggctgc      1080 catcctgctt actagcaccc tcaatatgct cattcctagc gctgccagag tccactatgg      1140
ctgcgtcatt ttcgtcagga tactgcaggg cttggtggag ggtgtgacgt atcccgcatg      1200
tcatggcatt tggagcaaat gggctccacc tttggagagg agcaggctgg ccacaaccag      1260
cttctgtgga tcctatgcag gcgccgtgat tgctatgccc ctggctggta ttctcgtcca      1320
gtacactggg tggtcctctg tcttttacgt gtatggcagc tttgggatgg tctggtacat      1380
gttctggctg cttgtgagct acgaaagtcc agccaagcat ccgaccatta cggatgaaga      1440
gcgtcggtac attgaggagt ctattggcga atctgccaat ctgttgggag ctatggagaa      1500
gtttaagact ccatggcgca aattcttcac aagcatgccc gtatatgcaa tcatcgttgc      1560
caatttctgc agatcctgga ccttttatct gctgttgatt tctcaacccg cgtatttga      1620 ggaggtgttt gggttcgaaa tcagcaaggt gggaatgctt tcagcagttc cacacctggt      1680
gatgacaatc atcgtaccca taggagggca aattgctgac tttctgcgca gtaaacagat      1740
cctgagtacc acaactgtcc gaaagattat gaactgtgga ggattcggca tggaagccac      1800
cctcctgctt gtggttggct atagccatac cagaggtgtc gccatctcat ttctggttct      1860
ggcggtaggt ttcagtggat ttgccatctc cggtttcaat gttaaccacc tcgacatcgc      1920
accccgttat gctagcattc tgatgggcat cagcaatggc gtgggcacac tcagcggaat      1980
ggtatgccca attatcgtag gcgccatgac taagaacaaa tcacgcgaag agtggcagta      2040
cgtgtttctg attgcagcac tggtgcatta tggtggggtc attttctacg cgatctttgc      2100
ttcaggggaa aagcaaccgt gggcagatcc tgaagagact agtgaggaga agtgcggttt      2160
catccatgag gacgaactgg acgaggaaac aggagacata acacagaact acatcaacta      2220
tggaacgacg aaatcctacg gggccaccac tcaggccaat ggaggctggc cttctgggtg      2280
ggaaaagaag gaggaatttg tgcaagggga ggtgcaggat ccccactcct ataaggaccg      2340
agttgattat tcataatcga gcaccaccat caccatcacc atcactaagt gattaacctc      2400
aggtgcaggc tgcctatcag aaggtggtgg ctggtgtggc caatgccctg gctcacaaat      2460
accactgaga tcgatctttt tccctctgcc aaaaattatg gggacatcat gaagccctt       2520 gagcatctga cttctggcta ataaaggaaa tttattttca ttgcaatagt gtgttggaat      2580
```

```
tttttgtgtc tctcactcgg aaggacatat gggagggcaa atcatttaaa acatcagaat   2640
gagtatttgg tttagagttt ggcaacatat gcccatatgt aactagcata accccttggg   2700
gcctctaaac gggtcttgag gggttttttg ctgaaagcat gcggaggaaa ttctccttga   2760
agtttccctg gtgttcaaag taaaggagtt tgcaccagac gcacctctgt tcactggtcc   2820
ggcgtattaa aacacgatac attgttatta gtacatttat taagcgctag attctgtgcg   2880
ttgttgattt acagacaatt gttgtacgta ttttaataat tcattaaatt tataatcttt   2940
agggtggtat gttagagcga aaatcaaatg attttcagcg tctttatatc tgaatttaaa   3000
tattaaatcc tcaatagatt tgtaaaatag gtttcgatta gtttcaaaca agggttgttt   3060
ttccgaaccg atggctggac tatctaatgg attttcgctc aacgccacaa aacttgccaa   3120
atcttgtagc agcaatctag ctttgtcgat attcgtttgt gttttgtttt gtaataaagg   3180
ttcgacgtcg ttcaaaatat tatgcgcttt tgtatttctt tcatcactgt cgttagtgta   3240
caattgactc gacgtaaaca cgttaaatag agcttggaca tatttaacat cgggcgtgtt   3300
agctttatta ggccgattat cgtcgtcgtc ccaaccctcg tcgttagaag ttgcttccga   3360
agacgatttt gccatagcca cacgacgcct attaattgtg tcggctaaca cgtccgcgat   3420
caaatttgta gttgagcttt ttggaattat ttctgattgc gggcgttttt gggcgggttt   3480
caatctaact gtgcccgatt ttaattcaga caacacgtta gaaagcgatg gtgcaggcgg   3540
tggtaacatt tcagacggca aatctactaa tggcggcggt ggtggagctg atgataaatc   3600
taccatcggt ggaggcgcag gcggggctgg cggcggaggc ggaggcggag gtggtggcgg   3660
tgatgcagac ggcggtttag gctcaaatgt ctcttaggc  aacacagtcg gcacctcaac   3720
tattgtactg gtttcgggcg ccgttttttgg tttgaccggt ctgagacgag tgcgattttt   3780
ttcgtttcta atagcttcca acaattgttg tctgtcgtct aaaggtgcag cgggttgagg   3840
ttccgtcggc attggtggag cgggcggcaa ttcagacatc gatggtggtg gtggtggtgg   3900
aggcgctgga atgttaggca cgggagaagg tggtggcggc ggtgccgccg gtataatttg   3960
ttctggttta gtttgttcgc gcacgattgt gggcaccggc gcaggcgccg ctggctgcac   4020
aacggaaggt cgtctgcttc gaggcagcgc ttggggtggt ggcaattcaa tattataatt   4080
ggaatacaaa tcgtaaaaat ctgctataag cattgtaatt tcgctatcgt ttaccgtgcc   4140
gatatttaac aaccgctcaa tgtaagcaat tgtattgtaa agagattgtc tcaagctcgg   4200
aacgctgcgc tcggtcgttc ggctgcggcg agcggtatca gctcactcaa aggcggtaat   4260
acggttatcc acagaatcag gggataacgc aggaaagaac atgtgagcaa aaggccagca   4320
aaaggccagg aaccgtaaaa aggccgcgtt gctggcgttt ttccataggc tccgcccccc   4380
tgacgagcat cacaaaaatc gacgctcaag tcagaggtgg cgaaacccga caggactata   4440
aagataccag gcgtttcccc ctggaagctc cctcgtgcgc tctcctgttc cgaccctgcc   4500
gcttaccgga tacctgtccg cctttctccc ttcgggaagc gtggcgcttt ctcaatgctc   4560
acgctgtagg tatctcagtt cggtgtaggt cgttcgctcc aagctgggct gtgtgcacga   4620
accccccgtt cagcccgacc gctgcgcctt atccggtaac tatcgtcttg agtccaaccc   4680
ggtaagacac gacttatcgc cactggcagc agccactggt aacaggatta gcagagcgag   4740
gtatgtaggc ggtgctacag agttcttgaa gtggtggcct aactacggct acactagaag   4800
gacagtattt ggtatctgcg ctctgctgaa gccagttacc ttcggaaaaa gagttggtag   4860
ctcttgatcc ggcaaacaaa ccaccgctgg tagcggtggt ttttttgttt gcaagcagca   4920
gattacgcgc agaaaaaaag gatctcaaga agatcctttg ttaccaatgc ttaatcagtg   4980
```

```
aggcacctat ctcagcgatc tgtctatttc gttcatccat agttgcctga ctccccgtcg    5040
tgtagataac tacgatacgg gagggcttac catctggccc cagtgctgca atgataccgc    5100
gagacccacg ctcaccggct ccagatttat cagcaataaa ccagccagcc ggaagggccg    5160
agcgcagaag tggtcctgca actttatccg cctccatcca gtctattaat tgttgccggg    5220
aagctagagt aagtagttcg ccagttaata gtttgcgcaa cgttgttgcc attgctacag    5280
gcatcgtggt gtcacgctcg tcgtttggta tggcttcatt cagctccggt tcccaacgat    5340
caaggcgagt tacatgatcc cccatgttgt gcaaaaaagc ggttagctcc ttcggtcctc    5400
cgatcgttgt cagaagtaag ttggccgcag tgttatcact catggttatg gcagcactgc    5460
ataattctct tactgtcatg ccatccgtaa gatgcttttc tgtgactggt gagtactcaa    5520
ccaagtcatt ctgagaatag tgtatgcggc gaccgagttg ctcttgcccg cgtcaatac    5580 gggataatac cgcgccacat agcagaactt taaaagtgct catcattgga aaacgttctt    5640
cggggcgaaa actctcaagg atcttaccgc tgttgagatc cagttcgatg taacccactc    5700
gtgcacccaa ctgatcttca gcatctttta ctttcaccag cgtttctggg tgagcaaaaa    5760
caggaaggca aaatgccgca aaaaagggaa taagggcgac acggaaatgt tgaatactca    5820
tactcttcct ttttcaatat tattgaagca tttatcaggg ttattgtctc atgtccgcgc    5880
gtttcctgca tcttttaatc aaatcccaag atgtgtataa accaccaaac tgccaaaaaa    5940
tgaaaactgt cgacaagctc tgtccgtttg ctggcaactg caagggtctc aatcctattt    6000
gtaattattg aataataaaa caattataaa tgtcaaattt gtttttttatt aacgatacaa    6060 accaaacgca acaagaacat ttgtagtatt atctataatt gaaaacgcgt agttataatc    6120
gctgaggtaa tatttaaaat catttttcaaa tgattcacag ttaatttgcg acaatataat    6180
tttattttca cataaactag acgccttgtc gtcttcttct tcgtattcct tctcttttc    6240 atttttctct tcataaaaat taacatagtt attatcgtat ccatatatgt atctatcgta    6300
tagagtaaat tttttgttgt cataaatata tatgtctttt ttaatggggt gtatagtacc    6360
gctgcgcata gtttttctgt aatttacaac agtgctattt tctggtagtt cttcggagtg    6420
tgttgcttta attattaaat ttatataatc aatgaatttg ggatcgtcgg ttttgtacaa    6480
tatgttgccg gcatagtacg cagcttcttc tagttcaatt acaccatttt ttagcagcac    6540
cggattaaca taacttttcca aaatgttgta cgaaccgtta aacaaaaaca gttcacctcc    6600
cttttctata ctattgtctg cgagcagttg tttgttgtta aaaataacag ccattgtaat    6660
gagacgcaca aactaatatc acaaactgga aatgtctatc aatatatagt tgctctagtt    6720
attaatagta atcaattacg gggtcattag ttcatagccc atatatggag ttccgcgtta    6780
cataacttac ggtaaatggc ccgcctggct gaccgcccaa cgacccccgc ccattgacgt    6840
caataatgac gtatgttccc atagtaacgc caatagggac tttccattga cgtcaatggg    6900
tggactattt acggtaaact gcccacttgg cagtacatca agtgtatcat atgccaagta    6960
cgccccctat tgacgtcaat gacggtaaat ggcccgcctg gcattatgcc cagtacatga    7020
ccttatggga ctttcctact tggcagtaca tctacgtatt agtcatcgct attaccatgc    7080
atggtcgagg tgagccccac gttctgcttc actctcccca tctccccccc ctccccaccc    7140 ccaatttttgt attttatttat ttttaattta ttttgtgcag cgatgggggc ggggggggg    7200 ggggggcgcg cgccaggcgg ggcggggcgg ggcgagggc ggggcggggc gaggcggaga    7260
ggtgcggcgg cagccaatca gagcggcgcg ctccgaaagt ttccttttat ggcgaggcgg    7320
```
cggcggcggc ggccctataa aaagcgaagc gcgcggcggg cg                              7362

<210> SEQ ID NO 10
<211> LENGTH: 582
<212> TYPE: PRT
<213> ORGANISM: Homo sapiens

<400> SEQUENCE: 10

Met Glu Ser Val Lys Gln Arg Ile Leu Ala Pro Gly Lys Glu Gly Leu
1               5                   10                  15

Lys Asn Phe Ala Gly Lys Ser Leu Gly Gln Ile Tyr Arg Val Leu Glu
                20                  25                  30

Lys Lys Gln Asp Thr Gly Glu Thr Ile Glu Leu Thr Glu Asp Gly Lys
            35                  40                  45

Pro Leu Glu Val Pro Glu Arg Lys Ala Pro Leu Cys Asp Cys Thr Cys
        50                  55                  60

Phe Gly Leu Pro Arg Arg Tyr Ile Ile Ala Ile Met Ser Gly Leu Gly
65                  70                  75                  80

Phe Cys Ile Ser Phe Gly Ile Arg Cys Asn Leu Gly Val Ala Ile Val
                85                  90                  95

Asp Met Val Asn Asn Ser Thr Ile His Arg Gly Gly Lys Val Ile Lys
            100                 105                 110

Glu Lys Ala Lys Phe Asn Trp Asp Pro Glu Thr Val Gly Met Ile His
        115                 120                 125

Gly Ser Phe Phe Trp Gly Tyr Ile Ile Thr Gln Ile Pro Gly Gly Tyr
    130                 135                 140

Ile Ala Ser Arg Leu Ala Ala Asn Arg Val Phe Gly Ala Ala Ile Leu
145                 150                 155                 160

Leu Thr Ser Thr Leu Asn Met Leu Ile Pro Ser Ala Ala Arg Val His
                165                 170                 175

Tyr Gly Cys Val Ile Phe Val Arg Ile Leu Gln Gly Leu Val Glu Gly
            180                 185                 190

Val Thr Tyr Pro Ala Cys His Gly Ile Trp Ser Lys Trp Ala Pro Pro
        195                 200                 205

Leu Glu Arg Ser Arg Leu Ala Thr Thr Ser Phe Cys Gly Ser Tyr Ala
    210                 215                 220

Gly Ala Val Ile Ala Met Pro Leu Ala Gly Ile Leu Val Gln Tyr Thr
225                 230                 235                 240

Gly Trp Ser Ser Val Phe Tyr Val Tyr Gly Ser Phe Gly Met Val Trp
                245                 250                 255

Tyr Met Phe Trp Leu Leu Val Ser Tyr Glu Ser Pro Ala Lys His Pro
            260                 265                 270

Thr Ile Thr Asp Glu Glu Arg Arg Tyr Ile Glu Ser Ile Gly Glu
        275                 280                 285

Ser Ala Asn Leu Leu Gly Ala Met Glu Lys Phe Lys Thr Pro Trp Arg
    290                 295                 300

Lys Phe Phe Thr Ser Met Pro Val Tyr Ala Ile Val Ala Asn Phe
305                 310                 315                 320

Cys Arg Ser Trp Thr Phe Tyr Leu Leu Leu Ile Ser Gln Pro Ala Tyr
                325                 330                 335

Phe Glu Glu Val Phe Gly Phe Glu Ile Ser Lys Val Gly Met Leu Ser
            340                 345                 350

Ala Val Pro His Leu Val Met Thr Ile Ile Val Pro Ile Gly Gly Gln
        355                 360                 365

```
Ile Ala Asp Phe Leu Arg Ser Lys Gln Ile Leu Ser Thr Thr Thr Val
    370                 375                 380

Arg Lys Ile Met Asn Cys Gly Gly Phe Gly Met Glu Ala Thr Leu Leu
385                 390                 395                 400

Leu Val Val Gly Tyr Ser His Thr Arg Gly Val Ala Ile Ser Phe Leu
                405                 410                 415

Val Leu Ala Val Gly Phe Ser Gly Phe Ala Ile Ser Gly Phe Asn Val
                420                 425                 430

Asn His Leu Asp Ile Ala Pro Arg Tyr Ala Ser Ile Leu Met Gly Ile
            435                 440                 445

Ser Asn Gly Val Gly Thr Leu Ser Gly Met Val Cys Pro Ile Ile Val
450                 455                 460

Gly Ala Met Thr Lys Asn Lys Ser Arg Glu Glu Trp Gln Tyr Val Phe
465                 470                 475                 480

Leu Ile Ala Ala Leu Val His Tyr Gly Gly Val Ile Phe Tyr Ala Ile
                485                 490                 495

Phe Ala Ser Gly Glu Lys Gln Pro Trp Ala Asp Pro Glu Glu Thr Ser
            500                 505                 510

Glu Glu Lys Cys Gly Phe Ile His Glu Asp Glu Leu Asp Glu Glu Thr
        515                 520                 525

Gly Asp Ile Thr Gln Asn Tyr Ile Asn Tyr Gly Thr Thr Lys Ser Tyr
    530                 535                 540

Gly Ala Thr Thr Gln Ala Asn Gly Gly Trp Pro Ser Gly Trp Glu Lys
545                 550                 555                 560

Lys Glu Glu Phe Val Gln Gly Glu Val Gln Asp Ser His Ser Tyr Lys
                565                 570                 575

Asp Arg Val Asp Tyr Ser
            580

<210> SEQ ID NO 11
<211> LENGTH: 7360
<212> TYPE: DNA
<213> ORGANISM: Artificial Sequence
<220> FEATURE:
<223> OTHER INFORMATION: pTriEx-1-VGLUT2 [human]-His

<400> SEQUENCE: 11
ggagtcgctg cgacgctgcc ttcgccccgt gccccgctcc gccgccgcct cgcgccgccc      60
gccccggctc tgactgaccg cgttactccc acaggtgagc gggcgggacg gcccttctcc     120
ttcgggctgt aattagcgct tggtttaatg acggcttgtt tcttttctgt ggctgcgtga     180
aagccttgag gggctccggg agggcccttt gtgcgggggg agcggctcgg ggctgtccgc     240 gggggggacgg ctgccttcgg gggggacggg gcagggcggg gttcggcttc tgcgtgtga     300 ccggcggctc tagagcctct gctaaccatg ttcatgcctt cttcttttc ctacagctcc     360 tgggcaacgt gctggttatt gtgctgtctc atcattttgg caaagaattg gatcggaccg     420
aaattaatac gactcactat aggggaattg tgagcggata acaattcccc ggagttaatc     480
cgggaccttt aattcaaccc aacacaatat attatagtta aataagaatt attatcaaat     540
catttgtata ttaattaaaa tactatactg taaattcat tttatttaca atcaaaggag     600
atataccatg gaatccgtaa acaaaggat tttggcacct ggcaaagaag ggctgaagaa     660 cttttgccggt aagtcactcg gccagattta ccgagtgctg gagaagaagc aggacactgg     720
agaaaccatc gagcttacag aggatgggaa accgttggag gtgcccgaaa ggaaggcccc     780
actgtgtgat tgcacctgtt tcggtctgcc tcggcggtat attatagcga tcatgtctgg     840
```

```
actgggcttt tgcatatcct ttgggatcag atgcaatctc ggggttgcca tagtggacat      900
ggtgaacaac tccaccatcc acagaggagg caaagtcata aaagagaaag ctaagttcaa      960
ctgggatcct gaaacagtgg gcatgatcca cggttctttc ttctggggat acatcatcac     1020
ccagataccc ggcggctaca tcgctagtcg cttggccgca aatcgggttt cggggctgc      1080 catcctgctt actagcaccc tcaatatgct cattcctagc gctgccagag tccactatgg     1140
ctgcgtcatt ttcgtcagga tactgcaggg cttggtggag ggtgtgacgt atcccgcatg     1200
tcatggcatt tggagcaaat gggctccacc tttggagagg agcaggctgg ccacaaccag     1260
cttctgtgga tcctatgcag gcgccgtgat tgctatgccc ctggctggta ttctcgtcca     1320
gtacactggg tggtcctctg tcttttacgt gtatggcagc tttgggatgg tctggtacat     1380
gttctggctg cttgtgagct acgaaagtcc agccaagcat ccgaccatta cggatgaaga     1440
gcgtcggtac attgaggagt ctattggcga atctgccaat ctgttgggag ctatggagaa     1500
gtttaagact ccatggcgca aattcttcac aagcatgccc gtatatgcaa tcatcgttgc     1560
caatttctgc agatcctgga ccttttatct gctgttgatt tctcaacccg cgtattttga     1620
ggaggtgttt gggttcgaaa tcagcaaggt gggaatgctt tcagcagttc cacacctggt     1680
gatgacaatc atcgtaccca taggagggca aattgctgac tttctgcgca gtaaacagat     1740
cctgagtacc acaactgtcc gaaagattat gaactgtgga ggattcggca tggaagccac     1800
cctcctgctt gtggttggct atagccatac cagaggtgtc gccatctcat ttctggttct     1860
ggcggtaggt ttcagtggat ttgccatctc cggtttcaat gttaaccacc tcgacatcgc     1920
accccgttat gctagcattc tgatgggcat cagcaatggc gtgggcacac tcagcggaat     1980
ggtatgccca attatcgtag gcgccatgac taagaacaaa tcacgcgaag agtggcagta     2040
cgtgtttctg attgcagcac tggtgcatta tggtggggtc attttctacg cgatctttgc     2100
ttcaggggaa aagcaaccgt gggcagatcc tgaagagact agtgaggaga agtgcggttt     2160
catccatgag gacgaactgg acgaggaaac aggagacata acacagaact acatcaacta     2220
tggaacgacg aaatcctacg gggccaccac tcaggccaat ggaggctggc cttctgggtg     2280
ggaaaagaag gaggaatttg tgcaagggga ggtgcaggat tcccacagct ataaggaccg     2340
agttgattat tcactcgagc accaccatca ccatcaccat cactaagtga ttaacctcag     2400
gtgcaggctg cctatcagaa ggtggtggct ggtgtggcca atgccctggc tcacaaatac     2460
cactgagatc gatctttttc cctctgccaa aaattatggg gacatcatga agccccttga     2520
gcatctgact tctggctaat aaaggaaatt tattttcatt gcaatagtgt gttggaatttt    2580 tttgtgtctc tcactcggaa ggacatatgg gagggcaaat catttaaaac atcagaatga    2640
gtatttggtt tagagtttgg caacatatgc ccatatgtaa ctagcataac cccttggggc    2700
ctctaaacgg gtcttgaggg gttttttgct gaaagcatgc ggaggaaatt ctccttgaag    2760
tttccctggt gttcaaagta aaggagtttg caccagacgc acctctgttc actggtccgg    2820
cgtattaaaa cacgatacat tgttattagt acatttatta agcgctagat tctgtgcgtt    2880
gttgatttac agacaattgt tgtacgtatt ttaataattc attaaattta taatctttag    2940
ggtggtatgt tagagcgaaa atcaaatgat tttcagcgtc tttatatctg aatttaaata    3000
ttaaatcctc aatagatttg taaaataggt ttcgattagt ttcaaacaag ggttgttttt    3060
ccgaaccgat ggctggacta tctaatggat tttcgctcaa cgcccacaaaa cttgccaaat   3120 cttgtagcag caatctagct ttgtcgatat tcgtttgtgt tttgttttgt aataaaggtt    3180
```

```
cgacgtcgtt caaaatatta tgcgcttttg tatttctttc atcactgtcg ttagtgtaca   3240
attgactcga cgtaaacacg ttaaatagag cttggacata tttaacatcg ggcgtgttag   3300
ctttattagg ccgattatcg tcgtcgtccc aaccctcgtc gttagaagtt gcttccgaag   3360
acgattttgc catagccaca cgacgcctat taattgtgtc ggctaacacg tccgcgatca   3420
aatttgtagt tgagcttttt ggaattattt ctgattgcgg gcgttttggg gcgggtttca   3480
atctaactgt gcccgatttt aattcagaca acacgttaga aagcgatggt gcaggcggtg   3540
gtaacatttc agacggcaaa tctactaatg gcggcggtgg tggagctgat gataaatcta   3600
ccatcggtgg aggcgcaggc ggggctggcg cggaggcgg aggcggaggt ggtggcggtg    3660
atgcagacgg cggtttaggc tcaaatgtct ctttaggcaa cacagtcggc acctcaacta   3720
ttgtactggt ttcgggcgcc gttttttggtt tgaccggtct gagacgagtg cgattttttt   3780
cgtttctaat agcttccaac aattgttgtc tgtcgtctaa aggtgcagcg ggttgaggtt    3840
ccgtcggcat tggtggagcg ggcggcaatt cagacatcga tggtggtggt ggtggtggag   3900
gcgctggaat gttaggcacg ggagaaggtg gtggcggcg tgccgccggt ataatttgtt    3960
ctggtttagt ttgttcgcgc acgattgtgg gcaccggcgc aggcgccgct ggctgcacaa   4020
cggaaggtcg tctgcttcga ggcagcgctt ggggtggtgg caattcaata ttataattgg   4080
aatacaaatc gtaaaaatct gctataagca ttgtaatttc gctatcgttt accgtgccga   4140
tatttaacaa ccgctcaatg taagcaattg tattgtaaag agattgtctc aagctcggaa   4200
cgctgcgctc ggtcgttcgg ctgcggcgag cggtatcagc tcactcaaag gcggtaatac   4260
ggttatccac agaatcaggg gataacgcag gaaagaacat gtgagcaaaa ggccagcaaa   4320
aggccaggaa ccgtaaaaag gccgcgttgc tggcgttttt ccataggctc cgcccccctg   4380
acgagcatca caaaaatcga cgctcaagtc agaggtggcg aaacccgaca ggactataaa   4440
gataccaggc gtttccccct ggaagctccc tcgtgcgctc tcctgttccg accctgccgc   4500
ttaccggata cctgtccgcc tttctccctt cgggaagcgt ggcgctttct caatgctcac   4560
gctgtaggta tctcagttcg gtgtaggtcg ttcgctccaa gctgggctgt gtgcacgaac   4620
cccccgttca gcccgaccgc tgcgccttat ccggtaacta tcgtcttgag tccaacccgg   4680
taagacacga cttatcgcca ctggcagcag ccactggtaa caggattagc agagcgaggt   4740
atgtaggcgg tgctacagag ttcttgaagt ggtggcctaa ctacggctac actagaagga   4800
cagtatttgg tatctgcgct ctgctgaagc cagttacctt cggaaaaaga gttggtagct   4860
cttgatccgg caaacaaacc accgctggta gcggtggttt ttttgtttgc aagcagcaga   4920
ttacgcgcag aaaaaaagga tctcaagaag atcctttgtt accaatgctt aatcagtgag   4980
gcacctatct cagcgatctg tctatttcgt tcatccatag ttgcctgact ccccgtcgtg   5040
tagataacta cgatacggga gggcttacca tctggcccca gtgctgcaat gataccgcga   5100
gacccacgct caccggctcc agatttatca gcaataaacc agccagccgg aagggccgag   5160
cgcagaagtg gtcctgcaac tttatccgcc tccatccagt ctattaattg ttgccgggaa   5220
gctagagtaa gtagttcgcc agttaatagt ttgcgcaacg ttgttgccat tgctacaggc   5280
atcgtggtgt cacgctcgtc gtttggtatg gcttcattca gctccggttc ccaacgatca   5340
aggcgagtta catgatcccc catgttgtgc aaaaaagcgg ttagctcctt cggtcctccg   5400
atcgttgtca gaagtaagtt ggccgcagtg ttatcactca tggttatggc agcactgcat   5460
aattctctta ctgtcatgcc atccgtaaga tgcttttctg tgactggtga gtactcaacc   5520
aagtcattct gagaatagtg tatgcggcga ccgagttgct cttgcccggc gtcaatacgg   5580
```

-continued

```
gataataccg cgccacatag cagaacttta aaagtgctca tcattggaaa acgttcttcg   5640
gggcgaaaac tctcaaggat cttaccgctg ttgagatcca gttcgatgta acccactcgt   5700
gcacccaact gatcttcagc atcttttact ttcaccagcg tttctgggtg agcaaaaaca   5760
ggaaggcaaa atgccgcaaa aagggaata agggcgacac ggaaatgttg aatactcata    5820
ctcttccttt ttcaatatta ttgaagcatt tatcagggtt attgtctcat gtccgcgcgt   5880
ttcctgcatc ttttaatcaa atcccaagat gtgtataaac caccaaactg ccaaaaatg    5940 aaaactgtcg acaagctctg tccgtttgct ggcaactgca agggtctcaa tcctatttgt   6000
aattattgaa taataaaaca attataaatg tcaaatttgt tttttattaa cgatacaaac   6060
caaacgcaac aagaacattt gtagtattat ctataattga aaacgcgtag ttataatcgc   6120
tgaggtaata tttaaaatca ttttcaaatg attcacagtt aatttgcgac aatataattt   6180
tattttcaca taaactagac gccttgtcgt cttcttcttc gtattccttc tcttttcat    6240 ttttctcttc ataaaaatta acatagttat tatcgtatcc atatatgtat ctatcgtata   6300
gagtaaattt tttgttgtca taaatatata tgtcttttt aatgggtgt atagtaccgc     6360 tgcgcatagt ttttctgtaa tttacaacag tgctattttc tggtagttct tcggagtgtg   6420
ttgctttaat tattaaattt atataatcaa tgaatttggg atcgtcggtt ttgtacaata   6480
tgttgccggc atagtacgca gcttcttcta gttcaattac ccatttttt agcagcaccg    6540 gattaacata actttccaaa atgttgtacg aaccgttaaa caaaaacagt tcacctccct   6600
tttctatact attgtctgcg agcagttgtt tgttgttaaa ataacagcc attgtaatga    6660 gacgcacaaa ctaatatcac aaactggaaa tgtctatcaa tatatagttg ctctagttat   6720
taatagtaat caattacggg gtcattagtt catagcccat atatggagtt ccgcgttaca   6780
taacttacgg taaatggccc gcctggctga ccgcccaacg accccgccc attgacgtca    6840 ataatgacgt atgttcccat agtaacgcca tagggactt tccattgacg tcaatgggtg    6900
gactatttac ggtaaactgc ccacttggca gtacatcaag tgtatcatat gccaagtacg   6960 cccctattg acgtcaatga cggtaaatgg cccgcctggc attatgccca gtacatgacc    7020
ttatgggact ttcctacttg gcagtacatc tacgtattag tcatcgctat taccatgcat   7080
ggtcgaggtg agccccacgt tctgcttcac tctccccatc tcccccccct ccccacccc    7140 aattttgtat ttatttattt tttaattatt ttgtgcagcg atggggcgg gggggggg     7200 ggggcgcgcg ccaggcgggg cggggcgggg cgaggggcgg ggcggggcga ggcggagagg   7260
tgcggcggca gccaatcaga gcggcgcgct ccgaaagttt ccttttatgg cgaggcggcg   7320
gcggcggcgg ccctataaaa agcgaagcgc gcggcgggcg                         7360
```

<210> SEQ ID NO 12
<211> LENGTH: 592
<212> TYPE: PRT
<213> ORGANISM: Artificial Sequence
<220> FEATURE:
<223> OTHER INFORMATION: VGLUT2 [human]-H8

<400> SEQUENCE: 12

```
Met Glu Ser Val Lys Gln Arg Ile Leu Ala Pro Gly Lys Glu Gly Leu
1               5                   10                  15

Lys Asn Phe Ala Gly Lys Ser Leu Gly Gln Ile Tyr Arg Val Leu Glu
            20                  25                  30

Lys Lys Gln Asp Thr Gly Glu Thr Ile Glu Leu Thr Glu Asp Gly Lys
        35                  40                  45
```

```
Pro Leu Glu Val Pro Glu Arg Lys Ala Pro Leu Cys Asp Cys Thr Cys
        50                  55                  60

Phe Gly Leu Pro Arg Arg Tyr Ile Ile Ala Ile Met Ser Gly Leu Gly
 65                  70                  75                  80

Phe Cys Ile Ser Phe Gly Ile Arg Cys Asn Leu Gly Val Ala Ile Val
                85                  90                  95

Asp Met Val Asn Asn Ser Thr Ile His Arg Gly Gly Lys Val Ile Lys
            100                 105                 110

Glu Lys Ala Lys Phe Asn Trp Asp Pro Glu Thr Val Gly Met Ile His
        115                 120                 125

Gly Ser Phe Phe Trp Gly Tyr Ile Ile Thr Gln Ile Pro Gly Gly Tyr
        130                 135                 140

Ile Ala Ser Arg Leu Ala Ala Asn Arg Val Phe Gly Ala Ala Ile Leu
145                 150                 155                 160

Leu Thr Ser Thr Leu Asn Met Leu Ile Pro Ser Ala Ala Arg Val His
                165                 170                 175

Tyr Gly Cys Val Ile Phe Val Arg Ile Leu Gln Gly Leu Val Glu Gly
                180                 185                 190

Val Thr Tyr Pro Ala Cys His Gly Ile Trp Ser Lys Trp Ala Pro Pro
        195                 200                 205

Leu Glu Arg Ser Arg Leu Ala Thr Thr Ser Phe Cys Gly Ser Tyr Ala
        210                 215                 220

Gly Ala Val Ile Ala Met Pro Leu Ala Gly Ile Leu Val Gln Tyr Thr
225                 230                 235                 240

Gly Trp Ser Ser Val Phe Tyr Val Tyr Gly Ser Phe Gly Met Val Trp
                245                 250                 255

Tyr Met Phe Trp Leu Leu Val Ser Tyr Glu Ser Pro Ala Lys His Pro
                260                 265                 270

Thr Ile Thr Asp Glu Glu Arg Arg Tyr Ile Glu Glu Ser Ile Gly Glu
            275                 280                 285

Ser Ala Asn Leu Leu Gly Ala Met Glu Lys Phe Lys Thr Pro Trp Arg
        290                 295                 300

Lys Phe Phe Thr Ser Met Pro Val Tyr Ala Ile Ile Val Ala Asn Phe
305                 310                 315                 320

Cys Arg Ser Trp Thr Phe Tyr Leu Leu Leu Ile Ser Gln Pro Ala Tyr
                325                 330                 335

Phe Glu Glu Val Phe Gly Phe Glu Ile Ser Lys Val Gly Met Leu Ser
                340                 345                 350

Ala Val Pro His Leu Val Met Thr Ile Ile Val Pro Ile Gly Gly Gln
        355                 360                 365

Ile Ala Asp Phe Leu Arg Ser Lys Gln Ile Leu Ser Thr Thr Thr Val
        370                 375                 380

Arg Lys Ile Met Asn Cys Gly Gly Phe Gly Met Glu Ala Thr Leu Leu
385                 390                 395                 400

Leu Val Val Gly Tyr Ser His Thr Arg Gly Val Ala Ile Ser Phe Leu
                405                 410                 415

Val Leu Ala Val Gly Phe Ser Gly Phe Ala Ile Ser Gly Phe Asn Val
                420                 425                 430

Asn His Leu Asp Ile Ala Pro Arg Tyr Ala Ser Ile Leu Met Gly Ile
        435                 440                 445

Ser Asn Gly Val Gly Thr Leu Ser Gly Met Val Cys Pro Ile Ile Val
        450                 455                 460
```

```
Gly Ala Met Thr Lys Asn Lys Ser Arg Glu Glu Trp Gln Tyr Val Phe
465                 470                 475                 480

Leu Ile Ala Ala Leu Val His Tyr Gly Gly Val Ile Phe Tyr Ala Ile
                485                 490                 495

Phe Ala Ser Gly Glu Lys Gln Pro Trp Ala Asp Pro Glu Glu Thr Ser
                500                 505                 510

Glu Glu Lys Cys Gly Phe Ile His Glu Asp Glu Leu Asp Glu Glu Thr
                515                 520                 525

Gly Asp Ile Thr Gln Asn Tyr Ile Asn Tyr Gly Thr Thr Lys Ser Tyr
                530                 535                 540

Gly Ala Thr Thr Gln Ala Asn Gly Gly Trp Pro Ser Gly Trp Glu Lys
545                 550                 555                 560

Lys Glu Glu Phe Val Gln Gly Glu Val Gln Asp Ser His Ser Tyr Lys
                565                 570                 575

Asp Arg Val Asp Tyr Ser Leu Glu His His His His His His
                580                 585                 590

<210> SEQ ID NO 13
<211> LENGTH: 560
<212> TYPE: PRT
<213> ORGANISM: Homo sapiens

<400> SEQUENCE: 13

Met Glu Phe Arg Gln Glu Phe Arg Lys Leu Ala Gly Arg Ala Leu
1               5                   10                  15

Gly Lys Leu His Arg Leu Leu Glu Lys Arg Gln Glu Gly Ala Glu Thr
                20                  25                  30

Leu Glu Leu Ser Ala Asp Gly Arg Pro Val Thr Thr Gln Thr Arg Asp
                35                  40                  45

Pro Pro Val Val Asp Cys Thr Cys Phe Gly Leu Pro Arg Arg Tyr Ile
                50                  55                  60

Ile Ala Ile Met Ser Gly Leu Gly Phe Cys Ile Ser Phe Gly Ile Arg
65                  70                  75                  80

Cys Asn Leu Gly Val Ala Ile Val Ser Met Val Asn Asn Ser Thr Thr
                85                  90                  95

His Arg Gly Gly His Val Val Gln Lys Ala Gln Phe Ser Trp Asp
                100                 105                 110

Pro Glu Thr Val Gly Leu Ile His Gly Ser Phe Phe Trp Gly Tyr Ile
                115                 120                 125

Val Thr Gln Ile Pro Gly Gly Phe Ile Cys Gln Lys Phe Ala Ala Asn
                130                 135                 140

Arg Val Phe Gly Phe Ala Ile Val Ala Thr Ser Thr Leu Asn Met Leu
145                 150                 155                 160

Ile Pro Ser Ala Ala Arg Val His Tyr Gly Cys Val Ile Phe Val Arg
                165                 170                 175

Ile Leu Gln Gly Leu Val Glu Gly Val Thr Tyr Pro Ala Cys His Gly
                180                 185                 190

Ile Trp Ser Lys Trp Ala Pro Pro Leu Glu Arg Ser Arg Leu Ala Thr
                195                 200                 205

Thr Ala Phe Cys Gly Ser Tyr Ala Gly Ala Val Val Ala Met Pro Leu
                210                 215                 220

Ala Gly Val Leu Val Gln Tyr Ser Gly Trp Ser Ser Val Phe Tyr Val
225                 230                 235                 240

Tyr Gly Ser Phe Gly Ile Phe Trp Tyr Leu Phe Trp Leu Leu Val Ser
                245                 250                 255
```

```
Tyr Glu Ser Pro Ala Leu His Pro Ser Ile Ser Glu Glu Arg Lys
            260                 265                 270

Tyr Ile Glu Asp Ala Ile Gly Glu Ser Ala Lys Leu Met Asn Pro Leu
        275                 280                 285

Thr Lys Phe Ser Thr Pro Trp Arg Arg Phe Phe Thr Ser Met Pro Val
    290                 295                 300

Tyr Ala Ile Ile Val Ala Asn Phe Cys Arg Ser Trp Thr Phe Tyr Leu
305                 310                 315                 320

Leu Leu Ile Ser Gln Pro Ala Tyr Phe Glu Glu Val Phe Gly Phe Glu
                325                 330                 335

Ile Ser Lys Val Gly Leu Val Ser Ala Leu Pro His Leu Val Met Thr
            340                 345                 350

Ile Ile Val Pro Ile Gly Gly Gln Ile Ala Asp Phe Leu Arg Ser Arg
        355                 360                 365

Arg Ile Met Ser Thr Thr Asn Val Arg Lys Leu Met Asn Cys Gly Gly
    370                 375                 380

Phe Gly Met Glu Ala Thr Leu Leu Leu Val Val Gly Tyr Ser His Ser
385                 390                 395                 400

Lys Gly Val Ala Ile Ser Phe Leu Val Leu Ala Val Gly Phe Ser Gly
                405                 410                 415

Phe Ala Ile Ser Gly Phe Asn Val Asn His Leu Asp Ile Ala Pro Arg
            420                 425                 430

Tyr Ala Ser Ile Leu Met Gly Ile Ser Asn Gly Val Gly Thr Leu Ser
        435                 440                 445

Gly Met Val Cys Pro Ile Ile Val Gly Ala Met Thr Lys His Lys Thr
    450                 455                 460

Arg Glu Glu Trp Gln Tyr Val Phe Leu Ile Ala Ser Leu Val His Tyr
465                 470                 475                 480

Gly Gly Val Ile Phe Tyr Gly Val Phe Ala Ser Gly Glu Lys Gln Pro
                485                 490                 495

Trp Ala Glu Pro Glu Glu Met Ser Glu Glu Lys Cys Gly Phe Val Gly
            500                 505                 510

His Asp Gln Leu Ala Gly Ser Asp Asp Ser Glu Met Glu Asp Glu Ala
        515                 520                 525

Glu Pro Pro Gly Ala Pro Pro Ala Pro Pro Ser Tyr Gly Ala Thr
    530                 535                 540

His Ser Thr Phe Gln Pro Pro Arg Pro Pro Pro Val Arg Asp Tyr
545                 550                 555                 560

<210> SEQ ID NO 14
<211> LENGTH: 589
<212> TYPE: PRT
<213> ORGANISM: Homo sapiens

<400> SEQUENCE: 14

Met Pro Phe Lys Ala Phe Asp Thr Phe Lys Glu Lys Ile Leu Lys Pro
1               5                   10                  15

Gly Lys Glu Gly Val Lys Asn Ala Val Gly Asp Ser Leu Gly Ile Leu
            20                  25                  30

Gln Arg Lys Ile Asp Gly Thr Thr Glu Glu Glu Asp Asn Ile Glu Leu
        35                  40                  45

Asn Glu Glu Gly Arg Pro Val Gln Thr Ser Arg Pro Ser Pro Pro Leu
    50                  55                  60

Cys Asp Cys His Cys Cys Gly Leu Pro Lys Arg Tyr Ile Ile Ala Ile
```

```
                65                  70                  75                  80
            Met Ser Gly Leu Gly Phe Cys Ile Ser Phe Gly Ile Arg Cys Asn Leu
                            85                  90                  95
            Gly Val Ala Ile Val Glu Met Val Asn Asn Ser Thr Val Tyr Val Asp
                            100                 105                 110
            Gly Lys Pro Glu Ile Gln Thr Ala Gln Phe Asn Trp Asp Pro Glu Thr
                            115                 120                 125
            Val Gly Leu Ile His Gly Ser Phe Phe Trp Gly Tyr Ile Met Thr Gln
                            130                 135                 140
            Ile Pro Gly Gly Phe Ile Ser Asn Lys Phe Ala Ala Asn Arg Val Phe
            145                 150                 155                 160
            Gly Ala Ala Ile Phe Leu Thr Ser Thr Leu Asn Met Phe Ile Pro Ser
                                165                 170                 175
            Ala Ala Arg Val His Tyr Gly Cys Val Met Cys Val Arg Ile Leu Gln
                            180                 185                 190
            Gly Leu Val Glu Gly Val Thr Tyr Pro Ala Cys His Gly Met Trp Ser
                            195                 200                 205
            Lys Trp Ala Pro Pro Leu Glu Arg Ser Arg Leu Ala Thr Thr Ser Phe
                            210                 215                 220
            Cys Gly Ser Tyr Ala Gly Ala Val Val Ala Met Pro Leu Ala Gly Val
            225                 230                 235                 240
            Leu Val Gln Tyr Ile Gly Trp Ser Ser Val Phe Tyr Ile Tyr Gly Met
                                245                 250                 255
            Phe Gly Ile Ile Trp Tyr Met Phe Trp Leu Leu Gln Ala Tyr Glu Cys
                            260                 265                 270
            Pro Ala Ala His Pro Thr Ile Ser Asn Glu Glu Lys Thr Tyr Ile Glu
                            275                 280                 285
            Thr Ser Ile Gly Glu Gly Ala Asn Val Val Ser Leu Ser Lys Phe Ser
                            290                 295                 300
            Thr Pro Trp Lys Arg Phe Phe Thr Ser Leu Pro Val Tyr Ala Ile Ile
            305                 310                 315                 320
            Val Ala Asn Phe Cys Arg Ser Trp Thr Phe Tyr Leu Leu Leu Ile Ser
                                325                 330                 335
            Gln Pro Ala Tyr Phe Glu Glu Val Phe Gly Phe Ala Ile Ser Lys Val
                            340                 345                 350
            Gly Leu Leu Ser Ala Val Pro His Met Val Met Thr Ile Val Val Pro
                            355                 360                 365
            Ile Gly Gly Gln Leu Ala Asp Tyr Leu Arg Ser Arg Gln Ile Leu Thr
                            370                 375                 380
            Thr Thr Ala Val Arg Lys Ile Met Asn Cys Gly Gly Phe Gly Met Glu
            385                 390                 395                 400
            Ala Thr Leu Leu Leu Val Val Gly Phe Ser His Thr Lys Gly Val Ala
                                405                 410                 415
            Ile Ser Phe Leu Val Leu Ala Val Gly Phe Ser Gly Phe Ala Ile Ser
                            420                 425                 430
            Gly Phe Asn Val Asn His Leu Asp Ile Ala Pro Arg Tyr Ala Ser Ile
                            435                 440                 445
            Leu Met Gly Ile Ser Asn Gly Val Gly Thr Leu Ser Gly Met Val Cys
                            450                 455                 460
            Pro Leu Ile Val Gly Ala Met Thr Arg His Lys Thr Arg Glu Glu Trp
            465                 470                 475                 480
            Gln Asn Val Phe Leu Ile Ala Ala Leu Val His Tyr Ser Gly Val Ile
                                485                 490                 495
```

Phe Tyr Gly Val Phe Ala Ser Gly Glu Lys Gln Glu Trp Ala Asp Pro
                500                 505                 510

Glu Asn Leu Ser Glu Glu Lys Cys Gly Ile Ile Asp Gln Asp Glu Leu
            515                 520                 525

Ala Glu Glu Ile Glu Leu Asn His Glu Ser Phe Ala Ser Pro Lys Lys
530                 535                 540

Lys Met Ser Tyr Gly Ala Thr Ser Gln Asn Cys Glu Val Gln Lys Lys
545                 550                 555                 560

Glu Trp Lys Gly Gln Arg Gly Ala Thr Leu Asp Glu Glu Leu Thr
                565                 570                 575

Ser Tyr Gln Asn Glu Glu Arg Asn Phe Ser Thr Ile Ser
            580                 585

<210> SEQ ID NO 15
<211> LENGTH: 595
<212> TYPE: PRT
<213> ORGANISM: Artificial Sequence
<220> FEATURE:
<223> OTHER INFORMATION: consensus sequence from human VGLUT1, VGLUT2,
      VGLUT3
<220> FEATURE:
<221> NAME/KEY: misc_feature
<222> LOCATION: (1)..(18)
<223> OTHER INFORMATION: Xaa can be any naturally occurring amino acid
<220> FEATURE:
<221> NAME/KEY: misc_feature
<222> LOCATION: (20)..(25)
<223> OTHER INFORMATION: Xaa can be any naturally occurring amino acid
<220> FEATURE:
<221> NAME/KEY: misc_feature
<222> LOCATION: (27)..(28)
<223> OTHER INFORMATION: Xaa can be any naturally occurring amino acid
<220> FEATURE:
<221> NAME/KEY: misc_feature
<222> LOCATION: (31)..(33)
<223> OTHER INFORMATION: Xaa can be any naturally occurring amino acid
<220> FEATURE:
<221> NAME/KEY: misc_feature
<222> LOCATION: (35)..(46)
<223> OTHER INFORMATION: Xaa can be any naturally occurring amino acid
<220> FEATURE:
<221> NAME/KEY: misc_feature
<222> LOCATION: (49)..(51)
<223> OTHER INFORMATION: Xaa can be any naturally occurring amino acid
<220> FEATURE:
<221> NAME/KEY: misc_feature
<222> LOCATION: (53)..(53)
<223> OTHER INFORMATION: Xaa can be any naturally occurring amino acid
<220> FEATURE:
<221> NAME/KEY: misc_feature
<222> LOCATION: (55)..(62)
<223> OTHER INFORMATION: Xaa can be any naturally occurring amino acid
<220> FEATURE:
<221> NAME/KEY: misc_feature
<222> LOCATION: (64)..(65)
<223> OTHER INFORMATION: Xaa can be any naturally occurring amino acid
<220> FEATURE:
<221> NAME/KEY: misc_feature
<222> LOCATION: (68)..(68)
<223> OTHER INFORMATION: Xaa can be any naturally occurring amino acid
<220> FEATURE:
<221> NAME/KEY: misc_feature
<222> LOCATION: (70)..(70)
<223> OTHER INFORMATION: Xaa can be any naturally occurring amino acid
<220> FEATURE:
<221> NAME/KEY: misc_feature
<222> LOCATION: (74)..(74)
<223> OTHER INFORMATION: Xaa can be any naturally occurring amino acid
<220> FEATURE:
<221> NAME/KEY: misc_feature
<222> LOCATION: (102)..(102)
<223> OTHER INFORMATION: Xaa can be any naturally occurring amino acid -continued

```
<220> FEATURE:
<221> NAME/KEY: misc_feature
<222> LOCATION: (109)..(112)
<223> OTHER INFORMATION: Xaa can be any naturally occurring amino acid
<220> FEATURE:
<221> NAME/KEY: misc_feature
<222> LOCATION: (114)..(119)
<223> OTHER INFORMATION: Xaa can be any naturally occurring amino acid
<220> FEATURE:
<221> NAME/KEY: misc_feature
<222> LOCATION: (121)..(121)
<223> OTHER INFORMATION: Xaa can be any naturally occurring amino acid
<220> FEATURE:
<221> NAME/KEY: misc_feature
<222> LOCATION: (123)..(123)
<223> OTHER INFORMATION: Xaa can be any naturally occurring amino acid
<220> FEATURE:
<221> NAME/KEY: misc_feature
<222> LOCATION: (131)..(131)
<223> OTHER INFORMATION: Xaa can be any naturally occurring amino acid
<220> FEATURE:
<221> NAME/KEY: misc_feature
<222> LOCATION: (142)..(142)
<223> OTHER INFORMATION: Xaa can be any naturally occurring amino acid
<220> FEATURE:
<221> NAME/KEY: misc_feature
<222> LOCATION: (149)..(149)
<223> OTHER INFORMATION: Xaa can be any naturally occurring amino acid
<220> FEATURE:
<221> NAME/KEY: misc_feature
<222> LOCATION: (151)..(154)
<223> OTHER INFORMATION: Xaa can be any naturally occurring amino acid
<220> FEATURE:
<221> NAME/KEY: misc_feature
<222> LOCATION: (162)..(162)
<223> OTHER INFORMATION: Xaa can be any naturally occurring amino acid
<220> FEATURE:
<221> NAME/KEY: misc_feature
<222> LOCATION: (165)..(166)
<223> OTHER INFORMATION: Xaa can be any naturally occurring amino acid
<220> FEATURE:
<221> NAME/KEY: misc_feature
<222> LOCATION: (173)..(173)
<223> OTHER INFORMATION: Xaa can be any naturally occurring amino acid
<220> FEATURE:
<221> NAME/KEY: misc_feature
<222> LOCATION: (186)..(187)
<223> OTHER INFORMATION: Xaa can be any naturally occurring amino acid
<220> FEATURE:
<221> NAME/KEY: misc_feature
<222> LOCATION: (206)..(206)
<223> OTHER INFORMATION: Xaa can be any naturally occurring amino acid
<220> FEATURE:
<221> NAME/KEY: misc_feature
<222> LOCATION: (223)..(223)
<223> OTHER INFORMATION: Xaa can be any naturally occurring amino acid
<220> FEATURE:
<221> NAME/KEY: misc_feature
<222> LOCATION: (233)..(233)
<223> OTHER INFORMATION: Xaa can be any naturally occurring amino acid
<220> FEATURE:
<221> NAME/KEY: misc_feature
<222> LOCATION: (240)..(240)
<223> OTHER INFORMATION: Xaa can be any naturally occurring amino acid
<220> FEATURE:
<221> NAME/KEY: misc_feature
<222> LOCATION: (245)..(245)
<223> OTHER INFORMATION: Xaa can be any naturally occurring amino acid
<220> FEATURE:
<221> NAME/KEY: misc_feature
<222> LOCATION: (253)..(253)
<223> OTHER INFORMATION: Xaa can be any naturally occurring amino acid
<220> FEATURE:
<221> NAME/KEY: misc_feature
<222> LOCATION: (256)..(256)
<223> OTHER INFORMATION: Xaa can be any naturally occurring amino acid
<220> FEATURE:
<221> NAME/KEY: misc_feature
<222> LOCATION: (259)..(260)
```

```
<223> OTHER INFORMATION: Xaa can be any naturally occurring amino acid
<220> FEATURE:
<221> NAME/KEY: misc_feature
<222> LOCATION: (263)..(263)
<223> OTHER INFORMATION: Xaa can be any naturally occurring amino acid
<220> FEATURE:
<221> NAME/KEY: misc_feature
<222> LOCATION: (268)..(269)
<223> OTHER INFORMATION: Xaa can be any naturally occurring amino acid
<220> FEATURE:
<221> NAME/KEY: misc_feature
<222> LOCATION: (272)..(272)
<223> OTHER INFORMATION: Xaa can be any naturally occurring amino acid
<220> FEATURE:
<221> NAME/KEY: misc_feature
<222> LOCATION: (275)..(275)
<223> OTHER INFORMATION: Xaa can be any naturally occurring amino acid
<220> FEATURE:
<221> NAME/KEY: misc_feature
<222> LOCATION: (278)..(278)
<223> OTHER INFORMATION: Xaa can be any naturally occurring amino acid
<220> FEATURE:
<221> NAME/KEY: misc_feature
<222> LOCATION: (280)..(281)
<223> OTHER INFORMATION: Xaa can be any naturally occurring amino acid
<220> FEATURE:
<221> NAME/KEY: misc_feature
<222> LOCATION: (284)..(285)
<223> OTHER INFORMATION: Xaa can be any naturally occurring amino acid
<220> FEATURE:
<221> NAME/KEY: misc_feature
<222> LOCATION: (289)..(290)
<223> OTHER INFORMATION: Xaa can be any naturally occurring amino acid
<220> FEATURE:
<221> NAME/KEY: misc_feature
<222> LOCATION: (294)..(294)
<223> OTHER INFORMATION: Xaa can be any naturally occurring amino acid
<220> FEATURE:
<221> NAME/KEY: misc_feature
<222> LOCATION: (296)..(302)
<223> OTHER INFORMATION: Xaa can be any naturally occurring amino acid
<220> FEATURE:
<221> NAME/KEY: misc_feature
<222> LOCATION: (305)..(305)
<223> OTHER INFORMATION: Xaa can be any naturally occurring amino acid
<220> FEATURE:
<221> NAME/KEY: misc_feature
<222> LOCATION: (309)..(310)
<223> OTHER INFORMATION: Xaa can be any naturally occurring amino acid
<220> FEATURE:
<221> NAME/KEY: misc_feature
<222> LOCATION: (315)..(315)
<223> OTHER INFORMATION: Xaa can be any naturally occurring amino acid
<220> FEATURE:
<221> NAME/KEY: misc_feature
<222> LOCATION: (349)..(349)
<223> OTHER INFORMATION: Xaa can be any naturally occurring amino acid
<220> FEATURE:
<221> NAME/KEY: misc_feature
<222> LOCATION: (355)..(356)
<223> OTHER INFORMATION: Xaa can be any naturally occurring amino acid
<220> FEATURE:
<221> NAME/KEY: misc_feature
<222> LOCATION: (359)..(359)
<223> OTHER INFORMATION: Xaa can be any naturally occurring amino acid
<220> FEATURE:
<221> NAME/KEY: misc_feature
<222> LOCATION: (362)..(362)
<223> OTHER INFORMATION: Xaa can be any naturally occurring amino acid
<220> FEATURE:
<221> NAME/KEY: misc_feature
<222> LOCATION: (367)..(367)
<223> OTHER INFORMATION: Xaa can be any naturally occurring amino acid
<220> FEATURE:
<221> NAME/KEY: misc_feature
<222> LOCATION: (374)..(374)
<223> OTHER INFORMATION: Xaa can be any naturally occurring amino acid
<220> FEATURE:
<221> NAME/KEY: misc_feature
```

```
<222> LOCATION: (377)..(377)
<223> OTHER INFORMATION: Xaa can be any naturally occurring amino acid
<220> FEATURE:
<221> NAME/KEY: misc_feature
<222> LOCATION: (381)..(382)
<223> OTHER INFORMATION: Xaa can be any naturally occurring amino acid
<220> FEATURE:
<221> NAME/KEY: misc_feature
<222> LOCATION: (384)..(385)
<223> OTHER INFORMATION: Xaa can be any naturally occurring amino acid
<220> FEATURE:
<221> NAME/KEY: misc_feature
<222> LOCATION: (388)..(388)
<223> OTHER INFORMATION: Xaa can be any naturally occurring amino acid
<220> FEATURE:
<221> NAME/KEY: misc_feature
<222> LOCATION: (392)..(392)
<223> OTHER INFORMATION: Xaa can be any naturally occurring amino acid
<220> FEATURE:
<221> NAME/KEY: misc_feature
<222> LOCATION: (410)..(410)
<223> OTHER INFORMATION: Xaa can be any naturally occurring amino acid
<220> FEATURE:
<221> NAME/KEY: misc_feature
<222> LOCATION: (413)..(414)
<223> OTHER INFORMATION: Xaa can be any naturally occurring amino acid
<220> FEATURE:
<221> NAME/KEY: misc_feature
<222> LOCATION: (467)..(467)
<223> OTHER INFORMATION: Xaa can be any naturally occurring amino acid
<220> FEATURE:
<221> NAME/KEY: misc_feature
<222> LOCATION: (474)..(475)
<223> OTHER INFORMATION: Xaa can be any naturally occurring amino acid
<220> FEATURE:
<221> NAME/KEY: misc_feature
<222> LOCATION: (477)..(477)
<223> OTHER INFORMATION: Xaa can be any naturally occurring amino acid
<220> FEATURE:
<221> NAME/KEY: misc_feature
<222> LOCATION: (483)..(483)
<223> OTHER INFORMATION: Xaa can be any naturally occurring amino acid
<220> FEATURE:
<221> NAME/KEY: misc_feature
<222> LOCATION: (489)..(489)
<223> OTHER INFORMATION: Xaa can be any naturally occurring amino acid
<220> FEATURE:
<221> NAME/KEY: misc_feature
<222> LOCATION: (494)..(494)
<223> OTHER INFORMATION: Xaa can be any naturally occurring amino acid
<220> FEATURE:
<221> NAME/KEY: misc_feature
<222> LOCATION: (500)..(501)
<223> OTHER INFORMATION: Xaa can be any naturally occurring amino acid
<220> FEATURE:
<221> NAME/KEY: misc_feature
<222> LOCATION: (509)..(509)
<223> OTHER INFORMATION: Xaa can be any naturally occurring amino acid
<220> FEATURE:
<221> NAME/KEY: misc_feature
<222> LOCATION: (512)..(512)
<223> OTHER INFORMATION: Xaa can be any naturally occurring amino acid
<220> FEATURE:
<221> NAME/KEY: misc_feature
<222> LOCATION: (515)..(516)
<223> OTHER INFORMATION: Xaa can be any naturally occurring amino acid
<220> FEATURE:
<221> NAME/KEY: misc_feature
<222> LOCATION: (523)..(526)
<223> OTHER INFORMATION: Xaa can be any naturally occurring amino acid
<220> FEATURE:
<221> NAME/KEY: misc_feature
<222> LOCATION: (528)..(528)
<223> OTHER INFORMATION: Xaa can be any naturally occurring amino acid
<220> FEATURE:
<221> NAME/KEY: misc_feature
<222> LOCATION: (530)..(552)
<223> OTHER INFORMATION: Xaa can be any naturally occurring amino acid
<220> FEATURE:
```

<221> NAME/KEY: misc_feature
<222> LOCATION: (558)..(595)
<223> OTHER INFORMATION: Xaa can be any naturally occurring amino acid

<400> SEQUENCE: 15

```
Xaa Xaa Xaa Xaa Xaa Xaa Xaa Xaa Xaa Xaa Xaa Xaa Xaa Xaa
1               5                   10                  15

Xaa Xaa Glu Xaa Xaa Xaa Xaa Gly Xaa Xaa Leu Gly Xaa Xaa
            20                  25              30

Xaa Arg Xaa Xaa Xaa Xaa Xaa Xaa Xaa Xaa Xaa Xaa Glu Leu
        35                  40                  45

Xaa Xaa Xaa Gly Xaa Pro Xaa Xaa Xaa Xaa Xaa Xaa Pro Xaa
50                  55                  60

Xaa Asp Cys Xaa Cys Xaa Gly Leu Pro Xaa Arg Tyr Ile Ala Ile
65              70                  75                  80

Met Ser Gly Leu Gly Phe Cys Ile Ser Phe Gly Ile Arg Cys Asn Leu
                85                  90                  95

Gly Val Ala Ile Val Xaa Met Val Asn Asn Ser Thr Xaa Xaa Xaa Xaa
                100             105                 110

Gly Xaa Xaa Xaa Xaa Xaa Ala Xaa Phe Xaa Trp Asp Pro Glu Thr
    115                 120                 125

Val Gly Xaa Ile His Gly Ser Phe Phe Trp Gly Tyr Ile Xaa Thr Gln
130                 135                 140

Ile Pro Gly Gly Xaa Ile Xaa Xaa Xaa Ala Ala Asn Arg Val Phe
145                 150                 155                 160

Gly Xaa Ala Ile Xaa Xaa Thr Ser Thr Leu Asn Met Xaa Ile Pro Ser
                165                 170                 175

Ala Ala Arg Val His Tyr Gly Cys Val Xaa Xaa Val Arg Ile Leu Gln
                180                 185                 190

Gly Leu Val Glu Gly Val Thr Tyr Pro Ala Cys His Gly Xaa Trp Ser
            195                 200                 205

Lys Trp Ala Pro Pro Leu Glu Arg Ser Arg Leu Ala Thr Thr Xaa Phe
210                 215                 220

Cys Gly Ser Tyr Ala Gly Ala Val Xaa Ala Met Pro Leu Ala Gly Xaa
225                 230                 235                 240

Leu Val Gln Tyr Xaa Gly Trp Ser Ser Val Phe Tyr Xaa Tyr Gly Xaa
                245                 250                 255

Phe Gly Xaa Xaa Trp Tyr Xaa Phe Trp Leu Leu Xaa Xaa Tyr Glu Xaa
            260                 265                 270

Pro Ala Xaa His Pro Xaa Ile Xaa Xaa Glu Glu Xaa Xaa Tyr Ile Glu
            275                 280                 285

Xaa Xaa Ile Gly Glu Xaa Ala Xaa Xaa Xaa Xaa Xaa Xaa Lys Phe
290                 295                 300

Xaa Thr Pro Trp Xaa Xaa Phe Phe Thr Ser Xaa Pro Val Tyr Ala Ile
305                 310                 315                 320

Ile Val Ala Asn Phe Cys Arg Ser Trp Thr Phe Tyr Leu Leu Leu Ile
                325                 330                 335

Ser Gln Pro Ala Tyr Phe Glu Glu Val Phe Gly Phe Xaa Ile Ser Lys
                340                 345                 350

Val Gly Xaa Xaa Ser Ala Xaa Pro His Xaa Val Met Thr Ile Xaa Val
            355                 360                 365

Pro Ile Gly Gly Gln Xaa Ala Asp Xaa Leu Arg Ser Xaa Xaa Ile Xaa
370                 375                 380

Xaa Thr Thr Xaa Val Arg Lys Xaa Met Asn Cys Gly Gly Phe Gly Met
```

```
                385                 390                 395                 400
        Glu Ala Thr Leu Leu Val Val Gly Xaa Ser His Xaa Xaa Gly Val
                        405                 410                 415
        Ala Ile Ser Phe Leu Val Leu Ala Val Gly Phe Ser Gly Phe Ala Ile
                        420                 425                 430
        Ser Gly Phe Asn Val Asn His Leu Asp Ile Ala Pro Arg Tyr Ala Ser
                        435                 440                 445
        Ile Leu Met Gly Ile Ser Asn Gly Val Gly Thr Leu Ser Gly Met Val
                        450                 455                 460
        Cys Pro Xaa Ile Val Gly Ala Met Thr Xaa Xaa Lys Xaa Arg Glu Glu
        465                 470                 475                 480
        Trp Gln Xaa Val Phe Leu Ile Ala Xaa Leu Val His Tyr Xaa Gly Val
                        485                 490                 495
        Ile Phe Tyr Xaa Xaa Phe Ala Ser Gly Glu Lys Gln Xaa Trp Ala Xaa
                        500                 505                 510
        Pro Glu Xaa Xaa Ser Glu Glu Lys Cys Gly Xaa Xaa Xaa Asp Xaa
                        515                 520                 525
        Leu Xaa Xaa Xaa Xaa Xaa Xaa Xaa Xaa Xaa Xaa Xaa Xaa
                        530                 535                 540
        Xaa Xaa Xaa Xaa Xaa Xaa Xaa Ser Tyr Gly Ala Thr Xaa Xaa Xaa
        545                 550                 555                 560
        Xaa Xaa Xaa Xaa Xaa Xaa Xaa Xaa Xaa Xaa Xaa Xaa Xaa Xaa Xaa
                        565                 570                 575
        Xaa Xaa Xaa Xaa Xaa Xaa Xaa Xaa Xaa Xaa Xaa Xaa Xaa Xaa Xaa
                        580                 585                 590
        Xaa Xaa Xaa
                595

<210> SEQ ID NO 16
<211> LENGTH: 71
<212> TYPE: PRT
<213> ORGANISM: Artificial Sequence
<220> FEATURE:
<223> OTHER INFORMATION: VGLUT2 human aa1-71

<400> SEQUENCE: 16

Met Glu Ser Val Lys Gln Arg Ile Leu Ala Pro Gly Lys Glu Gly Leu
1               5                   10                  15
Lys Asn Phe Ala Gly Lys Ser Leu Gly Gln Ile Tyr Arg Val Leu Glu
                20                  25                  30
Lys Lys Gln Asp Thr Gly Glu Thr Ile Glu Leu Thr Glu Asp Gly Lys
            35                  40                  45
Pro Leu Glu Val Pro Glu Arg Lys Ala Pro Leu Cys Asp Cys Thr Cys
        50                  55                  60
Phe Gly Leu Pro Arg Arg Tyr
65                  70

<210> SEQ ID NO 17
<211> LENGTH: 33
<212> TYPE: PRT
<213> ORGANISM: Artificial Sequence
<220> FEATURE:
<223> OTHER INFORMATION: VGLUT2 human aa93-125

<400> SEQUENCE: 17

Val Ala Ile Val Asp Met Val Asn Asn Ser Thr Ile His Arg Gly Gly
1               5                   10                  15
```

```
Lys Val Ile Lys Glu Lys Ala Lys Phe Asn Trp Asp Pro Glu Thr Val
            20                  25                  30

Gly

<210> SEQ ID NO 18
<211> LENGTH: 45
<212> TYPE: PRT
<213> ORGANISM: Artificial Sequence
<220> FEATURE:
<223> OTHER INFORMATION: VGLUT2 human aa266 -310

<400> SEQUENCE: 18

Glu Ser Pro Ala Lys His Pro Thr Ile Thr Asp Glu Glu Arg Arg Tyr
1               5                   10                  15

Ile Glu Glu Ser Ile Gly Glu Ser Ala Asn Leu Leu Gly Ala Met Glu
            20                  25                  30

Lys Phe Lys Thr Pro Trp Arg Lys Phe Phe Thr Ser Met
        35                  40                  45

<210> SEQ ID NO 19
<211> LENGTH: 84
<212> TYPE: PRT
<213> ORGANISM: Artificial Sequence
<220> FEATURE:
<223> OTHER INFORMATION: VGLUT2 human aa499-582

<400> SEQUENCE: 19

Ser Gly Glu Lys Gln Pro Trp Ala Asp Pro Glu Glu Thr Ser Glu Glu
1               5                   10                  15

Lys Cys Gly Phe Ile His Glu Asp Leu Asp Glu Glu Thr Gly Asp
            20                  25                  30

Ile Thr Gln Asn Tyr Ile Asn Tyr Gly Thr Thr Lys Ser Tyr Gly Ala
        35                  40                  45

Thr Thr Gln Ala Asn Gly Gly Trp Pro Ser Gly Trp Glu Lys Lys Glu
    50                  55                  60

Glu Phe Val Gln Gly Glu Val Gln Asp Ser His Ser Tyr Lys Asp Arg
65                  70                  75                  80

Val Asp Tyr Ser

<210> SEQ ID NO 20
<211> LENGTH: 560
<212> TYPE: PRT
<213> ORGANISM: Rattus norvegicus

<400> SEQUENCE: 20

Met Glu Phe Arg Gln Glu Glu Phe Arg Lys Leu Ala Gly Arg Ala Leu
1               5                   10                  15

Gly Arg Leu His Arg Leu Leu Glu Lys Arg Gln Glu Gly Ala Glu Thr
            20                  25                  30

Leu Glu Leu Ser Ala Asp Gly Arg Pro Val Thr Thr His Thr Arg Asp
        35                  40                  45

Pro Pro Val Val Asp Cys Thr Cys Phe Gly Leu Pro Arg Arg Tyr Ile
    50                  55                  60

Ile Ala Ile Met Ser Gly Leu Gly Phe Cys Ile Ser Phe Gly Ile Arg
65                  70                  75                  80

Cys Asn Leu Gly Val Ala Ile Val Ser Met Val Asn Asn Ser Thr Thr
            85                  90                  95

His Arg Gly Gly His Val Val Val Gln Lys Ala Gln Phe Asn Trp Asp
            100                 105                 110
```

```
Pro Glu Thr Val Gly Leu Ile His Gly Ser Phe Phe Trp Gly Tyr Ile
            115                 120                 125

Val Thr Gln Ile Pro Gly Gly Phe Ile Cys Gln Lys Phe Ala Ala Asn
    130                 135                 140

Arg Val Phe Gly Phe Ala Ile Val Ala Thr Ser Thr Leu Asn Met Leu
145                 150                 155                 160

Ile Pro Ser Ala Ala Arg Val His Tyr Gly Cys Val Ile Phe Val Arg
                165                 170                 175

Ile Leu Gln Gly Leu Val Glu Gly Val Thr Tyr Pro Ala Cys His Gly
                180                 185                 190

Ile Trp Ser Lys Trp Ala Pro Pro Leu Glu Arg Ser Arg Leu Ala Thr
        195                 200                 205

Thr Ala Phe Cys Gly Ser Tyr Ala Gly Ala Val Val Ala Met Pro Leu
        210                 215                 220

Ala Gly Val Leu Val Gln Tyr Ser Gly Trp Ser Ser Val Phe Tyr Val
225                 230                 235                 240

Tyr Gly Ser Phe Gly Ile Phe Trp Tyr Leu Phe Trp Leu Leu Val Ser
                245                 250                 255

Tyr Glu Ser Pro Ala Leu His Pro Ser Ile Ser Glu Glu Glu Arg Lys
            260                 265                 270

Tyr Ile Glu Asp Ala Ile Gly Glu Ser Ala Lys Leu Met Asn Pro Val
        275                 280                 285

Thr Lys Phe Asn Thr Pro Trp Arg Arg Phe Phe Thr Ser Met Pro Val
        290                 295                 300

Tyr Ala Ile Ile Val Ala Asn Phe Cys Arg Ser Trp Thr Phe Tyr Leu
305                 310                 315                 320

Leu Leu Ile Ser Gln Pro Ala Tyr Phe Glu Glu Val Phe Gly Phe Glu
                325                 330                 335

Ile Ser Lys Val Gly Leu Val Ser Ala Leu Pro His Leu Val Met Thr
            340                 345                 350

Ile Ile Val Pro Ile Gly Gly Gln Ile Ala Asp Phe Leu Arg Ser Arg
        355                 360                 365

His Ile Met Ser Thr Thr Asn Val Arg Lys Leu Met Asn Cys Gly Gly
        370                 375                 380

Phe Gly Met Glu Ala Thr Leu Leu Val Val Gly Tyr Ser His Ser
385                 390                 395                 400

Lys Gly Val Ala Ile Ser Phe Leu Val Leu Ala Val Gly Phe Ser Gly
                405                 410                 415

Phe Ala Ile Ser Gly Phe Asn Val Asn His Leu Asp Ile Ala Pro Arg
            420                 425                 430

Tyr Ala Ser Ile Leu Met Gly Ile Ser Asn Gly Val Gly Thr Leu Ser
        435                 440                 445

Gly Met Val Cys Pro Ile Ile Val Gly Ala Met Thr Lys His Lys Thr
450                 455                 460

Arg Glu Glu Trp Gln Tyr Val Phe Leu Ile Ala Ser Leu Val His Tyr
465                 470                 475                 480

Gly Gly Val Ile Phe Tyr Gly Val Phe Ala Ser Gly Glu Lys Gln Pro
                485                 490                 495

Trp Ala Glu Pro Glu Glu Met Ser Glu Glu Lys Cys Gly Phe Val Gly
            500                 505                 510

His Asp Gln Leu Ala Gly Ser Asp Glu Ser Glu Met Glu Asp Glu Val
        515                 520                 525
```

-continued

```
Glu Pro Pro Gly Ala Pro Ala Pro Pro Ser Tyr Gly Ala Thr
    530             535             540

His Ser Thr Val Gln Pro Pro Arg Pro Pro Pro Val Arg Asp Tyr
545             550             555             560
```

<210> SEQ ID NO 21
<211> LENGTH: 582
<212> TYPE: PRT
<213> ORGANISM: Rattus norvegicus

<400> SEQUENCE: 21

```
Met Glu Ser Val Lys Gln Arg Ile Leu Ala Pro Gly Lys Glu Gly Ile
1               5                   10                  15

Lys Asn Phe Ala Gly Lys Ser Leu Gly Gln Ile Tyr Arg Val Leu Glu
                20                  25                  30

Lys Lys Gln Asp Asn Arg Glu Thr Ile Glu Leu Thr Glu Asp Gly Lys
            35                  40                  45

Pro Leu Glu Val Pro Glu Lys Lys Ala Pro Leu Cys Asp Cys Thr Cys
    50                  55                  60

Phe Gly Leu Pro Arg Arg Tyr Ile Ile Ala Ile Met Ser Gly Leu Gly
65              70                  75                  80

Phe Cys Ile Ser Phe Gly Ile Arg Cys Asn Leu Gly Val Ala Ile Val
                85                  90                  95

Asp Met Val Asn Asn Ser Thr Ile His Arg Gly Gly Lys Val Ile Lys
            100                 105                 110

Glu Lys Ala Lys Phe Asn Trp Asp Pro Glu Thr Val Gly Met Ile His
        115                 120                 125

Gly Ser Phe Phe Trp Gly Tyr Ile Ile Thr Gln Ile Pro Gly Gly Tyr
    130                 135                 140

Ile Ala Ser Arg Leu Ala Ala Asn Arg Val Phe Gly Ala Ala Ile Leu
145                 150                 155                 160

Leu Thr Ser Thr Leu Asn Met Leu Ile Pro Ser Ala Ala Arg Val His
                165                 170                 175

Tyr Gly Cys Val Ile Phe Val Arg Ile Leu Gln Gly Leu Val Glu Gly
            180                 185                 190

Val Thr Tyr Pro Ala Cys His Gly Ile Trp Ser Lys Trp Ala Pro Pro
        195                 200                 205

Leu Glu Arg Ser Arg Leu Ala Thr Thr Ser Phe Cys Gly Ser Tyr Ala
    210                 215                 220

Gly Ala Val Ile Ala Met Pro Leu Ala Gly Ile Leu Val Gln Tyr Thr
225                 230                 235                 240

Gly Trp Ser Ser Val Phe Tyr Val Tyr Gly Ser Phe Gly Met Val Trp
                245                 250                 255

Tyr Met Phe Trp Leu Leu Val Ser Tyr Glu Ser Pro Ala Lys His Pro
            260                 265                 270

Thr Ile Thr Asp Glu Glu Arg Arg Tyr Ile Glu Glu Ser Ile Gly Glu
        275                 280                 285

Ser Ala Asn Leu Leu Gly Ala Met Glu Lys Phe Lys Thr Pro Trp Arg
    290                 295                 300

Lys Phe Phe Thr Ser Met Pro Val Tyr Ala Ile Ile Val Ala Asn Phe
305                 310                 315                 320

Cys Arg Ser Trp Thr Phe Tyr Leu Leu Leu Ile Ser Gln Pro Ala Tyr
                325                 330                 335

Phe Glu Glu Val Phe Gly Phe Glu Ile Ser Lys Val Gly Met Leu Ser
            340                 345                 350
```

```
Ala Val Pro His Leu Val Met Thr Ile Ile Val Pro Ile Gly Gly Gln
            355                 360                 365

Ile Ala Asp Phe Leu Arg Ser Lys Gln Ile Leu Ser Thr Thr Thr Val
370                 375                 380

Arg Lys Ile Met Asn Cys Gly Phe Gly Met Glu Ala Thr Leu Leu
385                 390                 395                 400

Leu Val Val Gly Tyr Ser His Thr Arg Gly Val Ala Ile Ser Phe Leu
                405                 410                 415

Val Leu Ala Val Gly Phe Ser Gly Phe Ala Ile Ser Gly Phe Asn Val
            420                 425                 430

Asn His Leu Asp Ile Ala Pro Arg Tyr Ala Ser Ile Leu Met Gly Ile
            435                 440                 445

Ser Asn Gly Val Gly Thr Leu Ser Gly Met Val Cys Pro Ile Ile Val
            450                 455                 460

Gly Ala Met Thr Lys Asn Lys Ser Arg Glu Glu Trp Gln Tyr Val Phe
465                 470                 475                 480

Leu Ile Ala Ala Leu Val His Tyr Gly Gly Val Ile Phe Tyr Ala Leu
                485                 490                 495

Phe Ala Ser Gly Glu Lys Gln Pro Trp Ala Asp Pro Glu Glu Thr Ser
            500                 505                 510

Glu Glu Lys Cys Gly Phe Ile His Glu Asp Glu Leu Asp Glu Glu Thr
            515                 520                 525

Gly Asp Ile Thr Gln Asn Tyr Ile Asn Tyr Gly Thr Thr Lys Ser Tyr
            530                 535                 540

Gly Ala Thr Ser Gln Glu Asn Gly Gly Trp Pro Asn Gly Trp Glu Lys
545                 550                 555                 560

Lys Glu Glu Phe Val Gln Glu Ser Ala Gln Asp Ala Tyr Ser Tyr Lys
                565                 570                 575

Asp Arg Asp Asp Tyr Ser
            580

<210> SEQ ID NO 22
<211> LENGTH: 588
<212> TYPE: PRT
<213> ORGANISM: Rattus norvegicus

<400> SEQUENCE: 22

Met Pro Phe Asn Ala Phe Asp Thr Phe Lys Glu Lys Ile Leu Lys Pro
1               5                   10                  15

Gly Lys Glu Gly Val Lys Asn Ala Val Gly Asp Ser Leu Gly Ile Leu
            20                  25                  30

Gln Arg Lys Leu Asp Gly Thr Asn Glu Glu Gly Asp Ala Ile Glu Leu
        35                  40                  45

Ser Glu Glu Gly Arg Pro Val Gln Thr Ser Arg Ala Arg Ala Pro Val
50                  55                  60

Cys Asp Cys Ser Cys Cys Gly Ile Pro Lys Arg Tyr Ile Ile Ala Val
65                  70                  75                  80

Met Ser Gly Leu Gly Phe Cys Ile Ser Phe Gly Ile Arg Cys Asn Leu
                85                  90                  95

Gly Val Ala Ile Val Glu Met Val Asn Asn Ser Thr Val Tyr Val Asp
            100                 105                 110

Gly Lys Pro Glu Ile Gln Thr Ala Gln Phe Asn Trp Asp Pro Glu Thr
        115                 120                 125

Val Gly Leu Ile His Gly Ser Phe Phe Trp Gly Tyr Ile Val Thr Gln
```

```
            130                 135                 140
Ile Pro Gly Gly Phe Ile Ser Asn Lys Phe Ala Ala Asn Arg Val Phe
145                 150                 155                 160

Gly Ala Ala Ile Phe Leu Thr Ser Thr Leu Asn Met Phe Ile Pro Ser
                165                 170                 175

Ala Ala Arg Val His Tyr Gly Cys Val Met Cys Val Arg Ile Leu Gln
                180                 185                 190

Gly Leu Val Glu Gly Val Thr Tyr Pro Ala Cys His Gly Met Trp Ser
                195                 200                 205

Lys Trp Ala Pro Pro Leu Glu Arg Ser Arg Leu Ala Thr Thr Ser Phe
210                 215                 220

Cys Gly Ser Tyr Ala Gly Ala Val Val Ala Met Pro Leu Ala Gly Val
225                 230                 235                 240

Leu Val Gln Tyr Ile Gly Trp Ala Ser Val Phe Tyr Ile Tyr Gly Met
                245                 250                 255

Phe Gly Ile Ile Trp Tyr Met Phe Trp Leu Leu Gln Ala Tyr Glu Cys
                260                 265                 270

Pro Ala Val His Pro Thr Ile Ser Asn Glu Glu Arg Thr Tyr Ile Glu
                275                 280                 285

Thr Ser Ile Gly Glu Gly Ala Asn Leu Ala Ser Leu Ser Lys Phe Asn
290                 295                 300

Thr Pro Trp Arg Arg Phe Phe Thr Ser Leu Pro Val Tyr Ala Ile Ile
305                 310                 315                 320

Val Ala Asn Phe Cys Arg Ser Trp Thr Phe Tyr Leu Leu Leu Ile Ser
                325                 330                 335

Gln Pro Ala Tyr Phe Glu Glu Val Phe Gly Phe Ala Ile Ser Lys Val
                340                 345                 350

Gly Leu Leu Ser Ala Val Pro His Met Val Met Thr Ile Val Val Pro
                355                 360                 365

Ile Gly Gly Gln Leu Ala Asp Tyr Leu Arg Ser Arg Lys Ile Leu Thr
                370                 375                 380

Thr Thr Ala Val Arg Lys Ile Met Asn Cys Gly Gly Phe Gly Met Glu
385                 390                 395                 400

Ala Thr Leu Leu Leu Val Val Gly Phe Ser His Thr Lys Gly Val Ala
                405                 410                 415

Ile Ser Phe Leu Val Leu Ala Val Gly Phe Ser Gly Phe Ala Ile Ser
                420                 425                 430

Gly Phe Asn Val Asn His Leu Asp Ile Ala Pro Arg Tyr Ala Ser Ile
                435                 440                 445

Leu Met Gly Ile Ser Asn Gly Val Gly Thr Leu Ser Gly Met Val Cys
450                 455                 460

Pro Leu Ile Val Gly Ala Met Thr Lys His Lys Thr Arg Glu Glu Trp
465                 470                 475                 480

Gln Asn Val Phe Leu Ile Ala Ala Leu Val His Tyr Ser Gly Val Ile
                485                 490                 495

Phe Tyr Gly Val Phe Ala Ser Gly Glu Lys Gln Asp Trp Ala Asp Pro
                500                 505                 510

Glu Asn Leu Ser Glu Glu Lys Cys Gly Ile Ile Asp Gln Asp Glu Leu
                515                 520                 525

Ala Glu Glu Thr Glu Leu Asn His Glu Ala Phe Val Ser Pro Arg Lys
                530                 535                 540

Lys Met Ser Tyr Gly Ala Thr Thr Gln Asn Cys Glu Val Gln Lys Thr
545                 550                 555                 560
```

Asp Arg Arg Gln Gln Arg Glu Ser Ala Phe Glu Gly Glu Glu Pro Leu
            565                 570                 575

Ser Tyr Gln Asn Glu Glu Asp Phe Ser Glu Thr Ser
            580                 585

<210> SEQ ID NO 23
<211> LENGTH: 377
<212> TYPE: PRT
<213> ORGANISM: Artificial Sequence
<220> FEATURE:
<223> OTHER INFORMATION: consensus sequence from immunoglobulin heavy
      constant gamma 1, 2, 3, 4
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (20)..(21)
<223> OTHER INFORMATION: Xaa can be any naturally occurring amino acid
<220> FEATURE:
<221> NAME/KEY: misc_feature
<222> LOCATION: (75)..(76)
<223> OTHER INFORMATION: Xaa can be any naturally occurring amino acid
<220> FEATURE:
<221> NAME/KEY: misc_feature
<222> LOCATION: (79)..(79)
<223> OTHER INFORMATION: Xaa can be any naturally occurring amino acid
<220> FEATURE:
<221> NAME/KEY: misc_feature
<222> LOCATION: (82)..(82)
<223> OTHER INFORMATION: Xaa can be any naturally occurring amino acid
<220> FEATURE:
<221> NAME/KEY: misc_feature
<222> LOCATION: (86)..(86)
<223> OTHER INFORMATION: Xaa can be any naturally occurring amino acid
<220> FEATURE:
<221> NAME/KEY: misc_feature
<222> LOCATION: (97)..(97)
<223> OTHER INFORMATION: Xaa can be any naturally occurring amino acid
<220> FEATURE:
<221> NAME/KEY: misc_feature
<222> LOCATION: (100)..(155)
<223> OTHER INFORMATION: Xaa can be any naturally occurring amino acid
<220> FEATURE:
<221> NAME/KEY: misc_feature
<222> LOCATION: (158)..(158)
<223> OTHER INFORMATION: Xaa can be any naturally occurring amino acid
<220> FEATURE:
<221> NAME/KEY: misc_feature
<222> LOCATION: (163)..(166)
<223> OTHER INFORMATION: Xaa can be any naturally occurring amino acid
<220> FEATURE:
<221> NAME/KEY: misc_feature
<222> LOCATION: (198)..(198)
<223> OTHER INFORMATION: Xaa can be any naturally occurring amino acid
<220> FEATURE:
<221> NAME/KEY: misc_feature
<222> LOCATION: (204)..(204)
<223> OTHER INFORMATION: Xaa can be any naturally occurring amino acid
<220> FEATURE:
<221> NAME/KEY: misc_feature
<222> LOCATION: (206)..(206)
<223> OTHER INFORMATION: Xaa can be any naturally occurring amino acid
<220> FEATURE:
<221> NAME/KEY: misc_feature
<222> LOCATION: (226)..(226)
<223> OTHER INFORMATION: Xaa can be any naturally occurring amino acid
<220> FEATURE:
<221> NAME/KEY: misc_feature
<222> LOCATION: (230)..(230)
<223> OTHER INFORMATION: Xaa can be any naturally occurring amino acid

```
<220> FEATURE:
<221> NAME/KEY: misc_feature
<222> LOCATION: (239)..(239)
<223> OTHER INFORMATION: Xaa can be any naturally occurring amino acid
<220> FEATURE:
<221> NAME/KEY: misc_feature
<222> LOCATION: (257)..(257)
<223> OTHER INFORMATION: Xaa can be any naturally occurring amino acid
<220> FEATURE:
<221> NAME/KEY: misc_feature
<222> LOCATION: (260)..(261)
<223> OTHER INFORMATION: Xaa can be any naturally occurring amino acid
<220> FEATURE:
<221> NAME/KEY: misc_feature
<222> LOCATION: (269)..(269)
<223> OTHER INFORMATION: Xaa can be any naturally occurring amino acid
<220> FEATURE:
<221> NAME/KEY: misc_feature
<222> LOCATION: (285)..(286)
<223> OTHER INFORMATION: Xaa can be any naturally occurring amino acid
<220> FEATURE:
<221> NAME/KEY: misc_feature
<222> LOCATION: (288)..(288)
<223> OTHER INFORMATION: Xaa can be any naturally occurring amino acid
<220> FEATURE:
<221> NAME/KEY: misc_feature
<222> LOCATION: (308)..(308)
<223> OTHER INFORMATION: Xaa can be any naturally occurring amino acid
<220> FEATURE:
<221> NAME/KEY: misc_feature
<222> LOCATION: (314)..(314)
<223> OTHER INFORMATION: Xaa can be any naturally occurring amino acid
<220> FEATURE:
<221> NAME/KEY: misc_feature
<222> LOCATION: (322)..(322)
<223> OTHER INFORMATION: Xaa can be any naturally occurring amino acid
<220> FEATURE:
<221> NAME/KEY: misc_feature
<222> LOCATION: (327)..(327)
<223> OTHER INFORMATION: Xaa can be any naturally occurring amino acid
<220> FEATURE:
<221> NAME/KEY: misc_feature
<222> LOCATION: (339)..(339)
<223> OTHER INFORMATION: Xaa can be any naturally occurring amino acid
<220> FEATURE:
<221> NAME/KEY: misc_feature
<222> LOCATION: (349)..(349)
<223> OTHER INFORMATION: Xaa can be any naturally occurring amino acid
<220> FEATURE:
<221> NAME/KEY: misc_feature
<222> LOCATION: (352)..(352)
<223> OTHER INFORMATION: Xaa can be any naturally occurring amino acid
<220> FEATURE:
<221> NAME/KEY: misc_feature
<222> LOCATION: (365)..(366)
<223> OTHER INFORMATION: Xaa can be any naturally occurring amino acid
<220> FEATURE:
<221> NAME/KEY: misc_feature
<222> LOCATION: (375)..(375)
<223> OTHER INFORMATION: Xaa can be any naturally occurring amino acid

<400> SEQUENCE: 23

Ala Ser Thr Lys Gly Pro Ser Val Phe Pro Leu Ala Pro Xaa Ser Xaa
1               5                   10                  15

Ser Thr Ser Xaa Xaa Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Xaa Xaa Gly Thr Xaa Thr
65                  70                  75                  80

Tyr Xaa Cys Asn Val Xaa His Lys Pro Ser Asn Thr Lys Val Asp Lys
```

85                  90                  95
Xaa Val Glu Xaa Xaa Xaa Xaa Xaa Xaa Xaa Xaa Xaa Xaa Xaa
                100                 105                 110

Xaa Xaa Xaa Xaa Xaa Xaa Xaa Xaa Xaa Xaa Xaa Xaa Xaa Xaa
            115                 120                 125

Xaa Xaa Xaa Xaa Xaa Xaa Xaa Xaa Xaa Xaa Xaa Xaa Xaa Xaa
        130                 135                 140

Xaa Xaa Xaa Xaa Xaa Xaa Xaa Xaa Xaa Cys Pro Xaa Cys Pro
145                 150                 155                 160

Ala Pro Xaa Xaa Xaa Xaa Gly Pro Ser Val Phe Leu Phe Pro Lys
                165                 170                 175

Pro Lys Asp Thr Leu Met Ile Ser Arg Thr Pro Glu Val Thr Cys Val
                180                 185                 190

Val Val Asp Val Ser Xaa Glu Asp Pro Glu Val Xaa Phe Xaa Trp Tyr
                195                 200                 205

Val Asp Gly Val Glu Val His Asn Ala Lys Thr Lys Pro Arg Glu Glu
            210                 215                 220

Gln Xaa Asn Ser Thr Xaa Arg Val Val Ser Val Leu Thr Val Xaa His
225                 230                 235                 240

Gln Asp Trp Leu Asn Gly Lys Glu Tyr Lys Cys Lys Val Ser Asn Lys
                245                 250                 255

Xaa Leu Pro Xaa Xaa Ile Glu Lys Thr Ile Ser Lys Xaa Lys Gly Gln
                260                 265                 270

Pro Arg Glu Pro Gln Val Tyr Thr Leu Pro Pro Ser Xaa Xaa Glu Xaa
            275                 280                 285

Thr Lys Asn Gln Val Ser Leu Thr Cys Leu Val Lys Gly Phe Tyr Pro
290                 295                 300

Ser Asp Ile Xaa Val Glu Trp Glu Ser Xaa Gly Gln Pro Glu Asn Asn
305                 310                 315                 320

Tyr Xaa Thr Thr Pro Pro Xaa Leu Asp Ser Asp Gly Ser Phe Phe Leu
                325                 330                 335

Tyr Ser Xaa Leu Thr Val Asp Lys Ser Arg Trp Gln Xaa Gly Asn Xaa
            340                 345                 350

Phe Ser Cys Ser Val Met His Glu Ala Leu His Asn Xaa Xaa Thr Gln
                355                 360                 365

Lys Ser Leu Ser Leu Ser Xaa Gly Lys
            370                 375

<210> SEQ ID NO 24
<211> LENGTH: 39
<212> TYPE: DNA
<213> ORGANISM: Artificial Sequence
<220> FEATURE:
<223> OTHER INFORMATION: sense VGLUT2-1-71

<400> SEQUENCE: 24
atacgtctca catggaatcc gtaaaacaaa ggattttgg                        39

<210> SEQ ID NO 25
<211> LENGTH: 42
<212> TYPE: DNA
<213> ORGANISM: Artificial Sequence
<220> FEATURE:
<223> OTHER INFORMATION: asense VGLUT2-1-71

<400> SEQUENCE: 25
atacgtctcc tcgattaata ccgccgaggc agaccgaaac ag                    42

<210> SEQ ID NO 26
<211> LENGTH: 38
<212> TYPE: DNA
<213> ORGANISM: Artificial Sequence
<220> FEATURE:
<223> OTHER INFORMATION: sense VGLUT2-93-125

<400> SEQUENCE: 26
atacgtctca catggttgcc atagtggaca tggtgaac         38

<210> SEQ ID NO 27
<211> LENGTH: 42
<212> TYPE: DNA
<213> ORGANISM: Artificial Sequence
<220> FEATURE:
<223> OTHER INFORMATION: asense VGLUT2-93-125

<400> SEQUENCE: 27
atacgtctcc tcgattagcc cactgtttca ggatcccagt tg         42

<210> SEQ ID NO 28
<211> LENGTH: 38
<212> TYPE: DNA
<213> ORGANISM: Artificial Sequence
<220> FEATURE:
<223> OTHER INFORMATION: sense VGLUT2-266-310

<400> SEQUENCE: 28
atacgtctca catggaaagt ccagccaagc atccgacc         38

<210> SEQ ID NO 29
<211> LENGTH: 43
<212> TYPE: DNA
<213> ORGANISM: Artificial Sequence
<220> FEATURE:
<223> OTHER INFORMATION: asense VGLUT2-266-310

<400> SEQUENCE: 29
atacgtctcc tcgattacat gcttgtgaag aatttgcgcc atg         43

<210> SEQ ID NO 30
<211> LENGTH: 39
<212> TYPE: DNA
<213> ORGANISM: Artificial Sequence
<220> FEATURE:
<223> OTHER INFORMATION: sense VGLUT2-499-582

<400> SEQUENCE: 30
atacgtctca catgtcaggg gaaaagcaac cgtgggcag         39

<210> SEQ ID NO 31
<211> LENGTH: 42
<212> TYPE: DNA
<213> ORGANISM: Artificial Sequence
<220> FEATURE:
<223> OTHER INFORMATION: asense VGLUT2-499-582

<400> SEQUENCE: 31
atacgtctcc tcgattatga ataatcaact cggtccttat ag         42

<210> SEQ ID NO 32
<211> LENGTH: 40
<212> TYPE: DNA
<213> ORGANISM: Artificial Sequence
<220> FEATURE:

```
<223> OTHER INFORMATION: sense VGLUT2-520-582

<400> SEQUENCE: 32
atacgtctca catgcatgag gacgaactgg acgaggaaac                    40

<210> SEQ ID NO 33
<211> LENGTH: 43
<212> TYPE: DNA
<213> ORGANISM: Artificial Sequence
<220> FEATURE:
<223> OTHER INFORMATION: asense VGLUT2-520-564

<400> SEQUENCE: 33
atacgtctcc tcgattaaaa ttcctccttc ttttcccacc cag                43

<210> SEQ ID NO 34
<211> LENGTH: 38
<212> TYPE: DNA
<213> ORGANISM: Artificial Sequence
<220> FEATURE:
<223> OTHER INFORMATION: sense VGLUT2-543-582

<400> SEQUENCE: 34
atacgtctca catgtcctac ggggccacca ctcaggcc                      38

<210> SEQ ID NO 35
<211> LENGTH: 38
<212> TYPE: DNA
<213> ORGANISM: Artificial Sequence
<220> FEATURE:
<223> OTHER INFORMATION: sense VGLUT2-565-582

<400> SEQUENCE: 35
atacgtctca catggtgcaa ggggaggtgc aggattcc                      38

<210> SEQ ID NO 36
<211> LENGTH: 42
<212> TYPE: DNA
<213> ORGANISM: Artificial Sequence
<220> FEATURE:
<223> OTHER INFORMATION: asense VGLUT2-499-542

<400> SEQUENCE: 36
atacgtctcc tcgattattt cgtcgttcca tagttgatgt ag                 42

<210> SEQ ID NO 37
<211> LENGTH: 54
<212> TYPE: DNA
<213> ORGANISM: Artificial Sequence
<220> FEATURE:
<223> OTHER INFORMATION: sense mutant-1_1

<400> SEQUENCE: 37
tgaccagctg gctggcagtg acgacagcat aacacagaac tacatcaact atgg    54

<210> SEQ ID NO 38
<211> LENGTH: 53
<212> TYPE: DNA
<213> ORGANISM: Artificial Sequence
<220> FEATURE:
<223> OTHER INFORMATION: sense mutant-1_2

<400> SEQUENCE: 38
atacgtctca catgttcatt ggccatgacc agctggctgg cagtgacgac agc     53
```

```
<210> SEQ ID NO 39
<211> LENGTH: 54
<212> TYPE: DNA
<213> ORGANISM: Artificial Sequence
<220> FEATURE:
<223> OTHER INFORMATION: asense mutant-2_1

<400> SEQUENCE: 39
agtcccggac aggggtgggg ggcctgggcc acccagaagg ccagcctcca ttgg        54

<210> SEQ ID NO 40
<211> LENGTH: 55
<212> TYPE: DNA
<213> ORGANISM: Artificial Sequence
<220> FEATURE:
<223> OTHER INFORMATION: asense mutant-2_2

<400> SEQUENCE: 40
atacgtctcc tcgagttatc actgcacgta gtcccggaca gggggtgggg gcctg       55

<210> SEQ ID NO 41
<211> LENGTH: 57
<212> TYPE: DNA
<213> ORGANISM: Artificial Sequence
<220> FEATURE:
<223> OTHER INFORMATION: sense mutant-3_1

<400> SEQUENCE: 41
aggacgaact ggacgaggaa acaggagatg aaatggagga tgaggctgag ccccgg      57

<210> SEQ ID NO 42
<211> LENGTH: 59
<212> TYPE: DNA
<213> ORGANISM: Artificial Sequence
<220> FEATURE:
<223> OTHER INFORMATION: asense mutant-3_2

<400> SEQUENCE: 42
atacgtctcc tcgattaaaa ttcctccttc ttttcgggct gaaatgtgct gtgtgtggc   59

<210> SEQ ID NO 43
<211> LENGTH: 48
<212> TYPE: DNA
<213> ORGANISM: Artificial Sequence
<220> FEATURE:
<223> OTHER INFORMATION: sense mutant-4_1

<400> SEQUENCE: 43
gaggaagctg aagaaattga aggagacata acacagaact acatcaac              48

<210> SEQ ID NO 44
<211> LENGTH: 45
<212> TYPE: DNA
<213> ORGANISM: Artificial Sequence
<220> FEATURE:
<223> OTHER INFORMATION: sense mutant-4_2

<400> SEQUENCE: 44
atacgtctca catgcatgac gaggaagctg aagaaattga aggag                 45

<210> SEQ ID NO 45
<211> LENGTH: 41
<212> TYPE: DNA
<213> ORGANISM: Artificial Sequence
<220> FEATURE:
<223> OTHER INFORMATION: sense VGLUT1-IF1
```

<400> SEQUENCE: 45
ataggtctca catggagttc cgccaggagg agtttcggaa g         41

<210> SEQ ID NO 46
<211> LENGTH: 43
<212> TYPE: DNA
<213> ORGANISM: Artificial Sequence
<220> FEATURE:
<223> OTHER INFORMATION: asense VGLUT1-IF1

<400> SEQUENCE: 46
ataggtctcc tcgaggtagt cccggacagg gggtgggggc ctg       43

<210> SEQ ID NO 47
<211> LENGTH: 42
<212> TYPE: DNA
<213> ORGANISM: Artificial Sequence
<220> FEATURE:
<223> OTHER INFORMATION: asense VGLUT1-IF1-Stop

<400> SEQUENCE: 47
ataggtctcc tcgagttatc agtagtcccg gacaggggt gg         42

<210> SEQ ID NO 48
<211> LENGTH: 50
<212> TYPE: DNA
<213> ORGANISM: Artificial Sequence
<220> FEATURE:
<223> OTHER INFORMATION: sense VGLUT3-IF1-F1-1

<400> SEQUENCE: 48
atacgtctcg agtaaattta gtaccccatg gaaaagattt ttcacatctt    50

<210> SEQ ID NO 49
<211> LENGTH: 50
<212> TYPE: DNA
<213> ORGANISM: Artificial Sequence
<220> FEATURE:
<223> OTHER INFORMATION: sense VGLUT3-IF1-F1-2

<400> SEQUENCE: 49
caatcattgt ggcaaatttt tgcagaagct ggacctttta tttgctcctc    50

<210> SEQ ID NO 50
<211> LENGTH: 35
<212> TYPE: DNA
<213> ORGANISM: Artificial Sequence
<220> FEATURE:
<223> OTHER INFORMATION: sense VGLUT3-IF1-F1-3

<400> SEQUENCE: 50
gcttattttg aagaggtctt tggatttgca ataag          35

<210> SEQ ID NO 51
<211> LENGTH: 39
<212> TYPE: DNA
<213> ORGANISM: Artificial Sequence
<220> FEATURE:
<223> OTHER INFORMATION: asense VGLUT3-IF1-F1-4

<400> SEQUENCE: 51
atacgtctcc ttacttattg caaatccaaa gacctcttc      39

<210> SEQ ID NO 52
<211> LENGTH: 52

```
<212> TYPE: DNA
<213> ORGANISM: Artificial Sequence
<220> FEATURE:
<223> OTHER INFORMATION: asense VGLUT3-IF1-F1-5

<400> SEQUENCE: 52
aagacctctt caaaataagc aggctgactt atgaggagca aataaaaggt cc        52

<210> SEQ ID NO 53
<211> LENGTH: 54
<212> TYPE: DNA
<213> ORGANISM: Artificial Sequence
<220> FEATURE:
<223> OTHER INFORMATION: asense VGLUT3-IF1-F1-6

<400> SEQUENCE: 53
caaaaatttg ccacaatgat tgcgtaaacc ggcaaagatg tgaaaaatct tttc      54

<210> SEQ ID NO 54
<211> LENGTH: 38
<212> TYPE: DNA
<213> ORGANISM: Artificial Sequence
<220> FEATURE:
<223> OTHER INFORMATION: sense VGLUT3-IF1-F2

<400> SEQUENCE: 54
atacgtctca catgcctttt aaagcatttg ataccttc                        38

<210> SEQ ID NO 55
<211> LENGTH: 38
<212> TYPE: DNA
<213> ORGANISM: Artificial Sequence
<220> FEATURE:
<223> OTHER INFORMATION: asense VGLUT3-IF1-F2

<400> SEQUENCE: 55
atacgtctca tacttagact aaccacgttg gccccctc                        38

<210> SEQ ID NO 56
<211> LENGTH: 42
<212> TYPE: DNA
<213> ORGANISM: Artificial Sequence
<220> FEATURE:
<223> OTHER INFORMATION: sense VGLUT3-IF1-F3

<400> SEQUENCE: 56
atacgtctca gtaaggtggg tctcttgtca gcagtcccac ac                   42

<210> SEQ ID NO 57
<211> LENGTH: 42
<212> TYPE: DNA
<213> ORGANISM: Artificial Sequence
<220> FEATURE:
<223> OTHER INFORMATION: asense VGLUT3-IF1-F3

<400> SEQUENCE: 57
atacgtctcc tcgagggata tagttgagaa gtttctctct tc                   42

<210> SEQ ID NO 58
<211> LENGTH: 43
<212> TYPE: DNA
<213> ORGANISM: Artificial Sequence
<220> FEATURE:
<223> OTHER INFORMATION: asense VGLUT3-IF1-F3-Stop

<400> SEQUENCE: 58
```
atacgtctcc tcgagtcatt aggatatagt tgagaagttt ctc                    43

<210> SEQ ID NO 59
<211> LENGTH: 39
<212> TYPE: DNA
<213> ORGANISM: Artificial Sequence
<220> FEATURE:
<223> OTHER INFORMATION: sense VGLUT1-491-560

<400> SEQUENCE: 59
ataggtctca catgtctgga gagaagcagc cgtgggcag                         39

<210> SEQ ID NO 60
<211> LENGTH: 39
<212> TYPE: DNA
<213> ORGANISM: Artificial Sequence
<220> FEATURE:
<223> OTHER INFORMATION: sense VGLUT3-503-589

<400> SEQUENCE: 60
atacgtctca catgtctggg gagaaacagg agtgggctg                         39

<210> SEQ ID NO 61
<211> LENGTH: 308
<212> TYPE: PRT
<213> ORGANISM: Artificial Sequence
<220> FEATURE:
<223> OTHER INFORMATION: H8-GST-(PSc)-VGLUT2-aa1-71

<400> SEQUENCE: 61

Met Ser His His His His His His His Met Ser Pro Ile Leu Gly
1               5                   10                  15

Tyr Trp Lys Ile Lys Gly Leu Val Gln Pro Thr Arg Leu Leu Leu Glu
                20                  25                  30

Tyr Leu Glu Glu Lys Tyr Glu Glu His Leu Tyr Glu Arg Asp Glu Gly
            35                  40                  45

Asp Lys Trp Arg Asn Lys Lys Phe Glu Leu Gly Leu Glu Phe Pro Asn
        50                  55                  60

Leu Pro Tyr Tyr Ile Asp Gly Asp Val Lys Leu Thr Gln Ser Met Ala
65                  70                  75                  80

Ile Ile Arg Tyr Ile Ala Asp Lys His Asn Met Leu Gly Gly Cys Pro
                85                  90                  95

Lys Glu Arg Ala Glu Ile Ser Met Leu Glu Gly Ala Val Leu Asp Ile
            100                 105                 110

Arg Tyr Gly Val Ser Arg Ile Ala Tyr Ser Lys Asp Phe Glu Thr Leu
        115                 120                 125

Lys Val Asp Phe Leu Ser Lys Leu Pro Glu Met Leu Lys Met Phe Glu
    130                 135                 140

Asp Arg Leu Cys His Lys Thr Tyr Leu Asn Gly Asp His Val Thr His
145                 150                 155                 160

Pro Asp Phe Met Leu Tyr Asp Ala Leu Asp Val Val Leu Tyr Met Asp
                165                 170                 175

Pro Met Cys Leu Asp Ala Phe Pro Lys Leu Val Cys Phe Lys Lys Arg
            180                 185                 190

Ile Glu Ala Ile Pro Gln Ile Asp Lys Tyr Leu Lys Ser Ser Lys Tyr
        195                 200                 205

Ile Ala Trp Pro Leu Gln Gly Trp Gln Ala Thr Phe Gly Gly Gly Asp
    210                 215                 220

His Pro Pro Lys Leu Glu Val Leu Phe Gln Gly Pro Ala Met Glu Ser

```
                    225                 230                 235                 240

Val Lys Gln Arg Ile Leu Ala Pro Gly Lys Glu Gly Leu Lys Asn Phe
                245                 250                 255

Ala Gly Lys Ser Leu Gly Gln Ile Tyr Arg Val Leu Glu Lys Lys Gln
                260                 265                 270

Asp Thr Gly Glu Thr Ile Glu Leu Thr Glu Asp Gly Lys Pro Leu Glu
                275                 280                 285

Val Pro Glu Arg Lys Ala Pro Leu Cys Asp Cys Thr Cys Phe Gly Leu
                290                 295                 300

Pro Arg Arg Tyr
305

<210> SEQ ID NO 62
<211> LENGTH: 271
<212> TYPE: PRT
<213> ORGANISM: Artificial Sequence
<220> FEATURE:
<223> OTHER INFORMATION: H8-GST-(PSc)-VGLUT2-aa93-125

<400> SEQUENCE: 62

Met Ser His His His His His His His Met Ser Pro Ile Leu Gly
1               5                   10                  15

Tyr Trp Lys Ile Lys Gly Leu Val Gln Pro Thr Arg Leu Leu Leu Glu
                20                  25                  30

Tyr Leu Glu Glu Lys Tyr Glu Glu His Leu Tyr Glu Arg Asp Glu Gly
                35                  40                  45

Asp Lys Trp Arg Asn Lys Lys Phe Glu Leu Gly Leu Glu Phe Pro Asn
50                  55                  60

Leu Pro Tyr Tyr Ile Asp Gly Asp Val Lys Leu Thr Gln Ser Met Ala
65                  70                  75                  80

Ile Ile Arg Tyr Ile Ala Asp Lys His Asn Met Leu Gly Gly Cys Pro
                85                  90                  95

Lys Glu Arg Ala Glu Ile Ser Met Leu Glu Gly Ala Val Leu Asp Ile
                100                 105                 110

Arg Tyr Gly Val Ser Arg Ile Ala Tyr Ser Lys Asp Phe Glu Thr Leu
                115                 120                 125

Lys Val Asp Phe Leu Ser Lys Leu Pro Glu Met Leu Lys Met Phe Glu
                130                 135                 140

Asp Arg Leu Cys His Lys Thr Tyr Leu Asn Gly Asp His Val Thr His
145                 150                 155                 160

Pro Asp Phe Met Leu Tyr Asp Ala Leu Asp Val Val Leu Tyr Met Asp
                165                 170                 175

Pro Met Cys Leu Asp Ala Phe Pro Lys Leu Val Cys Phe Lys Lys Arg
                180                 185                 190

Ile Glu Ala Ile Pro Gln Ile Asp Lys Tyr Leu Lys Ser Ser Lys Tyr
                195                 200                 205

Ile Ala Trp Pro Leu Gln Gly Trp Gln Ala Thr Phe Gly Gly Gly Asp
                210                 215                 220

His Pro Pro Lys Leu Glu Val Leu Phe Gln Gly Pro Ala Met Val Ala
225                 230                 235                 240

Ile Val Asp Met Val Asn Asn Ser Thr Ile His Arg Gly Gly Lys Val
                245                 250                 255

Ile Lys Glu Lys Ala Lys Phe Asn Trp Asp Pro Glu Thr Val Gly
                260                 265                 270
```

-continued

```
<210> SEQ ID NO 63
<211> LENGTH: 283
<212> TYPE: PRT
<213> ORGANISM: Artificial Sequence
<220> FEATURE:
<223> OTHER INFORMATION: H8-GST-(PSc)-VGLUT2-aa266-310

<400> SEQUENCE: 63

Met Ser His His His His His His His Met Ser Pro Ile Leu Gly
1               5                   10                  15

Tyr Trp Lys Ile Lys Gly Leu Val Gln Pro Thr Arg Leu Leu Leu Glu
            20                  25                  30

Tyr Leu Glu Glu Lys Tyr Glu Glu His Leu Tyr Glu Arg Asp Glu Gly
        35                  40                  45

Asp Lys Trp Arg Asn Lys Lys Phe Glu Leu Gly Leu Glu Phe Pro Asn
    50                  55                  60

Leu Pro Tyr Tyr Ile Asp Gly Asp Val Lys Leu Thr Gln Ser Met Ala
65                  70                  75                  80

Ile Ile Arg Tyr Ile Ala Asp Lys His Asn Met Leu Gly Gly Cys Pro
                85                  90                  95

Lys Glu Arg Ala Glu Ile Ser Met Leu Glu Gly Ala Val Leu Asp Ile
            100                 105                 110

Arg Tyr Gly Val Ser Arg Ile Ala Tyr Ser Lys Asp Phe Glu Thr Leu
        115                 120                 125

Lys Val Asp Phe Leu Ser Lys Leu Pro Glu Met Leu Lys Met Phe Glu
    130                 135                 140

Asp Arg Leu Cys His Lys Thr Tyr Leu Asn Gly Asp His Val Thr His
145                 150                 155                 160

Pro Asp Phe Met Leu Tyr Asp Ala Leu Asp Val Val Leu Tyr Met Asp
                165                 170                 175

Pro Met Cys Leu Asp Ala Phe Pro Lys Leu Val Cys Phe Lys Lys Arg
            180                 185                 190

Ile Glu Ala Ile Pro Gln Ile Asp Lys Tyr Leu Lys Ser Ser Lys Tyr
        195                 200                 205

Ile Ala Trp Pro Leu Gln Gly Trp Gln Ala Thr Phe Gly Gly Gly Asp
    210                 215                 220

His Pro Pro Lys Leu Glu Val Leu Phe Gln Gly Pro Ala Met Glu Ser
225                 230                 235                 240

Pro Ala Lys His Pro Thr Ile Thr Asp Glu Glu Arg Arg Tyr Ile Glu
                245                 250                 255

Glu Ser Ile Gly Glu Ser Ala Asn Leu Leu Gly Ala Met Glu Lys Phe
            260                 265                 270

Lys Thr Pro Trp Arg Lys Phe Phe Thr Ser Met
        275                 280

<210> SEQ ID NO 64
<211> LENGTH: 322
<212> TYPE: PRT
<213> ORGANISM: Artificial Sequence
<220> FEATURE:
<223> OTHER INFORMATION: H8-GST-(PSc)-VGLUT2-aa499-582

<400> SEQUENCE: 64

Met Ser His His His His His His His Met Ser Pro Ile Leu Gly
1               5                   10                  15

Tyr Trp Lys Ile Lys Gly Leu Val Gln Pro Thr Arg Leu Leu Leu Glu
            20                  25                  30
```

```
Tyr Leu Glu Glu Lys Tyr Glu Glu His Leu Tyr Glu Arg Asp Glu Gly
         35                  40                  45

Asp Lys Trp Arg Asn Lys Lys Phe Glu Leu Gly Leu Glu Phe Pro Asn
 50                  55                  60

Leu Pro Tyr Tyr Ile Asp Gly Asp Val Lys Leu Thr Gln Ser Met Ala
 65                  70                  75                  80

Ile Ile Arg Tyr Ile Ala Asp Lys His Asn Met Leu Gly Gly Cys Pro
                 85                  90                  95

Lys Glu Arg Ala Glu Ile Ser Met Leu Glu Gly Ala Val Leu Asp Ile
            100                 105                 110

Arg Tyr Gly Val Ser Arg Ile Ala Tyr Ser Lys Asp Phe Glu Thr Leu
            115                 120                 125

Lys Val Asp Phe Leu Ser Lys Leu Pro Glu Met Leu Lys Met Phe Glu
130                 135                 140

Asp Arg Leu Cys His Lys Thr Tyr Leu Asn Gly Asp His Val Thr His
145                 150                 155                 160

Pro Asp Phe Met Leu Tyr Asp Ala Leu Asp Val Val Leu Tyr Met Asp
                165                 170                 175

Pro Met Cys Leu Asp Ala Phe Pro Lys Leu Val Cys Phe Lys Lys Arg
            180                 185                 190

Ile Glu Ala Ile Pro Gln Ile Asp Lys Tyr Leu Lys Ser Ser Lys Tyr
            195                 200                 205

Ile Ala Trp Pro Leu Gln Gly Trp Gln Ala Thr Phe Gly Gly Gly Asp
            210                 215                 220

His Pro Pro Lys Leu Glu Val Leu Phe Gln Gly Pro Ala Met Ser Gly
225                 230                 235                 240

Glu Lys Gln Pro Trp Ala Asp Pro Glu Glu Thr Ser Glu Glu Lys Cys
                245                 250                 255

Gly Phe Ile His Glu Asp Glu Leu Asp Glu Glu Thr Gly Asp Ile Thr
            260                 265                 270

Gln Asn Tyr Ile Asn Tyr Gly Thr Thr Lys Ser Tyr Gly Ala Thr Thr
            275                 280                 285

Gln Ala Asn Gly Gly Trp Pro Ser Gly Trp Glu Lys Lys Glu Glu Phe
290                 295                 300

Val Gln Gly Glu Val Gln Asp Ser His Ser Tyr Lys Asp Arg Val Asp
305                 310                 315                 320

Tyr Ser

<210> SEQ ID NO 65
<211> LENGTH: 301
<212> TYPE: PRT
<213> ORGANISM: Artificial Sequence
<220> FEATURE:
<223> OTHER INFORMATION: H8-GST-(PSc)-VGLUT2-aa520-582

<400> SEQUENCE: 65

Met Ser His His His His His His His Met Ser Pro Ile Leu Gly
  1               5                  10                  15

Tyr Trp Lys Ile Lys Gly Leu Val Gln Pro Thr Arg Leu Leu Leu Glu
                 20                  25                  30

Tyr Leu Glu Glu Lys Tyr Glu Glu His Leu Tyr Glu Arg Asp Glu Gly
             35                  40                  45

Asp Lys Trp Arg Asn Lys Lys Phe Glu Leu Gly Leu Glu Phe Pro Asn
 50                  55                  60

Leu Pro Tyr Tyr Ile Asp Gly Asp Val Lys Leu Thr Gln Ser Met Ala
```

65                  70                  75                  80
Ile Ile Arg Tyr Ile Ala Asp Lys His Asn Met Leu Gly Gly Cys Pro
                    85                  90                  95

Lys Glu Arg Ala Glu Ile Ser Met Leu Glu Gly Ala Val Leu Asp Ile
            100                 105                 110

Arg Tyr Gly Val Ser Arg Ile Ala Tyr Ser Lys Asp Phe Glu Thr Leu
        115                 120                 125

Lys Val Asp Phe Leu Ser Lys Leu Pro Glu Met Leu Lys Met Phe Glu
    130                 135                 140

Asp Arg Leu Cys His Lys Thr Tyr Leu Asn Gly Asp His Val Thr His
145                 150                 155                 160

Pro Asp Phe Met Leu Tyr Asp Ala Leu Asp Val Val Leu Tyr Met Asp
                165                 170                 175

Pro Met Cys Leu Asp Ala Phe Pro Lys Leu Val Cys Phe Lys Lys Arg
            180                 185                 190

Ile Glu Ala Ile Pro Gln Ile Asp Lys Tyr Leu Lys Ser Ser Lys Tyr
        195                 200                 205

Ile Ala Trp Pro Leu Gln Gly Trp Gln Ala Thr Phe Gly Gly Gly Asp
    210                 215                 220

His Pro Pro Lys Leu Glu Val Leu Phe Gln Gly Pro Ala Met His Glu
225                 230                 235                 240

Asp Glu Leu Asp Glu Glu Thr Gly Asp Ile Thr Gln Asn Tyr Ile Asn
                245                 250                 255

Tyr Gly Thr Thr Lys Ser Tyr Gly Ala Thr Thr Gln Ala Asn Gly Gly
            260                 265                 270

Trp Pro Ser Gly Trp Glu Lys Lys Glu Glu Phe Val Gln Gly Glu Val
        275                 280                 285

Gln Asp Ser His Ser Tyr Lys Asp Arg Val Asp Tyr Ser
    290                 295                 300

<210> SEQ ID NO 66
<211> LENGTH: 283
<212> TYPE: PRT
<213> ORGANISM: Artificial Sequence
<220> FEATURE:
<223> OTHER INFORMATION: H8-GST-(PSc)-VGLUT2-aa520-564

<400> SEQUENCE: 66

Met Ser His His His His His His His Met Ser Pro Ile Leu Gly
1               5                   10                  15

Tyr Trp Lys Ile Lys Gly Leu Val Gln Pro Thr Arg Leu Leu Leu Glu
                20                  25                  30

Tyr Leu Glu Glu Lys Tyr Glu Glu His Leu Tyr Glu Arg Asp Glu Gly
            35                  40                  45

Asp Lys Trp Arg Asn Lys Lys Phe Glu Leu Gly Leu Glu Phe Pro Asn
        50                  55                  60

Leu Pro Tyr Tyr Ile Asp Gly Asp Val Lys Leu Thr Gln Ser Met Ala
65                  70                  75                  80

Ile Ile Arg Tyr Ile Ala Asp Lys His Asn Met Leu Gly Gly Cys Pro
                85                  90                  95

Lys Glu Arg Ala Glu Ile Ser Met Leu Glu Gly Ala Val Leu Asp Ile
            100                 105                 110

Arg Tyr Gly Val Ser Arg Ile Ala Tyr Ser Lys Asp Phe Glu Thr Leu
        115                 120                 125

Lys Val Asp Phe Leu Ser Lys Leu Pro Glu Met Leu Lys Met Phe Glu

```
                130                 135                 140
Asp Arg Leu Cys His Lys Thr Tyr Leu Asn Gly Asp His Val Thr His
145                 150                 155                 160

Pro Asp Phe Met Leu Tyr Asp Ala Leu Asp Val Val Leu Tyr Met Asp
                165                 170                 175

Pro Met Cys Leu Asp Ala Phe Pro Lys Leu Val Cys Phe Lys Lys Arg
            180                 185                 190

Ile Glu Ala Ile Pro Gln Ile Asp Lys Tyr Leu Lys Ser Ser Lys Tyr
            195                 200                 205

Ile Ala Trp Pro Leu Gln Gly Trp Gln Ala Thr Phe Gly Gly Gly Asp
            210                 215                 220

His Pro Pro Lys Leu Glu Val Leu Phe Gln Gly Pro Ala Met His Glu
225                 230                 235                 240

Asp Glu Leu Asp Glu Glu Thr Gly Asp Ile Thr Gln Asn Tyr Ile Asn
                245                 250                 255

Tyr Gly Thr Thr Lys Ser Tyr Gly Ala Thr Thr Gln Ala Asn Gly Gly
                260                 265                 270

Trp Pro Ser Gly Trp Glu Lys Lys Glu Glu Phe
            275                 280

<210> SEQ ID NO 67
<211> LENGTH: 278
<212> TYPE: PRT
<213> ORGANISM: Artificial Sequence
<220> FEATURE:
<223> OTHER INFORMATION: H8-GST-(PSc)-VGLUT2-aa543-582

<400> SEQUENCE: 67

Met Ser His His His His His His His Met Ser Pro Ile Leu Gly
1               5                   10                  15

Tyr Trp Lys Ile Lys Gly Leu Val Gln Pro Thr Arg Leu Leu Leu Glu
                20                  25                  30

Tyr Leu Glu Glu Lys Tyr Glu Glu His Leu Tyr Glu Arg Asp Glu Gly
                35                  40                  45

Asp Lys Trp Arg Asn Lys Lys Phe Glu Leu Gly Leu Glu Phe Pro Asn
50                  55                  60

Leu Pro Tyr Tyr Ile Asp Gly Asp Val Lys Leu Thr Gln Ser Met Ala
65                  70                  75                  80

Ile Ile Arg Tyr Ile Ala Asp Lys His Asn Met Leu Gly Gly Cys Pro
                85                  90                  95

Lys Glu Arg Ala Glu Ile Ser Met Leu Glu Gly Ala Val Leu Asp Ile
            100                 105                 110

Arg Tyr Gly Val Ser Arg Ile Ala Tyr Ser Lys Asp Phe Glu Thr Leu
            115                 120                 125

Lys Val Asp Phe Leu Ser Lys Leu Pro Glu Met Leu Lys Met Phe Glu
            130                 135                 140

Asp Arg Leu Cys His Lys Thr Tyr Leu Asn Gly Asp His Val Thr His
145                 150                 155                 160

Pro Asp Phe Met Leu Tyr Asp Ala Leu Asp Val Val Leu Tyr Met Asp
                165                 170                 175

Pro Met Cys Leu Asp Ala Phe Pro Lys Leu Val Cys Phe Lys Lys Arg
            180                 185                 190

Ile Glu Ala Ile Pro Gln Ile Asp Lys Tyr Leu Lys Ser Ser Lys Tyr
            195                 200                 205

Ile Ala Trp Pro Leu Gln Gly Trp Gln Ala Thr Phe Gly Gly Gly Asp
```

His Pro Pro Lys Leu Glu Val Leu Phe Gln Gly Pro Ala Met Ser Tyr
225                 230                 235                 240

Gly Ala Thr Thr Gln Ala Asn Gly Gly Trp Pro Ser Gly Trp Glu Lys
            245                 250                 255

Lys Glu Glu Phe Val Gln Gly Glu Val Gln Asp Ser His Ser Tyr Lys
            260                 265                 270

Asp Arg Val Asp Tyr Ser
            275

<210> SEQ ID NO 68
<211> LENGTH: 256
<212> TYPE: PRT
<213> ORGANISM: Artificial Sequence
<220> FEATURE:
<223> OTHER INFORMATION: H8-GST-(PSc)-VGLUT2-aa565-582

<400> SEQUENCE: 68

Met Ser His His His His His His His Met Ser Pro Ile Leu Gly
1               5                   10                  15

Tyr Trp Lys Ile Lys Gly Leu Val Gln Pro Thr Arg Leu Leu Leu Glu
            20                  25                  30

Tyr Leu Glu Glu Lys Tyr Glu Glu His Leu Tyr Glu Arg Asp Glu Gly
        35                  40                  45

Asp Lys Trp Arg Asn Lys Lys Phe Glu Leu Gly Leu Glu Phe Pro Asn
50                  55                  60

Leu Pro Tyr Tyr Ile Asp Gly Asp Val Lys Leu Thr Gln Ser Met Ala
65                  70                  75                  80

Ile Ile Arg Tyr Ile Ala Asp Lys His Asn Met Leu Gly Gly Cys Pro
                85                  90                  95

Lys Glu Arg Ala Glu Ile Ser Met Leu Glu Gly Ala Val Leu Asp Ile
            100                 105                 110

Arg Tyr Gly Val Ser Arg Ile Ala Tyr Ser Lys Asp Phe Glu Thr Leu
        115                 120                 125

Lys Val Asp Phe Leu Ser Lys Leu Pro Glu Met Leu Lys Met Phe Glu
130                 135                 140

Asp Arg Leu Cys His Lys Thr Tyr Leu Asn Gly Asp His Val Thr His
145                 150                 155                 160

Pro Asp Phe Met Leu Tyr Asp Ala Leu Asp Val Val Leu Tyr Met Asp
                165                 170                 175

Pro Met Cys Leu Asp Ala Phe Pro Lys Leu Val Cys Phe Lys Lys Arg
            180                 185                 190

Ile Glu Ala Ile Pro Gln Ile Asp Lys Tyr Leu Lys Ser Ser Lys Tyr
        195                 200                 205

Ile Ala Trp Pro Leu Gln Gly Trp Gln Ala Thr Phe Gly Gly Gly Asp
210                 215                 220

His Pro Pro Lys Leu Glu Val Leu Phe Gln Gly Pro Ala Met Val Gln
225                 230                 235                 240

Gly Glu Val Gln Asp Ser His Ser Tyr Lys Asp Arg Val Asp Tyr Ser
                245                 250                 255

<210> SEQ ID NO 69
<211> LENGTH: 282
<212> TYPE: PRT
<213> ORGANISM: Artificial Sequence
<220> FEATURE:
<223> OTHER INFORMATION: H8-GST-(PSc)-VGLUT2-aa499-542

```
<400> SEQUENCE: 69

Met Ser His His His His His His His Met Ser Pro Ile Leu Gly
1               5                   10                  15

Tyr Trp Lys Ile Lys Gly Leu Val Gln Pro Thr Arg Leu Leu Leu Glu
            20                  25                  30

Tyr Leu Glu Glu Lys Tyr Glu Glu His Leu Tyr Glu Arg Asp Glu Gly
        35                  40                  45

Asp Lys Trp Arg Asn Lys Lys Phe Glu Leu Gly Leu Glu Phe Pro Asn
50                  55                  60

Leu Pro Tyr Tyr Ile Asp Gly Asp Val Lys Leu Thr Gln Ser Met Ala
65                  70                  75                  80

Ile Ile Arg Tyr Ile Ala Asp Lys His Asn Met Leu Gly Gly Cys Pro
                85                  90                  95

Lys Glu Arg Ala Glu Ile Ser Met Leu Glu Gly Ala Val Leu Asp Ile
            100                 105                 110

Arg Tyr Gly Val Ser Arg Ile Ala Tyr Ser Lys Asp Phe Glu Thr Leu
        115                 120                 125

Lys Val Asp Phe Leu Ser Lys Leu Pro Glu Met Leu Lys Met Phe Glu
130                 135                 140

Asp Arg Leu Cys His Lys Thr Tyr Leu Asn Gly Asp His Val Thr His
145                 150                 155                 160

Pro Asp Phe Met Leu Tyr Asp Ala Leu Asp Val Val Leu Tyr Met Asp
                165                 170                 175

Pro Met Cys Leu Asp Ala Phe Pro Lys Leu Val Cys Phe Lys Lys Arg
            180                 185                 190

Ile Glu Ala Ile Pro Gln Ile Asp Lys Tyr Leu Lys Ser Ser Lys Tyr
        195                 200                 205

Ile Ala Trp Pro Leu Gln Gly Trp Gln Ala Thr Phe Gly Gly Gly Asp
210                 215                 220

His Pro Pro Lys Leu Glu Val Leu Phe Gln Gly Pro Ala Met Ser Gly
225                 230                 235                 240

Glu Lys Gln Pro Trp Ala Asp Pro Glu Glu Thr Ser Glu Glu Lys Cys
                245                 250                 255

Gly Phe Ile His Glu Asp Glu Leu Asp Glu Glu Thr Gly Asp Ile Thr
            260                 265                 270

Gln Asn Tyr Ile Asn Tyr Gly Thr Thr Lys
        275                 280

<210> SEQ ID NO 70
<211> LENGTH: 304
<212> TYPE: PRT
<213> ORGANISM: Artificial Sequence
<220> FEATURE:
<223> OTHER INFORMATION: H8-GST-(PSc)-VGLUT2-aa499-564

<400> SEQUENCE: 70

Met Ser His His His His His His His Met Ser Pro Ile Leu Gly
1               5                   10                  15

Tyr Trp Lys Ile Lys Gly Leu Val Gln Pro Thr Arg Leu Leu Leu Glu
            20                  25                  30

Tyr Leu Glu Glu Lys Tyr Glu Glu His Leu Tyr Glu Arg Asp Glu Gly
        35                  40                  45

Asp Lys Trp Arg Asn Lys Lys Phe Glu Leu Gly Leu Glu Phe Pro Asn
50                  55                  60
```

Leu Pro Tyr Tyr Ile Asp Gly Asp Val Lys Leu Thr Gln Ser Met Ala
65                  70                  75                  80

Ile Ile Arg Tyr Ile Ala Asp Lys His Asn Met Leu Gly Gly Cys Pro
            85                  90                  95

Lys Glu Arg Ala Glu Ile Ser Met Leu Glu Gly Ala Val Leu Asp Ile
            100                 105                 110

Arg Tyr Gly Val Ser Arg Ile Ala Tyr Ser Lys Asp Phe Glu Thr Leu
            115                 120                 125

Lys Val Asp Phe Leu Ser Lys Leu Pro Glu Met Leu Lys Met Phe Glu
            130                 135                 140

Asp Arg Leu Cys His Lys Thr Tyr Leu Asn Gly Asp His Val Thr His
145                 150                 155                 160

Pro Asp Phe Met Leu Tyr Asp Ala Leu Asp Val Val Leu Tyr Met Asp
                165                 170                 175

Pro Met Cys Leu Asp Ala Phe Pro Lys Leu Val Cys Phe Lys Lys Arg
                180                 185                 190

Ile Glu Ala Ile Pro Gln Ile Asp Lys Tyr Leu Lys Ser Ser Lys Tyr
            195                 200                 205

Ile Ala Trp Pro Leu Gln Gly Trp Gln Ala Thr Phe Gly Gly Gly Asp
210                 215                 220

His Pro Pro Lys Leu Glu Val Leu Phe Gln Gly Pro Ala Met Ser Gly
225                 230                 235                 240

Glu Lys Gln Pro Trp Ala Asp Pro Glu Glu Thr Ser Glu Glu Lys Cys
                245                 250                 255

Gly Phe Ile His Glu Asp Glu Leu Asp Glu Glu Thr Gly Asp Ile Thr
                260                 265                 270

Gln Asn Tyr Ile Asn Tyr Gly Thr Thr Lys Ser Tyr Gly Ala Thr Thr
            275                 280                 285

Gln Ala Asn Gly Gly Trp Pro Ser Gly Trp Glu Lys Lys Glu Glu Phe
            290                 295                 300

<210> SEQ ID NO 71
<211> LENGTH: 285
<212> TYPE: PRT
<213> ORGANISM: Artificial Sequence
<220> FEATURE:
<223> OTHER INFORMATION: H8-GST-(PSc)-VGLUT2-mutant-1

<400> SEQUENCE: 71

Met Ser His His His His His His His Met Ser Pro Ile Leu Gly
1               5                   10                  15

Tyr Trp Lys Ile Lys Gly Leu Val Gln Pro Thr Arg Leu Leu Leu Glu
            20                  25                  30

Tyr Leu Glu Glu Lys Tyr Glu Glu His Leu Tyr Glu Arg Asp Glu Gly
            35                  40                  45

Asp Lys Trp Arg Asn Lys Lys Phe Glu Leu Gly Leu Glu Phe Pro Asn
        50                  55                  60

Leu Pro Tyr Tyr Ile Asp Gly Asp Val Lys Leu Thr Gln Ser Met Ala
65                  70                  75                  80

Ile Ile Arg Tyr Ile Ala Asp Lys His Asn Met Leu Gly Gly Cys Pro
            85                  90                  95

Lys Glu Arg Ala Glu Ile Ser Met Leu Glu Gly Ala Val Leu Asp Ile
            100                 105                 110

Arg Tyr Gly Val Ser Arg Ile Ala Tyr Ser Lys Asp Phe Glu Thr Leu
            115                 120                 125

```
Lys Val Asp Phe Leu Ser Lys Leu Pro Glu Met Leu Lys Met Phe Glu
    130                 135                 140

Asp Arg Leu Cys His Lys Thr Tyr Leu Asn Gly Asp His Val Thr His
145                 150                 155                 160

Pro Asp Phe Met Leu Tyr Asp Ala Leu Asp Val Val Leu Tyr Met Asp
                165                 170                 175

Pro Met Cys Leu Asp Ala Phe Pro Lys Leu Val Cys Phe Lys Lys Arg
            180                 185                 190

Ile Glu Ala Ile Pro Gln Ile Asp Lys Tyr Leu Lys Ser Ser Lys Tyr
        195                 200                 205

Ile Ala Trp Pro Leu Gln Gly Trp Gln Ala Thr Phe Gly Gly Gly Asp
    210                 215                 220

His Pro Pro Lys Leu Glu Val Leu Phe Gln Gly Pro Ala Met Phe Ile
225                 230                 235                 240

Gly His Asp Gln Leu Ala Gly Ser Asp Asp Ser Ile Thr Gln Asn Tyr
                245                 250                 255

Ile Asn Tyr Gly Thr Thr Lys Ser Tyr Gly Ala Thr Thr Gln Ala Asn
            260                 265                 270

Gly Gly Trp Pro Ser Gly Trp Glu Lys Lys Glu Glu Phe
        275                 280                 285

<210> SEQ ID NO 72
<211> LENGTH: 289
<212> TYPE: PRT
<213> ORGANISM: Artificial Sequence
<220> FEATURE:
<223> OTHER INFORMATION: H8-GST-(PSc)-VGLUT2-mutant-2

<400> SEQUENCE: 72

Met Ser His His His His His His His Met Ser Pro Ile Leu Gly
1               5                   10                  15

Tyr Trp Lys Ile Lys Gly Leu Val Gln Pro Thr Arg Leu Leu Leu Glu
            20                  25                  30

Tyr Leu Glu Glu Lys Tyr Glu Glu His Leu Tyr Glu Arg Asp Glu Gly
        35                  40                  45

Asp Lys Trp Arg Asn Lys Lys Phe Glu Leu Gly Leu Glu Phe Pro Asn
    50                  55                  60

Leu Pro Tyr Tyr Ile Asp Gly Asp Val Lys Leu Thr Gln Ser Met Ala
65                  70                  75                  80

Ile Ile Arg Tyr Ile Ala Asp Lys His Asn Met Leu Gly Gly Cys Pro
                85                  90                  95

Lys Glu Arg Ala Glu Ile Ser Met Leu Glu Gly Ala Val Leu Asp Ile
            100                 105                 110

Arg Tyr Gly Val Ser Arg Ile Ala Tyr Ser Lys Asp Phe Glu Thr Leu
        115                 120                 125

Lys Val Asp Phe Leu Ser Lys Leu Pro Glu Met Leu Lys Met Phe Glu
    130                 135                 140

Asp Arg Leu Cys His Lys Thr Tyr Leu Asn Gly Asp His Val Thr His
145                 150                 155                 160

Pro Asp Phe Met Leu Tyr Asp Ala Leu Asp Val Val Leu Tyr Met Asp
                165                 170                 175

Pro Met Cys Leu Asp Ala Phe Pro Lys Leu Val Cys Phe Lys Lys Arg
            180                 185                 190

Ile Glu Ala Ile Pro Gln Ile Asp Lys Tyr Leu Lys Ser Ser Lys Tyr
        195                 200                 205
```

```
Ile Ala Trp Pro Leu Gln Gly Trp Gln Ala Thr Phe Gly Gly Gly Asp
    210                 215                 220

His Pro Pro Lys Leu Glu Val Leu Phe Gln Gly Pro Ala Met His Glu
225                 230                 235                 240

Asp Glu Leu Asp Glu Glu Thr Gly Asp Ile Thr Gln Asn Tyr Ile Asn
                245                 250                 255

Tyr Gly Thr Thr Lys Ser Tyr Gly Ala Thr Thr Gln Ala Asn Gly Gly
            260                 265                 270

Trp Pro Ser Gly Trp Pro Arg Pro Pro Pro Val Arg Asp Tyr Val
            275                 280                 285

Gln

<210> SEQ ID NO 73
<211> LENGTH: 283
<212> TYPE: PRT
<213> ORGANISM: Artificial Sequence
<220> FEATURE:
<223> OTHER INFORMATION: H8-GST-(PSc)-VGLUT2-mutant-3

<400> SEQUENCE: 73

Met Ser His His His His His His His Met Ser Pro Ile Leu Gly
1               5                   10                  15

Tyr Trp Lys Ile Lys Gly Leu Val Gln Pro Thr Arg Leu Leu Leu Glu
                20                  25                  30

Tyr Leu Glu Glu Lys Tyr Glu Glu His Leu Tyr Glu Arg Asp Glu Gly
            35                  40                  45

Asp Lys Trp Arg Asn Lys Lys Phe Glu Leu Gly Leu Glu Phe Pro Asn
50                  55                  60

Leu Pro Tyr Tyr Ile Asp Gly Asp Val Lys Leu Thr Gln Ser Met Ala
65                  70                  75                  80

Ile Ile Arg Tyr Ile Ala Asp Lys His Asn Met Leu Gly Gly Cys Pro
                85                  90                  95

Lys Glu Arg Ala Glu Ile Ser Met Leu Glu Gly Ala Val Leu Asp Ile
            100                 105                 110

Arg Tyr Gly Val Ser Arg Ile Ala Tyr Ser Lys Asp Phe Glu Thr Leu
        115                 120                 125

Lys Val Asp Phe Leu Ser Lys Leu Pro Glu Met Leu Lys Met Phe Glu
130                 135                 140

Asp Arg Leu Cys His Lys Thr Tyr Leu Asn Gly Asp His Val Thr His
145                 150                 155                 160

Pro Asp Phe Met Leu Tyr Asp Ala Leu Asp Val Val Leu Tyr Met Asp
                165                 170                 175

Pro Met Cys Leu Asp Ala Phe Pro Lys Leu Val Cys Phe Lys Lys Arg
            180                 185                 190

Ile Glu Ala Ile Pro Gln Ile Asp Lys Tyr Leu Lys Ser Ser Lys Tyr
        195                 200                 205

Ile Ala Trp Pro Leu Gln Gly Trp Gln Ala Thr Phe Gly Gly Gly Asp
    210                 215                 220

His Pro Pro Lys Leu Glu Val Leu Phe Gln Gly Pro Ala Met His Glu
225                 230                 235                 240

Asp Glu Leu Asp Glu Glu Thr Gly Asp Glu Met Glu Asp Glu Ala Glu
                245                 250                 255

Pro Pro Gly Ala Pro Pro Ala Pro Pro Ser Tyr Gly Ala Thr His
            260                 265                 270

Ser Thr Phe Gln Pro Glu Lys Lys Glu Glu Phe
```

-continued

```
                275                 280

<210> SEQ ID NO 74
<211> LENGTH: 283
<212> TYPE: PRT
<213> ORGANISM: Artificial Sequence
<220> FEATURE:
<223> OTHER INFORMATION: H8-GST-(PSc)-VGLUT2-mutant-4

<400> SEQUENCE: 74

Met Ser His His His His His His His Met Ser Pro Ile Leu Gly
1               5                   10                  15

Tyr Trp Lys Ile Lys Gly Leu Val Gln Pro Thr Arg Leu Leu Leu Glu
            20                  25                  30

Tyr Leu Glu Glu Lys Tyr Glu Glu His Leu Tyr Glu Arg Asp Glu Gly
        35                  40                  45

Asp Lys Trp Arg Asn Lys Lys Phe Glu Leu Gly Leu Glu Phe Pro Asn
    50                  55                  60

Leu Pro Tyr Tyr Ile Asp Gly Asp Val Lys Leu Thr Gln Ser Met Ala
65                  70                  75                  80

Ile Ile Arg Tyr Ile Ala Asp Lys His Asn Met Leu Gly Gly Cys Pro
                85                  90                  95

Lys Glu Arg Ala Glu Ile Ser Met Leu Glu Gly Ala Val Leu Asp Ile
            100                 105                 110

Arg Tyr Gly Val Ser Arg Ile Ala Tyr Ser Lys Asp Phe Glu Thr Leu
        115                 120                 125

Lys Val Asp Phe Leu Ser Lys Leu Pro Glu Met Leu Lys Met Phe Glu
    130                 135                 140

Asp Arg Leu Cys His Lys Thr Tyr Leu Asn Gly Asp His Val Thr His
145                 150                 155                 160

Pro Asp Phe Met Leu Tyr Asp Ala Leu Asp Val Val Leu Tyr Met Asp
                165                 170                 175

Pro Met Cys Leu Asp Ala Phe Pro Lys Leu Val Cys Phe Lys Lys Arg
            180                 185                 190

Ile Glu Ala Ile Pro Gln Ile Asp Lys Tyr Leu Lys Ser Ser Lys Tyr
        195                 200                 205

Ile Ala Trp Pro Leu Gln Gly Trp Gln Ala Thr Phe Gly Gly Gly Asp
    210                 215                 220

His Pro Pro Lys Leu Glu Val Leu Phe Gln Gly Pro Ala Met His Asp
225                 230                 235                 240

Glu Glu Ala Glu Glu Ile Glu Gly Asp Ile Thr Gln Asn Tyr Ile Asn
                245                 250                 255

Tyr Gly Thr Thr Lys Ser Tyr Gly Ala Thr Thr Gln Ala Asn Gly Gly
            260                 265                 270

Trp Pro Ser Gly Trp Glu Lys Lys Glu Glu Phe
        275                 280

<210> SEQ ID NO 75
<211> LENGTH: 570
<212> TYPE: PRT
<213> ORGANISM: Artificial Sequence
<220> FEATURE:
<223> OTHER INFORMATION: VGLUT1-isoform1-H8

<400> SEQUENCE: 75

Met Glu Phe Arg Gln Glu Glu Phe Arg Lys Leu Ala Gly Arg Ala Leu
1               5                   10                  15
```

```
Gly Lys Leu His Arg Leu Leu Glu Lys Arg Gln Glu Gly Ala Glu Thr
             20                  25                  30

Leu Glu Leu Ser Ala Asp Gly Arg Pro Val Thr Thr Gln Thr Arg Asp
         35                  40                  45

Pro Pro Val Val Asp Cys Thr Cys Phe Gly Leu Pro Arg Arg Tyr Ile
 50                  55                  60

Ile Ala Ile Met Ser Gly Leu Gly Phe Cys Ile Ser Phe Gly Ile Arg
 65                  70                  75                  80

Cys Asn Leu Gly Val Ala Ile Val Ser Met Val Asn Asn Ser Thr Thr
                 85                  90                  95

His Arg Gly Gly His Val Val Gln Lys Ala Gln Phe Ser Trp Asp
                100                 105                 110

Pro Glu Thr Val Gly Leu Ile His Gly Ser Phe Phe Trp Gly Tyr Ile
         115                 120                 125

Val Thr Gln Ile Pro Gly Gly Phe Ile Cys Gln Lys Phe Ala Ala Asn
130                 135                 140

Arg Val Phe Gly Phe Ala Ile Val Ala Thr Ser Thr Leu Asn Met Leu
145                 150                 155                 160

Ile Pro Ser Ala Ala Arg Val His Tyr Gly Cys Val Ile Phe Val Arg
                165                 170                 175

Ile Leu Gln Gly Leu Val Glu Gly Val Thr Tyr Pro Ala Cys His Gly
         180                 185                 190

Ile Trp Ser Lys Trp Ala Pro Pro Leu Glu Arg Ser Arg Leu Ala Thr
         195                 200                 205

Thr Ala Phe Cys Gly Ser Tyr Ala Gly Ala Val Val Ala Met Pro Leu
210                 215                 220

Ala Gly Val Leu Val Gln Tyr Ser Gly Trp Ser Ser Val Phe Tyr Val
225                 230                 235                 240

Tyr Gly Ser Phe Gly Ile Phe Trp Tyr Leu Phe Trp Leu Leu Val Ser
                245                 250                 255

Tyr Glu Ser Pro Ala Leu His Pro Ser Ile Ser Glu Glu Arg Lys
         260                 265                 270

Tyr Ile Glu Asp Ala Ile Gly Glu Ser Ala Lys Leu Met Asn Pro Leu
275                 280                 285

Thr Lys Phe Ser Thr Pro Trp Arg Arg Phe Phe Thr Ser Met Pro Val
290                 295                 300

Tyr Ala Ile Ile Val Ala Asn Phe Cys Arg Ser Trp Thr Phe Tyr Leu
305                 310                 315                 320

Leu Leu Ile Ser Gln Pro Ala Tyr Phe Glu Glu Val Phe Gly Phe Glu
                325                 330                 335

Ile Ser Lys Val Gly Leu Val Ser Ala Leu Pro His Leu Val Met Thr
         340                 345                 350

Ile Ile Val Pro Ile Gly Gly Gln Ile Ala Asp Phe Leu Arg Ser Arg
         355                 360                 365

Arg Ile Met Ser Thr Thr Asn Val Arg Lys Leu Met Asn Cys Gly Gly
370                 375                 380

Phe Gly Met Glu Ala Thr Leu Leu Val Val Gly Tyr Ser His Ser
385                 390                 395                 400

Lys Gly Val Ala Ile Ser Phe Leu Val Leu Ala Val Gly Phe Ser Gly
                405                 410                 415

Phe Ala Ile Ser Gly Phe Asn Val Asn His Leu Asp Ile Ala Arg Arg
         420                 425                 430

Tyr Ala Ser Ile Leu Met Gly Ile Ser Asn Gly Val Gly Thr Leu Ser
```

```
                435                 440                 445
Gly Met Val Cys Pro Ile Ile Val Gly Ala Met Thr Lys His Lys Thr
    450                 455                 460
Arg Glu Glu Trp Gln Tyr Val Phe Leu Ile Ala Ser Leu Val His Tyr
465                 470                 475                 480
Gly Gly Val Ile Phe Tyr Gly Val Phe Ala Ser Gly Glu Lys Gln Pro
                485                 490                 495
Trp Ala Glu Pro Glu Glu Met Ser Glu Lys Cys Gly Phe Val Gly
            500                 505                 510
His Asp Gln Leu Ala Gly Ser Asp Asp Ser Glu Met Glu Asp Glu Ala
            515                 520                 525
Glu Pro Pro Gly Ala Pro Pro Ala Pro Pro Ser Tyr Gly Ala Thr
    530                 535                 540
His Ser Thr Phe Gln Pro Pro Arg Pro Pro Pro Val Arg Asp Tyr
545                 550                 555                 560
Leu Glu His His His His His His His His
                565                 570

<210> SEQ ID NO 76
<211> LENGTH: 560
<212> TYPE: PRT
<213> ORGANISM: Artificial Sequence
<220> FEATURE:
<223> OTHER INFORMATION: VGLUT1-isoform1

<400> SEQUENCE: 76

Met Glu Phe Arg Gln Glu Glu Phe Arg Lys Leu Ala Gly Arg Ala Leu
1               5                   10                  15
Gly Lys Leu His Arg Leu Leu Glu Lys Arg Gln Glu Gly Ala Glu Thr
            20                  25                  30
Leu Glu Leu Ser Ala Asp Gly Arg Pro Val Thr Thr Gln Thr Arg Asp
        35                  40                  45
Pro Pro Val Val Asp Cys Thr Cys Phe Gly Leu Pro Arg Arg Tyr Ile
    50                  55                  60
Ile Ala Ile Met Ser Gly Leu Gly Phe Cys Ile Ser Phe Gly Ile Arg
65                  70                  75                  80
Cys Asn Leu Gly Val Ala Ile Val Ser Met Val Asn Asn Ser Thr Thr
                85                  90                  95
His Arg Gly Gly His Val Val Gln Lys Ala Gln Phe Ser Trp Asp
            100                 105                 110
Pro Glu Thr Val Gly Leu Ile His Gly Ser Phe Phe Trp Gly Tyr Ile
        115                 120                 125
Val Thr Gln Ile Pro Gly Gly Phe Ile Cys Gln Lys Phe Ala Ala Asn
    130                 135                 140
Arg Val Phe Gly Phe Ala Ile Val Ala Thr Ser Thr Leu Asn Met Leu
145                 150                 155                 160
Ile Pro Ser Ala Ala Arg Val His Tyr Gly Cys Val Ile Phe Val Arg
                165                 170                 175
Ile Leu Gln Gly Leu Val Glu Gly Val Thr Tyr Pro Ala Cys His Gly
            180                 185                 190
Ile Trp Ser Lys Trp Ala Pro Pro Leu Glu Arg Ser Arg Leu Ala Thr
        195                 200                 205
Thr Ala Phe Cys Gly Ser Tyr Ala Gly Ala Val Val Ala Met Pro Leu
    210                 215                 220
Ala Gly Val Leu Val Gln Tyr Ser Gly Trp Ser Ser Val Phe Tyr Val
```

```
            225                 230                 235                 240
Tyr Gly Ser Phe Gly Ile Phe Trp Tyr Leu Phe Trp Leu Leu Val Ser
                    245                 250                 255

Tyr Glu Ser Pro Ala Leu His Pro Ser Ile Ser Glu Glu Arg Lys
            260                 265                 270

Tyr Ile Glu Asp Ala Ile Gly Glu Ser Ala Lys Leu Met Asn Pro Leu
                275                 280                 285

Thr Lys Phe Ser Thr Pro Trp Arg Arg Phe Phe Thr Ser Met Pro Val
            290                 295                 300

Tyr Ala Ile Ile Val Ala Asn Phe Cys Arg Ser Trp Thr Phe Tyr Leu
305                 310                 315                 320

Leu Leu Ile Ser Gln Pro Ala Tyr Phe Glu Glu Val Phe Gly Phe Glu
                325                 330                 335

Ile Ser Lys Val Gly Leu Val Ser Ala Leu Pro His Leu Val Met Thr
            340                 345                 350

Ile Ile Val Pro Ile Gly Gly Gln Ile Ala Asp Phe Leu Arg Ser Arg
                355                 360                 365

Arg Ile Met Ser Thr Thr Asn Val Arg Lys Leu Met Asn Cys Gly Gly
        370                 375                 380

Phe Gly Met Glu Ala Thr Leu Leu Leu Val Val Gly Tyr Ser His Ser
385                 390                 395                 400

Lys Gly Val Ala Ile Ser Phe Leu Val Leu Ala Val Gly Phe Ser Gly
                    405                 410                 415

Phe Ala Ile Ser Gly Phe Asn Val Asn His Leu Asp Ile Ala Arg Arg
                420                 425                 430

Tyr Ala Ser Ile Leu Met Gly Ile Ser Asn Gly Val Gly Thr Leu Ser
            435                 440                 445

Gly Met Val Cys Pro Ile Ile Val Gly Ala Met Thr Lys His Lys Thr
        450                 455                 460

Arg Glu Glu Trp Gln Tyr Val Phe Leu Ile Ala Ser Leu Val His Tyr
465                 470                 475                 480

Gly Gly Val Ile Phe Tyr Gly Val Phe Ala Ser Gly Glu Lys Gln Pro
                    485                 490                 495

Trp Ala Glu Pro Glu Glu Met Ser Glu Glu Lys Cys Gly Phe Val Gly
                500                 505                 510

His Asp Gln Leu Ala Gly Ser Asp Asp Ser Glu Met Glu Asp Glu Ala
            515                 520                 525

Glu Pro Pro Gly Ala Pro Pro Ala Pro Pro Ser Tyr Gly Ala Thr
        530                 535                 540

His Ser Thr Phe Gln Pro Pro Arg Pro Pro Pro Val Arg Asp Tyr
545                 550                 555                 560
```

<210> SEQ ID NO 77
<211> LENGTH: 599
<212> TYPE: PRT
<213> ORGANISM: Artificial Sequence
<220> FEATURE:
<223> OTHER INFORMATION: VGLUT3-isoform1-H8

<400> SEQUENCE: 77

```
Met Pro Phe Lys Ala Phe Asp Thr Phe Lys Glu Lys Ile Leu Lys Pro
1                   5                   10                  15

Gly Lys Glu Gly Val Lys Asn Ala Val Gly Asp Ser Leu Gly Ile Leu
            20                  25                  30

Gln Arg Lys Ile Asp Gly Thr Thr Glu Glu Glu Asp Asn Ile Glu Leu
```

```
                35                  40                  45
Asn Glu Glu Gly Arg Pro Val Gln Thr Ser Arg Pro Ser Pro Pro Leu
 50                  55                  60
Cys Asp Cys His Cys Cys Gly Leu Pro Lys Arg Tyr Ile Ile Ala Ile
 65                  70                  75                  80
Met Ser Gly Leu Gly Phe Cys Ile Ser Phe Gly Ile Arg Cys Asn Leu
                 85                  90                  95
Gly Val Ala Ile Val Glu Met Val Asn Asn Ser Thr Val Tyr Val Asp
                100                 105                 110
Gly Lys Pro Glu Ile Gln Thr Ala Gln Phe Asn Trp Asp Pro Glu Thr
                115                 120                 125
Val Gly Leu Ile His Gly Ser Phe Phe Trp Gly Tyr Ile Met Thr Gln
                130                 135                 140
Ile Pro Gly Gly Phe Ile Ser Asn Lys Phe Ala Ala Asn Arg Val Phe
145                 150                 155                 160
Gly Ala Ala Ile Phe Leu Thr Ser Thr Leu Asn Met Phe Ile Pro Ser
                165                 170                 175
Ala Ala Arg Val His Tyr Gly Cys Val Met Cys Val Arg Ile Leu Gln
                180                 185                 190
Gly Leu Val Glu Gly Val Thr Tyr Pro Ala Cys His Gly Met Trp Ser
                195                 200                 205
Lys Trp Ala Pro Pro Leu Glu Arg Ser Arg Leu Ala Thr Thr Ser Phe
                210                 215                 220
Cys Gly Ser Tyr Ala Gly Ala Val Val Ala Met Pro Leu Ala Gly Val
225                 230                 235                 240
Leu Val Gln Tyr Ile Gly Trp Ser Ser Val Phe Tyr Ile Tyr Gly Met
                245                 250                 255
Phe Gly Ile Ile Trp Tyr Met Phe Trp Leu Leu Gln Ala Tyr Glu Cys
                260                 265                 270
Pro Ala Ala His Pro Thr Ile Ser Asn Glu Glu Lys Thr Tyr Ile Glu
                275                 280                 285
Thr Ser Ile Gly Glu Gly Ala Asn Val Val Ser Leu Ser Lys Phe Ser
290                 295                 300
Thr Pro Trp Lys Arg Phe Phe Thr Ser Leu Pro Val Tyr Ala Ile Ile
305                 310                 315                 320
Val Ala Asn Phe Cys Arg Ser Trp Thr Phe Tyr Leu Leu Leu Ile Ser
                325                 330                 335
Gln Pro Ala Tyr Phe Glu Glu Val Phe Gly Phe Ala Ile Ser Lys Val
                340                 345                 350
Gly Leu Leu Ser Ala Val Pro His Met Val Met Thr Ile Val Val Pro
                355                 360                 365
Ile Gly Gly Gln Leu Ala Asp Tyr Leu Arg Ser Arg Gln Ile Leu Thr
                370                 375                 380
Thr Thr Ala Val Arg Lys Ile Met Asn Cys Gly Gly Phe Gly Met Glu
385                 390                 395                 400
Ala Thr Leu Leu Leu Val Val Gly Phe Ser His Thr Lys Gly Val Ala
                405                 410                 415
Ile Ser Phe Leu Val Leu Ala Val Gly Phe Ser Gly Phe Ala Ile Ser
                420                 425                 430
Gly Phe Asn Val Asn His Leu Asp Ile Ala Pro Arg Tyr Ala Ser Ile
                435                 440                 445
Leu Met Gly Ile Ser Asn Gly Val Gly Thr Leu Ser Gly Met Val Cys
                450                 455                 460
```

```
Pro Leu Ile Val Gly Ala Met Thr Arg His Lys Thr Arg Glu Glu Trp
465                 470                 475                 480

Gln Asn Val Phe Leu Ile Ala Ala Leu Val His Tyr Ser Gly Val Ile
            485                 490                 495

Phe Tyr Gly Val Phe Ala Ser Gly Glu Lys Gln Glu Trp Ala Asp Pro
        500                 505                 510

Glu Asn Leu Ser Glu Glu Lys Cys Gly Ile Ile Asp Gln Asp Glu Leu
    515                 520                 525

Ala Glu Glu Ile Glu Leu Asn His Glu Ser Phe Ala Ser Pro Lys Lys
530                 535                 540

Lys Met Ser Tyr Gly Ala Thr Ser Gln Asn Cys Glu Val Gln Lys Lys
545                 550                 555                 560

Glu Trp Lys Gly Gln Arg Gly Ala Thr Leu Asp Glu Glu Leu Thr
                565                 570                 575

Ser Tyr Gln Asn Glu Glu Arg Asn Phe Ser Thr Ile Ser Leu Glu His
            580                 585                 590

His His His His His His
        595

<210> SEQ ID NO 78
<211> LENGTH: 589
<212> TYPE: PRT
<213> ORGANISM: Artificial Sequence
<220> FEATURE:
<223> OTHER INFORMATION: VGLUT3-isoform1

<400> SEQUENCE: 78

Met Pro Phe Lys Ala Phe Asp Thr Phe Lys Glu Lys Ile Leu Lys Pro
1               5                   10                  15

Gly Lys Glu Gly Val Lys Asn Ala Val Gly Asp Ser Leu Gly Ile Leu
            20                  25                  30

Gln Arg Lys Ile Asp Gly Thr Thr Glu Glu Asp Asn Ile Glu Leu
        35                  40                  45

Asn Glu Glu Gly Arg Pro Val Gln Thr Ser Arg Pro Ser Pro Pro Leu
50                  55                  60

Cys Asp Cys His Cys Cys Gly Leu Pro Lys Arg Tyr Ile Ile Ala Ile
65                  70                  75                  80

Met Ser Gly Leu Gly Phe Cys Ile Ser Phe Gly Ile Arg Cys Asn Leu
                85                  90                  95

Gly Val Ala Ile Val Glu Met Val Asn Asn Ser Thr Val Tyr Val Asp
            100                 105                 110

Gly Lys Pro Glu Ile Gln Thr Ala Gln Phe Asn Trp Asp Pro Glu Thr
        115                 120                 125

Val Gly Leu Ile His Gly Ser Phe Phe Trp Gly Tyr Ile Met Thr Gln
130                 135                 140

Ile Pro Gly Gly Phe Ile Ser Asn Lys Phe Ala Ala Asn Arg Val Phe
145                 150                 155                 160

Gly Ala Ala Ile Phe Leu Thr Ser Thr Leu Asn Met Phe Ile Pro Ser
                165                 170                 175

Ala Ala Arg Val His Tyr Gly Cys Val Met Cys Val Arg Ile Leu Gln
            180                 185                 190

Gly Leu Val Glu Gly Val Thr Tyr Pro Ala Cys His Gly Met Trp Ser
        195                 200                 205

Lys Trp Ala Pro Pro Leu Glu Arg Ser Arg Leu Ala Thr Thr Ser Phe
210                 215                 220
```

Cys Gly Ser Tyr Ala Gly Ala Val Val Ala Met Pro Leu Ala Gly Val
225                 230                 235                 240

Leu Val Gln Tyr Ile Gly Trp Ser Ser Val Phe Tyr Ile Tyr Gly Met
            245                 250                 255

Phe Gly Ile Ile Trp Tyr Met Phe Trp Leu Leu Gln Ala Tyr Glu Cys
        260                 265                 270

Pro Ala Ala His Pro Thr Ile Ser Asn Glu Glu Lys Thr Tyr Ile Glu
    275                 280                 285

Thr Ser Ile Gly Glu Gly Ala Asn Val Val Ser Leu Ser Lys Phe Ser
290                 295                 300

Thr Pro Trp Lys Arg Phe Phe Thr Ser Leu Pro Val Tyr Ala Ile Ile
305                 310                 315                 320

Val Ala Asn Phe Cys Arg Ser Trp Thr Phe Tyr Leu Leu Leu Ile Ser
                325                 330                 335

Gln Pro Ala Tyr Phe Glu Glu Val Phe Gly Phe Ala Ile Ser Lys Val
            340                 345                 350

Gly Leu Leu Ser Ala Val Pro His Met Val Met Thr Ile Val Val Pro
        355                 360                 365

Ile Gly Gly Gln Leu Ala Asp Tyr Leu Arg Ser Arg Gln Ile Leu Thr
    370                 375                 380

Thr Thr Ala Val Arg Lys Ile Met Asn Cys Gly Gly Phe Gly Met Glu
385                 390                 395                 400

Ala Thr Leu Leu Leu Val Val Gly Phe Ser His Thr Lys Gly Val Ala
                405                 410                 415

Ile Ser Phe Leu Val Leu Ala Val Gly Phe Ser Gly Phe Ala Ile Ser
            420                 425                 430

Gly Phe Asn Val Asn His Leu Asp Ile Ala Pro Arg Tyr Ala Ser Ile
        435                 440                 445

Leu Met Gly Ile Ser Asn Gly Val Gly Thr Leu Ser Gly Met Val Cys
    450                 455                 460

Pro Leu Ile Val Gly Ala Met Thr Arg His Lys Thr Arg Glu Glu Trp
465                 470                 475                 480

Gln Asn Val Phe Leu Ile Ala Ala Leu Val His Tyr Ser Gly Val Ile
                485                 490                 495

Phe Tyr Gly Val Phe Ala Ser Gly Glu Lys Gln Glu Trp Ala Asp Pro
            500                 505                 510

Glu Asn Leu Ser Glu Glu Lys Cys Gly Ile Ile Asp Gln Asp Glu Leu
        515                 520                 525

Ala Glu Glu Ile Glu Leu Asn His Glu Ser Phe Ala Ser Pro Lys Lys
    530                 535                 540

Lys Met Ser Tyr Gly Ala Thr Ser Gln Asn Cys Glu Val Gln Lys Lys
545                 550                 555                 560

Glu Trp Lys Gly Gln Arg Gly Ala Thr Leu Asp Glu Glu Leu Thr
                565                 570                 575

Ser Tyr Gln Asn Glu Glu Arg Asn Phe Ser Thr Ile Ser
            580                 585

<210> SEQ ID NO 79
<211> LENGTH: 325
<212> TYPE: PRT
<213> ORGANISM: Artificial Sequence
<220> FEATURE:
<223> OTHER INFORMATION: H8-GST-(PSc)-VGLUT3-aa503-589

<400> SEQUENCE: 79

```
Met Ser His His His His His His Met Ser Pro Ile Leu Gly
1               5                       10                  15

Tyr Trp Lys Ile Lys Gly Leu Val Gln Pro Thr Arg Leu Leu Leu Glu
                20                  25                  30

Tyr Leu Glu Glu Lys Tyr Glu Glu His Leu Tyr Glu Arg Asp Glu Gly
            35                  40                  45

Asp Lys Trp Arg Asn Lys Lys Phe Glu Leu Gly Leu Glu Phe Pro Asn
    50                  55                  60

Leu Pro Tyr Tyr Ile Asp Gly Asp Val Lys Leu Thr Gln Ser Met Ala
65              70                  75                  80

Ile Ile Arg Tyr Ile Ala Asp Lys His Asn Met Leu Gly Gly Cys Pro
                85                  90                  95

Lys Glu Arg Ala Glu Ile Ser Met Leu Glu Gly Ala Val Leu Asp Ile
            100                 105                 110

Arg Tyr Gly Val Ser Arg Ile Ala Tyr Ser Lys Asp Phe Glu Thr Leu
        115                 120                 125

Lys Val Asp Phe Leu Ser Lys Leu Pro Glu Met Leu Lys Met Phe Glu
130                 135                 140

Asp Arg Leu Cys His Lys Thr Tyr Leu Asn Gly Asp His Val Thr His
145                 150                 155                 160

Pro Asp Phe Met Leu Tyr Asp Ala Leu Asp Val Val Leu Tyr Met Asp
                165                 170                 175

Pro Met Cys Leu Asp Ala Phe Pro Lys Leu Val Cys Phe Lys Lys Arg
            180                 185                 190

Ile Glu Ala Ile Pro Gln Ile Asp Lys Tyr Leu Lys Ser Ser Lys Tyr
        195                 200                 205

Ile Ala Trp Pro Leu Gln Gly Trp Gln Ala Thr Phe Gly Gly Gly Asp
210                 215                 220

His Pro Pro Lys Leu Glu Val Leu Phe Gln Gly Pro Ala Met Ser Gly
225                 230                 235                 240

Glu Lys Gln Glu Trp Ala Asp Pro Glu Asn Leu Ser Glu Glu Lys Cys
                245                 250                 255

Gly Ile Ile Asp Gln Asp Glu Leu Ala Glu Glu Ile Glu Leu Asn His
            260                 265                 270

Glu Ser Phe Ala Ser Pro Lys Lys Lys Met Ser Tyr Gly Ala Thr Ser
        275                 280                 285

Gln Asn Cys Glu Val Gln Lys Lys Glu Trp Lys Gly Gln Arg Gly Ala
    290                 295                 300

Thr Leu Asp Glu Glu Glu Leu Thr Ser Tyr Gln Asn Glu Glu Arg Asn
305                 310                 315                 320

Phe Ser Thr Ile Ser
                325

<210> SEQ ID NO 80
<211> LENGTH: 6158
<212> TYPE: DNA
<213> ORGANISM: Artificial Sequence
<220> FEATURE:
<223> OTHER INFORMATION: pET24d-N-GST-(PSc)-VGLUT2[human](aa1-71)

<400> SEQUENCE: 80
ggggaattgt gagcggataa caattcccct ctagaaataa ttttgtttaa ctttaagaag      60
gagtatataa tgagccatca tcatcatcat catcatcata tgtcccctat actaggttat     120
tggaaaatta agggccttgt gcaacccact cgacttcttt tggaatatct tgaagaaaaa     180
```

```
tatgaagagc atttgtatga gcgcgatgaa ggtgataaat ggcgaaacaa aaagtttgaa    240
ttgggtttgg agtttcccaa tcttccttat tatattgatg gtgatgttaa attaacacag    300
tctatggcca tcatacgtta tatagctgac aagcacaaca tgttgggtgg ttgtccaaaa    360
gagcgtgcag agatttcaat gcttgaagga gcggttttgg atattagata cggtgtttcg    420
agaattgcat atagtaaaga ctttgaaact ctcaaagttg attttcttag caagctacct    480
gaaatgctga aaatgttcga agatcgttta tgtcataaaa catatttaaa tggtgatcat    540
gtaacccatc ctgacttcat gttgtatgac gctcttgatg ttgttttata catggaccca    600
atgtgcctgg atgcgttccc aaaattagtt tgttttaaaa aacgtattga agctatccca    660
caaattgata agtacttgaa atccagcaag tatatagcat ggcctttgca gggctggcaa    720
gccacgtttg gtggtggcga ccatcctcca aaattggaag tgctgtttca gggtccagcc    780
atggaatccg taaaacaaag gattttggca cctggcaaag aagggctgaa gaactttgcc    840
ggtaagtcac tcggccagat ttaccgagtg ctggagaaga agcaggacac tggagaaacc    900
atcgagctta cagaggatgg gaaaccgttg gaggtgcccg aaaggaaggc cccactgtgt    960
gattgcacct gttccggtct gcctcggcgg tattaatcga gcaccaccac caccaccact    1020
gagatccggc tgctaacaaa gcccgaaagg aagctgagtt ggctgctgcc accgctgagc    1080
aataactagc ataaccccctt ggggcctcta acgggtctt gaggggtttt ttgctgaaag    1140
gaggaactat atccggattg gcgaatggga cgcgccctgt agcggcgcat taagcgcggc    1200
gggtgtggtg gttacgcgca gcgtgaccgc tacacttgcc agcgccctag cgcccgctcc    1260
tttcgctttc ttcccttcct ttctcgccac gttcgccggc tttccccgtc aagctctaaa    1320 tcggggctc cctttagggt tccgatttag tgctttacgg cacctcgacc ccaaaaaact    1380
tgattagggt gatggttcac gtagtgggcc atcgccctga tagacggttt ttcgcccttt    1440
gacgttggag tccacgttct ttaatagtgg actcttgttc caaactggaa caacactcaa    1500
ccctatctcg gtctattctt ttgatttata agggattttg ccgatttcgg cctattggtt    1560
aaaaaatgag ctgatttaac aaaaatttaa cgcgaatttt aacaaaatat taacgtttac    1620
aatttcaggt ggcacttttc ggggaaatgt gcgcggaacc cctatttgtt tatttttcta    1680
aatacattca aatatgtatc cgctcatgaa ttaattctta gaaaaactca tcgagcatca    1740
aatgaaactg caatttattc atatcaggat tatcaatacc atattttga aaaagccgtt    1800 tctgtaatga aggagaaaac tcaccgaggc agttccatag gatggcaaga tcctggtatc    1860
ggtctgcgat tccgactcgt ccaacatcaa tacaacctat taatttcccc tcgtcaaaaa    1920
taaggttatc aagtgagaaa tcaccatgag tgacgactga atccggtgag aatggcaaaa    1980
gtttatgcat ttctttccag acttgttcaa caggccagcc attacgctcg tcatcaaaat    2040
cactcgcatc aaccaaaccg ttattcattc gtgattgcgc ctgagcgaga cgaaatacgc    2100
gatcgctgtt aaaaggacaa ttacaaacag gaatcgaatg caaccggcgc aggaacactg    2160
ccagcgcatc aacaatattt tcacctgaat caggatattc ttctaatacc tggaatgctg    2220
ttttcccggg gatcgcagtg gtgagtaacc atgcatcatc aggagtacgg ataaaatgct    2280
tgatggtcga agaggcata aattccgtca gccagtttag tctgaccatc tcatctgtaa    2340
catcattggc aacgctacct ttgccatgtt tcagaaacaa ctctggcgca tcgggcttcc    2400
catacaatcg atagattgtc gcacctgatt gcccgacatt atcgcgagcc catttatacc    2460
catataaatc agcatccatg ttggaattta atcgcggcct agagcaagac gtttcccgtt    2520
```

```
gaatatggct cataacaccc cttgtattac tgtttatgta agcagacagt tttattgttc    2580
atgaccaaaa tcccttaacg tgagttttcg ttccactgag cgtcagaccc cgtagaaaag    2640
atcaaaggat cttcttgaga tcctttttt ctgcgcgtaa tctgctgctt gcaaacaaaa    2700
aaaccaccgc taccagcggt ggtttgtttg ccggatcaag agctaccaac tcttttccg    2760 aaggtaactg gcttcagcag agcgcagata ccaaatactg tccttctagt gtagccgtag    2820
ttaggccacc acttcaagaa ctctgtagca ccgcctacat acctcgctct gctaatcctg    2880
ttaccagtgg ctgctgccag tggcgataag tcgtgtctta ccgggttgga ctcaagacga    2940
tagttaccgg ataaggcgca gcggtcgggc tgaacggggg gttcgtgcac acagcccagc    3000
ttggagcgaa cgacctacac cgaactgaga tacctacagc gtgagctatg agaaagcgcc    3060
acgcttcccg aagggagaaa ggcggacagg tatccggtaa gcggcagggt cggaacagga    3120
gagcgcacga gggagcttcc aggggggaaac gcctggtatc tttatagtcc tgtcgggttt    3180
cgccacctct gacttgagcg tcgatttttg tgatgctcgt caggggggcg agcctatgg    3240 aaaaacgcca gcaacgcggc cttttacgg ttcctggcct tttgctggcc ttttgctcac    3300
atgttctttc ctgcgttatc ccctgattct gtggataacc gtattaccgc ctttgagtga    3360
gctgataccg ctcgccgcag ccgaacgacc gagcgcagcg agtcagtgag cgaggaagcg    3420
gaagagcgcc tgatgcggta ttttctcctt acgcatctgt gcggtatttc acaccgcata    3480
tatggtgcac tctcagtaca atctgctctg atgccgcata gttaagccag tatacactcc    3540
gctatcgcta cgtgactggg tcatggctgc gccccgacac ccgccaacac ccgctgacgc    3600
gccctgacgg gcttgtctgc tcccggcatc cgcttacaga caagctgtga ccgtctccgg    3660
gagctgcatg tgtcagaggt tttcaccgtc atcaccgaaa cgcgcgaggc agctgcggta    3720
aagctcatca gcgtggtcgt gaagcgattc acagatgtct gcctgttcat ccgcgtccag    3780
ctcgttgagt ttctccagaa gcgttaatgt ctggcttctg ataaagcggg ccatgttaag    3840
ggcggttttt tcctgtttgg tcactgatgc ctccgtgtaa ggggattttc tgttcatggg    3900
ggtaatgata ccgatgaaac gagagaggat gctcacgata cgggttactg atgatgaaca    3960
tgcccggtta ctggaacgtt gtgagggtaa acaactggcg tatggatgc ggcgggacca    4020 gagaaaaatc actcagggtc aatgccagcg cttcgttaat acagatgtag gtgttccaca    4080
gggtagccag cagcatcctg cgatgcagat ccggaacata atggtgcagg cgctgactt    4140 ccgcgtttcc agactttacg aaacacggaa accgaagacc attcatgttg ttgctcaggt    4200
cgcagacgtt tgcagcagc agtcgcttca cgttcgctcg cgtatcggtg attcattctg    4260
ctaaccagta aggcaacccc gccagcctag ccgggtcctc aacgacagga gcacgatcat    4320
gcgcacccgt ggggccgcca tgccggcgat aatggcctgc ttctcgccga aacgtttggt    4380
ggcgggacca gtgacgaagg cttgagcgag ggcgtgcaag attccgaata ccgcaagcga    4440
caggccgatc atcgtcgcgc tccagcgaaa gcggtcctcg ccgaaaatga cccagagcgc    4500
tgccggcacc tgtcctacga gttgcatgat aaagaagaca gtcataagtg cggcgacgat    4560
agtcatgccc cgcgcccacc ggaaggagct gactgggttg aaggctctca agggcatcgg    4620
tcgagatccc ggtgcctaat gagtgagcta acttacatta attgcgttgc gctcactgcc    4680
cgctttccag tcgggaaacc tgtcgtgcca gctgcattaa tgaatcggcc aacgcgcggg    4740
gagaggcggt ttgcgtattg ggcgccaggg tggttttct tttcaccagt gagacgggca    4800
acagctgatt gcccttcacc gcctggccct gagagagttg cagcaagcgg tccacgctgg    4860
tttgccccag caggcgaaaa tcctgtttga tggtggttaa cggcgggata taacatgagc    4920
```

```
tgtcttcggt atcgtcgtat cccactaccg agatatccgc accaacgcgc agcccggact    4980
cggtaatggc gcgcattgcg cccagcgcca tctgatcgtt ggcaaccagc atcgcagtgg    5040
gaacgatgcc ctcattcagc atttgcatgg tttgttgaaa accggacatg gcactccagt    5100
cgccttcccg ttccgctatc ggctgaattt gattgcgagt gagatattta tgccagccag    5160
ccagacgcag acgcgccgag acagaactta atgggcccgc taacagcgcg atttgctggt    5220
gacccaatgc gaccagatgc tccacgccca gtcgcgtacc gtcttcatgg agaaaaataa    5280
tactgttgat gggtgtctgg tcagagacat caagaaataa cgccggaaca ttagtgcagg    5340
cagcttccac agcaatggca tcctggtcat ccagcggata gttaatgatc agcccactga    5400
cgcgttgcgc gagaagattg tgcaccgccg ctttacaggc ttcgacgccg cttcgttcta    5460
ccatcgacac caccacgctg gcacccagtt gatcggcgcg agatttaatc gccgcgacaa    5520
tttgcgacgg cgcgtgcagg ccagactgga aggtggcaac gccaatcagc aacgactgtt    5580
tgcccgccag ttgttgtgcc acgcggttgg gaatgtaatt cagctccgcc atcgccgctt    5640 ccacttttc ccgcgttttc gcagaaacgt ggctggcctg gttcaccacg cgggaaacgg    5700
tctgataaga gacaccggca tactctgcga catcgtataa cgttactggt ttcacattca    5760
ccaccctgaa ttgactctct tccgggcgct atcatgccat accgcgaaag gttttgcgcc    5820
attcgatggt gtccgggatc tcgacgctct cccttatgcg actcctgcat taggaagcag    5880
cccagtagta ggttgaggcc gttgagcacc gccgccgcaa ggaatggtgc atgcaaggag    5940
atggcgccca acagtcccc ggccacgggg cctgccacca tacccacgcc gaaacaagcg    6000
ctcatgagcc cgaagtggcg agcccgatct tccccatcgg tgatgtcggc gatataggcg    6060
ccagcaaccg cacctgtggc gccggtgatg ccggccacga tgcgtccggc gtagaggatc    6120
gagatctcga tcccgcgaaa ttaatacgac tcactata                           6158
```

<210> SEQ ID NO 81
<211> LENGTH: 6047
<212> TYPE: DNA
<213> ORGANISM: Artificial Sequence
<220> FEATURE:
<223> OTHER INFORMATION: pET24d-N-GST-(PSc)-VGLUT2[human](aa93-125)

<400> SEQUENCE: 81

```
ggggaattgt gagcggataa caattcccct ctagaaataa ttttgtttaa ctttaagaag     60
gagtatataa tgagccatca tcatcatcat catcatcata tgtcccctat actaggttat    120
tggaaaatta agggccttgt gcaacccact cgacttcttt tggaatatct tgaagaaaaa    180
tatgaagagc atttgtatga gcgcgatgaa ggtgataaat ggcgaaacaa aaagtttgaa    240
ttgggtttgg agtttcccaa tcttccttat tatattgatg gtgatgttaa attaacacag    300
tctatggcca tcatacgtta tatagctgac aagcacaaca tgttgggtgg ttgtccaaaa    360
gagcgtgcag agatttcaat gcttgaagga gcggttttgg atattagata cggtgtttcg    420
agaattgcat atagtaaaga ctttgaaact ctcaaagttg attttcttag caagctacct    480
gaaatgctga aaatgttcga agatcgttta tgtcataaaa catatttaaa tggtgatcat    540
gtaacccatc ctgacttcat gttgtatgac gctcttgatg ttgttttata catggaccca    600
atgtgcctgg atgcgttccc aaaattagtt tgttttaaaa aacgtattga agctatccca    660
caaattgata agtacttgaa atccagcaag tatatagcat ggcctttgca gggctggcaa    720
gccacgtttg gtggtggcga ccatcctcca aaattggaag tgctgtttca gggtccagcc    780
```

```
atggttgcca tagtggacat ggtgaacaac tccaccatcc acagaggagg caaagtcata     840
aaagagaaag ctaagttcaa ctgggatcct gaaacagtgg gctaatcgag caccaccacc     900
accaccactg agatccggct gctaacaaag cccgaaagga agctgagttg gctgctgcca     960
ccgctgagca taactagca taaccccttg gggcctctaa acgggtcttg agggggttttt    1020 tgctgaaagg aggaactata tccggattgg cgaatgggac gcgccctgta gcggcgcatt    1080
aagcgcggcg ggtgtggtgg ttacgcgcag cgtgaccgct acacttgcca gcgccctagc    1140
gcccgctcct ttcgctttct tcccttcctt tctcgccacg ttcgccggct ttccccgtca    1200
agctctaaat cgggggctcc ctttaggggtt ccgatttagt gctttacggc acctcgaccc    1260
caaaaaactt gattagggtg atggttcacg tagtgggcca tcgccctgat agacggtttt    1320
tcgccctttg acgttggagt ccacgttctt aatagtgga ctcttgttcc aaactggaac    1380
aacactcaac cctatctcgg tctattcttt tgatttataa gggattttgc cgatttcggc    1440
ctattggtta aaaatgagc tgatttaaca aaaatttaac gcgaatttta acaaaatatt    1500
aacgtttaca atttcaggtg cacttttcg gggaaatgtg cgcggaaccc ctatttgttt    1560 attttttctaa atacattcaa atatgtatcc gctcatgaat taattcttag aaaaactcat    1620
cgagcatcaa atgaaactgc aatttattca tatcaggatt atcaatacca tatttttgaa    1680
aaagccgttt ctgtaatgaa ggagaaaact caccgaggca gttccatagg atggcaagat    1740
cctggtatcg gtctgcgatt ccgactcgtc caacatcaat acaacctatt aatttcccct    1800
cgtcaaaaat aaggttatca agtgagaaat caccatgagt gacgactgaa tccggtgaga    1860
atggcaaaag tttatgcatt tctttccaga cttgttcaac aggccagcca ttacgctcgt    1920
catcaaaatc actcgcatca accaaaccgt tattcattcg tgattgcgcc tgagcgagac    1980
gaaatacgcg atcgctgtta aaaggacaat tacaaacagg aatcgaatgc aaccggcgca    2040
ggaacactgc cagcgcatca acaatatttt cacctgaatc aggatattct tctaatacct    2100
ggaatgctgt ttcccgggg atcgcagtgg tgagtaacca tgcatcatca ggagtacgga    2160
taaaatgctt gatggtcgga agaggcataa attccgtcag ccagtttagt ctgaccatct    2220
catctgtaac atcattggca acgctacctt tgccatgttt cagaaacaac tctggcgcat    2280
cgggcttccc atacaatcga tagattgtcg cacctgattg cccgacatta tcgcgagccc    2340
atttataccc atataaatca gcatccatgt tggaatttaa tcgcggccta gagcaagacg    2400
tttcccgttg aatatggctc ataacacccc ttgtattact gtttatgtaa gcagacagtt    2460
ttattgttca tgaccaaaat cccttaacgt gagttttcgt tccactgagc gtcagacccc    2520
gtagaaaaga tcaaaggatc ttcttgagat cctttttttc tgcgcgtaat ctgctgcttg    2580
caaacaaaaa aaccaccgct accagcggtg gtttgtttgc cggatcaaga gctaccaact    2640
ctttttccga aggtaactgg cttcagcaga gcgcagatac caaatactgt ccttctagtg    2700
tagccgtagt taggccacca cttcaagaac tctgtagcac cgcctacata cctcgctctg    2760
ctaatcctgt taccagtggc tgctgccagt ggcgataagt cgtgtcttac cgggttggac    2820
tcaagacgat agttaccgga taaggcgcag cggtcgggct gaacggggggg ttcgtgcaca    2880 cagcccagct tggagcgaac gacctacacc gaactgagat acctacagcg tgagctatga    2940
gaaagcgcca cgcttcccga agggagaaag gcggacaggt atccggtaag cggcagggtc    3000
ggaacaggag agcgcacgag ggagcttcca gggggaaacg cctggtatct ttatagtcct    3060
gtcgggtttc gccacctctg acttgagcgt cgatttttgt gatgctcgtc aggggggcgg    3120
agcctatgga aaaacgccag caacgcggcc ttttacggt tcctggcctt ttgctggcct    3180
```

-continued

```
tttgctcaca tgttctttcc tgcgttatcc cctgattctg tggataaccg tattaccgcc    3240
tttgagtgag ctgataccgc tcgccgcagc cgaacgaccg agcgcagcga gtcagtgagc    3300
gaggaagcgg aagagcgcct gatgcggtat tttctcctta cgcatctgtg cggtatttca    3360
caccgcatat atggtgcact ctcagtacaa tctgctctga tgccgcatag ttaagccagt    3420
atacactccg ctatcgctac gtgactgggt catggctgcg ccccgacacc cgccaacacc    3480
cgctgacgcg ccctgacggg cttgtctgct cccggcatcc gcttacagac aagctgtgac    3540
cgtctccggg agctgcatgt gtcagaggtt ttcaccgtca tcaccgaaac gcgcgaggca    3600
gctgcggtaa agctcatcag cgtggtcgtg aagcgattca cagatgtctg cctgttcatc    3660
cgcgtccagc tcgttgagtt tctccagaag cgttaatgtc tggcttctga taaagcgggc    3720
catgttaagg gcggtttttt cctgtttggt cactgatgcc tccgtgtaag ggggatttct    3780
gttcatgggg gtaatgatac cgatgaaacg agagaggatg ctcacgatac gggttactga    3840
tgatgaacat gcccggttac tggaacgttg tgagggtaaa caactggcgg tatggatgcg    3900
gcgggaccag agaaaaatca ctcagggtca atgccagcgc ttcgttaata cagatgtagg    3960
tgttccacag ggtagccagc agcatcctgc gatgcagatc cggaacataa tggtgcaggg    4020
cgctgacttc cgcgtttcca gactttacga aacacggaaa ccgaagacca ttcatgttgt    4080
tgctcaggtc gcagacgttt tgcagcagca gtcgcttcac gttcgctcgc gtatcggtga    4140
ttcattctgc taaccagtaa ggcaaccccg ccagcctagc cgggtcctca acgacaggag    4200
cacgatcatg cgcacccgtg gggccgccat gccggcgata atggcctgct tctcgccgaa    4260
acgtttggtg gcgggaccag tgacgaaggc ttgagcgagg gcgtgcaaga ttccgaatac    4320
cgcaagcgac aggccgatca tcgtcgcgct ccagcgaaag cggtcctcgc cgaaaatgac    4380
ccagagcgct gccggcacct gtcctacgag ttgcatgata aagaagacag tcataagtgc    4440
ggcgacgata gtcatgcccc gcgcccaccg gaaggagctg actgggttga aggctctcaa    4500
gggcatcggt cgagatcccg gtgcctaatg agtgagctaa cttacattaa ttgcgttgcg    4560
ctcactgccc gctttccagt cgggaaacct gtcgtgccag ctgcattaat gaatcggcca    4620
acgcgcgggg agaggcggtt tgcgtattgg gcgccagggt ggttttcctt ttcaccagtg    4680
agacgggcaa cagctgattg ccccttcaccg cctggccctg agagagttgc agcaagcggt    4740
ccacgctggt ttgccccagc aggcgaaaat cctgtttgat ggtggttaac ggcgggatat    4800
aacatgagct gtcttcggta tcgtcgtatc ccactaccga gatatccgca ccaacgcgca    4860
gcccggactc ggtaatggcg cgcattgcgc ccagcgccat ctgatcgttg caaccagca    4920 tcgcagtggg aacgatgccc tcattcagca tttgcatggt ttgttgaaaa ccggacatgg    4980
cactccagtc gccttcccgt tccgctatcg gctgaatttg attgcgagtg agatatttat    5040
gccagccagc cagacgcaga cgcgccgaga cagaacttaa tgggcccgct aacagcgcga    5100
tttgctggtg acccaatgcg accagatgct ccacgcccag tcgcgtaccg tcttcatggg    5160
agaaaataat actgttgatg ggtgtctggt cagagacatc aagaaataac gccggaacat    5220
tagtgcaggc agcttccaca gcaatggcat cctggtcatc cagcggatag ttaatgatca    5280
gcccactgac gcgttgcgcg agaagattgt gcaccgccgc tttacaggct tcgacgccgc    5340
ttcgttctac catcgacacc accacgctgg cacccagttg atcggcgcga gatttaatcg    5400
ccgcgacaat ttgcgacggc gcgtgcaggg ccagactgga ggtggcaacg ccaatcagca    5460
acgactgttt gcccgccagt tgttgtgcca cgcggttggg aatgtaattc agctccgcca    5520
```

```
tcgccgcttc cacttttcc cgcgttttcg cagaaacgtg gctggcctgg ttcaccacgc    5580
gggaaacggt ctgataagag acaccggcat actctgcgac atcgtataac gttactggtt    5640
tcacattcac caccctgaat tgactctctt ccgggcgcta tcatgccata ccgcgaaagg    5700
ttttgcgcca ttcgatggtg tccgggatct cgacgctctc ccttatgcga ctcctgcatt    5760
aggaagcagc ccagtagtag gttgaggccg ttgagcaccg ccgccgcaag gaatggtgca    5820
tgcaaggaga tggcgcccaa cagtcccccg gccacgggc ctgccaccat acccacgccg    5880
aaacaagcgc tcatgagccc gaagtggcga gcccgatctt ccccatcggt gatgtcggcg    5940
atataggcgc cagcaaccgc acctgtggcg ccggtgatgc cggccacgat gcgtccggcg    6000
tagaggatcg agatctcgat cccgcgaaat taatacgact cactata    6047
```

<210> SEQ ID NO 82
<211> LENGTH: 6083
<212> TYPE: DNA
<213> ORGANISM: Artificial Sequence
<220> FEATURE:
<223> OTHER INFORMATION: pET24d-N-GST-(PSc)-VGLUT2[human](aa266-310)

<400> SEQUENCE: 82

```
ggggaattgt gagcggataa caattcccct ctagaaataa ttttgtttaa ctttaagaag      60
gagtatataa tgagccatca tcatcatcat catcatcata tgtcccctat actaggttat     120
tggaaaatta agggccttgt gcaacccact cgacttcttt ggaatatctt tgaagaaaaa     180
tatgaagagc atttgtatga gcgcgatgaa ggtgataaat ggcgaaacaa aaagtttgaa     240
ttgggtttgg agtttcccaa tcttccttat tatattgatg gtgatgttaa attaacacag     300
tctatggcca tcatacgtta tatagctgac aagcacaaca tgttgggtgg ttgtccaaaa     360
gagcgtgcag agatttcaat gcttgaagga gcggttttgg atattagata cggtgtttcg     420
agaattgcat atagtaaaga ctttgaaact ctcaaagttg atttttcttag caagctacct     480 gaaatgctga aaatgttcga agatcgttta tgtcataaaa catatttaaa tggtgatcat     540
gtaacccatc ctgacttcat gttgtatgac gctcttgatg ttgttttata catggaccca     600
atgtgcctgg atgcgttccc aaaattagtt tgttttaaaa aacgtattga agctatccca     660
caaattgata agtacttgaa atccagcaag tatatagcat ggccttttgca gggctggcaa     720 gccacgtttg gtggtggcga ccatcctcca aaattggaag tgctgtttca gggtccagcc     780
atggaaagtc cagccaagca tccgaccatt acggatgaag agcgtcggta cattgaggag     840
tctattggcg aatctgccaa tctgttggga gctatgagag agtttaagac tccatggcgc     900
aaattcttca caagcatgta atcgagcacc accaccacca ccactgagat ccggctgcta     960
acaaagcccg aaaggaagct gagttggctg ctgccaccgc tgagcaataa ctagcataac    1020
cccttggggc ctctaaacgg gtcttgaggg gttttttgct gaaaggagga actatatccg    1080
gattggcgaa tgggacgcgc cctgtagcgg cgcattaagc gcggcgggtg tggtggttac    1140
gcgcagcgtg accgctacac ttgccagcgc cctagcgccc gctcctttcg ctttcttccc    1200
ttcctttctc gccacgttcg ccggcttttcc ccgtcaagct ctaaatcggg gctccctttt    1260
agggttccga tttagtgctt tacggcacct cgaccccaaa aaacttgatt agggtgatgg    1320
ttcacgtagt gggccatcgc cctgatagac ggtttttcgc cctttgacgt tggagtccac    1380
gttctttaat agtggactct tgttccaaac tggaacaaca ctcaacccta tctcggtcta    1440
ttcttttgat ttataaggga ttttgccgat ttcggcctat tggttaaaaa atgagctgat    1500
ttaacaaaaa tttaacgcga attttaacaa aatattaacg tttacaattt caggtggcac    1560
```

```
ttttcgggga aatgtgcgcg gaaccccctat ttgtttattt ttctaaatac attcaaatat    1620
gtatccgctc atgaattaat tcttagaaaa actcatcgag catcaaatga aactgcaatt    1680
tattcatatc aggattatca ataccatatt tttgaaaaag ccgtttctgt aatgaaggag    1740
aaaactcacc gaggcagttc cataggatgg caagatcctg gtatcggtct gcgattccga    1800
ctcgtccaac atcaatacaa cctattaatt tcccctcgtc aaaaataagg ttatcaagtg    1860
agaaatcacc atgagtgacg actgaatccg gtgagaatgg caaaagttta tgcatttctt    1920
tccagacttg ttcaacaggc cagccattac gctcgtcatc aaaatcactc gcatcaacca    1980
aaccgttatt cattcgtgat tgcgcctgag cgagacgaaa tacgcgatcg ctgttaaaag    2040
gacaattaca acaggaatc gaatgcaacc ggcgcaggaa cactgccagc gcatcaacaa    2100
tattttcacc tgaatcagga tattcttcta atacctggaa tgctgttttc ccggggatcg    2160
cagtggtgag taaccatgca tcatcaggag tacggataaa atgcttgatg gtcggaagag    2220
gcataaattc cgtcagccag tttagtctga ccatctcatc tgtaacatca ttggcaacgc    2280
tacctttgcc atgtttcaga acaactctg gcgcatcggg cttcccatac aatcgataga    2340
ttgtcgcacc tgattgcccg acattatcgc gagcccattt atacccatat aaatcagcat    2400
ccatgttgga atttaatcgc ggcctagagc aagacgtttc ccgttgaata tggctcataa    2460
caccccttgt attactgttt atgtaagcag acagttttat tgttcatgac caaaatccct    2520
taacgtgagt tttcgttcca ctgagcgtca gaccccgtag aaaagatcaa aggatcttct    2580
tgagatcctt ttttctgcg cgtaatctgc tgcttgcaaa caaaaaaacc accgctacca    2640
gcggtggttt gtttgccgga tcaagagcta ccaactcttt ttccgaaggt aactggcttc    2700
agcagagcgc agataccaaa tactgtcctt ctagtgtagc cgtagttagg ccaccacttc    2760
aagaactctg tagcaccgcc tacatacctc gctctgctaa tcctgttacc agtggctgct    2820
gccagtggcg ataagtcgtg tcttaccggg ttggactcaa gacgatagtt accggataag    2880
gcgcagcggt cgggctgaac ggggggttcg tgcacacagc ccagcttgga gcgaacgacc    2940
tacaccgaac tgagatacct acagcgtgag ctatgagaaa gcgccacgct tcccgaaggg    3000
agaaaggcgg acaggtatcc ggtaagcggc agggtcggaa caggagagcg cacgagggag    3060
cttccagggg gaaacgcctg gtatctttat agtcctgtcg ggtttcgcca cctctgactt    3120
gagcgtcgat ttttgtgatg ctcgtcaggg gggcggagcc tatggaaaaa cgccagcaac    3180
gcggcctttt tacggttcct ggccttttgc tggccttttg ctcacatgtt ctttcctgcg    3240
ttatcccctg attctgtgga taaccgtatt accgcctttg agtgagctga taccgctcgc    3300
cgcagccgaa cgaccgagcg cagcgagtca gtgagcgagg aagcggaaga gcgcctgatg    3360
cggtattttc tccttacgca tctgtgcggt atttcacacc gcatatatgg tgcactctca    3420
gtacaatctg ctctgatgcc gcatagttaa gccagtatac actccgctat cgctacgtga    3480
ctgggtcatg gctgcgcccc gacacccgcc aacacccgct gacgcgccct gacgggcttg    3540
tctgctcccg gcatccgctt acagacaagc tgtgaccgtc tccgggagct gcatgtgtca    3600
gaggttttca ccgtcatcac cgaaacgcgc gaggcagctg cggtaaagct catcagcgtg    3660
gtcgtgaagc gattcacaga tgtctgcctg ttcatccgcg tccagctcgt tgagtttctc    3720
cagaagcgtt aatgtctggc ttctgataaa gcgggccatg ttaagggcgg ttttttcctg    3780
tttggtcact gatgcctccg tgtaagggg atttctgttc atgggggtaa tgataccgat    3840
gaaacgagag aggatgctca cgatacgggt tactgatgat gaacatgccc ggttactgga    3900
```

```
acgttgtgag ggtaaacaac tggcggtatg gatgcggcgg gaccagagaa aaatcactca    3960
gggtcaatgc cagcgcttcg ttaatacaga tgtaggtgtt ccacagggta gccagcagca    4020
tcctgcgatg cagatccgga acataatggt gcagggcgct gacttccgcg tttccagact    4080
ttacgaaaca cggaaaccga agaccattca tgttgttgct caggtcgcag acgttttgca    4140
gcagcagtcg cttcacgttc gctcgcgtat cggtgattca ttctgctaac cagtaaggca    4200
accccgccag cctagccggg tcctcaacga caggagcacg atcatgcgca cccgtggggc    4260
cgccatgccg gcgataatgg cctgcttctc gccgaaacgt ttggtggcgg gaccagtgac    4320
gaaggcttga gcgagggcgt gcaagattcc gaataccgca agcgacaggc cgatcatcgt    4380
cgcgctccag cgaaagcggt cctcgccgaa aatgacccag agcgctgccg gcacctgtcc    4440
tacgagttgc atgataaaga agacagtcat aagtgcggcg acgatagtca tgccccgcgc    4500
ccaccggaag gagctgactg ggttgaaggc tctcaagggc atcggtcgag atcccggtgc    4560
ctaatgagtg agctaactta cattaattgc gttgcgctca ctgcccgctt tccagtcggg    4620
aaacctgtcg tgccagctgc attaatgaat cggccaacgc gcggggagag gcggtttgcg    4680
tattgggcgc cagggtggtt tttcttttca ccagtgagac gggcaacagc tgattgccct    4740
tcaccgcctg gccctgagag agttgcagca agcggtccac gctggtttgc cccagcaggc    4800
gaaaatcctg tttgatggtg gttaacggcg ggatataaca tgagctgtct tcggtatcgt    4860
cgtatcccac taccgagata tccgcaccaa cgcgcagccc ggactcggta atggcgcgca    4920
ttgcgcccag cgccatctga tcgttggcaa ccagcatcgc agtgggaacg atgccctcat    4980
tcagcatttg catggtttgt tgaaaaccgg acatggcact ccagtcgcct tcccgttccg    5040
ctatcggctg aatttgattg cgagtgagat atttatgcca gccagccaga cgcagacgcg    5100
ccgagacaga acttaatggg cccgctaaca gcgcgatttg ctggtgaccc aatgcgacca    5160
gatgctccac gcccagtcgc gtaccgtctt catgggagaa aataatactg ttgatgggtg    5220
tctggtcaga gacatcaaga aataacgccg gaacattagt gcaggcagct tccacagcaa    5280
tggcatcctg gtcatccagc ggatagttaa tgatcagccc actgacgcgt tgcgcgagaa    5340
gattgtgcac cgccgcttta caggcttcga cgccgcttcg ttctaccatc gacaccacca    5400
cgctggcacc cagttgatcg gcgcgagatt taatcgccgc gacaatttgc gacggcgcgt    5460
gcagggccag actggaggtg gcaacgccaa tcagcaacga ctgtttgccc gccagttgtt    5520
gtgccacgcg gttgggaatg taattcagct ccgccatcgc cgcttccact tttcccgcg    5580 ttttcgcaga aacgtggctg gcctggttca ccacgcggga aacggtctga taagagacac    5640
cggcatactc tgcgacatcg tataacgtta ctggtttcac attcaccacc ctgaattgac    5700
tctcttccgg cgctatcat gccataccgc gaaaggtttt gcgccattcg atggtgtccg    5760
ggatctcgac gctctcccctt atgcgactcc tgcattagga agcagcccag tagtaggttg    5820
aggccgttga gcaccgccgc cgcaaggaat ggtgcatgca aggagatggc gcccaacagt    5880 ccccccggcca cggggcctgc caccataccc acgccgaaac aagcgctcat gagcccgaag    5940
tggcgagccc gatcttcccc atcggtgatg tcggcgatat aggcgccagc aaccgcacct    6000
gtggcgccgg tgatgccggc cacgatgcgt ccggcgtaga ggatcgagat ctcgatcccg    6060
cgaaattaat acgactcact ata                                             6083
```

<210> SEQ ID NO 83
<211> LENGTH: 6200
<212> TYPE: DNA
<213> ORGANISM: Artificial Sequence
<220> FEATURE:
<223> OTHER INFORMATION: pET24d-N-GST-(PSc)-VGLUT2[human](aa499-582)

<400> SEQUENCE: 83

| | |
|---|---|
| ggggaattgt gagcggataa caattcccct ctagaaataa ttttgtttaa ctttaagaag | 60 |
| gagtatataa tgagccatca tcatcatcat catcatcata tgtccectat actaggttat | 120 |
| tggaaaatta agggccttgt gcaacccact cgacttcttt tggaatatct tgaagaaaaa | 180 |
| tatgaagagc atttgtatga gcgcgatgaa ggtgataaat ggcgaaacaa aaagtttgaa | 240 |
| ttgggtttgg agtttcccaa tcttccttat tatattgatg gtgatgttaa attaacacag | 300 |
| tctatggcca tcatacgtta tatagctgac aagcacaaca tgttgggtgg ttgtccaaaa | 360 |
| gagcgtgcag agatttcaat gcttgaagga gcggttttgg atattagata cggtgtttcg | 420 |
| agaattgcat atagtaaaga ctttgaaact ctcaaagttg attttcttag caagctacct | 480 |
| gaaatgctga aaatgttcga agatcgttta tgtcataaaa catatttaaa tggtgatcat | 540 |
| gtaacccatc ctgacttcat gttgtatgac gctcttgatg ttgttttata catggaccca | 600 |
| atgtgcctgg atgcgttccc aaaattagtt tgttttaaaa aacgtattga agctatccca | 660 |
| caaattgata agtacttgaa atccagcaag tatatagcat ggcctttgca gggctggcaa | 720 |
| gccacgtttg gtggtggcga ccatcctcca aaattggaag tgctgtttca gggtccagcc | 780 |
| atgtcagggg aaaagcaacc gtgggcagat cctgaagaga ctagtgagga gaagtgcggt | 840 |
| ttcatccatg aggacgaact ggacgaggaa acaggagaca taacacagaa ctacatcaac | 900 |
| tatgaacga cgaaatccta cggggccacc actcaggcca atggaggctg gccttctggg | 960 |
| tgggaaaaga aggaggaatt tgtgcaaggg gaggtgcagg attcccactc ctataaggac | 1020 |
| cgagttgatt attcataatc gagcaccacc accaccacca ctgagatccg gctgctaaca | 1080 |
| aagcccgaaa ggaagctgag ttggctgctg ccaccgctga gcaataacta gcataacccc | 1140 |
| ttggggcctc taaacgggtc ttgaggggtt ttttgctgaa aggaggaact atatccggat | 1200 |
| tggcgaatgg gacgcgccct gtagcggcgc attaagcgcg gcgggtgtgg tggttacgcg | 1260 |
| cagcgtgacc gctacacttg ccagcgccct agcgcccgct cctttcgctt tcttcccttc | 1320 |
| ctttctcgcc acgttcgccg gctttccccg tcaagctcta aatcggggc tccctttagg | 1380 |
| gttccgattt agtgctttac ggcacctcga ccccaaaaaa cttgattagg gtgatggttc | 1440 |
| acgtagtggg ccatcgccct gatagacggt ttttcgccct tgacgttgg agtccacgtt | 1500 |
| ctttaatagt ggactcttgt tccaaactgg aacaacactc aaccctatct cggtctattc | 1560 |
| ttttgattta taagggattt tgccgatttc ggcctattgg ttaaaaaatg agctgattta | 1620 |
| acaaaaattt aacgcgaatt ttaacaaaat attaacgttt acaatttcag gtggcacttt | 1680 |
| tcggggaaat gtgcgcggaa cccctatttg tttatttttc taaatacatt caaatatgta | 1740 |
| tccgctcatg aattaattct tagaaaaact catcgagcat caaatgaaac tgcaatttat | 1800 |
| tcatatcagg attatcaata ccatattttt gaaaagccg tttctgtaat gaaggagaaa | 1860 |
| actcaccgag gcagttccat aggatggcaa gatcctggta tcggtctgcg attccgactc | 1920 |
| gtccaacatc aatacaacct attaatttcc cctcgtcaaa aataaggtta tcaagtgaga | 1980 |
| aatcaccatg agtgacgact gaatccggtg agaatggcaa aagtttatgc atttctttcc | 2040 |
| agacttgttc aacaggccag ccattacgct cgtcatcaaa atcactcgca tcaaccaaac | 2100 |
| cgttattcat tcgtgattgc gcctgagcga cgaaatac gcgatcgctg ttaaaaggac | 2160 |
| aattacaaac aggaatcgaa tgcaaccggc gcaggaacac tgccagcgca tcaacaatat | 2220 |

```
tttcacctga atcaggatat tcttctaata cctggaatgc tgttttcccg gggatcgcag    2280
tggtgagtaa ccatgcatca tcaggagtac ggataaaatg cttgatggtc ggaagaggca    2340
taaattccgt cagccagttt agtctgacca tctcatctgt aacatcattg caacgctac     2400
ctttgccatg tttcagaaac aactctggcg catcgggctt cccatacaat cgatagattg    2460
tcgcacctga ttgcccgaca ttatcgcgag cccatttata cccatataaa tcagcatcca    2520
tgttggaatt taatcgcggc ctagagcaag acgtttcccg ttgaatatgg ctcataacac    2580
cccttgtatt actgtttatg taagcagaca gttttattgt tcatgaccaa aatcccttaa    2640
cgtgagtttt cgttccactg agcgtcagac cccgtagaaa agatcaaagg atcttcttga    2700
gatccttttt ttctgcgcgt aatctgctgc ttgcaaacaa aaaaaccacc gctaccagcg    2760
gtggtttgtt tgccggatca agagctacca actctttttc cgaaggtaac tggcttcagc    2820
agagcgcaga taccaaatac tgtccttcta gtgtagccgt agttaggcca ccacttcaag    2880
aactctgtag caccgcctac atacctcgct ctgctaatcc tgttaccagt ggctgctgcc    2940
agtggcgata agtcgtgtct taccgggttg gactcaagac gatagttacc ggataaggcg    3000
cagcggtcgg gctgaacggg gggttcgtgc acacagccca gcttggagcg aacgacctac    3060
accgaactga gatacctaca gcgtgagcta tgagaaagcg ccacgcttcc cgaagggaga    3120
aaggcggaca ggtatccggt aagcggcagg gtcggaacag gagagcgcac gagggagctt    3180
ccagggggaa acgcctggta tctttatagt cctgtcgggt ttcgccacct ctgacttgag    3240
cgtcgatttt tgtgatgctc gtcagggggg cggagcctat ggaaaaacgc cagcaacgcg    3300
gcctttttac ggttcctggc cttttgctgg ccttttgctc acatgttctt tcctgcgtta    3360
tcccctgatt ctgtggataa ccgtattacc gcctttgagt gagctgatac cgctcgccgc    3420
agccgaacga ccgagcgcag cgagtcagtg agcgaggaag cggaagagcg cctgatgcgg    3480
tattttctcc ttacgcatct gtgcggtatt tcacaccgca tatatggtgc actctcagta    3540
caatctgctc tgatgccgca tagttaagcc agtatacact ccgctatcgc tacgtgactg    3600
ggtcatggct gcgccccgac acccgccaac acccgctgac gcgccctgac gggcttgtct    3660
gctcccggca tccgcttaca gacaagctgt gaccgtctcc gggagctgca tgtgtcagag    3720
gttttcaccg tcatcaccga aacgcgcgag gcagctgcgg taaagctcat cagcgtggtc    3780
gtgaagcgat tcacagatgt ctgcctgttc atccgcgtcc agctcgttga gtttctccag    3840
aagcgttaat gtctggcttc tgataaagcg ggccatgtta agggcggttt tttcctgttt    3900
ggtcactgat gcctccgtgt aagggggatt tctgttcatg ggggtaatga taccgatgaa    3960
acgagagagg atgctcacga tacgggttac tgatgatgaa catgcccggt tactggaacg    4020
ttgtgagggt aaacaactgg cggtatggat gcggcgggac cagagaaaaa tcactcaggg    4080
tcaatgccag cgcttcgtta atacagatgt aggtgttcca cagggtagcc agcagcatcc    4140
tgcgatgcag atccggaaca taatggtgca gggcgctgac ttccgcgttt ccagacttta    4200
cgaaacacgg aaaccgaaga ccattcatgt tgttgctcag gtcgcagacg ttttgcagca    4260
gcagtcgctt cacgttcgct cgcgtatcgg tgattcattc tgctaaccag taaggcaacc    4320
ccgccagcct agccgggtcc tcaacgacag gagcacgatc atgcgcaccc gtggggccgc    4380
catgccggcg ataatggcct gcttctcgcc gaaacgtttg gtggcgggac cagtgacgaa    4440
ggcttgagcg agggcgtgca agattccgaa taccgcaagc gacaggccga tcatcgtcgc    4500
gctccagcga aagcggtcct cgccgaaaat gacccagagc gctgccggca cctgtcctac    4560
gagttgcatg ataaagaaga cagtcataag tgcggcgacg atagtcatgc cccgcgccca    4620
```

```
ccggaaggag ctgactgggt tgaaggctct caagggcatc ggtcgagatc ccggtgccta    4680
atgagtgagc taacttacat taattgcgtt gcgctcactg cccgctttcc agtcgggaaa    4740
cctgtcgtgc cagctgcatt aatgaatcgg ccaacgcgcg gggagaggcg gtttgcgtat    4800
tgggcgccag ggtggttttt cttttcacca gtgagacggg caacagctga ttgcccttca    4860
ccgcctggcc ctgagagagt tgcagcaagc ggtccacgct ggtttgcccc agcaggcgaa    4920
aatcctgttt gatggtggtt aacggcggga tataacatga gctgtcttcg gtatcgtcgt    4980
atcccactac cgagatatcc gcaccaacgc gcagcccgga ctcggtaatg gcgcgcattg    5040
cgcccagcgc catctgatcg ttggcaacca gcatcgcagt gggaacgatg ccctcattca    5100
gcatttgcat ggtttgttga aaccggaca tggcactcca gtcgccttcc cgttccgcta    5160
tcggctgaat ttgattgcga gtgagatatt tatgccagcc agccagacgc agacgcgccg    5220
agacagaact taatgggccc gctaacagcg cgatttgctg gtgacccaat gcgaccagat    5280
gctccacgcc cagtcgcgta ccgtcttcat gggagaaaat aatactgttg atgggtgtct    5340
ggtcagagac atcaagaaat aacgccggaa cattagtgca ggcagcttcc acagcaatgg    5400
catcctggtc atccagcgga tagttaatga tcagcccact gacgcgttgc gcgagaagat    5460
tgtgcaccgc cgctttacag gcttcgacgc cgcttcgttc taccatcgac accaccacgc    5520
tggcacccag ttgatcggcg cgagatttaa tcgccgcgac aatttgcgac ggcgcgtgca    5580
gggccagact ggaggtggca acgccaatca gcaacgactg tttgcccgcc agttgttgtg    5640
ccacgcggtt gggaatgtaa ttcagctccg ccatcgccgc ttccactttt tcccgcgttt    5700
tcgcagaaac gtggctggcc tggttcacca cgcgggaaac ggtctgataa gagacaccgg    5760
catactctgc gacatcgtat aacgttactg gtttcacatt caccaccctg aattgactct    5820
cttccgggcg ctatcatgcc ataccgcgaa aggttttgcg ccattcgatg gtgtccggga    5880
tctcgacgct ctcccttatg cgactcctgc attaggaagc agcccagtag taggttgagg    5940
ccgttgagca ccgccgccgc aaggaatggt gcatgcaagg agatggcgcc caacagtccc    6000
ccggccacgg ggcctgccac catacccacg ccgaaacaag cgctcatgag cccgaagtgg    6060
cgagcccgat cttcccatc ggtgatgtcg gcgatatagg cgccagcaac cgcacctgtg    6120
gcgccggtga tgccggccac gatgcgtccg gcgtagagga tcgagatctc gatcccgcga    6180
aattaatacg actcactata                                                6200
```

<210> SEQ ID NO 84
<211> LENGTH: 6137
<212> TYPE: DNA
<213> ORGANISM: Artificial Sequence
<220> FEATURE:
<223> OTHER INFORMATION: pET24d-N-GST-(PSc)-VGLUT2[human](aa520-582)

<400> SEQUENCE: 84

```
ggggaattgt gagcggataa caattcccct ctagaaataa ttttgtttaa ctttaagaag     60
gagtatataa tgagccatca tcatcatcat catcatcata tgtcccctat actaggttat    120
tggaaaatta agggccttgt gcaacccact cgacttcttt tggaatatct tgaagaaaaa    180
tatgaagagc atttgtatga gcgcgatgaa ggtgataaat ggcgaaacaa aaagtttgaa    240
ttgggtttgg agtttcccaa tcttccttat tatattgatg gtgatgttaa attaacacag    300
tctatggcca tcatacgtta tatagctgac aagcacaaca tgttgggtgg ttgtccaaaa    360
gagcgtgcag agatttcaat gcttgaagga gcggttttgg atattagata cggtgtttcg    420
```

```
agaattgcat atagtaaaga cttttgaaact ctcaaagttg attttcttag caagctacct    480
gaaatgctga aaatgttcga agatcgttta tgtcataaaa catatttaaa tggtgatcat    540
gtaacccatc ctgacttcat gttgtatgac gctcttgatg ttgttttata catggaccca    600
atgtgcctgg atgcgttccc aaaattagtt tgttttaaaa aacgtattga agctatccca    660
caaattgata agtacttgaa atccagcaag tatatagcat ggcctttgca gggctggcaa    720
gccacgtttg gtggtggcga ccatcctcca aaattggaag tgctgtttca gggtccagcc    780
atgcatgagg acgaactgga cgaggaaaca ggagacataa cacagaacta catcaactat    840
ggaacgacga aatcctacgg ggccaccact caggccaatg gaggctggcc ttctgggtgg    900
gaaagaagg aggaatttgt gcaaggggag gtgcaggatt cccactccta aaggaccga    960
gttgattatt cataatcgag caccaccacc accaccactg agatccggct gctaacaaag    1020
cccgaaagga agctgagttg gctgctgcca ccgctgagca ataactagca taccccttg    1080
gggcctctaa acgggtcttg aggggttttt tgctgaaagg aggaactata tccggattgg    1140
cgaatgggac gcgccctgta gcggcgcatt aagcgcggcg ggtgtggtgg ttacgcgcag    1200
cgtgaccgct acacttgcca gcgccctagc gcccgctcct ttcgctttct tcccttcctt    1260
tctcgccacg ttcgccggct ttccccgtca agctctaaat cggggggctcc ctttagggtt    1320
ccgatttagt gctttacggc acctcgaccc caaaaaactt gatagggtg atggttcacg    1380
tagtgggcca tcgccctgat agacggtttt tcgccctttg acgttggagt ccacgttctt    1440
taatagtgga ctcttgttcc aaactggaac aacactcaac cctatctcgg tctattcttt    1500
tgatttataa gggattttgc cgatttcggc ctattggtta aaaaatgagc tgatttaaca    1560
aaaatttaac gcgaattta acaaaatatt aacgtttaca atttcaggtg cactttcg    1620
gggaaatgtg cgcggaaccc ctatttgttt attttctaa atacattcaa atatgtatcc    1680
gctcatgaat taattcttag aaaaactcat cgagcatcaa atgaaactgc aatttattca    1740
tatcaggatt atcaatacca tattttgaa aaagccgttt ctgtaatgaa ggagaaaact    1800
caccgaggca gttccatagg atggcaagat cctggtatcg gtctgcgatt ccgactcgtc    1860
caacatcaat acaacctatt aatttcccct cgtcaaaaat aaggttatca agtgagaaat    1920
caccatgagt gacgactgaa tccggtgaga atggcaaaag tttatgcatt tctttccaga    1980
cttgttcaac aggccagcca ttacgctcgt catcaaaatc actcgcatca accaaaccgt    2040
tattcattcg tgattgcgcc tgagcgagac gaaatacgcg atcgctgtta aaaggacaat    2100
tacaaacagg aatcgaatgc aaccggcgca ggaacactgc cagcgcatca acaatatttt    2160
cacctgaatc aggatattct tctaatacct ggaatgctgt tttcccgggg atcgcagtgg    2220
tgagtaacca tgcatcatca ggagtacgga taaaatgctt gatggtcgga agaggcataa    2280
attccgtcag ccagtttagt ctgaccatct catctgtaac atcattggca acgctacctt    2340
tgccatgttt cagaaacaac tctggcgcat cgggcttccc atacaatcga tagattgtcg    2400
cacctgattg cccgacatta tcgcgagccc atttataccc atataaatca gcatccatgt    2460
tggaatttaa tcgcggccta gagcaagacg tttcccgttg aatatggctc ataacacccc    2520
ttgtattact gtttatgtaa gcagacagtt ttattgttca tgaccaaaat cccttaacgt    2580
gagttttcgt tccactgagc gtcagacccc gtagaaaaga tcaaaggatc ttcttgagat    2640
ccttttttc tgcgcgtaat ctgctgcttg caaacaaaaa aaccaccgct accagcggtg    2700
gtttgtttgc cggatcaaga gctaccaact ctttttccga aggtaactgg cttcagcaga    2760
gcgcagatac caaatactgt ccttctagtg tagccgtagt taggccacca cttcaagaac    2820
```

```
tctgtagcac cgcctacata cctcgctctg ctaatcctgt taccagtggc tgctgccagt   2880
ggcgataagt cgtgtcttac cgggttggac tcaagacgat agttaccgga taaggcgcag   2940
cggtcgggct gaacgggggg ttcgtgcaca cagcccagct tggagcgaac gacctacacc   3000
gaactgagat acctcagcg tgagctatga gaaagcgcca cgcttcccga agggagaaag   3060
gcggacaggt atccggtaag cggcagggtc ggaacaggag agcgcacgag ggagcttcca   3120
gggggaaacg cctggtatct ttatagtcct gtcgggtttc gccacctctg acttgagcgt   3180 cgattttgt gatgctcgtc aggggggcgg agcctatgga aaaacgccag caacgcggcc   3240
tttttacggt tcctggcctt tgctggcct tttgctcaca tgttctttcc tgcgttatcc   3300
cctgattctg tggataaccg tattaccgcc tttgagtgag ctgataccgc tcgccgcagc   3360
cgaacgaccg agcgcagcga gtcagtgagc gaggaagcgg aagagcgcct gatgcggtat   3420
tttctcctta cgcatctgtg cggtatttca caccgcatat atggtgcact ctcagtacaa   3480
tctgctctga tgccgcatag ttaagccagt atacactccg ctatcgctac gtgactgggt   3540
catggctgcg ccccgacacc cgccaacacc cgctgacgcg ccctgacggg cttgtctgct   3600
cccggcatcc gcttacagac aagctgtgac cgtctccggg agctgcatgt gtcagaggtt   3660
ttcaccgtca tcaccgaaac gcgcgaggca gctgcggtaa agctcatcag cgtggtcgtg   3720
aagcgattca cagatgtctg cctgttcatc cgcgtccagc tcgttgagtt tctccagaag   3780
cgttaatgtc tggcttctga taaagcgggc catgttaagg gcggtttttt cctgtttggt   3840
cactgatgcc tccgtgtaag ggggatttct gttcatgggg gtaatgatac cgatgaaacg   3900
agagaggatg ctcacgatac gggttactga tgatgaacat gcccggttac tggaacgttg   3960
tgagggtaaa caactggcgg tatggatgcg gcgggaccag agaaaaatca ctcagggtca   4020
atgccagcgc ttcgttaata cagatgtagg tgttccacag ggtagccagc agcatcctgc   4080
gatgcagatc cggaacataa tggtgcaggg cgctgacttc cgcgtttcca gactttacga   4140
aacacggaaa ccgaagacca ttcatgttgt tgctcaggtc gcagacgttt tgcagcagca   4200
gtcgcttcac gttcgctcgc gtatcggtga ttcattctgc taaccagtaa ggcaaccccg   4260
ccagcctagc cgggtcctca acgacaggag cacgatcatg cgcacccgtg gggccgccat   4320
gccggcgata atggcctgct tctcgccgaa acgtttggtg gcgggaccag tgacgaaggc   4380
ttgagcgagg gcgtgcaaga ttccgaatac cgcaagcgac aggccgatca tcgtcgcgct   4440
ccagcgaaag cggtcctcgc cgaaaatgac ccagagcgct gccggcacct gtcctacgag   4500
ttgcatgata aagaagacag tcataagtgc ggcgacgata tcatgccccgcgcccaccg   4560 gaaggagctg actgggttga aggctctcaa gggcatcggt cgagatcccg gtgcctaatg   4620
agtgagctaa cttacattaa ttgcgttgcg ctcactgccc gctttccagt cgggaaacct   4680
gtcgtgccag ctgcattaat gaatcggcca acgcgcgggg agaggcggtt tgcgtattgg   4740
gcgccagggt ggtttttctt ttcaccagtg agacgggcaa cagctgattg ccttcaccg   4800 cctggccctg agagagttgc agcaagcggt ccacgctggt ttgccccagc aggcgaaaat   4860
cctgtttgat ggtggttaac ggcgggatat aacatgagct gtcttcggta tcgtcgtatc   4920
ccactaccga gatatccgca ccaacgcgca gcccggactc ggtaatggcg cgcattgcgc   4980
ccagcgccat ctgatcgttg gcaaccagca tcgcagtggg aacgatgccc tcattcagca   5040
tttgcatggt ttgttgaaaa ccggacatgg cactccagtc gccttcccgt tccgctatcg   5100
gctgaatttg attgcgagtg agatatttat gccagccagc cagacgcaga cgcgccgaga   5160
```

```
cagaacttaa tgggcccgct aacagcgcga tttgctggtg acccaatgcg accagatgct   5220
ccacgcccag tcgcgtaccg tcttcatggg agaaaataat actgttgatg ggtgtctggt   5280
cagagacatc aagaaataac gccggaacat tagtgcaggc agcttccaca gcaatggcat   5340
cctggtcatc cagcggatag ttaatgatca gcccactgac gcgttgcgcg agaagattgt   5400
gcaccgccgc tttacaggct tcgacgccgc ttcgttctac catcgacacc accacgctgg   5460
cacccagttg atcggcgcga gatttaatcg ccgcgacaat ttgcgacggc gcgtgcaggg   5520
ccagactgga ggtggcaacg ccaatcagca acgactgttt gcccgccagt tgttgtgcca   5580
cgcggttggg aatgtaattc agctccgcca tcgccgcttc acttttttcc cgcgttttcg   5640
cagaaacgtg gctggcctgg ttcaccacgc gggaaacggt ctgataagag acaccggcat   5700
actctgcgac atcgtataac gttactggtt tcacattcac caccctgaat tgactctctt   5760
ccgggcgcta tcatgccata ccgcgaaagg ttttgcgcca ttcgatggtg tccgggatct   5820
cgacgctctc ccttatgcga ctcctgcatt aggaagcagc ccagtagtag gttgaggccg   5880
ttgagcaccg ccgccgcaag gaatggtgca tgcaaggaga tggcgcccaa cagtcccccg   5940
gccacggggc ctgccaccat acccacgccg aaacaagcgc tcatgagccc gaagtggcga   6000
gcccgatctt ccccatcgt gatgtcgcg atataggcgc cagcaaccgc acctgtggcg   6060
ccggtgatgc cggccacgat gcgtccggcg tagaggatcg agatctcgat cccgcgaaat   6120
taatacgact cactata                                                  6137

<210> SEQ ID NO 85
<211> LENGTH: 6083
<212> TYPE: DNA
<213> ORGANISM: Artificial Sequence
<220> FEATURE:
<223> OTHER INFORMATION: pET24d-N-GST-(PSc)-VGLUT2[human](aa520-564)

<400> SEQUENCE: 85
ggggaattgt gagcggataa caattcccct ctagaaataa ttttgtttaa ctttaagaag     60
gagtatataa tgagccatca tcatcatcat catcatcata tgtcccctat actaggttat    120
tggaaaatta agggccttgt gcaacccact cgacttcttt tggaatatct tgaagaaaaa    180
tatgaagagc atttgtatga gcgcgatgaa ggtgataaat ggcgaaacaa aaagtttgaa    240
ttgggttttg agtttcccaa tcttccttat tatattgatg gtgatgttaa attaacacag    300
tctatggcca tcatacgtta tatagctgac aagcacaaca tgttgggtgg ttgtccaaaa    360
gagcgtgcag agatttcaat gcttgaagga gcggttttgg atattagata cggtgtttcg    420
agaattgcat atagtaaaga ctttgaaact ctcaaagttg attttcttag caagctacct    480
gaaatgctga aaatgttcga agatcgttta tgtcataaaa catatttaaa tggtgatcat    540
gtaacccatc ctgacttcat gttgtatgac gctcttgatg ttgttttata catggaccca    600
atgtgcctgg atgcgttccc aaaattagtt tgttttaaaa aacgtattga agctatccca    660
caaattgata agtacttgaa atccagcaag tatatagcat ggcctttgca gggctggcaa    720
gccacgtttg gtggtggcga ccatcctcca aaattggaag tgctgttttca gggtccagcc    780 atgcatgagc acgaactgga cgaggaaaca ggagacataa cacagaacta catcaactat    840
ggaacgacga atcctacgg ggccaccact caggccaatg gaggctggcc ttctgggtgg    900
gaaaagaagg aggaatttta atcgagcacc accaccacca ccactgagat ccggctgcta    960
acaaagcccg aaaggaagct gagttggctg ctgccaccgc tgagcaataa ctagcataac   1020
cccttggggc ctctaaacgg gtcttgaggg gttttttgct gaaaggagga actatatccg   1080
```

```
gattggcgaa tgggacgcgc cctgtagcgg cgcattaagc gcggcgggtg tggtggttac   1140
gcgcagcgtg accgctacac ttgccagcgc cctagcgccc gctcctttcg ctttcttccc   1200
ttcctttctc gccacgttcg ccggcttttcc ccgtcaagct ctaaatcggg gctcccttt   1260 agggttccga tttagtgctt tacggcacct cgaccccaaa aaacttgatt agggtgatgg   1320
ttcacgtagt gggccatcgc cctgatagac ggttttttcgc cctttgacgt tggagtccac   1380
gttctttaat agtggactct tgttccaaac tggaacaaca ctcaaccctat ctcggtcta    1440 ttcttttgat ttataaggga ttttgccgat ttcggcctat tggttaaaaa atgagctgat   1500
ttaacaaaaa tttaacgcga attttaacaa aatattaacg tttacaattt caggtggcac   1560
ttttcgggga aatgtgcgcg gaaccccatat ttgttatttt ttctaaatac attcaaatat   1620
gtatccgctc atgaattaat tcttagaaaa actcatcgag catcaaatga actgcaatt    1680 tattcatatc aggattatca ataccatatt tttgaaaaag ccgtttctgt aatgaaggag   1740
aaaactcacc gaggcagttc cataggatgg caagatcctg gtatcggtct gcgattccga   1800
ctcgtccaac atcaatacaa cctattaatt tcccctcgtc aaaaataagg ttatcaagtg   1860
agaaatcacc atgagtgacg actgaatccg gtgagaatgg caaaagttta tgcatttctt   1920
tccagacttg ttcaacaggc cagccattac gctcgtcatc aaaatcactc gcatcaacca   1980
aaccgttatt cattcgtgat tgcgcctgag cgagacgaaa tacgcgatcg ctgttaaaag   2040
gacaattaca aacaggaatc gaatgcaacc ggcgcaggaa cactgccagc gcatcaacaa   2100
tattttcacc tgaatcagga tattcttcta atacctggaa tgctgttttc ccggggatcg   2160
cagtggtgag taaccatgca tcatcaggag tacggataaa atgcttgatg gtcggaagag   2220
gcataaattc cgtcagccag tttagtctga ccatctcatc tgtaacatca ttggcaacgc   2280 taccttttgcc atgtttcaga aacaactctg gcgcatcggg cttcccatac aatcgataga   2340
ttgtcgcacc tgattgcccg acattatcgc gagcccattt ataccatat aaatcagcat    2400 ccatgttgga atttaatcgc ggcctagagc aagacgtttc ccgttgaata tggctcataa   2460
caccccttgt attactgttt atgtaagcag acagttttat tgttcatgac caaaatccct   2520
taacgtgagt tttcgttcca ctgagcgtca gaccccgtag aaaagatcaa aggatcttct   2580
tgagatcctt ttttttctgcg cgtaatctgc tgcttgcaaa caaaaaaacc accgctacca   2640
gcggtggttt gtttgccgga tcaagagcta ccaactcttt ttccgaaggt aactggcttc   2700
agcagagcgc agataccaaa tactgtcctt ctagtgtagc cgtagttagg ccaccacttc   2760
aagaactctg tagcaccgcc tacatacctc gctctgctaa tcctgttacc agtggctgct   2820
gccagtggcg ataagtcgtg tcttaccggg ttggactcaa gacgatagtt accggataag   2880
gcgcagcggt cgggctgaac ggggggttcg tgcacacagc ccagcttgga gcgaacgacc   2940
tacaccgaac tgagatacct acagcgtgag ctatgagaaa gcgccacgct cccgaaggg    3000 agaaaggcgg acaggtatcc ggtaagcggc agggtcggaa caggagagcg cacgagggag   3060
cttccagggg gaaacgcctg gtatctttat agtcctgtcg ggtttcgcca cctctgactt   3120
gagcgtcgat ttttgtgatg ctcgtcaggg gggcggagcc tatggaaaaa cgccagcaac   3180
gcggcctttt tacggttcct ggccttttgc tggccttttg ctcacatgtt ctttcctgcg   3240
ttatcccctg attctgtgga taaccgtatt accgcctttg agtgagctga taccgctcgc   3300
cgcagccgaa cgaccgagcg cagcgagtca gtgagcgagg aagcggaaga gcgcctgatg   3360
cggtattttc tccttacgca tctgtgcggt atttcacacc gcatatatgg tgcactctca   3420
```

| | |
|---|---|
| gtacaatctg ctctgatgcc gcatagttaa gccagtatac actccgctat cgctacgtga | 3480 |
| ctgggtcatg gctgcgcccc gacacccgcc aacacccgct gacgcgccct gacgggcttg | 3540 |
| tctgctcccg gcatccgctt acagacaagc tgtgaccgtc tccgggagct gcatgtgtca | 3600 |
| gaggttttca ccgtcatcac cgaaacgcgc gaggcagctg cggtaaagct catcagcgtg | 3660 |
| gtcgtgaagc gattcacaga tgtctgcctg ttcatccgcg tccagctcgt tgagtttctc | 3720 |
| cagaagcgtt aatgtctggc ttctgataaa gcgggccatg ttaagggcgg ttttttcctg | 3780 |
| tttggtcact gatgcctccg tgtaaggggg atttctgttc atggggtaa tgataccgat | 3840 |
| gaaacgagag aggatgctca cgatacgggt tactgatgat gaacatgccc ggttactgga | 3900 |
| acgttgtgag ggtaaacaac tggcggtatg gatgcggcgg gaccagagaa aaatcactca | 3960 |
| gggtcaatgc cagcgcttcg ttaatacaga tgtaggtgtt ccacagggta gccagcagca | 4020 |
| tcctgcgatg cagatccgga acataatggt gcagggcgct gacttccgcg tttccagact | 4080 |
| ttacgaaaca cggaaaccga agaccattca tgttgttgct caggtcgcag acgttttgca | 4140 |
| gcagcagtcg cttcacgttc gctcgcgtat cggtgattca ttctgctaac cagtaaggca | 4200 |
| accccgccag cctagccggg tcctcaacga caggagcacg atcatgcgca cccgtggggc | 4260 |
| cgccatgccg gcgataatgg cctgcttctc gccgaaacgt ttggtggcgg gaccagtgac | 4320 |
| gaaggcttga gcgagggcgt gcaagattcc gaataccgca agcgacaggc cgatcatcgt | 4380 |
| cgcgctccag cgaaagcggt cctcgccgaa aatgacccag agcgctgccg gcacctgtcc | 4440 |
| tacgagttgc atgataaaga agacagtcat aagtgcggcg acgatagtca tgccccgcgc | 4500 |
| ccaccggaag gagctgactg ggttgaaggc tctcaagggc atcggtcgag atcccggtgc | 4560 |
| ctaatgagtg agctaactta cattaattgc gttgcgctca ctgcccgctt tccagtcggg | 4620 |
| aaacctgtcg tgccagctgc attaatgaat cggccaacgc gcggggagag gcggtttgcg | 4680 |
| tattgggcgc cagggtggtt tttcttttca ccagtgagac gggcaacagc tgattgccct | 4740 |
| tcaccgcctg gccctgagag agttgcagca agcggtccac gctggtttgc cccagcaggc | 4800 |
| gaaaatcctg tttgatggtg gttaacggcg ggatataaca tgagctgtct tcggtatcgt | 4860 |
| cgtatcccac taccgagata tccgcaccaa cgcgcagccc ggactcggta atggcgcgca | 4920 |
| ttgcgcccag cgccatctga tcgttggcaa ccagcatcgc agtgggaacg atgccctcat | 4980 |
| tcagcatttg catggtttgt tgaaaaccgg acatggcact ccagtcgcct tcccgttccg | 5040 |
| ctatcggctg aatttgattg cgagtgagat atttatgcca gccagccaga cgcagacgcg | 5100 |
| ccgagacaga acttaatggg cccgctaaca gcgcgatttg ctggtgaccc aatgcgacca | 5160 |
| gatgctccac gcccagtcgc gtaccgtctt catgggagaa aataatactg ttgatgggtg | 5220 |
| tctggtcaga gacatcaaga ataacgccg gaacattagt gcaggcagct tccacagcaa | 5280 |
| tggcatcctg gtcatccagc ggatagttaa tgatcagccc actgacgcgt tgcgcgagaa | 5340 |
| gattgtgcac cgccgcttta caggcttcga cgccgcttcg ttctaccatc gacaccacca | 5400 |
| cgctggcacc cagttgatcg gcgcgagatt taatcgccgc gacaatttgc gacggcgcgt | 5460 |
| gcagggccag actggaggtg gcaacgccaa tcagcaacga ctgtttgccc gccagttgtt | 5520 |
| gtgccacgcg gttgggaatg taattcagct ccgccatcgc cgcttccact ttttcccgcg | 5580 |
| ttttcgcaga aacgtggctg gcctggttca ccacgcggga aacggtctga taagagacac | 5640 |
| cggcatactc tgcgacatcg tataacgtta ctggtttcac attcaccacc ctgaattgac | 5700 |
| tctcttccgg gcgctatcat gccataccgc gaaaggtttt gcgccattcg atggtgtccg | 5760 |
| ggatctcgac gctctccctt atgcgactcc tgcattagga agcagcccag tagtaggttg | 5820 |

```
aggccgttga gcaccgccgc cgcaaggaat ggtgcatgca aggagatggc gcccaacagt    5880 ccccggcca cggggcctgc caccataccc acgccgaaac aagcgctcat gagcccgaag     5940
tggcgagccc gatcttcccc atcggtgatg tcggcgatat aggcgccagc aaccgcacct    6000
gtggcgccgg tgatgccggc cacgatgcgt ccggcgtaga ggatcgagat ctcgatcccg    6060
cgaaattaat acgactcact ata                                            6083

<210> SEQ ID NO 86
<211> LENGTH: 6068
<212> TYPE: DNA
<213> ORGANISM: Artificial Sequence
<220> FEATURE:
<223> OTHER INFORMATION: pET24d-N-GST-(PSc)-VGLUT2[human](aa543-582)

<400> SEQUENCE: 86
ggggaattgt gagcggataa caattcccct ctagaaataa ttttgtttaa ctttaagaag      60
gagtatataa tgagccatca tcatcatcat catcatcata tgtcccctat actaggttat     120
tggaaaatta agggccttgt gcaacccact cgacttcttt tggaatatct tgaagaaaaa     180
tatgaagagc atttgtatga gcgcgatgaa ggtgataaat ggcgaaacaa aaagtttgaa     240
ttgggtttgg agtttcccaa tcttccttat tatattgatg gtgatgttaa attaacacag     300
tctatggcca tcatacgtta tatagctgac aagcacaaca tgttgggtgg ttgtccaaaa     360
gagcgtgcag agatttcaat gcttgaagga gcggttttgg atattagata cggtgtttcg     420
agaattgcat atagtaaaga ctttgaaact ctcaaagttg attttcttag caagctacct     480
gaaatgctga aatgttcga agatcgttta tgtcataaaa catatttaaa tggtgatcat     540
gtaacccatc ctgacttcat gttgtatgac gctcttgatg ttgttttata catggaccca     600
atgtgcctgg atgcgttccc aaaattagtt tgttttaaaa acgtattga agctatccca     660 caaattgata agtacttgaa atccagcaag tatatagcat ggcctttgca gggctggcaa     720
gccacgtttg gtggtggcga ccatcctcca aaattggaag tgctgtttca gggtccagcc     780
atgtcctacg ggccaccac tcaggccaat ggaggctggc cttctgggtg gaaaagaag     840 gaggaatttg tgcaagggga ggtgcaggat tcccactcct ataaggaccg agttgattat     900
tcataatcga gcaccaccac caccaccact gagatccggc tgctaacaaa gcccgaaagg     960
aagctgagtt ggctgctgcc accgctgagc aataactagc ataacccctt ggggcctcta    1020
aacgggtctt gaggggtttt ttgctgaaag gaggaactat atccggattg gcgaatggga    1080
cgcgccctgt agcggcgcat taagcgcggc gggtgtggtg gttacgcgca gcgtgaccgc    1140
tacacttgcc agcgccctag cgcccgctcc tttcgctttc ttcccttcct ttctcgccac    1200
gttcgccggc tttccccgtc aagctctaaa tcggggctc cctttagggt tccgatttag    1260
tgctttacgg cacctcgacc ccaaaaaact tgattagggt gatggttcac gtagtgggcc    1320
atcgccctga tagacggttt ttcgcccttt gacgttggag tccacgttct ttaatagtgg    1380
actcttgttc caaactggaa caacactcaa ccctatctcg gtctattctt tgatttata    1440 agggattttg ccgatttcgg cctattggtt aaaaaatgag ctgatttaac aaaaatttaa    1500
cgcgaatttt aacaaaatat taacgtttac aatttcaggt ggcactttc ggggaaatgt    1560 gcgcggaacc cctatttgtt tatttttcta aatacattca aatatgtatc cgctcatgaa    1620
ttaattctta gaaaaactca tcgagcatca aatgaaactg caattattc atatcaggat    1680 tatcaatacc atatttttga aaagccgttt ctgtaatga aggagaaaac tcaccgaggc    1740
```

```
agttccatag gatggcaaga tcctggtatc ggtctgcgat tccgactcgt ccaacatcaa   1800
tacaacctat taatttcccc tcgtcaaaaa taaggttatc aagtgagaaa tcaccatgag   1860
tgacgactga atccggtgag aatggcaaaa gtttatgcat ttctttccag acttgttcaa   1920
caggccagcc attacgctcg tcatcaaaat cactcgcatc aaccaaaccg ttattcattc   1980
gtgattgcgc ctgagcgaga cgaaatacgc gatcgctgtt aaaaggacaa ttacaaacag   2040
gaatcgaatg caaccggcgc aggaacactg ccagcgcatc aacaatattt tcacctgaat   2100
caggatattc ttctaatacc tggaatgctg ttttcccggg gatcgcagtg gtgagtaacc   2160
atgcatcatc aggagtacgg ataaaatgct tgatggtcgg aagaggcata aattccgtca   2220
gccagtttag tctgaccatc tcatctgtaa catcattggc aacgctacct ttgccatgtt   2280
tcagaaacaa ctctggcgca tcgggcttcc catacaatcg atagattgtc gcacctgatt   2340
gcccgacatt atcgcgagcc catttatacc catataaatc agcatccatg ttggaattta   2400
atcgcggcct agagcaagac gtttcccgtt gaatatggct cataacaccc cttgtattac   2460
tgtttatgta agcagacagt tttattgttc atgaccaaaa tcccttaacg tgagttttcg   2520
ttccactgag cgtcagaccc cgtagaaaag atcaaaggat cttcttgaga tccttttttt   2580
ctgcgcgtaa tctgctgctt gcaaacaaaa aaaccaccgc taccagcggt ggtttgtttg   2640
ccggatcaag agctaccaac tcttttccg aaggtaactg gcttcagcag agcgcagata   2700
ccaaatactg tccttctagt gtagccgtag ttaggccacc acttcaagaa ctctgtagca   2760
ccgcctacat acctcgctct gctaatcctg ttaccagtgg ctgctgccag tggcgataag   2820
tcgtgtctta ccgggttgga ctcaagacga tagttaccgg ataaggcgca gcggtcgggc   2880
tgaacggggg gttcgtgcac acagcccagc ttggagcgaa cgacctacac cgaactgaga   2940
tacctacagc gtgagctatg agaaagcgcc acgcttcccg aagggagaaa ggcggacagg   3000
tatccggtaa gcggcagggt cggaacagga gagcgcacga gggagcttcc agggggaaac   3060
gcctggtatc tttatagtcc tgtcgggttt cgccacctct gacttgagcg tcgatttttg   3120
tgatgctcgt caggggggcg gagcctatgg aaaaacgcca gcaacgcggc ctttttacgg   3180
ttcctggcct tttgctggcc ttttgctcac atgttcttc ctgcgttatc ccctgattct   3240
gtggataacc gtattaccgc ctttgagtga gctgataccg ctcgccgcag ccgaacgacc   3300
gagcgcagcg agtcagtgag cgaggaagcg gaagagcgcc tgatgcggta ttttctcctt   3360
acgcatctgt gcggtatttc acaccgcata tatggtgcac tctcagtaca atctgctctg   3420
atgccgcata gttaagccag tatacactcc gctatcgcta cgtgactggg tcatggctgc   3480
gccccgacac ccgccaacac ccgctgacgc gccctgacgg gcttgtctgc tcccggcatc   3540
cgcttacaga caagctgtga ccgtctccgg gagctgcatg tgtcagaggt tttcaccgtc   3600
atcaccgaaa cgcgcgaggc agctgcggta agctcatca gcgtggtcgt gaagcgattc   3660
acagatgtct gcctgttcat ccgcgtccag ctcgttgagt ttctccagaa gcgttaatgt   3720
ctggcttctg ataaagcggg ccatgttaag gcggtttttt cctgtttggt cactgatgc   3780 ctccgtgtaa gggggatttc tgttcatggg ggtaatgata ccgatgaaac gagagaggat   3840
gctcacgata cgggttactg atgatgaaca tgcccggtta ctggaacgtt gtgagggtaa   3900
acaactggcg gtatggatgc ggcgggacca gagaaaaatc actcagggtc aatgccagcg   3960
cttcgttaat acagatgtag gtgttccaca gggtagccag cagcatcctg cgatgcagat   4020
ccggaacata atggtgcagg gcgctgactt ccgcgtttcc agactttacg aaacacggaa   4080
accgaagacc attcatgttg ttgctcaggt cgcagacgtt ttgcagcagc agtcgcttca   4140
```

```
cgttcgctcg cgtatcggtg attcattctg ctaaccagta aggcaacccc gccagcctag   4200
ccgggtcctc aacgacagga gcacgatcat gcgcacccgt ggggccgcca tgccggcgat   4260
aatggcctgc ttctcgccga aacgtttggt ggcgggacca gtgacgaagg cttgagcgag   4320
ggcgtgcaag attccgaata ccgcaagcga caggccgatc atcgtcgcgc tccagcgaaa   4380
gcggtcctcg ccgaaaatga cccagagcgc tgccggcacc tgtcctacga gttgcatgat   4440
aaagaagaca gtcataagtg cggcgacgat agtcatgccc cgcgcccacc ggaaggagct   4500
gactgggttg aaggctctca agggcatcgg tcgagatccc ggtgcctaat gagtgagcta   4560
acttacatta attgcgttgc gctcactgcc cgctttccag tcgggaaacc tgtcgtgcca   4620
gctgcattaa tgaatcggcc aacgcgcggg gagaggcggt ttgcgtattg ggcgccaggg   4680 tggttttttct tttcaccagt gagacgggca acagctgatt gcccttcacc gcctggccct   4740
gagagagttg cagcaagcgg tccacgctgg tttgccccag caggcgaaaa tcctgtttga   4800
tggtggttaa cggcgggata taacatgagc tgtcttcggt atcgtcgtat cccactaccg   4860
agatatccgc accaacgcgc agcccggact cggtaatggc gcgcattgcg cccagcgcca   4920
tctgatcgtt ggcaaccagc atcgcagtgg gaacgatgcc ctcattcagc atttgcatgg   4980
tttgttgaaa accggacatg gcactccagt cgccttcccg ttccgctatc ggctgaattt   5040
gattgcgagt gagatattta tgccagccag ccagacgcag acgcgccgag acagaactta   5100
atgggcccgc taacagcgcg atttgctggt gacccaatgc gaccagatgc tccacgccca   5160
gtcgcgtacc gtcttcatgg gagaaaataa tactgttgat gggtgtctgg tcagagacat   5220
caagaaataa cgccggaaca ttagtgcagg cagcttccac agcaatggca tcctggtcat   5280
ccagcggata gttaatgatc agcccactga cgcgttgcgc gagaagattg tgcaccgccg   5340
ctttacaggc ttcgacgccg cttcgttcta ccatcgacac caccacgctg gcacccagtt   5400
gatcggcgcg agatttaatc gccgcgacaa tttgcgacgg cgcgtgcagg ccagactgg   5460 aggtggcaac gccaatcagc aacgactgtt tgcccgccag ttgttgtgcc acgcggttgg   5520
gaatgtaatt cagctccgcc atcgccgctt ccacttttc ccgcgttttc gcagaaacgt   5580
ggctggcctg gttcaccacg cgggaaacgg tctgataaga gacaccggca tactctgcga   5640
catcgtataa cgttactggt ttcacattca ccaccctgaa ttgactctct tccgggcgct   5700
atcatgccat accgcgaaag gttttgcgcc attcgatggt gtccgggatc tcgacgctct   5760 ccccttatgcg actcctgcat taggaagcag cccagtagta ggttgaggcc gttgagcacc   5820
gccgccgcaa ggaatggtgc atgcaaggag atggcgccca acagtccccc ggccacgggg   5880
cctgccacca tacccacgcc gaaacaagcg ctcatgagcc cgaagtggcg agcccgatct   5940
tccccatcgg tgatgtcggc gatataggcg ccagcaaccg cacctgtggc gccggtgatg   6000
ccggccacga tgcgtccggc gtagaggatc gagatctcga tcccgcgaaa ttaatacgac   6060
tcactata                                                            6068

<210> SEQ ID NO 87
<211> LENGTH: 6002
<212> TYPE: DNA
<213> ORGANISM: Artificial Sequence
<220> FEATURE:
<223> OTHER INFORMATION: pET24d-N-GST-(PSc)-VGLUT2[human](aa565-582)

<400> SEQUENCE: 87
ggggaattgt gagcggataa caattcccct ctagaaataa ttttgtttaa ctttaagaag   60
```

-continued

| | | | | | |
|---|---|---|---|---|---|
| gagtatataa | tgagccatca | tcatcatcat | catcatcata | tgtccctat | actaggttat | 120
| tggaaaatta | agggccttgt | gcaacccact | cgacttcttt | tggaatatct | tgaagaaaaa | 180
| tatgaagagc | atttgtatga | gcgcgatgaa | ggtgataaat | ggcgaaacaa | aaagtttgaa | 240
| ttgggtttgg | agtttcccaa | tcttccttat | tatattgatg | gtgatgttaa | attaacacag | 300
| tctatggcca | tcatacgtta | tatagctgac | aagcacaaca | tgttgggtgg | ttgtccaaaa | 360
| gagcgtgcag | agatttcaat | gcttgaagga | gcggttttgg | atattagata | cggtgtttcg | 420
| agaattgcat | atagtaaaga | ctttgaaact | ctcaaagttg | attttcttag | caagctacct | 480
| gaaatgctga | aaatgttcga | agatcgttta | tgtcataaaa | catatttaaa | tggtgatcat | 540
| gtaacccatc | ctgacttcat | gttgtatgac | gctcttgatg | ttgttttata | catggaccca | 600
| atgtgcctgg | atgcgttccc | aaaattagtt | tgttttaaaa | aacgtattga | agctatccca | 660
| caaattgata | agtacttgaa | atccagcaag | tatatagcat | ggcctttgca | gggctggcaa | 720
| gccacgtttg | gtggtggcga | ccatcctcca | aaattggaag | tgctgtttca | gggtccagcc | 780
| atggtgcaag | gggaggtgca | ggattcccac | tcctataagg | accgagttga | ttattcataa | 840
| tcgagcacca | ccaccaccac | cactgagatc | cggctgctaa | caaagcccga | aaggaagctg | 900
| agttggctgc | tgccaccgct | gagcaataac | tagcataacc | ccttggggcc | tctaaacggg | 960
| tcttgagggg | ttttttgctg | aaaggaggaa | ctatatccgg | attggcgaat | gggacgcgcc | 1020
| ctgtagcggc | gcattaagcg | cggcgggtgt | ggtggttacg | cgcagcgtga | ccgctacact | 1080
| tgccagcgcc | ctagcgcccg | ctcctttcgc | tttcttccct | tcctttctcg | ccacgttcgc | 1140
| cggctttccc | cgtcaagctc | taaatcgggg | gctcccttta | gggttccgat | ttagtgcttt | 1200
| acggcacctc | gaccccaaaa | aacttgatta | gggtgatggt | tcacgtagtg | gccatcgcc | 1260
| ctgatagacg | gtttttcgcc | ctttgacgtt | ggagtccacg | ttctttaata | gtggactctt | 1320
| gttccaaact | ggaacaacac | tcaaccctat | ctcggtctat | tcttttgatt | tataagggat | 1380
| tttgccgatt | tcggcctatt | ggttaaaaaa | tgagctgatt | taacaaaaat | ttaacgcgaa | 1440
| ttttaacaaa | atattaacgt | ttacaatttc | aggtggcact | tttcggggaa | atgtgcgcgg | 1500
| aaccccctatt | tgtttatttt | tctaaataca | ttcaaatatg | tatccgctca | tgaattaatt | 1560
| cttagaaaaa | ctcatcgagc | atcaaatgaa | actgcaattt | attcatatca | ggattatcaa | 1620
| taccatattt | ttgaaaaagc | cgtttctgta | atgaaggaga | aaactcaccg | aggcagttcc | 1680
| ataggatggc | aagatcctgg | tatcggtctg | cgattccgac | tcgtccaaca | tcaatacaac | 1740
| ctattaattt | cccctcgtca | aaaataaggt | tatcaagtga | gaaatcacca | tgagtgacga | 1800
| ctgaatccgg | tgagaatggc | aaaagtttat | gcatttcttt | ccagacttgt | tcaacaggcc | 1860
| agccattacg | ctcgtcatca | aaatcactcg | catcaaccaa | accgttattc | attcgtgatt | 1920
| gcgcctgagc | gagacgaaat | acgcgatcgc | tgttaaaagg | acaattacaa | acaggaatcg | 1980
| aatgcaaccg | gcgcaggaac | actgccagcg | catcaacaat | attttcacct | gaatcaggat | 2040
| attcttctaa | tacctggaat | gctgttttcc | cggggatcgc | agtggtgagt | aaccatgcat | 2100
| catcaggagt | acggataaaa | tgcttgatgg | tcggaagagg | cataaattcc | gtcagccagt | 2160
| ttagtctgac | catctcatct | gtaacatcat | tggcaacgct | acctttgcca | tgtttcagaa | 2220
| acaactctgg | cgcatcgggc | ttcccataca | atcgatagat | tgtcgcacct | gattgcccga | 2280
| cattatcgcg | agcccattta | tacccatata | aatcagcatc | catgttggaa | tttaatcgcg | 2340
| gcctagagca | agacgtttcc | cgttgaatat | ggctcataac | accccttgta | ttactgttta | 2400
| tgtaagcaga | cagttttatt | gttcatgacc | aaaatccctt | aacgtgagtt | ttcgttccac | 2460

```
tgagcgtcag accccgtaga aaagatcaaa ggatcttctt gagatccttt ttttctgcgc    2520
gtaatctgct gcttgcaaac aaaaaaacca ccgctaccag cggtggtttg tttgccggat    2580
caagagctac caactctttt tccgaaggta actggcttca gcagagcgca gataccaaat    2640
actgtccttc tagtgtagcc gtagttaggc caccacttca agaactctgt agcaccgcct    2700
acatacctcg ctctgctaat cctgttacca gtggctgctg ccagtggcga taagtcgtgt    2760
cttaccgggt tggactcaag acgatagtta ccggataagg cgcagcggtc gggctgaacg    2820
gggggttcgt gcacacagcc cagcttggag cgaacgacct acaccgaact gagatacccta   2880 cagcgtgagc tatgagaaag cgccacgctt cccgaaggga gaaaggcgga caggtatccg    2940
gtaagcggca gggtcggaac aggagagcgc acgagggagc ttccaggggg aaacgcctgg    3000
tatctttata gtcctgtcgg gtttcgccac ctctgacttg agcgtcgatt tttgtgatgc    3060
tcgtcagggg ggcggagcct atggaaaaac gccagcaacg cggccttttt acggttcctg    3120
gccttttgct ggccttttgc tcacatgttc tttcctgcgt tatccctga ttctgtggat     3180 aaccgtatta ccgcctttga gtgagctgat accgctcgcc gcagccgaac gaccgagcgc    3240
agcgagtcag tgagcgagga agcggaagag cgcctgatgc ggtattttct ccttacgcat    3300
ctgtgcggta tttcacaccg catatatggt gcactctcag tacaatctgc tctgatgccg    3360
catagttaag ccagtataca ctccgctatc gctacgtgac tgggtcatgg ctgcgccccg    3420
acacccgcca cacccgctg acgcgcctg acgggcttgt ctgctcccgg catccgctta     3480
cagacaagct gtgaccgtct ccgggagctg catgtgtcag aggttttcac cgtcatcacc    3540
gaaacgcgcg aggcagctgc ggtaaagctc atcagcgtgg tcgtgaagcg attcacagat    3600
gtctgcctgt tcatccgcgt ccagctcgtt gagtttctcc agaagcgtta atgtctggct    3660
tctgataaag cgggccatgt taagggcggt ttttcctgt ttggtcactg atgcctccgt     3720
gtaaggggga tttctgttca tgggggtaat gataccgatg aaacgagaga ggatgctcac    3780
gatacgggtt actgatgatg aacatgcccg gttactggaa cgttgtgagg gtaaacaact    3840
ggcggtatgg atgcggcggg accagagaaa aatcactcag ggtcaatgcc agcgcttcgt    3900
taatacagat gtaggtgttc cacagggtag ccagcagcat cctgcgatgc agatccggaa    3960
cataatggtg cagggcgctg acttccgcgt ttccagactt tacgaaacac ggaaaccgaa    4020
gaccattcat gttgttgctc aggtcgcaga cgttttgcag cagcagtcgc ttcacgttcg    4080
ctcgcgtatc ggtgattcat tctgctaacc agtaaggcaa ccccgccagc ctagccgggt    4140
cctcaacgac aggagcacga tcatgcgcac ccgtggggcc gccatgccgg cgataatggc    4200
ctgcttctcg ccgaaacgtt tggtggcggg accagtgacg aaggcttgag cgagggcgtg    4260
caagattccg aataccgcaa gcgacaggcc gatcatcgtc gcgctccagc gaaagcggtc    4320
ctcgccgaaa atgacccaga gcgctgccgg cacctgtcct acgagttgca tgataaagaa    4380
gacagtcata agtgcggcga cgatagtcat gccccgcgcc caccggaagg agctgactgg    4440
gttgaaggct ctcaagggca tcggtcgaga tcccggtgcc taatgagtga gctaacttac    4500
attaattgcg ttgcgctcac tgcccgcttt ccagtcggga aacctgtcgt gccagctgca    4560
ttaatgaatc ggccaacgcg cggggagagg cggtttgcgt attgggcgcc agggtggttt    4620
ttcttttcac cagtgagacg ggcaacagct gattgccctt caccgcctgg ccctgagaga    4680
gttgcagcaa gcggtccacg ctggtttgcc ccagcaggcg aaaatcctgt ttgatggtgg    4740
ttaacggcgg gatataacat gagctgtctt cggtatcgtc gtatcccact accgagatat    4800
```

-continued

| | |
|---|---|
| ccgcaccaac gcgcagcccg gactcggtaa tggcgcgcat tgcgcccagc gccatctgat | 4860 |
| cgttggcaac cagcatcgca gtgggaacga tgccctcatt cagcatttgc atggtttgtt | 4920 |
| gaaaaccgga catggcactc cagtcgcctt cccgttccgc tatcggctga atttgattgc | 4980 |
| gagtgagata tttatgccag ccagccagac gcagacgcgc cgagacagaa cttaatgggc | 5040 |
| ccgctaacag cgcgatttgc tggtgaccca atgcgaccag atgctccacg cccagtcgcg | 5100 |
| taccgtcttc atgggagaaa ataatactgt tgatgggtgt ctggtcagag acatcaagaa | 5160 |
| ataacgccgg aacattagtg caggcagctt ccacagcaat ggcatcctgg tcatccagcg | 5220 |
| gatagttaat gatcagccca ctgacgcgtt gcgcagaag attgtgcacc gccgctttac | 5280 |
| aggcttcgac gccgcttcgt tctaccatcg acaccaccac gctggcaccc agttgatcgg | 5340 |
| cgcgagattt aatcgccgcg acaatttgcg acggcgcgtg cagggccaga ctggaggtgg | 5400 |
| caacgccaat cagcaacgac tgtttgcccg ccagttgttg tgccacgcgg ttgggaatgt | 5460 |
| aattcagctc cgccatcgcc gcttccactt tttcccgcgt tttcgcagaa cgtggctgg | 5520 |
| cctggttcac cacgcgggaa acggtctgat aagagacacc ggcatactct gcgacatcgt | 5580 |
| ataacgttac tggtttcaca ttcaccaccc tgaattgact ctcttccggg cgctatcatg | 5640 |
| ccataccgcg aaaggttttg cgccattcga tggtgtccgg gatctcgacg ctctccctta | 5700 |
| tgcgactcct gcattaggaa gcagcccagt agtaggttga ggccgttgag caccgccgcc | 5760 |
| gcaaggaatg tgcatgcaa ggagatggcg cccaacagtc ccccggccac ggggcctgcc | 5820 |
| accatacccca cgccgaaaca agcgctcatg agcccgaagt ggcgagcccg atcttcccca | 5880 |
| tcggtgatgt cggcgatata ggcgccagca accgcacctg tggcgccggt gatgccggcc | 5940 |
| acgatgcgtc cggcgtagag gatcgagatc tcgatcccgc gaaattaata cgactcacta | 6000 |
| ta | 6002 |

<210> SEQ ID NO 88
<211> LENGTH: 6080
<212> TYPE: DNA
<213> ORGANISM: Artificial Sequence
<220> FEATURE:
<223> OTHER INFORMATION: pET24d-N-GST-(PSc)-VGLUT2[human](aa499-542)

<400> SEQUENCE: 88

| | |
|---|---|
| ggggaattgt gagcggataa caattcccct ctagaaataa ttttgtttaa ctttaagaag | 60 |
| gagtatataa tgagccatca tcatcatcat catcatcata tgtccctat actaggttat | 120 |
| tggaaaatta agggccttgt gcaacccact cgacttcttt tggaatatct tgaagaaaaa | 180 |
| tatgaagagc atttgtatga gcgcgatgaa ggtgataaat ggcgaaacaa aagtttgaa | 240 |
| ttgggttttgg agtttcccaa tcttccttat tatattgatg gtgatgttaa attaacacag | 300 |
| tctatggcca tcatacgtta tatagctgac aagcacaaca tgttgggtgg ttgtccaaaa | 360 |
| gagcgtgcag agatttcaat gcttgaagga gcggttttgg atattagata cggtgtttcg | 420 |
| agaattgcat atagtaaaga ctttgaaact ctcaaagttg attttcttag caagctacct | 480 |
| gaaatgctga aaatgttcga agatcgttta tgtcataaaa catatttaaa tggtgatcat | 540 |
| gtaacccatc ctgacttcat gttgtatgac gctcttgatg ttgttttata catgaccca | 600 |
| atgtgcctgg atgcgttccc aaaattagtt tgttttaaaa aacgtattga agctatccca | 660 |
| caaattgata agtacttgaa atccagcaag tatatagcat ggcctttgca gggctggcaa | 720 |
| gccacgtttg gtggtggcga ccatcctcca aaattggaag tgctgtttca gggtccagcc | 780 |
| atgtcagggg aaaagcaacc gtgggcagat cctgaagaga ctagtgagga gaagtgcggt | 840 |

```
ttcatccatg aggacgaact ggacgaggaa acaggagaca taacacagaa ctacatcaac    900
tatggaacga cgaaataatc gagcaccacc accaccacca ctgagatccg gctgctaaca    960
aagcccgaaa ggaagctgag ttggctgctg ccaccgctga gcaataacta gcataacccc   1020
ttggggcctc taaacgggtc ttgaggggtt ttttgctgaa aggaggaact atatccggat   1080
tggcgaatgg gacgcgccct gtagcggcgc attaagcgcg gcgggtgtgg tggttacgcg   1140
cagcgtgacc gctacacttg ccagcgccct agcgcccgct cctttcgctt tcttcccttc   1200
ctttctcgcc acgttcgccg gctttccccg tcaagctcta atcgggggc tccctttagg   1260
gttccgattt agtgctttac ggcacctcga ccccaaaaaa cttgattagg gtgatggttc   1320
acgtagtggg ccatcgccct gatagacggt ttttcgccct tgacgttgg agtccacgtt   1380
ctttaatagt ggactcttgt tccaaactgg aacaacactc aaccctatct cggtctattc   1440
ttttgattta agggatttt tgccgatttc ggcctattgg ttaaaaaatg agctgattta   1500
acaaaatttt aacgcgaatt ttaacaaaat attaacgttt acaatttcag gtggcacttt   1560
tcggggaaat gtgcgcggaa cccctatttg tttatttttc taaatacatt caaatatgta   1620
tccgctcatg aattaattct tagaaaaact catcgagcat caaatgaaac tgcaatttat   1680
tcatatcagg attatcaata ccatattttt gaaaaagccg tttctgtaat gaaggagaaa   1740
actcaccgag gcagttccat aggatggcaa gatcctggta tcggtctgcg attccgactc   1800
gtccaacatc aatacaacct attaatttcc cctcgtcaaa aataaggtta tcaagtgaga   1860
aatcaccatg agtgacgact gaatccggtg agaatggcaa aagtttatgc atttctttcc   1920
agacttgttc aacaggccag ccattacgct cgtcatcaaa atcactcgca tcaaccaaac   1980
cgttattcat tcgtgattgc gcctgagcga cgcgaaatac gcgatcgctg ttaaaaggac   2040
aattacaaac aggaatcgaa tgcaaccggc gcaggaacac tgccagcgca tcaacaatat   2100
tttcacctga atcaggatat tcttctaata cctggaatgc tgttttcccg gggatcgcag   2160
tggtgagtaa ccatgcatca tcaggagtac ggataaaatg cttgatggtc ggaagaggca   2220
taaattccgt cagccagttt agtctgacca tctcatctgt aacatcattg gcaacgctac   2280
ctttgccatg tttcagaaac aactctggcg catcgggctt cccatacaat cgatagattg   2340
tcgcacctga ttgcccgaca ttatcgcgag cccatttata cccatataaa tcagcatcca   2400
tgttggaatt taatcgcggc ctagagcaag acgtttcccg ttgaatatgg ctcataacac   2460
cccttgtatt actgtttatg taagcagaca gttttattgt tcatgaccaa aatcccttaa   2520
cgtgagtttt cgttccactg agcgtcagac cccgtagaaa agatcaaagg atcttcttga   2580
gatccttttt ttctgcgcgt aatctgctgc ttgcaaacaa aaaaaccacc gctaccagcg   2640
gtggtttgtt tgccggatca agagctacca actcttttc cgaaggtaac tggcttcagc   2700
agagcgcaga taccaaatac tgtccttcta gtgtagccgt agttaggcca ccacttcaag   2760
aactctgtag caccgcctac atacctcgct ctgctaatcc tgttaccagt ggctgctgcc   2820
agtggcgata agtcgtgtct taccgggttg gactcaagac gatagttacc ggataaggcg   2880
cagcggtcgg gctgaacggg gggttcgtgc acacagccca gcttggagcg aacgacctac   2940
accgaactga gatacctaca gcgtgagcta tgagaaagcg ccacgcttcc cgaagggaga   3000
aaggcggaca ggtatccggt aagcggcagg gtcggaacag gagagcgcac gagggagctt   3060
ccagggggaa acgcctggta tctttatagt cctgtcgggt ttcgccacct ctgacttgag   3120
cgtcgatttt tgtgatgctc gtcagggggg cggagcctat ggaaaaacgc cagcaacgcg   3180
```

```
gcctttttac ggttcctggc cttttgctgg ccttttgctc acatgttctt tcctgcgtta    3240
tcccctgatt ctgtggataa ccgtattacc gcctttgagt gagctgatac cgctcgccgc    3300
agccgaacga ccgagcgcag cgagtcagtg agcgaggaag cggaagagcg cctgatgcgg    3360
tattttctcc ttacgcatct gtgcggtatt tcacaccgca tatatggtgc actctcagta    3420
caatctgctc tgatgccgca tagttaagcc agtatacact ccgctatcgc tacgtgactg    3480
ggtcatggct gcgccccgac acccgccaac acccgctgac gcgccctgac gggcttgtct    3540
gctcccggca tccgcttaca gacaagctgt gaccgtctcc gggagctgca tgtgtcagag    3600
gttttcaccg tcatcaccga aacgcgcgag gcagctgcgg taaagctcat cagcgtggtc    3660
gtgaagcgat tcacagatgt ctgcctgttc atccgcgtcc agctcgttga gtttctccag    3720
aagcgttaat gtctggcttc tgataaagcg ggccatgtta agggcggttt tttcctgttt    3780
ggtcactgat gcctccgtgt aagggggatt tctgttcatg ggggtaatga taccgatgaa    3840
acgagagagg atgctcacga tacgggttac tgatgatgaa catgcccggt tactggaacg    3900
ttgtgagggt aaacaactgg cggtatggat gcggcggaca cagagaaaaa tcactcaggg    3960
tcaatgccag cgcttcgtta atacagatgt aggtgttcca cagggtagcc agcagcatcc    4020
tgcgatgcag atccggaaca taatggtgca gggcgctgac ttccgcgttt ccagacttta    4080
cgaaacacgg aaaccgaaga ccattcatgt tgttgctcag gtcgcagacg ttttgcagca    4140
gcagtcgctt cacgttcgct cgcgtatcgg tgattcattc tgctaaccag taaggcaacc    4200
ccgccagcct agccgggtcc tcaacgacag gagcacgatc atgcgcaccc gtggggccgc    4260
catgccggcg ataatggcct gcttctcgcc gaaacgtttg gtggcgggac cagtgacgaa    4320
ggcttgagcg agggcgtgca agattccgaa taccgcaagc gacaggccga tcatcgtcgc    4380
gctccagcga aagcggtcct cgccgaaaat gacccagagc gctgccggca cctgtcctac    4440
gagttgcatg ataaagaaga cagtcataag tgcggcgacg atagtcatgc cccgcgccca    4500
ccggaaggag ctgactgggt tgaaggctct caagggcatc ggtcgagatc ccggtgccta    4560
atgagtgagc taacttacat taattgcgtt gcgctcactg cccgctttcc agtcgggaaa    4620
cctgtcgtgc cagctgcatt aatgaatcgg ccaacgcgcg gggagaggcg gtttgcgtat    4680
tgggcgccag ggtggttttt cttttcacca gtgagacggg caacagctga ttgcccttca    4740
ccgcctggcc ctgagagagt tgcagcaagc ggtccacgct ggtttgcccc agcaggcgaa    4800
aatcctgttt gatggtggtt aacggcggga tataacatga gctgtcttcg gtatcgtcgt    4860
atcccactac cgagatatcc gcaccaacgc gcagcccgga ctcggtaatg gcgcgcattg    4920
cgcccagcgc catctgatcg ttggcaacca gcatcgcagt gggaacgatg ccctcattca    4980
gcatttgcat ggtttgttga aaaccggaca tggcactcca gtcgccttcc cgttccgcta    5040
tcggctgaat ttgattgcga gtgagatatt tatgccagcc agccagacgc agacgcgccg    5100
agacagaact taatgggccc gctaacagcg cgatttgctg gtgacccaat gcgaccagat    5160
gctccacgcc cagtcgcgta ccgtcttcat gggagaaaat aatactgttg atgggtgtct    5220
ggtcagagac atcaagaaat aacgccggaa cattagtgca ggcagcttcc acagcaatgg    5280
catcctggtc atccagcgga tagttaatga tcagcccact gacgcgttgc gcgagaagat    5340
tgtgcaccgc cgctttacag gcttcgacgc cgcttcgttc taccatcgac accaccacgc    5400
tggcacccag ttgatcggcg cgagatttaa tcgccgcgac aatttgcgac ggcgcgtgca    5460
gggccagact ggaggtggca acgccaatca gcaacgactt tttgcccgcc agttgttgtg    5520
ccacgcggtt gggaatgtaa ttcagctccg ccatcgccgc ttccactttt tcccgcgttt    5580
```

```
tcgcagaaac gtggctggcc tggttcacca cgcgggaaac ggtctgataa gagacaccgg    5640
catactctgc gacatcgtat aacgttactg gtttcacatt caccaccctg aattgactct    5700
cttccgggcg ctatcatgcc ataccgcgaa aggttttgcg ccattcgatg tgtccggga     5760 tctcgacgct ctcccttatg cgactcctgc attaggaagc agcccagtag taggttgagg    5820
ccgttgagca ccgccgccgc aaggaatggt gcatgcaagg agatggcgcc aacagtccc     5880 ccggccacgg ggcctgccac catacccacg ccgaaacaag cgctcatgag cccgaagtgg    5940
cgagcccgat cttccccatc ggtgatgtcg gcgatatagg cgccagcaac cgcacctgtg    6000
gcgccggtga tgccggccac gatgcgtccg gcgtagagga tcgagatctc gatcccgcga    6060
aattaatacg actcactata                                                6080
```

<210> SEQ ID NO 89
<211> LENGTH: 6146
<212> TYPE: DNA
<213> ORGANISM: Artificial Sequence
<220> FEATURE:
<223> OTHER INFORMATION: pET24d-N-GST-(PSc)-VGLUT2[human](aa499-564)

<400> SEQUENCE: 89

```
ggggaattgt gagcggataa caattcccct ctagaaataa ttttgtttaa ctttaagaag      60
gagtatataa tgagccatca tcatcatcat catcatcata tgtcccctat actaggttat     120
tggaaaatta agggccttgt gcaacccact cgacttcttt tggaatatct tgaagaaaaa     180
tatgaagagc atttgtatga gcgcgatgaa ggtgataaat ggcgaaacaa aaagtttgaa     240
ttgggtttgg agtttcccaa tcttccttat tatattgatg gtgatgttaa attaacacag     300
tctatggcca tcatacgtta tatagctgac aagcacaaca tgttgggtgg ttgtccaaaa     360
gagcgtgcag agatttcaat gcttgaagga gcggttttgg atattagata cggtgtttcg     420
agaattgcat atagtaaaga ctttgaaact ctcaaagttg attttcttag caagctacct     480
gaaatgctga aaatgttcga agatcgttta tgtcataaaa catatttaaa tggtgatcat     540
gtaacccatc ctgacttcat gttgtatgac gctcttgatg ttgttttata catggaccca     600
atgtgcctgg atgcgttccc aaaaattagt tgttttaaaa acgtattga agctatccca     660 caaattgata agtacttgaa atccagcaag tatatagcat ggcctttgca gggctggcaa     720
gccacgtttg gtggtggcga ccatcctcca aaattggaag tgctgtttca gggtccagcc     780
atgtcagggg aaaagcaacc gtgggcagat cctgaagaga ctagtgagga gaagtgcggt     840
ttcatccatg aggacgaact ggacgaggaa acaggagaca taacacagaa ctacatcaac     900
tatggaacga cgaaatccta cggggccacc actcaggcca atggaggctg gccttctggg     960
tgggaaaaga aggaggaatt ttaatcgagc accaccacca ccaccactga gatccggctg    1020
ctaacaaagc ccgaaaggaa gctgagttgg ctgctgccac cgctgagcaa taactagcat    1080
aaccccttgg ggcctctaaa cgggtcttga ggggtttttt gctgaaagga ggaactatat    1140
ccggattggc gaatgggacg cgccctgtag cggcgcatta agcgcggcgg gtgtggtggt    1200
tacgcgcagc gtgaccgcta cacttgccag cgccctagcg cccgctcctt tcgctttctt    1260
cccttccttt ctcgccacgt tcgccggctt tccccgtcaa gctctaaatc ggggctccc     1320 tttagggttc cgatttagtg ctttacggca cctcgacccc aaaaaacttg attagggtga    1380
tggttcacgt agtgggccat cgccctgata ccggttttt cgcccttga cgttggagtc      1440 cacgttcttt aatagtggac tcttgttcca aactggaaca acactcaacc ctatctcggt    1500
```

```
ctattcttttt gatttataag ggattttgcc gatttcggcc tattggttaa aaaatgagct   1560
gatttaacaa aaatttaacg cgaattttaa caaaatatta acgtttacaa tttcaggtgg   1620 cactttctcgg ggaaatgtgc gcggaacccc tatttgttta ttttttctaaa tacattcaaa   1680 tatgtatccg ctcatgaatt aattcttaga aaaactcatc gagcatcaaa tgaaactgca   1740
atttattcat atcaggatta tcaataccat attttttgaaa aagccgtttc tgtaatgaag   1800
gagaaaactc accgaggcag ttccatagga tggcaagatc ctggtatcgg tctgcgattc   1860
cgactcgtcc aacatcaata caacctatta atttcccctc gtcaaaaata aggttatcaa   1920
gtgagaaatc accatgagtg acgactgaat ccggtgagaa tggcaaaagt ttatgcattt   1980
ctttccagac ttgttcaaca ggccagccat tacgctcgtc atcaaaatca ctcgcatcaa   2040
ccaaaccgtt attcattcgt gattgcgcct gagcgagacg aaatacgcga tcgctgttaa   2100
aaggacaatt acaaacagga atcgaatgca accggcgcag gaacactgcc agcgcatcaa   2160
caatattttc acctgaatca ggatattctt ctaatacctg gaatgctgtt ttcccgggga   2220
tcgcagtggt gagtaaccat gcatcatcag gagtacggat aaaatgcttg atggtcggaa   2280
gaggcataaa ttccgtcagc cagtttagtc tgaccatctc atctgtaaca tcattggcaa   2340
cgctaccttt gccatgtttc agaaacaact ctggcgcatc gggcttccca tacaatcgat   2400
agattgtcgc acctgattgc ccgacattat cgcgagccca tttataccca tataaatcag   2460
catccatgtt ggaatttaat cgcggcctag agcaagacgt ttcccgttga atatggctca   2520
taacacccct tgtattactg tttatgtaag cagacagttt tattgttcat gaccaaaatc   2580
ccttaacgtg agttttcgtt ccactgagcg tcagaccccg tagaaaagat caaaggatct   2640
tcttgagatc cttttttttct gcgcgtaatc tgctgcttgc aaacaaaaaa accaccgcta   2700
ccagcggtgg tttgtttgcc ggatcaagag ctaccaactc ttttttccgaa ggtaactggc   2760 ttcagcagag cgcagatacc aaatactgtc cttctagtgt agccgtagtt aggccaccac   2820
ttcaagaact ctgtagcacc gcctacatac ctcgctctgc taatcctgtt accagtggct   2880
gctgccagtg gcgataagtc gtgtcttacc gggttggact caagacgata gttaccggat   2940
aaggcgcagc ggtcgggctg aacggggggt tcgtgcacac agcccagctt ggagcgaacg   3000
acctacaccg aactgagata cctacagcgt gagctatgag aaagcgccac gcttcccgaa   3060
gggagaaagg cggacaggta tccggtaagc ggcagggtcg gaacaggaga gcgcacgagg   3120
gagcttccag ggggaaacgc ctggtatctt tatagtcctg tcgggtttcg ccacctctga   3180
cttgagcgtc gatttttgtg atgctcgtca gggggggcgga gcctatggaa aaacgccagc   3240
aacgcggcct ttttacggtt cctggccttt tgctggcctt ttgctcacat gttctttcct   3300
gcgttatccc ctgattctgt ggataaccgt attaccgcct ttgagtgagc tgataccgct   3360
cgccgcagcc gaacgaccga gcgcagcgag tcagtgagcg aggaagcgga agagcgcctg   3420
atgcggtatt ttctccttac gcatctgtgc ggtatttcac accgcatata tggtgcactc   3480
tcagtacaat ctgctctgat gccgcatagt taagccagta tacactccgc tatcgctacg   3540
tgactgggtc atggctgcgc cccgacaccc gccaacaccc gctgacgcgc cctgacgggc   3600
ttgtctgctc ccggcatccg cttacagaca agctgtgacc gtctccggga gctgcatgtg   3660
tcagaggttt tcaccgtcat caccgaaacg cgcgaggcag ctgcggtaaa gctcatcagc   3720
gtggtcgtga agcgattcac agatgtctgc ctgttcatcc gcgtccagct cgttgagttt   3780
ctccagaagc gttaatgtct ggcttctgat aaagcgggcc atgttaaggg cggttttttc   3840
ctgtttggtc actgatgcct ccgtgtaagg gggatttctg ttcatggggg taatgatacc   3900
```

```
gatgaaacga gagaggatgc tcacgatacg ggttactgat gatgaacatg cccggttact    3960
ggaacgttgt gagggtaaac aactggcggt atggatgcgg cgggaccaga gaaaaatcac    4020
tcagggtcaa tgccagcgct tcgttaatac agatgtaggt gttccacagg gtagccagca    4080
gcatcctgcg atgcagatcc ggaacataat ggtgcagggc gctgacttcc gcgtttccag    4140
actttacgaa acacggaaac cgaagaccat tcatgttgtt gctcaggtcg cagacgtttt    4200
gcagcagcag tcgcttcacg ttcgctcgcg tatcggtgat tcattctgct aaccagtaag    4260
gcaaccccgc cagcctagcc gggtcctcaa cgacaggagc acgatcatgc gcacccgtgg    4320
ggccgccatg ccggcgataa tggcctgctt ctcgccgaaa cgtttggtgg cgggaccagt    4380
gacgaaggct tgagcgaggg cgtgcaagat tccgaatacc gcaagcgaca ggccgatcat    4440
cgtcgcgctc cagcgaaagc ggtcctcgcc gaaaatgacc cagagcgctg ccggcacctg    4500
tcctacgagt tgcatgataa agaagacagt cataagtgcg gcgacgatag tcatgccccg    4560
cgcccaccgg aaggagctga ctgggttgaa ggctctcaag ggcatcggtc gagatcccgg    4620
tgcctaatga gtgagctaac ttacattaat tgcgttgcgc tcactgcccg ctttccagtc    4680
gggaaacctg tcgtgccagc tgcattaatg aatcggccaa cgcgcgggga gaggcggttt    4740
gcgtattggg cgccagggtg ttttttcttt tcaccagtga cgggcaac agctgattgc    4800 ccttcaccgc ctggccctga gagagttgca gcaagcggtc cacgctggtt tgccccagca    4860
ggcgaaaatc ctgtttgatg gtggttaacg gcgggatata acatgagctg tcttcggtat    4920
cgtcgtatcc cactaccgag atatccgcac caacgcgcag cccggactcg gtaatggcgc    4980
gcattgcgcc cagcgccatc tgatcgttgg caaccagcat cgcagtggga acgatgccct    5040
cattcagcat ttgcatggtt tgttgaaaac cggacatggc actccagtcg ccttcccgtt    5100
ccgctatcgg ctgaatttga ttgcgagtga gatatttatg ccagccagcc agacgcagac    5160
gcgccgagac agaacttaat gggcccgcta acagcgcgat ttgctggtga cccaatgcga    5220
ccagatgctc cacgcccagt cgcgtaccgt cttcatggga gaaaataata ctgttgatgg    5280
gtgtctggtc agagacatca agaaataacg ccggaacatt agtgcaggca gcttccacag    5340
caatggcatc ctggtcatcc agcggatagt taatgatcag cccactgacg cgttgcgcga    5400
gaagattgtg caccgccgct ttacaggctt cgacgccgct tcgttctacc atcgacacca    5460
ccacgctggc acccagttga tcggcgcgag atttaatcgc cgcgacaatt tgcgacggcg    5520
cgtgcagggc cagactggag gtggcaacgc caatcagcaa cgactgtttg cccgccagtt    5580
gttgtgccac gcggttggga atgtaattca gctccgccat cgccgcttcc acttttttccc    5640 gcgttttcgc agaaacgtgg ctggcctggt tcaccacgcg ggaaacggtc tgataagaga    5700
caccggcata ctctgcgaca tcgtataacg ttactggttt cacattcacc accctgaatt    5760
gactctcttc cgggcgctat catgccatac cgcgaaaggt tttgcgccat tcgatggtgt    5820
ccgggatctc gacgctctcc cttatgcgac tcctgcatta ggaagcagcc cagtagtagg    5880
ttgaggccgt tgagcaccgc cgccgcaagg aatggtgcat gcaaggagat ggcgcccaac    5940
agtcccccgg ccacgggggcc tgccaccata cccacgccga aacaagcgct catgagcccg    6000
aagtggcgag cccgatcttc cccatcggtg atgtcggcga tataggcgcc agcaaccgca    6060
cctgtggcgc cggtgatgcc ggccacgatg cgtccggcgt agaggatcga gatctcgatc    6120
ccgcgaaatt aatacgactc actata                                          6146
```

<210> SEQ ID NO 90

<211> LENGTH: 6089
<212> TYPE: DNA
<213> ORGANISM: Artificial Sequence
<220> FEATURE:
<223> OTHER INFORMATION: pET24d-N-GST-(PSc)-VGLUT2-mutant1

<400> SEQUENCE: 90

| | | | | | |
|---|---|---|---|---|---|
| ggggaattgt | gagcggataa | caattcccct | ctagaaataa | ttttgtttaa | ctttaagaag | 60 |
| gagtatataa | tgagccatca | tcatcatcat | catcatcata | tgtcccctat | actaggttat | 120 |
| tggaaaatta | agggccttgt | gcaacccact | cgacttcttt | tggaatatct | tgaagaaaaa | 180 |
| tatgaagagc | atttgtatga | gcgcgatgaa | ggtgataaat | ggcgaaacaa | aaagtttgaa | 240 |
| ttgggtttgg | agtttcccaa | tcttccttat | tatattgatg | gtgatgttaa | attaacacag | 300 |
| tctatggcca | tcatacgtta | tatagctgac | aagcacaaca | tgttgggtgg | ttgtccaaaa | 360 |
| gagcgtgcag | agatttcaat | gcttgaagga | gcggttttgg | atattagata | cggtgtttcg | 420 |
| agaattgcat | atagtaaaga | ctttgaaact | ctcaaagttg | atttcttag  | caagctacct | 480 |
| gaaatgctga | aaatgttcga | agatcgttta | tgtcataaaa | catatttaaa | tggtgatcat | 540 |
| gtaacccatc | ctgacttcat | gttgtatgac | gctcttgatg | ttgttttata | catggaccca | 600 |
| atgtgcctgg | atgcgttccc | aaaattagtt | tgttttaaaa | aacgtattga | agctatccca | 660 |
| caaattgata | agtacttgaa | atccagcaag | tatatagcat | ggcctttgca | gggctggcaa | 720 |
| gccacgtttg | gtggtggcga | ccatcctcca | aaattggaag | tgctgtttca | gggtccagcc | 780 |
| atgttcattg | gccatgacca | gctggctggc | agtgacgaca | gcataacaca | gaactacatc | 840 |
| aactatggaa | cgacgaaatc | ctacggggcc | accactcagg | ccaatggagg | ctggccttct | 900 |
| gggtgggaaa | agaaggagga | attttaatcg | agcaccacca | ccaccaccac | tgagatccgg | 960 |
| ctgctaacaa | agcccgaaag | gaagctgagt | tggctgctgc | caccgctgag | caataactag | 1020 |
| cataacccct | tggggcctct | aaacgggtct | tgaggggttt | tttgctgaaa | ggaggaacta | 1080 |
| tatccggatt | ggcgaatggg | acgcgccctg | tagcggcgca | ttaagcgcgg | cgggtgtggt | 1140 |
| ggttacgcgc | agcgtgaccg | ctacacttgc | cagcgcccta | gcgcccgctc | ctttcgcttt | 1200 |
| cttcccttcc | tttctcgcca | cgttcgccgg | ctttccccgt | caagctctaa | atcgggggct | 1260 |
| ccctttaggg | ttccgattta | gtgctttacg | gcacctcgac | cccaaaaaac | ttgattaggg | 1320 |
| tgatggttca | cgtagtgggc | catcgccctg | atagacggtt | tttcgccctt | tgacgttgga | 1380 |
| gtccacgttc | tttaatagtg | gactcttgtt | ccaaactgga | acaacactca | accctatctc | 1440 |
| ggtctattct | tttgatttat | aagggatttt | gccgatttcg | gcctattggt | taaaaaatga | 1500 |
| gctgatttaa | caaaaattta | acgcgaattt | taacaaaata | ttaacgttta | caatttcagg | 1560 |
| tggcactttt | cggggaaatg | tgcgcggaac | ccctatttgt | ttatttttct | aaatacattc | 1620 |
| aaatatgtat | ccgctcatga | attaattctt | agaaaaactc | atcgagcatc | aaatgaaact | 1680 |
| gcaatttatt | catatcagga | ttatcaatac | catattttg  | aaaaagccgt | ttctgtaatg | 1740 |
| aaggagaaaa | ctcaccgagg | cagttccata | ggatggcaag | atcctggtat | cggtctgcga | 1800 |
| ttccgactcg | tccaacatca | atacaaccta | ttaatttccc | ctcgtcaaaa | ataaggttat | 1860 |
| caagtgagaa | atcaccatga | gtgacgactg | aatccggtga | gaatggcaaa | agtttatgca | 1920 |
| tttctttcca | gacttgttca | acaggccagc | cattacgctc | gtcatcaaaa | tcactcgcat | 1980 |
| caaccaaacc | gttattcatt | cgtgattgcg | cctgagcgag | acgaaatacg | cgatcgctgt | 2040 |
| taaaaggaca | attacaaaca | ggaatcgaat | gcaaccggcg | caggaacact | gccagcgcat | 2100 |
| caacaatatt | ttcacctgaa | tcaggatatt | cttctaatac | ctggaatgct | gttttcccgg | 2160 |

-continued

```
ggatcgcagt ggtgagtaac catgcatcat caggagtacg gataaaatgc ttgatggtcg    2220
gaagaggcat aaattccgtc agccagttta gtctgaccat ctcatctgta acatcattgg    2280
caacgctacc tttgccatgt ttcagaaaca actctggcgc atcgggcttc ccatacaatc    2340
gatagattgt cgcacctgat tgcccgacat tatcgcgagc ccatttatac ccatataaat    2400
cagcatccat gttggaattt aatcgcggcc tagagcaaga cgtttcccgt tgaatatggc    2460
tcataacacc ccttgtatta ctgtttatgt aagcagacag ttttattgtt catgaccaaa    2520
atcccttaac gtgagttttc gttccactga gcgtcagacc ccgtagaaaa gatcaaagga    2580
tcttcttgag atccttttt tctgcgcgta atctgctgct tgcaaacaaa aaaaccaccg    2640
ctaccagcgg tggtttgttt gccggatcaa gagctaccaa ctcttttcc gaaggtaact    2700 ggcttcagca gagcgcagat accaaatact gtccttctag tgtagccgta gttaggccac    2760
cacttcaaga actctgtagc accgcctaca tacctcgctc tgctaatcct gttaccagtg    2820
gctgctgcca gtggcgataa gtcgtgtctt accgggttgg actcaagacg atagttaccg    2880
gataaggcgc agcggtcggg ctgaacgggg ggttcgtgca cacagcccag cttggagcga    2940
acgacctaca ccgaactgag atacctacag cgtgagctat gagaaagcgc cacgcttccc    3000
gaagggagaa aggcggacag gtatccggta agcggcaggg tcggaacagg agagcgcacg    3060
agggagcttc caggggggaaa cgcctggtat ctttatagtc ctgtcgggtt tcgccacctc    3120
tgacttgagc gtcgattttt gtgatgctcg tcaggggggc ggagcctatg gaaaaacgcc    3180
agcaacgcgg ccttttttacg gttcctggcc ttttgctggc cttttgctca catgttcttt    3240
cctgcgttat cccctgattc tgtggataac cgtattaccg cctttgagtg agctgatacc    3300
gctcgccgca gccgaacgac cgagcgcagc gagtcagtga gcgaggaagc ggaagagcgc    3360
ctgatgcggt attttctcct tacgcatctg tgcggtattt cacaccgcat atatggtgca    3420
ctctcagtac aatctgctct gatgccgcat agttaagcca gtatacactc cgctatcgct    3480
acgtgactgg gtcatggctg cgccccgaca cccgccaaca cccgctgacg cgccctgacg    3540
ggcttgtctg ctcccggcat ccgcttacag acaagctgtg accgtctccg ggagctgcat    3600
gtgtcagagg ttttcaccgt catcaccgaa acgcgcgagg cagctgcggt aaagctcatc    3660
agcgtggtcg tgaagcgatt cacagatgtc tgcctgttca tccgcgtcca gctcgttgag    3720
tttctccaga agcgttaatg tctggcttct gataaagcgg ccatgttaa gggcggtttt    3780 ttcctgtttg gtcactgatg cctccgtgta aggggggattt ctgttcatgg gggtaatgat    3840
accgatgaaa cgagagagga tgctcacgat acgggttact gatgatgaac atgcccggtt    3900
actggaacgt tgtgagggta acaactggc ggtatggatg cggcgggacc agagaaaaat    3960
cactcagggt caatgccagc gcttcgttaa tacagatgta ggtgttccac agggtagcca    4020
gcagcatcct gcgatgcaga tccggaacat aatggtgcag ggcgctgact tccgcgtttc    4080
cagactttac gaaacacgga aaccgaagac cattcatgtt gttgctcagg tcgcagacgt    4140
tttgcagcag cagtcgcttc acgttcgctc gcgtatcggt gattcattct gctaaccagt    4200
aaggcaaccc cgccagccta gccgggtcct caacgacagg agcacgatca tgcgcacccg    4260
tggggccgcc atgccggcga taatggcctg cttctcgccg aaacgtttgg tggcgggacc    4320
agtgacgaag gcttgagcga gggcgtgcaa gattccgaat accgcaagcg acaggccgat    4380
catcgtcgcg ctccagcgaa agcggtcctc gccgaaaatg acccagagcg ctgccggcac    4440
ctgtcctacg agttgcatga taagaagac agtcataagt gcggcgacga tagtcatgcc    4500
```

```
ccgcgcccac cggaaggagc tgactgggtt gaaggctctc aagggcatcg gtcgagatcc    4560
cggtgcctaa tgagtgagct aacttacatt aattgcgttg cgctcactgc ccgctttcca    4620
gtcgggaaac ctgtcgtgcc agctgcatta atgaatcggc caacgcgcgg ggagaggcgg    4680
tttgcgtatt gggcgccagg gtggtttttc ttttcaccag tgagacgggc aacagctgat    4740
tgcccttcac cgcctggccc tgagagagtt gcagcaagcg gtccacgctg gtttgcccca    4800
gcaggcgaaa atcctgtttg atggtggtta acggcgggat ataacatgag ctgtcttcgg    4860
tatcgtcgta tcccactacc gagatatccg caccaacgcg cagcccggac tcggtaatgg    4920
cgcgcattgc gcccagcgcc atctgatcgt tggcaaccag catcgcagtg gaacgatgc     4980
cctcattcag catttgcatg gtttgttgaa aaccggacat ggcactccag tcgccttccc    5040
gttccgctat cggctgaatt tgattgcgag tgagatattt atgccagcca gccagacgca    5100
gacgcgccga gacagaactt aatgggcccg ctaacagcgc gatttgctgg tgacccaatg    5160
cgaccagatg ctccacgccc agtcgcgtac cgtcttcatg ggagaaaata atactgttga    5220
tgggtgtctg gtcagagaca tcaagaaata acgccggaac attagtgcag gcagcttcca    5280
cagcaatggc atcctggtca tccagcggat agttaatgat cagcccactg acgcgttgcg    5340
cgagaagatt gtgcaccgcc gctttacagg cttcgacgcc gcttcgttct accatcgaca    5400
ccaccacgct ggcacccagt tgatcggcgc gagatttaat cgccgcgaca atttgcgacg    5460
gcgcgtgcag ggccagactg gaggtggcaa cgccaatcag caacgactgt ttgcccgcca    5520
gttgttgtgc cacgcggttg ggaatgtaat tcagctccgc catcgccgct tccactttt     5580
cccgcgtttt cgcagaaacg tggctggcct ggttcaccac gcgggaaacg gtctgataag    5640
agacaccggc atactctgcg acatcgtata cgttactggt ttcacattc accaccctga     5700
attgactctc ttccgggcgc tatcatgcca taccgcgaaa ggttttgcgc cattcgatgg    5760
tgtccgggat ctcgacgctc tcccttatgc gactcctgca ttaggaagca gcccagtagt    5820
aggttgaggc cgttgagcac cgccgccgca aggaatggtg catgcaagga gatggcgccc    5880
aacagtcccc cggccacggg gcctgccacc atacccacgc cgaaacaagc gctcatgagc    5940
ccgaagtggc gagcccgatc ttccccatcg gtgatgtcgg cgatataggc gccagcaacc    6000
gcacctgtgg cgccggtgat gccggccacg atgcgtccgg cgtagaggat cgagatctcg    6060
atcccgcgaa attaatacga ctcactata                                      6089
```

<210> SEQ ID NO 91
<211> LENGTH: 6105
<212> TYPE: DNA
<213> ORGANISM: Artificial Sequence
<220> FEATURE:
<223> OTHER INFORMATION: pET24d-N-GST-(PSc)-VGLUT2-mutant2

<400> SEQUENCE: 91

```
ggggaattgt gagcggataa caattcccct ctagaaataa ttttgtttaa ctttaagaag      60
gagtatataa tgagccatca tcatcatcat catcatcata tgtccctat actaggttat      120
tggaaaatta agggccttgt gcaacccact cgacttcttt tggaatatct tgaagaaaaa     180
tatgaagagc atttgtatga gcgcgatgaa ggtgataaat ggcgaaacaa aaagtttgaa     240
ttgggtttgg agtttcccaa tcttccttat tatattgatg gtgatgttaa attaacacag     300
tctatggcca tcatacgtta tatagctgac aagcacaaca tgttgggtgg ttgtccaaaa     360
gagcgtgcag agatttcaat gcttgaagga gcggttttgg atattagata cggtgtttcg     420
agaattgcat atagtaaaga ctttgaaact ctcaaagttg attttcttag caagctacct     480
```

```
gaaatgctga aaatgttcga agatcgttta tgtcataaaa catatttaaa tggtgatcat    540
gtaacccatc ctgacttcat gttgtatgac gctcttgatg ttgttttata catggaccca    600
atgtgcctgg atgcgttccc aaaattagtt tgttttaaaa aacgtattga agctatccca    660
caaattgata agtacttgaa atccagcaag tatatagcat ggcctttgca gggctggcaa    720
gccacgtttg gtggtggcga ccatcctcca aaattggaag tgctgtttca gggtccagcc    780
atgcatgagg acgaactgga cgaggaaaca ggagacataa cacagaacta catcaactat    840
ggaacgacga atcctacgg ggccaccact caggccaatg gaggctggcc ttctgggtgg    900
cccaggcccc cacccctgt ccgggactac gtgcagtgat aactcgagca ccaccaccac    960
caccactgag atccggctgc taacaaagcc cgaaaggaag ctgagttggc tgctgccacc   1020
gctgagcaat aactagcata ccccttggg gcctctaaac gggtcttgag gggtttttg    1080 ctgaaaggag gaactatatc cggattggcg aatgggacgc gccctgtagc ggcgcattaa   1140
gcgcggcggt tgtggtggtt acgcgcagcg tgaccgctac acttgccagc gccctagcgc   1200
ccgctccttt cgctttcttc ccttcctttc tcgccacgtt cgccggcttt ccccgtcaag   1260
ctctaaatcg ggggctccct ttagggttcc gatttagtgc tttacggcac ctcgacccca   1320
aaaaacttga ttagggtgat ggttcacgta gtgggccatc gccctgatag acggtttttc   1380 gcccttttgac gttggagtcc acgttcttta atagtggact cttgttccaa actgaacaa   1440 cactcaaccc tatctcggtc tattcttttg atttataagg gattttgccg atttcggcct   1500
attggttaaa aaatgagctg atttaacaaa aatttaacgc gaattttaac aaaatattaa   1560
cgtttacaat ttcaggtggc acttttcggg gaaatgtgcg cggaaccct atttgtttat   1620 ttttctaaat acattcaaat atgtatccgc tcatgaatta attcttagaa aaactcatcg   1680
agcatcaaat gaaactgcaa tttattcata tcaggattat caataccata ttttttgaaaa   1740 agccgtttct gtaatgaagg agaaaactca ccgaggcagt tccataggat ggcaagatcc   1800
tggtatcggt ctgcgattcc gactcgtcca acatcaatac aacctattaa tttcccctcg   1860
tcaaaaataa ggttatcaag tgagaaatca ccatgagtga cgactgaatc cggtgagaat   1920
ggcaaaagtt tatgcatttc tttccagact tgttcaacag gccagccatt acgctcgtca   1980
tcaaaatcac tcgcatcaac caaaccgtta ttcattcgtg attgcgcctg agcgagacga   2040
aatacgcgat cgctgttaaa aggacaatta caaacaggaa tcgaatgcaa ccggcgcagg   2100
aacactgcca gcgcatcaac aatattttca cctgaatcag gatattcttc taatacctgg   2160
aatgctgttt tcccggggat cgcagtggtg agtaaccatg catcatcagg agtacggata   2220
aaatgcttga tggtcggaag aggcataaat tccgtcagcc agtttagtct gaccatctca   2280
tctgtaacat cattggcaac gctacctttg ccatgtttca gaaacaactc tggcgcatcg   2340
ggcttcccat acaatcgata gattgtcgca cctgattgcc cgacattatc gcgagcccat   2400
ttatacccat ataaatcagc atccatgttg gaatttaatc gcggcctaga gcaagacgtt   2460
tcccgttgaa tatggctcat aacaccccct tgtattactg tttatgtaagc agacagtttt   2520 attgttcatg accaaaatcc cttaacgtga gttttcgttc cactgagcgt cagaccccgt   2580
agaaaagatc aaaggatctt cttgagatcc ttttttttctg cgcgtaatct gctgcttgca   2640
aacaaaaaaa ccaccgctac cagcggtggt ttgtttgccg gatcaagagc taccaactct   2700
ttttccgaag gtaactggct tcagcagagc gcagatacca aatactgtcc ttctagtgta   2760
gccgtagtta ggccaccact tcaagaactc tgtagcaccg cctacatacc tcgctctgct   2820
```

```
aatcctgtta ccagtggctg ctgccagtgg cgataagtcg tgtcttaccg ggttggactc    2880
aagacgatag ttaccggata aggcgcagcg gtcgggctga acgggggggtt cgtgcacaca   2940 gcccagcttg gagcgaacga cctacaccga actgagatac ctacagcgtg agctatgaga   3000
aagcgccacg cttcccgaag ggagaaaggc ggacaggtat ccggtaagcg gcagggtcgg   3060
aacaggagag cgcacgaggg agcttccagg gggaaacgcc tggtatcttt atagtcctgt   3120
cgggtttcgc cacctctgac ttgagcgtcg attttttgtga tgctcgtcag ggggcggag   3180 cctatggaaa aacgccagca acgcggcctt tttacggttc ctggccttttt gctggccttt  3240 tgctcacatg ttctttcctg cgttatcccc tgattctgtg gataaccgta ttaccgcctt   3300
tgagtgagct gataccgctc gccgcagccg aacgaccgag cgcagcgagt cagtgagcga   3360
ggaagcggaa gagcgcctga tgcggtattt tctccttacg catctgtgcg gtatttcaca   3420
ccgcatatat ggtgcactct cagtacaatc tgctctgatg ccgcatagtt aagccagtat   3480
acactccgct atcgctacgt gactgggtca tggctgcgcc ccgacacccg ccaacacccg   3540
ctgacgcgcc ctgacgggct tgtctgctcc cggcatccgc ttacagacaa gctgtgaccg   3600
tctccgggag ctgcatgtgt cagaggtttt caccgtcatc accgaaacgc gcgaggcagc   3660
tgcggtaaag ctcatcagcg tggtcgtgaa gcgattcaca gatgtctgcc tgttcatccg   3720
cgtccagctc gttgagtttc tccagaagcg ttaatgtctg gcttctgata aagcgggcca   3780
tgttaagggc ggttttttcc tgttttggtca ctgatgcctc cgtgtaaggg ggatttctgt   3840
tcatgggggt aatgataccg atgaaacgag agaggatgct cacgatacgg gttactgatg   3900
atgaacatgc ccggttactg gaacgttgtg agggtaaaca actggcggta tggatgcggc   3960
gggaccagag aaaaatcact cagggtcaat gccagcgctt cgttaataca gatgtaggtg   4020
ttccacaggg tagccagcag catcctgcga tgcagatccg gaacataatg gtgcagggcg   4080
ctgacttccg cgtttccaga ctttacgaaa cacggaaacc gaagaccatt catgttgttg   4140
ctcaggtcgc agacgttttg cagcagcagt cgcttcacgt tcgctcgcgt atcggtgatt   4200
cattctgcta accagtaagg caaccccgcc agcctagccg ggtcctcaac gacaggagca   4260
cgatcatgcg cacccgtggg gccgccatgc cggcgataat ggcctgcttc tcgccgaaac   4320
gtttggtggc gggaccagtg acgaaggctt gagcgagggc gtgcaagatt ccgaataccg   4380
caagcgacag gccgatcatc gtcgcgctcc agcgaaagcg gtcctcgccg aaaatgaccc   4440
agagcgctgc cggcacctgt cctacgagtt gcatgataaa gaagacagtc ataagtgcgg   4500
cgacgatagt catgccccgc gcccaccgga aggagctgac tgggttgaag gctctcaagg   4560
gcatcggtcg agatcccggt gcctaatgag tgagctaact tacattaatt gcgttgcgct   4620
cactgcccgc tttccagtcg ggaaacctgt cgtgccagct gcattaatga atcggccaac   4680
gcgcggggag aggcggtttg cgtattgggc gccagggtgg ttttcttttt caccagtgag   4740 acggcaaca gctgattgcc cttcaccgcc tggccctgag agagttgcag caagcggtcc   4800
acgctggttt gccccagcag gcgaaaatcc tgtttgatgg tggttaacgg cgggatataa   4860
catgagctgt cttcggtatc gtcgtatccc actaccgaga tatccgcacc aacgcgcagc   4920
ccggactcgg taatggcgcg cattgcgccc agcgccatct gatcgttggc aaccagcatc   4980
gcagtgggaa cgatgccctc attcagcatt tgcatggttt gttgaaaacc ggacatggca   5040
ctccagtcgc cttcccgttc cgctatcggc tgaatttgat tgcgagtgag atatttatgc   5100
cagccagcca gacgcagacg cgccgagaca gaacttaatg ggcccgctaa cagcgcgatt   5160
tgctggtgac ccaatgcgac cagatgctcc acgcccagtc gcgtaccgtc ttcatgggag   5220
```

```
aaaataatac tgttgatggg tgtctggtca gagacatcaa gaaataacgc cggaacatta      5280
gtgcaggcag cttccacagc aatggcatcc tggtcatcca gcggatagtt aatgatcagc      5340
ccactgacgc gttgcgcgag aagattgtgc accgccgctt tacaggcttc gacgccgctt      5400
cgttctacca tcgacaccac cacgctggca cccagttgat cggcgcgaga tttaatcgcc      5460
gcgacaattt gcgacggcgc gtgcagggcc agactggagg tggcaacgcc aatcagcaac      5520
gactgtttgc ccgccagttg ttgtgccacg cggttgggaa tgtaattcag ctccgccatc      5580
gccgcttcca cttttttccg cgttttcgca gaaacgtggc tggcctggtt caccacgcgg      5640
gaaacggtct gataagagac accggcatac tctgcgacat cgtataacgt tactggtttc      5700
acattcacca ccctgaattg actctcttcc gggcgctatc atgccatacc gcgaaaggtt      5760
ttgcgccatt cgatggtgtc cgggatctcg acgctctccc ttatgcgact cctgcattag      5820
gaagcagccc agtagtaggt tgaggccgtt gagcaccgcc gccgcaagga tggtgcatg      5880 caaggagatg cgcccaaca gtcccccggc acggggcct gccaccatac ccacgccgaa      5940
acaagcgctc atgagcccga gtggcgagc ccgatcttcc ccatcggtga tgtcggcgat      6000
ataggcgcca gcaaccgcac ctgtggcgcc ggtgatgccg gccacgatgc gtccggcgta      6060
gaggatcgag atctcgatcc cgcgaaatta atacgactca ctata                     6105

<210> SEQ ID NO 92
<211> LENGTH: 6083
<212> TYPE: DNA
<213> ORGANISM: Artificial Sequence
<220> FEATURE:
<223> OTHER INFORMATION: pET24d-N-GST-(PSc)-VGLUT2-mutant3

<400> SEQUENCE: 92
ggggaattgt gagcggataa caattcccct ctagaaataa ttttgtttaa ctttaagaag        60
gagtatataa tgagccatca tcatcatcat catcatcata tgtccccctat actaggttat      120 tggaaaatta agggccttgt gcaacccact cgacttcttt tggaatatct tgaagaaaaa      180
tatgaagagc atttgtatga gcgcgatgaa ggtgataaat ggcgaaacaa aaagtttgaa      240
ttgggtttgg agtttcccaa tcttccttat tatattgatg gtgatgttaa attaacacag      300
tctatggcca tcatacgtta tatagctgac aagcacaaca tgttgggtgg ttgtccaaaa      360
gagcgtgcag agatttcaat gcttgaagga gcggttttgg atattagata cggtgtttcg      420
agaattgcat atagtaaaga ctttgaaact ctcaaagttg attttcttag caagctacct      480
gaaatgctga aaatgttcga agatcgttta tgtcataaaa catatttaaa tggtgatcat      540
gtaacccatc ctgacttcat gttgtatgac gctcttgatg ttgttttata catggaccca      600
atgtgcctgg atgcgttccc aaaattagtt tgttttaaaa acgtattga agctatccca      660 caaattgata agtacttgaa atccagcaag tatatagcat ggcctttgca gggctggcaa      720
gccacgtttg gtggtggcga ccatcctcca aaattggaag tgctgtttca gggtccagcc      780
atgcatgagg acgaactgga cgaggaaaca ggagatgaaa tggaggatga ggctgagccc      840 ccggggcac cccctgcacc cccgccctcc tatgggccca cacacagcac atttcagccc      900
gaaaagaagg aggaatttta atcgagcacc accaccacca ccactgagat ccggctgcta      960
acaaagcccg aaaggaagct gagttggctg ctgccaccgc tgagcaataa ctagcataac     1020
cccttggggc ctctaaacgg gtcttgaggg gttttttgct gaaaggagga actatatccg     1080
gattggcgaa tgggacgcgc cctgtagcgg cgcattaagc gcggcgggtg tggtggttac     1140
```

```
gcgcagcgtg accgctacac ttgccagcgc cctagcgccc gctcctttcg ctttcttccc    1200
ttcctttctc gccacgttcg ccggcttttcc ccgtcaagct ctaaatcggg ggctcccttt    1260
agggttccga tttagtgctt tacggcacct cgaccccaaa aaacttgatt agggtgatgg    1320
ttcacgtagt gggccatcgc cctgatagac ggttttttcgc cctttgacgt tggagtccac    1380
gttctttaat agtggactct tgttccaaac tggaacaaca ctcaaccta tctcggtcta    1440 ttcttttgat ttataaggga ttttgccgat ttcggcctat tggttaaaaa atgagctgat    1500
ttaacaaaaa tttaacgcga attttaacaa aatattaacg tttacaattt caggtggcac    1560
ttttcgggga aatgtgcgcg gaacccctat ttgtttattt ttctaaatac attcaaatat    1620
gtatccgctc atgaattaat tcttagaaaa actcatcgag catcaaatga aactgcaatt    1680
tattcatatc aggattatca ataccatatt tttgaaaaag ccgtttctgt aatgaaggag    1740
aaaactcacc gaggcagttc cataggatgg caagatcctg gtatcggtct gcgattccga    1800
ctcgtccaac atcaatacaa cctattaatt tcccctcgtc aaaaataagg ttatcaagtg    1860
agaaatcacc atgagtgacg actgaatccg gtgagaatgg caaaagttta tgcatttctt    1920
tccagacttg ttcaacaggc cagccattac gctcgtcatc aaaatcactc gcatcaacca    1980
aaccgttatt cattcgtgat tgcgcctgag cgagacgaaa tacgcgatcg ctgttaaaag    2040
gacaattaca acaggaatc gaatgcaacc ggcgcaggaa cactgccagc gcatcaacaa    2100
tattttcacc tgaatcagga tattcttcta atacctggaa tgctgttttc ccggggatcg    2160
cagtggtgag taaccatgca tcatcaggag tacggataaa atgcttgatg gtcggaagag    2220
gcataaattc cgtcagccag tttagtctga ccatctcatc tgtaacatca ttggcaacgc    2280
tacctttgcc atgtttcaga aacaactctg gcgcatcggg cttcccatac aatcgataga    2340
ttgtcgcacc tgattgcccg acattatcgc gagcccattt atacccatat aaatcagcat    2400
ccatgttgga atttaatcgc ggcctagagc aagacgtttc ccgttgaata tggctcataa    2460
caccccttgt attactgttt atgtaagcag acagttttat tgttcatgac caaaatccct    2520
taacgtgagt tttcgttcca ctgagcgtca gaccccgtag aaaagatcaa aggatcttct    2580
tgagatcctt ttttttctgcg cgtaatctgc tgcttgcaaa caaaaaaacc accgctacca    2640
gcggtggttt gtttgccgga tcaagagcta ccaactcttt ttccgaaggt aactggcttc    2700
agcagagcgc agataccaaa tactgtcctt ctagtgtagc cgtagttagg ccaccacttc    2760
aagaactctg tagcaccgcc tacataccte gctctgctaa tcctgttacc agtggctgct    2820
gccagtggcg ataagtcgtg tcttaccggg ttggactcaa gacgatagtt accggataag    2880
gcgcagcggt cgggctgaac ggggggttcg tgcacacagc ccagcttgga gcgaacgacc    2940
tacaccgaac tgagatacct acagcgtgag ctatgagaaa gcgccacgct tcccgaaggg    3000
agaaaggcgg acaggtatcc ggtaagcggc agggtcggaa caggagagcg cacgagggag    3060
cttccagggg gaaacgcctg gtatctttat agtcctgtcg ggtttcgcca cctctgactt    3120
gagcgtcgat ttttgtgatg ctcgtcaggg ggcggagcc tatggaaaaa cgccagcaac    3180
gcggcctttt tacggttcct ggccttttgc tggccttttg ctcacatgtt ctttcctgcg    3240
ttatcccctg attctgtgga taaccgtatt accgcctttg agtgagctga taccgctcgc    3300
cgcagccgaa cgaccgagcg cagcgagtca gtgagcgagg aagcggaaga gcgcctgatg    3360
cggtattttc tccttacgca tctgtgcggt atttcacacc gcatatatgg tgcactctca    3420
gtacaatctg ctctgatgcc gcatagttaa gccagtatac actccgctat cgctacgtga    3480
ctgggtcatg gctgcgcccc gacacccgcc aacacccgct gacgcgccct gacgggcttg    3540
```

-continued

```
tctgctcccg gcatccgctt acagacaagc tgtgaccgtc tccgggagct gcatgtgtca    3600
gaggttttca ccgtcatcac cgaaacgcgc gaggcagctg cggtaaagct catcagcgtg    3660
gtcgtgaagc gattcacaga tgtctgcctg ttcatccgcg tccagctcgt tgagtttctc    3720
cagaagcgtt aatgtctggc ttctgataaa gcgggccatg ttaagggcgg ttttttcctg    3780
tttggtcact gatgcctccg tgtaaggggg atttctgttc atgggggtaa tgataccgat    3840
gaaacgagag aggatgctca cgatacgggt tactgatgat gaacatgccc ggttactgga    3900
acgttgtgag ggtaaacaac tggcggtatg gatgcggcgg gaccagagaa aaatcactca    3960
gggtcaatgc cagcgcttcg ttaatacaga tgtaggtgtt ccacagggta gccagcagca    4020
tcctgcgatg cagatccgga acataatggt gcagggcgct gacttccgcg tttccagact    4080
ttacgaaaca cggaaaccga agaccattca tgttgttgct caggtcgcag acgttttgca    4140
gcagcagtcg cttcacgttc gctcgcgtat cggtgattca ttctgctaac cagtaaggca    4200
accccgccag cctagccggg tcctcaacga caggagcacg atcatgcgca cccgtggggc    4260
cgccatgccg gcgataatgg cctgcttctc gccgaaacgt ttggtggcgg gaccagtgac    4320
gaaggcttga gcgagggcgt gcaagattcc gaataccgca agcgacaggc cgatcatcgt    4380
cgcgctccag cgaaagcggt cctcgccgaa aatgacccag agcgctgccg gcacctgtcc    4440
tacgagttgc atgataaaga agacagtcat aagtgcggcg acgatagtca tgccccgcgc    4500
ccaccggaag gagctgactg ggttgaaggc tctcaagggc atcggtcgag atcccggtgc    4560
ctaatgagtg agctaactta cattaattgc gttgcgctca ctgcccgctt tccagtcggg    4620
aaacctgtcg tgccagctgc attaatgaat cggccaacgc gcggggagag gcggtttgcg    4680
tattgggcgc cagggtggtt tttcttttca ccagtgagac gggcaacagc tgattgccct    4740
tcaccgcctg gccctgagag agttgcagca agcggtccac gctggtttgc cccagcaggc    4800
gaaaatcctg tttgatggtg gttaacggcg ggatataaca tgagctgtct tcggtatcgt    4860
cgtatcccac taccgagata tccgcaccaa cgcgcagccc ggactcggta atggcgcgca    4920
ttgcgcccag cgccatctga tcgttggcaa ccagcatcgc agtgggaacg atgccctcat    4980
tcagcatttg catggtttgt tgaaaaccgg acatggcact ccagtcgcct tcccgttccg    5040
ctatcggctg aatttgattg cgagtgagat atttatgcca gccagccaga cgcagacgcg    5100
ccgagacaga acttaatggg cccgctaaca gcgcgatttg ctggtgaccc aatgcgacca    5160
gatgctccac gcccagtcgc gtaccgtctt catgggagaa aataatactg ttgatgggtg    5220
tctggtcaga gacatcaaga ataacgccg gaacattagt gcaggcagct tccacagcaa    5280
tggcatcctg gtcatccagc ggatagttaa tgatcagccc actgacgcgt gcgcgagaa    5340
gattgtgcac cgccgcttta caggcttcga cgccgcttcg ttctaccatc gacaccacca    5400
cgctggcacc cagttgatcg gcgcgagatt taatcgccgc gacaatttgc gacggcgcgt    5460
gcagggccag actggaggtg gcaacgccaa tcagcaacga ctgtttgccc gccagttgtt    5520
gtgccacgcg gttgggaatg taattcagct ccgccatcgc cgcttccact tttcccgcg    5580
ttttcgcaga acgtggctg gcctggttca ccacgcggga aacggtctga taagagacac    5640
cggcatactc tgcgacatcg tataacgtta ctggtttcac attcaccacc ctgaattgac    5700
tctcttccgg cgctatcat gccataccgc gaaaggtttt gcgccattcg atggtgtccg    5760
ggatctcgac gctctccctt atgcgactcc tgcattagga agcagcccag tagtaggttg    5820
aggccgttga gcaccgccgc cgcaaggaat ggtgcatgca aggagatggc gcccaacagt    5880
```

```
cccccggcca cgggcctgc caccataccc acgccgaaac aagcgctcat gagcccgaag    5940
tggcgagccc gatcttcccc atcggtgatg tcggcgatat aggcgccagc aaccgcacct    6000
gtggcgccgg tgatgccggc cacgatgcgt ccggcgtaga ggatcgagat ctcgatcccg    6060
cgaaattaat acgactcact ata                                            6083

<210> SEQ ID NO 93
<211> LENGTH: 6083
<212> TYPE: DNA
<213> ORGANISM: Artificial Sequence
<220> FEATURE:
<223> OTHER INFORMATION: pET24d-N-GST-(PSc)-VGLUT2-mutant4

<400> SEQUENCE: 93
ggggaattgt gagcggataa caattcccct ctagaaataa ttttgtttaa ctttaagaag      60
gagtatataa tgagccatca tcatcatcat catcatcata tgtccctat actaggttat     120 tggaaaatta agggccttgt gcaacccact cgacttcttt tggaatatct tgaagaaaaa     180
tatgaagagc atttgtatga gcgcgatgaa ggtgataaat ggcgaaacaa aaagtttgaa     240
ttgggtttgg agtttcccaa tcttccttat tatattgatg gtgatgttaa attaacacag     300
tctatggcca tcatacgtta tatagctgac aagcacaaca tgttgggtgg ttgtccaaaa     360
gagcgtgcag agatttcaat gcttgaagga gcggttttgg atattagata cggtgtttcg     420
agaattgcat atagtaaaga ctttgaaact ctcaaagttg attttcttag caagctacct     480
gaaatgctga aatgttcga agatcgttta tgtcataaaa catatttaaa tggtgatcat     540
gtaacccatc ctgacttcat gttgtatgac gctcttgatg ttgttttata catggaccca     600
atgtgcctgg atgcgttccc aaaattagtt tgttttaaaa aacgtattga agctatccca     660
caaattgata agtacttgaa atccagcaag tatatagcat ggcctttgca gggctggcaa     720
gccacgtttg gtggtggcga ccatcctcca aaattggaag tgctgtttca gggtccagcc     780
atgcatgacg aggaagctga agaaattgaa ggagacataa cacagaacta catcaactat     840
ggaacgacga atcctacgg ggccaccact caggccaatg gaggctggcc ttctgggtgg     900
gaaaagaagg aggaatttta atcgagcacc accaccacca ccactgagat ccggctgcta     960
acaaagcccg aaggaagct gagttggctg ctgccaccgc tgagcaataa ctagcataac    1020 cccttgggc tctaaacgg tcttgaggg gttttttgct gaaaggagga actatatccg    1080
gattggcgaa tgggacgcgc cctgtagcgg cgcattaagc gcggcgggtg tggtggttac    1140
gcgcagcgtg accgctacac ttgccagcgc cctagcgccc gctcctttcg ctttcttccc    1200
ttcctttctc gccacgttcg ccggctttcc ccgtcaagct ctaaatcggg gctccctt     1260 agggttccga tttagtgctt tacgcacct cgaccccaaa aaacttgatt agggtgatgg    1320
ttcacgtagt gggccatcgc cctgatagac ggttttcgc cctttgacgt tggagtccac    1380
gttctttaat agtggactct tgttccaaac tggaacaaca ctcaacccta tctcggtcta    1440
ttcttttgat ttataaggga ttttgccgat ttcggcctat tggttaaaaa atgagctgat    1500
ttaacaaaaa tttaacgcga attttaacaa atattaacg tttacaattt caggtggcac    1560
ttttcgggga aatgtgcgcg gaaccccat ttgtttattt ttctaaatac attcaaatat    1620
gtatccgctc atgaattaat tcttagaaaa actcatcgag catcaaatga actgcaatt    1680 tattcatatc aggattatca ataccatatt tttgaaaaag ccgtttctgt aatgaaggag    1740
aaaactcacc gaggcagttc cataggatgg caagatcctg gtatcggtct gcgattccga    1800
ctcgtccaac atcaatacaa cctattaatt tcccctcgtc aaaaataagg ttatcaagtg    1860
```

```
agaaatcacc atgagtgacg actgaatccg gtgagaatgg caaaagttta tgcatttctt    1920
tccagacttg ttcaacaggc cagccattac gctcgtcatc aaaatcactc gcatcaacca    1980
aaccgttatt cattcgtgat tgcgcctgag cgagacgaaa tacgcgatcg ctgttaaaag    2040
gacaattaca aacaggaatc gaatgcaacc ggcgcaggaa cactgccagc gcatcaacaa    2100
tattttcacc tgaatcagga tattcttcta atacctggaa tgctgttttc ccggggatcg    2160
cagtggtgag taaccatgca tcatcaggag tacggataaa atgcttgatg gtcggaagag    2220
gcataaattc cgtcagccag tttagtctga ccatctcatc tgtaacatca ttggcaacgc    2280
tacctttgcc atgtttcaga aacaactctg gcgcatcggg cttcccatac aatcgataga    2340
ttgtcgcacc tgattgcccg acattatcgc gagcccattt atacccatat aaatcagcat    2400
ccatgttgga atttaatcgc ggcctagagc aagacgtttc ccgttgaata tggctcataa    2460 cacccttgt attactgttt atgtaagcag acagttttat tgttcatgac caaaatccct    2520
taacgtgagt tttcgttcca ctgagcgtca gaccccgtag aaaagatcaa aggatcttct    2580
tgagatcctt ttttttctgcg cgtaatctgc tgcttgcaaa caaaaaaacc accgctacca    2640
gcggtggttt gtttgccgga tcaagagcta ccaactcttt ttccgaaggt aactggcttc    2700
agcagagcgc agataccaaa tactgtcctt ctagtgtagc cgtagttagg ccaccacttc    2760
aagaactctg tagcaccgcc tacatacctc gctctgctaa tcctgttacc agtggctgct    2820
gccagtggcg ataagtcgtg tcttaccggg ttggactcaa gacgatagtt accggataag    2880
gcgcagcggt cgggctgaac ggggggttcg tgcacacagc ccagcttgga gcgaacgacc    2940
tacaccgaac tgagatacct acagcgtgag ctatgagaaa gcgccacgct tcccgaaggg    3000
agaaaggcgg acaggtatcc ggtaagcggc agggtcggaa caggagagcg cacgagggag    3060
cttccagggg gaaacgcctg gtatctttat agtcctgtcg ggtttcgcca cctctgactt    3120
gagcgtcgat ttttgtgatg ctcgtcaggg gggcggagcc tatggaaaaa cgccagcaac    3180
gcggcctttt tacggttcct ggccttttgc tggccttttg ctcacatgtt ctttcctgcg    3240
ttatcccctg attctgtgga taaccgtatt accgcctttg agtgagctga taccgctcgc    3300
cgcagccgaa cgaccgagcg cagcgagtca gtgagcgagg aagcggaaga gcgcctgatg    3360
cggtattttc tccttacgca tctgtgcggt atttcacacc gcatatatgg tgcactctca    3420
gtacaatctg ctctgatgcc gcatagttaa gccagtatac actccgctat cgctacgtga    3480
ctgggtcatg gctgcgcccc gacacccgcc aacacccgct gacgcgccct gacgggcttg    3540
tctgctcccg gcatccgctt acagacaagc tgtgaccgtc tccgggagct gcatgtgtca    3600
gaggttttca ccgtcatcac cgaaacgcgc gaggcagctg cggtaaagct catcagcgtg    3660
gtcgtgaagc gattcacaga tgtctgcctg ttcatccgcg tccagctcgt tgagtttctc    3720
cagaagcgtt aatgtctggc ttctgataaa gcgggccatg ttaagggcgg ttttttcctg    3780
tttggtcact gatgcctccg tgtaaggggg atttctgttc atgggggtaa tgataccgat    3840
gaaacgagag aggatgctca cgatacgggt tactgatgat gaacatgccc ggttactgga    3900
acgttgtgag ggtaaacaac tggcggtatg gatgcggcgg gaccagagaa aaatcactca    3960
gggtcaatgc cagcgcttcg ttaatacaga tgtaggtgtt ccacagggta gccagcagca    4020
tcctgcgatg cagatccgga acataatggt gcagggcgct gacttccgcg tttccagact    4080
ttacgaaaca cggaaaccga agaccattca tgttgttgct caggtcgcag acgttttgca    4140
gcagcagtcg cttcacgttc gctcgcgtat cggtgattca ttctgctaac cagtaaggca    4200
```

```
acccccgccag cctagccggg tcctcaacga caggagcacg atcatgcgca cccgtggggc    4260
cgccatgccg gcgataatgg cctgcttctc gccgaaacgt ttggtggcgg gaccagtgac    4320
gaaggcttga gcgagggcgt gcaagattcc gaataccgca agcgacaggc cgatcatcgt    4380
cgcgctccag cgaaagcggt cctcgccgaa aatgacccag agcgctgccg gcacctgtcc    4440
tacgagttgc atgataaaga agacagtcat aagtgcggcg acgatagtca tgccccgcgc    4500
ccaccggaag gagctgactg ggttgaaggc tctcaagggc atcggtcgag atcccggtgc    4560
ctaatgagtg agctaactta cattaattgc gttgcgctca ctgcccgctt ccagtcggg    4620
aaacctgtcg tgccagctgc attaatgaat cggccaacgc gcggggagag gcggtttgcg    4680
tattgggcgc cagggtggtt tttcttttca ccagtgagac gggcaacagc tgattgccct    4740
tcaccgcctg gccctgagag agttgcagca agcggtccac gctggtttgc cccagcaggc    4800
gaaaatcctg tttgatggtg gttaacggcg ggatataaca tgagctgtct tcggtatcgt    4860
cgtatcccac taccgagata tccgcaccaa cgcgcagccc ggactcggta atggcgcgca    4920
ttgcgcccag cgccatctga tcgttggcaa ccagcatcgc agtgggaacg atgccctcat    4980
tcagcatttg catggtttgt tgaaaaccgg acatggcact ccagtcgcct tcccgttccg    5040
ctatcggctg aatttgattg cgagtgagat atttatgcca gccagccaga cgcagacgcg    5100
ccgagacaga acttaatggg cccgctaaca gcgcgatttg ctggtgaccc aatgcgacca    5160
gatgctccac gcccagtcgc gtaccgtctt catgggagaa aataatactg ttgatgggtg    5220
tctggtcaga gacatcaaga ataacgccg gaacattagt gcaggcagct tccacagcaa    5280
tggcatcctg gtcatccagc ggatagttaa tgatcagccc actgacgcgt tgcgcgagaa    5340
gattgtgcac cgccgcttta caggcttcga cgccgcttcg ttctaccatc gacaccacca    5400
cgctggcacc cagttgatcg gcgcgagatt taatcgccgc gacaatttgc gacggcgcgt    5460
gcagggccag actggaggtg gcaacgccaa tcagcaacga ctgtttgccc gccagttgtt    5520
gtgccacgcg gttgggaatg taattcagct ccgccatcgc cgcttccact ttttcccgcg    5580
ttttcgcaga aacgtggctg gcctggttca ccacgcggga acggtctga taagagacac    5640
cggcatactc tgcgacatcg tataacgtta ctggtttcac attcaccacc ctgaattgac    5700
tctcttccgg gcgctatcat gccataccgc gaaaggtttt gcgccattcg atggtgtccg    5760
ggatctcgac gctctccctt atgcgactcc tgcattagga agcagcccag tagtaggttg    5820
aggccgttga gcaccgccgc cgcaaggaat ggtgcatgca aggagatggc gcccaacagt    5880
ccccggcca cggggcctgc caccataccc acgccgaaac aagcgctcat gagcccgaag    5940
tggcgagccc gatcttcccc atcggtgatg tcggcgatat aggcgccagc aaccgcacct    6000
gtggcgccgg tgatgccggc cacgatgcgt ccggcgtaga ggatcgagat ctcgatcccg    6060
cgaaattaat acgactcact ata                                             6083
```

<210> SEQ ID NO 94
<211> LENGTH: 7294
<212> TYPE: DNA
<213> ORGANISM: Artificial Sequence
<220> FEATURE:
<223> OTHER INFORMATION: pTriEx-1-VGLUT1[human]-IF1-H8

<400> SEQUENCE: 94

```
ggggaattgt gagcggataa caattccccg gagttaatcc gggacctta attcaaccca      60
acacaatata ttatagttaa ataagaatta ttatcaaatc atttgtatat taattaaaat    120
actatactgt aaattacatt ttatttacaa tcaaaggaga tataccatgg agttccgcca    180
```

```
ggaggagttt cggaagctag cgggtcgtgc tctcgggaag ctgcaccgcc ttctggagaa    240
gcggcaggaa ggcgcggaga cgctggagct gagtgcggat gggcgcccgg tgaccacgca    300
gacccgggac ccgccggtgg tggactgcac ctgcttcggc ctccctcgcc gctacattat    360
cgccatcatg agtggtctgg gcttctgcat cagctttggc atccgctgca acctgggcgt    420
ggccatcgtc tccatggtca ataacagcac gacccaccgc ggggccacg tggtggtgca     480
gaaagcccag ttcagctggg atccagagac tgtcggcctc atacacggct ccttttcctg    540
gggctacatt gtcactcaga ttccaggagg atttatctgt caaaaatttg cagccaacag    600
agttttcggc tttgctattg tggcaacatc cactctaaac atgctgatcc cctcagctgc    660
ccgcgtccac tatggctgtg tcatcttcgt gaggatcctg caggggttgg tagagggggt    720
cacataccc gcctgccatg ggatctggag caaatgggcc ccaccttag aacgagtcg      780
cctggcgacg acagcctttt gtggttccta tgctggggcg gtggtcgcga tgccctcgc    840
cggggtcctt gtgcagtact caggatggag ctctgttttc tacgtctacg gcagcttcgg    900
gatcttctgg tacctgttct ggctgctcgt ctcctacgag tccccgcgc tgcacccaag    960
catctcggag gaggagcgca agtacatcga ggacgccatc ggagagagcg cgaaactcat    1020
gaacccctc acgaagttta gcactccctg gcggcgcttc ttcacgtcta tgccagtcta    1080
tgccatcatc gtggccaact tctgccgcag ctggacgttc tacctgctgc tcatctccca    1140
gcccgcctac ttcgaagaag tgttcggctt cgagatcagc aaggtaggcc tggtgtccgc    1200
gctgccccac ctggtcatga ccatcatcgt gcccatcggc ggccagatcg cggacttcct    1260
gcggagccgc cgcatcatgt ccaccaccaa cgtgcgcaag ttgatgaact gcggaggctt    1320
cggcatggaa gccacgctgc tgttggtggt cggctactcg cactccaagg gcgtggccat    1380
ctccttcctg gtcctagccg tgggcttcag cggcttcgcc atctctgggt caacgtgaa    1440
ccacctggac atagcccggc gctacgccag catcctcatg ggcatctcca acggcgtggg    1500
cacactgtcg ggcatggtgt gccccatcat cgtggggcc atgactaagc acaagactcg    1560
ggaggagtgg cagtacgtgt tcctaattgc ctccctggtg cactatggag gtgtcatctt    1620
ctacggggtc tttgcttctg gagagaagca gccgtgggca gagcctgagg agatgagcga    1680
ggagaagtgt ggcttcgttg ccatgaccac gctggctggc agtgacgaca gcgaaatgga    1740
ggatgaggct gagccccgg gggcaccccc tgcacccccg ccctcctatg ggccacaca    1800
cagcacattt cagccccca ggccccacc ccctgtccgg gactacctcg agcaccacca     1860
tcaccatcac catcactaag tgattaacct caggtgcagg ctgcctatca aaggtggtg    1920
gctggtgtgg ccaatgccct ggctcacaaa taccactgag atcgatcttt ttccctctgc    1980
caaaaattat ggggacatca tgaagcccct tgagcatctg acttctggct aataaaggaa    2040
atttatttc attgcaatag tgtgttggaa ttttttgtgt ctctcactcg gaaggacata    2100
tgggagggca aatcatttaa aacatcagaa tgagtatttg gttagagtt tggcaacata    2160
tgcccatatg taactagcat aaccccttgg ggcctctaaa cgggtcttga ggggttttt     2220
gctgaaagca tgcggaggaa attctccttg aagtttccct ggtgttcaaa gtaaaggagt    2280
ttgcaccaga cgcacctctg ttcactggtc cggcgtatta aaacacgata cattgttatt    2340
agtacattta ttaagcgcta gattctgtgc gttgttgatt tacagacaat tgttgtacgt    2400
attttaataa ttcattaaat ttataatctt tagggtggta tgttagagcg aaaatcaaat    2460
gattttcagc gtctttatat ctgaatttaa atattaaatc ctcaatagat ttgtaaaata    2520
```

```
ggtttcgatt agtttcaaac aagggttgtt tttccgaacc gatggctgga ctatctaatg    2580
gattttcgct caacgccaca aaacttgcca aatcttgtag cagcaatcta gctttgtcga    2640
tattcgtttg tgttttgttt tgtaataaag gttcgacgtc gttcaaaata ttatgcgctt    2700
ttgtatttct ttcatcactg tcgttagtgt acaattgact cgacgtaaac acgttaaata    2760
gagcttggac atatttaaca tcgggcgtgt tagctttatt aggccgatta tcgtcgtcgt    2820
cccaaccctc gtcgttagaa gttgcttccg aagacgattt tgccatagcc acacgacgcc    2880
tattaattgt gtcggctaac acgtccgcga tcaaatttgt agttgagctt tttggaatta    2940
tttctgattg cgggcgtttt tgggcgggtt tcaatctaac tgtgcccgat tttaattcag    3000
acaacacgtt agaaagcgat ggtgcaggcg gtggtaacat ttcagacggc aaatctacta    3060
atggcggcgg tggtggagct gatgataaat ctaccatcgg tggaggcgca ggcggggctg    3120
gcggcggagg cggaggcgga ggtggtggcg gtgatgcaga cggcggttta ggctcaaatg    3180
tctctttagg caacacagtc ggcacctcaa ctattgtact ggtttcgggc gccgttttg    3240
gtttgaccgg tctgagacga gtgcgatttt tttcgtttct aatagcttcc aacaattgtt    3300
gtctgtcgtc taaaggtgca gcgggttgag gttccgtcgg cattggtgga gcgggcggca    3360
attcagacat cgatggtggt ggtggtggtg gaggcgctgg aatgttaggc acgggagaag    3420
gtggtggcgg cggtgccgcc ggtataattt gttctggttt agtttgttcg cgcacgattg    3480
tgggcaccgg cgcaggcgcc gctggctgca caacggaagg tcgtctgctt cgaggcagcg    3540
cttggggtgg tggcaattca atattataat tggaatacaa atcgtaaaaa tctgctataa    3600
gcattgtaat ttcgctatcg tttaccgtgc cgatatttaa caaccgctca atgtaagcaa    3660
ttgtattgta aagagattgt ctcaagctcg gaacgctgcg ctcggtcgtt cggctgcggc    3720
gagcggtatc agctcactca aaggcggtaa tacggttatc cacagaatca ggggataacg    3780
caggaaagaa catgtgagca aaaggccagc aaaaggccag gaaccgtaaa aaggccgcgt    3840
tgctggcgtt ttccataggc tccgcccccc tgacgagca tcacaaaaat cgacgctcaa    3900
gtcagaggtg gcgaaacccg acaggactat aaagatacca ggcgtttccc cctggaagct    3960
ccctcgtgcg ctctcctgtt ccgaccctgc cgcttaccgg atacctgtcc gcctttctcc    4020
cttcgggaag cgtggcgctt tctcaatgct cacgctgtag gtatctcagt tcggtgtagg    4080
tcgttcgctc caagctgggc tgtgtgcacg aaccccccgt tcagcccgac cgctgcgcct    4140
tatccggtaa ctatcgtctt gagtccaacc cggtaagaca cgacttatcg ccactggcag    4200
cagccactgg taacaggatt agcagagcga ggtatgtagg cggtgctaca gagttcttga    4260
agtggtggcc taactacggc tacactagaa ggacagtatt tggtatctgc gctctgctga    4320
agccagttac cttcggaaaa agagttggta gctcttgatc cggcaaacaa accaccgctg    4380
gtagcggtgg tttttttgtt tgcaagcagc agattacgcg cagaaaaaaa ggatctcaag    4440
aagatccttt gttaccaatg cttaatcagt gaggcaccta tctcagcgat ctgtctattt    4500
cgttcatcca tagttgcctg actccccgtc gtgtagataa ctacgatacg ggagggctta    4560
ccatctggcc ccagtgctgc aatgataccg cgagacccac gctcaccggc tccagattta    4620
tcagcaataa accagccagc cggaagggcc gagcgcagaa gtggtcctgc aactttatcc    4680
gcctccatcc agtctattaa ttgttgccgg gaagctagag taagtagttc gccagttaat    4740
agtttgcgca acgttgttgc cattgctaca ggcatcgtgg tgtcacgctc gtcgtttggt    4800
atggcttcat tcagctccgg ttcccaacga tcaaggcgag ttacatgatc ccccatgttg    4860
tgcaaaaaag cggttagctc cttcggtcct ccgatcgttg tcagaagtaa gttggccgca    4920
```

```
gtgttatcac tcatggttat ggcagcactg cataattctc ttactgtcat gccatccgta    4980
agatgctttt ctgtgactgg tgagtactca accaagtcat tctgagaata gtgtatgcgg    5040
cgaccgagtt gctcttgccc ggcgtcaata cgggataata ccgcgccaca tagcagaact    5100
ttaaaagtgc tcatcattgg aaaacgttct tcggggcgaa aactctcaag gatcttaccg    5160
ctgttgagat ccagttcgat gtaacccact cgtgcaccca actgatcttc agcatctttt    5220
actttcacca gcgtttctgg gtgagcaaaa acaggaaggc aaaatgccgc aaaaaaggga    5280
ataagggcga cacggaaatg ttgaatactc atactcttcc ttttcaata ttattgaagc     5340 atttatcagg gttattgtct catgtccgcg cgtttcctgc atcttttaat caaatcccaa    5400
gatgtgtata aaccaccaaa ctgccaaaaa atgaaaactg tcgacaagct ctgtccgttt    5460
gctggcaact gcaagggtct caatcctatt tgtaattatt gaataataaa acaattataa    5520
atgtcaaatt tgttttttat taacgataca aaccaaacgc aacaagaaca tttgtagtat    5580
tatctataat tgaaaacgcg tagttataat cgctgaggta atatttaaaa tcattttcaa    5640
atgattcaca gttaatttgc gacaatataa ttttattttc acataaacta gacgccttgt    5700
cgtcttcttc ttcgtattcc ttctcttttt cattttctc ttcataaaaa ttaacatagt      5760
tattatcgta tccatatatg tatctatcgt atagagtaaa tttttgttg tcataaatat      5820 atatgtcttt tttaatgggg tgtatagtac cgctgcgcat agttttctg taatttacaa     5880 cagtgctatt ttctggtagt tcttcggagt gtgttgcttt aattattaaa tttatataat    5940
caatgaattt gggatcgtcg gttttgtaca atatgttgcc ggcatagtac gcagcttctt    6000
ctagttcaat tacaccattt tttagcagca ccggattaac ataactttcc aaaatgttgt    6060
acgaaccgtt aaacaaaaac agttcacctc cctttctat actattgtct gcagcagtt     6120 gtttgttgtt aaaaataaca gccattgtaa tgagacgcac aaactaatat cacaaactgg    6180
aaatgtctat caatatatag ttgctctagt tattaatagt aatcaattac ggggtcatta    6240
gttcatagcc catatatgga gttccgcgtt acataactta cggtaaatgg cccgcctggc    6300
tgaccgccca cgaccccccg cccattgacg tcaataatga cgtatgttcc catagtaacg    6360
ccaataggga ctttccattg acgtcaatgg gtggactatt tacggtaaac tgcccacttg    6420
gcagtacatc aagtgtatca tatgccaagt acgcccccta ttgacgtcaa tgacggtaaa    6480
tggcccgcct ggcattatgc ccagtacatg accttatggg actttcctac ttggcagtac    6540
atctacgtat tagtcatcgc tattaccatg catggtcgag gtgagcccca cgttctgctt    6600
cactctcccc atctccccc cctccccacc cccaattttg tatttattta ttttttaatt     6660
attttgtgca gcgatggggg cggggggggg gggggggcgc gcgccaggcg gggcggggcg    6720
gggcgagggg cggggcgggg cgaggcggag aggtgcggcg gcagccaatc agagcggcgc    6780
gctccgaaag tttccttta tggcgaggcg gcggcggcgg cggccctata aaaagcgaag    6840
cgcgcggcgg gcgggagtcg ctgcgacgct gccttcgccc cgtgccccgc tccgccgccg    6900
cctcgcgccg cccgccccgg ctctgactga ccgcgttact cccacaggtg agcgggcggg    6960
acggcccttc tccttcgggc tgtaattagc gcttggttta atgacggctt gtttcttttc    7020
tgtggctgcg tgaaagcctt gaggggctcc ggagggccc tttgtgcggg gggagcggct     7080
cggggctgtc gcgggggga cggctgcctt cgggggggac ggggcagggc ggggttcggc    7140
ttctggcgtg tgaccggcgg ctctagagcc tctgctaacc atgttcatgc cttcttcttt    7200
ttcctacagc tcctgggcaa cgtgctggtt attgtgctgt ctcatcattt tggcaaagaa    7260
```
ttggatcgga ccgaaattaa tacgactcac tata 7294

<210> SEQ ID NO 95
<211> LENGTH: 7300
<212> TYPE: DNA
<213> ORGANISM: Artificial Sequence
<220> FEATURE:
<223> OTHER INFORMATION: pTriEx-1-VGLUT1[human]-IF1

<400> SEQUENCE: 95

| | |
|---|---|
| ggggaattgt gagcggataa caattccccg gagttaatcc gggaccttta attcaaccca | 60 |
| acacaatata ttatagttaa ataagaatta ttatcaaatc atttgtatat taattaaaat | 120 |
| actatactgt aaattacatt ttatttacaa tcaaaggaga tataccatgg agttccgcca | 180 |
| ggaggagttt cggaagctag cgggtcgtgc tctcgggaag ctgcaccgcc ttctggagaa | 240 |
| gcggcaggaa ggcgcggaga cgctggagct gagtgcggat gggcgcccgg tgaccacgca | 300 |
| gacccgggac cgccggtgg tggactgcac ctgcttcggc ctccctcgcc gctacattat | 360 |
| cgccatcatg agtggtctgg gcttctgcat cagctttggc atccgctgca acctgggcgt | 420 |
| ggccatcgtc tccatggtca ataacagcac gacccaccgc ggggccacg tggtggtgca | 480 |
| gaaagcccag ttcagctggg atccagagac tgtcggcctc atacacggct ccttttcctg | 540 |
| gggctacatt gtcactcaga ttccaggagg atttatctgt caaaaatttg cagccaacag | 600 |
| agttttcggc tttgctattg tggcaacatc cactctaaac atgctgatcc cctcagctgc | 660 |
| ccgcgtccac tatggctgtg tcatcttcgt gaggatcctg caggggttgg tagagggggt | 720 |
| cacatacccc gcctgccatg ggatctggag caaatgggcc ccacccttag aacggagtcg | 780 |
| cctggcgacg acagcctttt gtggttccta tgctggggcg gtggtcgcga tgccctcgc | 840 |
| cggggtcctt gtgcagtact caggatgag ctctgttttc tacgtctacg cagcttcgg | 900 |
| gatcttctgg tacctgttct ggctgctcgt ctcctacgag tccccgcgc tgcacccaag | 960 |
| catctcggag gaggagcgca agtacatcga ggacgccatc ggagagagcg cgaaactcat | 1020 |
| gaacccctc acgaagttta gcactccctg gcggcgcttc ttcacgtcta tgccagtcta | 1080 |
| tgccatcatc gtggccaact tctgccgcag ctggacgttc tacctgctgc tcatctccca | 1140 |
| gcccgcctac ttcgaagaag tgttcggctt cgagatcagc aaggtaggcc tggtgtccgc | 1200 |
| gctgccccac ctggtcatga ccatcatcgt gcccatcggc ggccagatcg cggcttcct | 1260 |
| gcggagccgc cgcatcatgt ccaccaccaa cgtgcgcaag ttgatgaact gcggaggctt | 1320 |
| cggcatggaa gccacgctgc tgttggtggt cggctactcg cactccaagg gcgtggccat | 1380 |
| ctccttcctg gtcctagccg tgggcttcag cggcttcgcc atctctgggt tcaacgtgaa | 1440 |
| ccacctggac atagcccggc gctacgccag catcctcatg ggcatctcca acggcgtggg | 1500 |
| cacactgtcg ggcatggtgt gccccatcat cgtgggggcc atgactaagc acaagactcg | 1560 |
| ggaggagtgg cagtacgtgt tcctaattgc ctccctggtg cactatggag tgtcatctt | 1620 |
| ctacgggggtc tttgcttctg agagaagca gccgtgggca gagcctgagg agatgagcga | 1680 |
| ggagaagtgt ggcttcgttg ccatgaccca gctggctggc agtgacgaca gcgaaatgga | 1740 |
| ggatgaggct gagccccgg gggcaccccc tgcaccccg ccctcctatg ggccacaca | 1800 |
| cagcacattt cagccccca ggcccccacc cctgtccgg gactactgat aactcgagca | 1860 |
| ccaccatcac catcaccatc actaagtgat taacctcagg tgcaggctgc ctatcagaag | 1920 |
| gtggtggctg gtgtggccaa tgccctggct cacaaatacc actgagatcg atctttttcc | 1980 |
| ctctgccaaa aattatgggg acatcatgaa gccccttgag catctgactt ctggctaata | 2040 |

```
aaggaaattt attttcattg caatagtgtg ttggaatttt ttgtgtctct cactcggaag    2100
gacatatggg agggcaaatc atttaaaaca tcagaatgag tatttggttt agagtttggc    2160
aacatatgcc catatgtaac tagcataacc ccttggggcc tctaaacggg tcttgagggg    2220 tttttttgctg aaagcatgcg gaggaaattc tccttgaagt ttccctggtg ttcaaagtaa    2280
aggagtttgc accagacgca cctctgttca ctggtccggc gtattaaaac acgatacatt    2340
gttattagta catttattaa gcgctagatt ctgtgcgttg ttgatttaca gacaattgtt    2400
gtacgtattt taataattca ttaaatttat aatctttagg gtggtatgtt agagcgaaaa    2460
tcaaatgatt ttcagcgtct ttatatctga atttaaatat taaatcctca atagatttgt    2520
aaaataggtt tcgattagtt tcaaacaagg gttgttttttc cgaaccgatg gctggactat    2580
ctaatggatt ttcgctcaac gccacaaaac ttgccaaatc ttgtagcagc aatctagctt    2640
tgtcgatatt cgtttgtgtt ttgttttgta ataaaggttc gacgtcgttc aaaatattat    2700
gcgcttttgt atttctttca tcactgtcgt tagtgtacaa ttgactcgac gtaaacacgt    2760
taaatagagc ttgacatat ttaacatcgg gcgtgttagc tttattaggc cgattatcgt    2820
cgtcgtccca accctcgtcg ttagaagttg cttccgaaga cgattttgcc atagccacac    2880
gacgcctatt aattgtgtcg gctaacacgt ccgcgatcaa atttgtagtt gagcttttttg    2940 gaattatttc tgattgcggg cgttttttggg cgggtttcaa tctaactgtg cccgatttta    3000
attcagacaa cacgttagaa agcgatggtg caggcggtgg taacatttca gacggcaaat    3060
ctactaatgg cggcggtggt ggagctgatg ataaatctac catcggtgga ggcgcaggcg    3120
gggctggcgg cggaggcgga ggcggaggtg gtggcggtga tgcagacggc ggtttaggct    3180
caaatgtctc tttaggcaac acagtcggca cctcaactat tgtactggtt tcgggcgccg    3240
tttttggttt gaccggtctg agacgagtgc gattttttttc gtttctaata gcttccaaca    3300
attgttgtct gtcgtctaaa ggtgcagcgg gttgaggttc cgtcggcatt ggtggagcgg    3360
gcggcaattc agacatcgat ggtggtggtg gtggtggagg cgctggaatg ttaggcacgg    3420
gagaaggtgg tggcggcggt gccgccggta aatttgttc tggtttagtt tgttcgcgca    3480
cgattgtggg caccggcgca ggcgccgctg gctgcacaac ggaaggtcgt ctgcttcgag    3540
gcagcgcttg gggtggtggc aattcaatat tataattgga atacaaatcg taaaaatctg    3600
ctataagcat tgtaatttcg ctatcgttta ccgtgccgat atttaacaac cgctcaatgt    3660
aagcaattgt attgtaaaga gattgtctca agctcggaac gctgcgctcg gtcgttcggc    3720
tgcggcgagc ggtatcagct cactcaaagg cggtaatacg gttatccaca gaatcagggg    3780
ataacgcagg aaagaacatg tgagcaaaag gccagcaaaa ggccaggaac cgtaaaaagg    3840
ccgcgttgct ggcgtttttc cataggctcc gcccccctga cgagcatcac aaaaatcgac    3900
gctcaagtca gaggtggcga aacccgacag gactataaag ataccaggcg tttccccctg    3960
gaagctccct cgtgcgctct cctgttccga ccctgccgct taccggatac ctgtccgcct    4020
ttctcccttc gggaagcgtg gcgctttctc aatgctcacg ctgtaggtat ctcagttcgg    4080
tgtaggtcgt tcgctccaag ctgggctgtg tgcacgaacc ccccgttcag cccgaccgct    4140
gcgccttatc cggtaactat cgtcttgagt ccaacccggt aagacacgac ttatcgccac    4200
tggcagcagc cactggtaac aggattagca gagcgaggta tgtaggcggt gctacagagt    4260
tcttgaagtg gtggcctaac tacggctaca ctagaaggac agtatttggt atctgcgctc    4320
tgctgaagcc agttaccttc ggaaaaagag ttggtagctc ttgatccggc aaacaaacca    4380
```

```
ccgctggtag cggtggtttt tttgtttgca agcagcagat tacgcgcaga aaaaaaggat    4440
ctcaagaaga tcctttgtta ccaatgctta atcagtgagg cacctatctc agcgatctgt    4500
ctatttcgtt catccatagt tgcctgactc cccgtcgtgt agataactac gatacgggag    4560
ggcttaccat ctggccccag tgctgcaatg ataccgcgag acccacgctc accggctcca    4620
gatttatcag caataaacca gccagccgga agggccgagc gcagaagtgg tcctgcaact    4680
ttatccgcct ccatccagtc tattaattgt tgccgggaag ctagagtaag tagttcgcca    4740
gttaatagtt tgcgcaacgt tgttgccatt gctacaggca tcgtggtgtc acgctcgtcg    4800
tttggtatgg cttcattcag ctccggttcc caacgatcaa ggcgagttac atgatccccc    4860
atgttgtgca aaaaagcggt tagctccttc ggtcctccga tcgttgtcag aagtaagttg    4920
gccgcagtgt tatcactcat ggttatggca gcactgcata attctcttac tgtcatgcca    4980
tccgtaagat gcttttctgt gactggtgag tactcaacca agtcattctg agaatagtgt    5040
atgcggcgac cgagttgctc ttgcccggcg tcaatacggg ataataccgc gccacatagc    5100
agaactttaa aagtgctcat cattggaaaa cgttcttcgg ggcgaaaact ctcaaggatc    5160
ttaccgctgt tgagatccag ttcgatgtaa cccactcgtg cacccaactg atcttcagca    5220
tcttttactt tcaccagcgt ttctgggtga gcaaaaacag gaaggcaaaa tgccgcaaaa    5280
aagggaataa gggcgacacg gaaatgttga atactcatac tcttcctttt tcaatattat    5340
tgaagcattt atcagggtta ttgtctcatg tccgcgcgtt tcctgcatct tttaatcaaa    5400
tcccaagatg tgtataaacc accaaactgc caaaaaatga aaactgtcga caagctctgt    5460
ccgtttgctg gcaactgcaa gggtctcaat cctatttgta attattgaat aataaaacaa    5520
ttataaatgt caaatttgtt tttattaac gatacaaacc aaacgcaaca gaacatttg     5580 tagtattatc tataattgaa aacgcgtagt tataatcgct gaggtaatat ttaaaatcat    5640
tttcaaatga ttcacagtta atttgcgaca atataatttt attttcacat aaactagacg    5700
ccttgtcgtc ttcttcttcg tattccttct ctttttcatt tttctcttca taaaaattaa    5760
catagttatt atcgtatcca tatatgtatc tatcgtatag agtaaatttt tgttgtcat    5820 aaatatatat gtcttttttta atggggtgta tagtaccgct gcgcatagtt tttctgtaat    5880
ttacaacagt gctattttct ggtagttctt cggagtgtgt tgctttaatt attaaattta    5940
tataatcaat gaatttggga tcgtcggttt tgtacaatat gttgccggca tagtacgcag    6000
cttcttctag ttcaattaca ccattttta gcagcaccgg attaacataa ctttccaaaa    6060
tgttgtacga accgttaaac aaaaacagtt cacctcccctt ttctatacta ttgtctgcga    6120
gcagttgttt gttgttaaaa ataacagcca ttgtaatgag acgcacaaac taatatcaca    6180
aactggaaat gtctatcaat atatagttgc tctagttatt aatagtaatc aattacgggg    6240
tcattagttc atagcccata tatggagttc cgcgttacat aacttacggt aaatggcccg    6300
cctggctgac cgcccaacga ccccccgccca ttgacgtcaa taatgacgta tgttcccata    6360
gtaacgccaa tagggacttt ccattgacgt caatgggtgg actatttacg gtaaactgcc    6420
cacttggcag tacatcaagt gtatcatatg ccaagtacgc cccctattga cgtcaatgac    6480
ggtaaatggc ccgcctggca ttatgcccag tacatgacct tatgggactt tcctacttgg    6540
cagtacatct acgtattagt catcgctatt accatgcatg gtcgaggtga ccccacgtt    6600 ctgcttcact ctccccatct cccccccctc cccaccccca attttgtatt tatttatttt    6660
ttaattattt tgtgcagcga tggggggcggg ggggggggg gggcgcgcgc caggcgggc     6720 ggggcgggc gaggggcggg gcggggcgag gcggagaggt gcggcggcag ccaatcagag    6780
```

| | |
|---|---|
| cggcgcgctc cgaaagtttc cttttatggc gaggcggcgg cggcggcggc cctataaaaa | 6840 |
| gcgaagcgcg cggcgggcgg gagtcgctgc gacgctgcct tcgccccgtg ccccgctccg | 6900 |
| ccgccgcctc gcgccgcccg ccccggctct gactgaccgc gttactccca caggtgagcg | 6960 |
| ggcgggacgg cccttctcct tcgggctgta attagcgctt ggtttaatga cggcttgttt | 7020 |
| cttttctgtg gctgcgtgaa agccttgagg ggctccggga gggccctttg tgcgggggga | 7080 |
| gcggctcggg gctgtccgcg gggggacggc tgccttcggg ggggacgggg cagggcgggg | 7140 |
| ttcggcttct ggcgtgtgac cggcggctct agagcctctg ctaaccatgt tcatgccttc | 7200 |
| ttcttttttcc tacagctcct gggcaacgtg ctggttattg tgctgtctca tcattttggc | 7260 |
| aaagaattgg atcggaccga aattaatacg actcactata | 7300 |

<210> SEQ ID NO 96
<211> LENGTH: 7381
<212> TYPE: DNA
<213> ORGANISM: Artificial Sequence
<220> FEATURE:
<223> OTHER INFORMATION: pTriEx-1-VGLUT3[human]-IF1-H8

<400> SEQUENCE: 96

| | |
|---|---|
| ggggaattgt gagcggataa caattccccg agttaatccc gggaccttta attcaaccca | 60 |
| acacaatata ttatagttaa ataagaatta ttatcaaatc atttgtatat taattaaaat | 120 |
| actatactgt aaattacatt ttatttacaa tcaaggaga tataccatgc cttttaaagc | 180 |
| atttgatacc ttcaaagaaa aaattctgaa acctgggaag gaaggagtga agaacgccgt | 240 |
| gggagattct ttgggaattt tacaaagaaa aatcgatggg acaactgagg aagaagataa | 300 |
| cattgagctg aatgaagaag gaaggccggt gcagacgtcc aggccaagcc ccccactctg | 360 |
| cgactgccac tgctgcggcc tccccaagcg ttacatcatt gctatcatga gtgggctggg | 420 |
| attctgcatt tccttttggga tccggtgcaa tcttggagtt gccattgtgg aaatggtcaa | 480 |
| caatagcacc gtatatgttg atggaaaacc ggaaattcag acagcacagt ttaactggga | 540 |
| tccagaaaca gtgggcctta tccatggatc ttttttctgg ggctatatta tgacacaaat | 600 |
| tccaggtggt ttcatttcaa acaagtttgc tgctaacagg gtctttggag ctgccatctt | 660 |
| cttaacatcg actctgaaca tgtttattcc ctctgcagcc agagtgcatt acggatgcgt | 720 |
| catgtgtgtc agaattctgc aaggtttagt ggagggtgtg acctacccag cctgccatgg | 780 |
| gatgtggagt aagtgggcac cacctttgga gagaagccga ctggccacaa cctcttttg | 840 |
| tggttcctat gcaggggcag tggttgccat gccctggct ggggtgttgg tgcagtacat | 900 |
| tggatggtcc tctgtctttt atatttatgg catgtttggg attatttggt acatgttttg | 960 |
| gctgttgcag gcctatgagt gcccagcagc tcatccaaca atatccaatg aggagaagac | 1020 |
| ctatatagag acaagcatag gagaggggc caacgtggtt agtctaagta aatttagtac | 1080 |
| cccatggaaa agatttttca catctttgcc ggtttacgca atcattgtgg caaattttg | 1140 |
| cagaagctgg acctttttatt tgctcctcat aagtcagcct gcttatttg aagaggtctt | 1200 |
| tggatttgca ataagtaagg tgggtctctt gtcagcagtc ccacacatgg ttatgacaat | 1260 |
| cgttgtacct attggaggac aattggctga ttatttaaga agcagacaaa ttttaaccac | 1320 |
| aactgctgtc agaaaaatca tgaactgtgg aggttttggc atggaggcaa ccttactcct | 1380 |
| ggtggttggc ttttcgcata ccaaaggggt ggctatctcc tttctggtac ttgctgtagg | 1440 |
| atttagtggc ttcgctattt caggttttaa tgtcaaccac ctggacattg ccccacgcta | 1500 |

```
tgccagcatt ctcatgggga tctcaaacgg agtgggaacc ctctctggaa tggtctgtcc    1560
cctcattgtc ggtgcaatga ccaggcacaa gacccgtgaa gaatggcaga atgtgttcct    1620
catagctgcc ctggtgcatt acagtggtgt gatcttctat ggggtctttg cttctgggga    1680
gaaacaggag tgggctgacc cagagaatct ctctgaggag aaatgtggaa tcattgacca    1740
ggacgaatta gctgaggaga tagaactcaa ccatgagagt tttgcgagtc ccaaaaagaa    1800
gatgtcttat ggagccacct cccagaattg tgaagtccag aagaaggaat ggaaaggaca    1860
gagaggagcg acccttgatg aggaagagct gacatcctac cagaatgaag agagaaactt    1920
ctcaactata tccctcgagc accaccatca ccatcaccat cactaagtga ttaacctcag    1980
gtgcaggctg cctatcagaa ggtggtggct ggtgtggcca atgccctggc tcacaaatac    2040
cactgagatc gatcttttc cctctgccaa aaattatggg gacatcatga agccccttga    2100
gcatctgact tctggctaat aaaggaaatt tattttcatt gcaatagtgt gttggaattt    2160
tttgtgtctc tcactcggaa ggacatatgg gagggcaaat catttaaaac atcagaatga    2220
gtatttggtt tagagtttgg caacatatgc ccatatgtaa ctagcataac cccttggggc    2280
ctctaaacgg gtcttgaggg gttttttgct gaaagcatgc ggaggaaatt ctccttgaag    2340
tttccctggt gttcaaagta aaggagtttg caccagacgc acctctgttc actggtccgg    2400
cgtattaaaa cacgatacat tgttattagt acatttatta gcgctagat tctgtgcgtt    2460
gttgatttac agacaattgt tgtacgtatt ttaataattc attaaattta taatctttag    2520
ggtggtatgt tagagcgaaa atcaaatgat tttcagcgtc tttatatctg aatttaaata    2580
ttaaatcctc aatagatttg taaaataggt ttcgattagt ttcaaacaag ggttgttttt    2640
ccgaaccgat ggctggacta tctaatggat tttcgctcaa cgccacaaaa cttgccaaat    2700
cttgtagcag caatctagct ttgtcgatat tcgtttgtgt tttgttttgt aataaaggtt    2760
cgacgtcgtt caaaatatta tgcgcttttg tatttctttc atcactgtcg ttagtgtaca    2820
attgactcga cgtaaacacg ttaaatagag cttggacata tttaacatcg ggcgtgttag    2880
ctttattagg ccgattatcg tcgtcgtccc aaccctcgtc gttagaagtt gcttccgaag    2940
acgattttgc catagccaca cgacgcctat taattgtgtc ggctaacacg tccgcgatca    3000
aatttgtagt tgagcttttt ggaattattt ctgattgcgg gcgttttgg gcgggtttca    3060
atctaactgt gcccgatttt aattcagaca acacgttaga aagcgatggt gcaggcggtg    3120
gtaacatttc agacggcaaa tctactaatg gcggcggtgg tggagctgat gataaatcta    3180
ccatcggtgg aggcgcaggc ggggctgcg gcggaggcgg aggcggaggt ggtggcggtg    3240
atgcagacgg cggtttaggc tcaaatgtct ctttaggcaa cacagtcggc acctcaacta    3300
ttgtactggt ttcgggcgcc gttttggtt tgaccggtct gagacgagtg cgattttttt    3360
cgtttctaat agcttccaac aattgttgtc tgtcgtctaa aggtgcagcg ggttgaggtt    3420
ccgtcggcat tggtggagcg ggcggcaatt cagacatcga tggtggtggt ggtggtggag    3480
gcgctggaat gttaggcacg ggagaaggtg gtggcggcgg tgccgccggt ataatttgtt    3540
ctggtttagt ttgttcgcgc acgattgtgg gcaccggcgc aggcgccgct ggctgcacaa    3600
cggaaggtcg tctgcttcga ggcagcgctt ggggtggtgg caattcaata ttataattgg    3660
aatacaaatc gtaaaaatct gctataagca ttgtaatttc gctatcgttt accgtgccga    3720
tatttaacaa ccgctcaatg taagcaattg tattgtaaag agattgtctc aagctcggaa    3780
cgctgcgctc ggtcgttcgg ctgcggcgag cggtatcagc tcactcaaag gcggtaatac    3840
ggttatccac agaatcaggg gataacgcag gaaagaacat gtgagcaaaa ggccagcaaa    3900
```

```
aggccaggaa ccgtaaaaag gccgcgttgc tggcgttttt ccataggctc cgccccctg    3960 acgagcatca caaaaatcga cgctcaagtc agaggtggcg aaacccgaca ggactataaa    4020
gataccaggc gtttccccct ggaagctccc tcgtgcgctc tcctgttccg accctgccgc    4080
ttaccggata cctgtccgcc tttctccctt cgggaagcgt ggcgctttct caatgctcac    4140
gctgtaggta tctcagttcg gtgtaggtcg ttcgctccaa gctgggctgt gtgcacgaac    4200
cccccgttca gcccgaccgc tgcgccttat ccggtaacta tcgtcttgag tccaacccgg    4260
taagacacga cttatcgcca ctggcagcag ccactggtaa caggattagc agagcgaggt    4320
atgtaggcgg tgctacagag ttcttgaagt ggtggcctaa ctacggctac actagaagga    4380
cagtatttgg tatctgcgct ctgctgaagc cagttacctt cggaaaaaga gttggtagct    4440
cttgatccgg caaacaaacc accgctggta gcggtggttt ttttgtttgc aagcagcaga    4500
ttacgcgcag aaaaaaagga tctcaagaag atcctttgtt accaatgctt aatcagtgag    4560
gcacctatct cagcgatctg tctatttcgt tcatccatag ttgcctgact ccccgtcgtg    4620
tagataacta cgatacggga gggcttacca tctggcccca gtgctgcaat gataccgcga    4680
gacccacgct caccggctcc agatttatca gcaataaacc agccagccgg aagggccgag    4740
cgcagaagtg gtcctgcaac tttatccgcc tccatccagt ctattaattg ttgccgggaa    4800
gctagagtaa gtagttcgcc agttaatagt ttgcgcaacg ttgttgccat tgctacaggc    4860
atcgtggtgt cacgctcgtc gtttggtatg gcttcattca gctccggttc ccaacgatca    4920
aggcgagtta catgatcccc catgttgtgc aaaaaagcgg ttagctcctt cggtcctccg    4980
atcgttgtca gaagtaagtt ggccgcagtg ttatcactca tggttatggc agcactgcat    5040
aattctctta ctgtcatgcc atccgtaaga tgcttttctg tgactggtga gtactcaacc    5100
aagtcattct gagaatagtg tatgcggcga ccgagttgct cttgcccggc gtcaatacgg    5160
gataataccg cgccacatag cagaacttta aaagtgctca tcattggaaa acgttcttcg    5220
gggcgaaaac tctcaaggat cttaccgctg ttgagatcca gttcgatgta acccactcgt    5280
gcacccaact gatcttcagc atcttttact tcaccagcg tttctgggtg agcaaaaaca    5340
ggaaggcaaa atgccgcaaa aaagggaata agggcgacac ggaaatgttg aatactcata    5400
ctcttccttt ttcaatatta ttgaagcatt tatcagggtt attgtctcat gtccgcgcgt    5460
ttcctgcatc ttttaatcaa atcccaagat gtgtataaac caccaaactg ccaaaaaatg    5520
aaaactgtcg acaagctctg tccgtttgct ggcaactgca agggtctcaa tcctatttgt    5580
aattattgaa taataaaaca attataaatg tcaaatttgt tttttattaa cgatacaaac    5640
caaacgcaac aagaacattt gtagtattat ctataattga aaacgcgtag ttataatcgc    5700
tgaggtaata tttaaaatca ttttcaaatg attcacagtt aatttgcgac aatataattt    5760
tattttcaca taaactagac gccttgtcgt cttcttcttc gtattccttc tcttttcat    5820 ttttctcttc ataaaaatta acatagttat tatcgtatcc atatatgtat ctatcgtata    5880
gagtaaattt tttgttgtca taaatatata tgtctttttt aatggggtgt atagtaccgc    5940
tgcgcatagt ttttctgtaa tttacaacag tgctattttc tggtagttct tcggagtgtg    6000
ttgctttaat tattaaattt atataatcaa tgaatttggg atcgtcggtt ttgtacaata    6060
tgttgccggc atagtacgca gcttcttcta gttcaattac accatttttt agcagcaccg    6120
gattaacata acttttccaaa atgttgtacg aaccgtaaaa caaaaacagt tcacctccct    6180
tttctatact attgtctgcg agcagttgtt tgttgttaaa aataacagcc attgtaatga    6240
```

-continued

```
gacgcacaaa ctaatatcac aaactggaaa tgtctatcaa tatatagttg ctctagttat    6300
taatagtaat caattacggg gtcattagtt catagcccat atatggagtt ccgcgttaca    6360
taacttacgg taaatggccc gcctggctga ccgcccaacg accccgccc attgacgtca    6420 ataatgacgt atgttcccat agtaacgcca tagggactt tccattgacg tcaatgggtg    6480
gactatttac ggtaaactgc ccacttggca gtacatcaag tgtatcatat gccaagtacg    6540 cccctattg acgtcaatga cggtaaatgg cccgcctggc attatgccca gtacatgacc    6600
ttatgggact ttcctacttg gcagtacatc tacgtattag tcatcgctat taccatgcat    6660
ggtcgaggtg agccccacgt tctgcttcac tctccccatc tccccccct ccccaccccc    6720 aattttgtat ttatttattt tttaattatt ttgtgcagcg atggggcgg gggggggg    6780 ggggcgcgcg ccaggcgggg cggggcgggg cgaggggcgg ggcggggcga ggcggagagg    6840
tgcggcggca gccaatcaga gcggcgcgct ccgaaagttt cctttatgg cgaggcggcg    6900 gcggcggcgg ccctataaaa agcgaagcgc gcggcgggcg ggagtcgctg cgacgctgcc    6960
ttcgccccgt gccccgctcc gccgccgcct cgcgccgccc gccccggctc tgactgaccg    7020
cgttactccc acaggtgagc gggcgggacg gcccttctcc ttcgggctgt aattagcgct    7080
tggtttaatg acgcttgtt tctttctgt ggctgcgtga aagccttgag gggctccggg    7140
agggcccttt gtgcgggggg agcggctcgg ggctgtccgc gggggacgg ctgccttcgg    7200 gggggacggg gcagggcggg gttcggcttc tggcgtgtga ccggcggctc tagagcctct    7260
gctaaccatg ttcatgcctt cttcttttc ctacagctcc tgggcaacgt gctggttatt    7320
gtgctgtctc atcatttgg caaagaattg atcggaccg aaattaatac gactcactat    7380
a                                                                  7381
```

<210> SEQ ID NO 97
<211> LENGTH: 7387
<212> TYPE: DNA
<213> ORGANISM: Artificial Sequence
<220> FEATURE:
<223> OTHER INFORMATION: pTriEx-1-VGLUT3[human]-IF1

<400> SEQUENCE: 97

```
ggggaattgt gagcggataa caattccccg gagttaatcc gggaccttta attcaaccca      60
acacaatata ttatagttaa ataagaatta ttatcaaatc atttgtatat taattaaaat     120
actatactgt aaattacatt ttatttacaa tcaaaggaga tataccatgc cttttaaagc     180
atttgatacc ttcaaagaaa aaattctgaa acctgggaag gaaggagtga agaacgccgt     240
gggagattct ttgggaattt tacaaagaaa aatcgatggg acaactgagg aagaagataa     300
cattgagctg aatgaagaag gaaggccggt gcagacgtcc aggccaagcc cccactctg     360 cgactgccac tgctgcggcc tccccaagcg ttacatcatt gctatcatga gtgggctggg     420
attctgcatt tcctttggga tccggtgcaa tcttggagtt gccattgtgg aaatggtcaa     480
caatagcacc gtatatgttg atggaaaacc ggaaattcag acagcacagt ttaactggga     540
tccagaaaca gtgggcctta tccatggatc ttttttctgg ggctatatta tgacacaaat     600
tccaggtggt tcattccaa acaagtttgc tgctaacagg gtctttggag ctgccatctt     660
cttaacatcg actctgaaca tgtttattcc ctctgcagcc agagtgcatt acggatgcgt     720
catgtgtgtc agaattctgc aaggtttagt ggagggtgtg acctacccag cctgccatgg     780
gatgtggagt aagtgggcac cacctttgga gagaagccga ctggccacaa cctctttttg     840
tggttcctat gcaggggcag tggttgccat gccctggct ggggtgttgg tgcagtacat     900
```

```
tggatggtcc tctgtctttt atatttatgg catgtttggg attatttggt acatgttttg     960
gctgttgcag gcctatgagt gcccagcagc tcatccaaca atatccaatg aggagaagac    1020
ctatatagag acaagcatag gagaggggggc caacgtggtt agtctaagta aatttagtac    1080
cccatggaaa agatttttca catctttgcc ggtttacgca atcattgtgg caaattttttg    1140 cagaagctgg acctttttatt tgctcctcat aagtcagcct gcttatttttg aagaggtctt    1200 tggatttgca ataagtaagg tgggtctctt gtcagcagtc ccacacatgg ttatgacaat    1260
cgttgtacct attggaggac aattggctga ttatttaaga agcagacaaa ttttaaccac    1320
aactgctgtc agaaaaatca tgaactgtgg aggttttggc atggaggcaa ccttactcct    1380
ggtggttggc ttttcgcata ccaagggggt ggctatctcc tttctggtac ttgctgtagg    1440
atttagtggc ttcgctattt caggttttaa tgtcaaccac ctggacattg ccccacgcta    1500
tgccagcatt tcatgggga tctcaaacgg agtgggaacc ctctctggaa tggtctgtcc    1560
cctcattgtc ggtgcaatga ccaggcacaa gacccgtgaa gatgggcaga atgtgttcct    1620
catagctgcc ctggtgcatt acagtggtgt gatcttctat ggggtctttg cttctgggga    1680
gaaacaggag tgggctgacc cagagaatct ctctgaggag aaatgtggaa tcattgacca    1740
ggacgaatta gctgaggaga tagaactcaa ccatgagagt tttgcgagtc caaaaagaa    1800 gatgtcttat ggagccacct cccagaattg tgaagtccag aagaaggaat ggaaaggaca    1860
gagaggagcg acccttgatg aggaagagct gacatcctac cagaatgaag agagaaactt    1920
ctcaactata tcctaatgac tcgagcacca ccatcaccat caccatcact aagtgattaa    1980
cctcaggtgc aggctgccta tcagaaggtg gtggctggtg tggccaatgc cctggctcac    2040
aaataccact gagatcgatc ttttttccctc tgccaaaaat tatggggaca tcatgaagcc    2100
ccttgagcat ctgacttctg gctaataaag gaaatttatt ttcattgcaa tagtgtgttg    2160 gaatttttttg tgtctctcac tcggaaggac atatgggagg gcaaatcatt taaaacatca    2220
gaatgagtat ttggtttaga gtttggcaac atatgcccat atgtaactag cataaccccct    2280 tggggcctct aaacgggtct tgaggggttt ttttgctgaaa gcatgcggag gaaattctcc    2340
ttgaagtttc cctggtgttc aaagtaaagg agtttgcacc agacgcacct ctgttcactg    2400
gtccggcgta ttaaaacacg atacattgtt attagtacat ttattaagcg ctagattctg    2460
tgcgttgttg atttacagac aattgttgta cgtatttttaa taattcatta aatttataat    2520
ctttagggtg gtatgttaga gcgaaaatca aatgattttttc agcgtcttta tatctgaatt    2580
taaatattaa atcctcaata gatttgtaaa ataggtttcg attagtttca acaagggtt    2640 gttttttccga accgatggct ggactatcta atggattttttc gctcaacgcc acaaaacttg    2700
ccaaatcttg tagcagcaat ctagctttgt cgatattcgt ttgtgttttg ttttgtaata    2760
aaggttcgac gtcgttcaaa atattatgcg ctttttgtatt tctttcatca ctgtcgttag    2820
tgtacaattg actcgacgta aacacgttaa atagagcttg acatatttta acatcgggcg    2880
tgttagcttt attaggccga ttatcgtcgt cgtcccaacc ctcgtcgtta aagttgctt    2940 ccgaagacga ttttgccata gccacacgac gcctattaat tgtgtcggct aacacgtccg    3000
cgatcaaatt tgtagttgag ctttttggaa ttatttctga ttgcgggcgt ttttgggcgg    3060
gtttcaatct aactgtgccc gattttaatt cagacaacac gttagaaagc gatggtgcag    3120
gcggtggtaa catttcagac ggcaaatcta ctaatggcgg cggtggtgga gctgatgata    3180
aatctaccat cggtggaggc gcaggcgggg ctggcggcgg aggcggaggc ggaggtggtg    3240
```

```
gcggtgatgc agacggcggt ttaggctcaa atgtctcttt aggcaacaca gtcggcacct    3300
caactattgt actggtttcg ggcgccgttt ttggtttgac cggtctgaga cgagtgcgat    3360
ttttttcgtt tctaatagct tccaacaatt gttgtctgtc gtctaaaggt gcagcgggtt    3420
gaggttccgt cggcattggt ggagcgggcg gcaattcaga catcgatggt ggtggtggtg    3480
gtggaggcgc tggaatgtta ggcacgggag aaggtggtgg cggcggtgcc gccggtataa    3540
tttgttctgg tttagtttgt tcgcgcacga ttgtgggcac cggcgcaggc gccgctggct    3600
gcacaacgga aggtcgtctg cttcgaggca gcgcttgggg tggtggcaat tcaatattat    3660
aattggaata caaatcgtaa aaatctgcta taagcattgt aatttcgcta tcgtttaccg    3720
tgccgatatt taacaaccgc tcaatgtaag caattgtatt gtaaagagat tgtctcaagc    3780
tcggaacgct gcgctcggtc gttcggctgc ggcgagcgt  atcagctcac tcaaaggcgg    3840
taatacggtt atccacagaa tcaggggata acgcaggaaa gaacatgtga gcaaaaggcc    3900
agcaaaaggc caggaaccgt aaaaaggccg cgttgctggc gttttccat aggctccgcc    3960 ccccctgacga gcatcacaaa aatcgacgct caagtcagag gtggcgaaac ccgacaggac    4020
tataaagata ccaggcgttt ccccctggaa gctccctcgt gcgctctcct gttccgaccc    4080
tgccgcttac cggatacctg tccgcctttc tcccttcggg aagcgtggcg ctttctcaat    4140
gctcacgctg taggtatctc agttcggtgt aggtcgttcg ctccaagctg ggctgtgtgc    4200
acgaaccccc cgttcagccc gaccgctgcg ccttatccgg taactatcgt cttgagtcca    4260
acccggtaag acacgactta tcgccactgg cagcagccac tggtaacagg attagcagag    4320
cgaggtatgt aggcggtgct acagagttct tgaagtggtg gcctaactac ggctacacta    4380
gaaggacagt atttggtatc tgcgctctgc tgaagccagt taccttcgga aaaagagttg    4440
gtagctcttg atccggcaaa caaaccaccg ctggtagcgg tggttttttt gtttgcaagc    4500
agcagattac gcgcagaaaa aaaggatctc aagaagatcc tttgttacca atgcttaatc    4560
agtgaggcac ctatctcagc gatctgtcta tttcgttcat ccatagttgc ctgactcccc    4620
gtcgtgtaga taactacgat acgggagggc ttaccatctg gccccagtgc tgcaatgata    4680
ccgcgagacc cacgctcacc ggctccagat ttatcagcaa taaaccagcc agccggaagg    4740
gccgagcgca gaagtggtcc tgcaacttta tccgcctcca tccagtctat taattgttgc    4800
cgggaagcta gagtaagtag ttcgccagtt aatagtttgc gcaacgttgt tgccattgct    4860
acaggcatcg tggtgtcacg ctcgtcgttt ggtatggctt cattcagctc cggttcccaa    4920
cgatcaaggc gagttacatg atcccccatg ttgtgcaaaa aagcggttag ctccttcggt    4980
cctccgatcg ttgtcagaag taagttggcc gcagtgttat cactcatggt tatggcagca    5040
ctgcataatt ctcttactgt catgccatcc gtaagatgct tttctgtgac tggtgagtac    5100
tcaaccaagt cattctgaga atagtgtatg cggcgaccga gttgctcttg cccggcgtca    5160
atacgggata taccgcgcc  acatagcaga actttaaaag tgctcatcat tggaaaacgt    5220
tcttcggggc gaaaactctc aaggatctta ccgctgttga tccagttc  gatgtaaccc    5280 actcgtgcac ccaactgatc ttcagcatct tttactttca ccagcgtttc tgggtgagca    5340
aaaacaggaa ggcaaaatgc cgcaaaaaag gaataagggc gacacggaaa atgttgaata    5400
ctcatactct tcctttttca atattattga agcatttatc agggttattg tctcatgtcc    5460 gcgcgttttcc tgcatctttt aatcaaatcc caagatgtgt ataaaccacc aaactgccaa    5520
aaaatgaaaa ctgtcgacaa gctctgtccg tttgctggca actgcaaggg tctcaatcct    5580
atttgtaatt attgaataat aaaacaatta taaatgtcaa atttgttttt tattaacgat    5640
```

-continued

```
acaaaccaaa cgcaacaaga acatttgtag tattatctat aattgaaaac gcgtagttat    5700
aatcgctgag gtaatattta aaatcatttt caaatgattc acagttaatt tgcgacaata    5760
taattttatt ttcacataaa ctagacgcct tgtcgtcttc ttcttcgtat tccttctctt    5820
tttcattttt ctcttcataa aaattaacat agttattatc gtatccatat atgtatctat    5880
cgtatagagt aaattttttg ttgtcataaa tatatatgtc ttttttaatg gggtgtatag    5940
taccgctgcg catagttttt ctgtaattta caacagtgct attttctggt agttcttcgg    6000
agtgtgttgc tttaattatt aaatttatat aatcaatgaa tttgggatcg tcggttttgt    6060
acaatatgtt gccggcatag tacgcagctt cttctagttc aattcaccca ttttttagca    6120
gcaccggatt aacataactt tccaaaatgt tgtacgaacc gttaaacaaa aacagttcac    6180
ctcccttttc tatactattg tctgcgagca gttgtttgtt gttaaaaata acagccattg    6240
taatgagacg cacaaactaa tatcacaaac tggaaatgtc tatcaatata tagttgctct    6300
agttattaat agtaatcaat tacggggtca ttagttcata gcccatatat ggagttccgc    6360
gttacataac ttacggtaaa tggcccgcct ggctgaccgc ccaacgaccc ccgcccattg    6420
acgtcaataa tgacgtatgt tcccatagta acgccaatag ggactttcca ttgacgtcaa    6480
tgggtggact atttacggta aactgcccac ttggcagtac atcaagtgta tcatatgcca    6540
agtacgcccc ctattgacgt caatgacggt aaatggcccg cctggcatta tgcccagtac    6600
atgaccttat gggactttcc tacttggcag tacatctacg tattagtcat cgctattacc    6660
atgcatggtc gaggtgagcc ccacgttctg cttcactctc cccatctccc ccccctcccc    6720 accccccaatt ttgtatttat ttatttttta attattttgt gcagcgatgg gggcgggggg    6780
gggggggggg cgcgcgccag gcggggcggg gcggggcgag gggcggggcg gggcgaggcg    6840
gagaggtgcg gcggcagcca atcagagcgg cgcgctccga aagtttcctt ttatggcgag    6900
gcggcggcgg cggcggccct ataaaaagcg aagcgcgcgg cgggcgggag tcgctgcgac    6960
gctgccttcg ccccgtgccc cgctccgccg ccgcctcgcg ccgcccgccc cggctctgac    7020
tgaccgcgtt actcccacag gtgagcgggc gggacggccc ttctccttcg gctgtaatt    7080 agcgcttggt ttaatgacgg cttgtttctt ttctgtggct gcgtgaaagc cttgaggggc    7140
tccgggaggg ccctttgtgc gggggagcg gctcggggct gtccgcgggg gacggctgc    7200 cttcgggggg gacggggcag ggcggggttc ggcttctggc gtgtgaccgg cggctctaga    7260
gcctctgcta accatgttca tgccttcttc ttttttcctac agctcctggg caacgtgctg    7320
gttattgtgc tgtctcatca ttttggcaaa gaattggatc ggaccgaaat taatacgact    7380
cactata                                                              7387
```

<210> SEQ ID NO 98
<211> LENGTH: 6162
<212> TYPE: DNA
<213> ORGANISM: Artificial Sequence
<220> FEATURE:
<223> OTHER INFORMATION: pET24d-N-GST-(PSc)-VGLUT1[human](aa491-560)

<400> SEQUENCE: 98

```
ggggaattgt gagcggataa caattcccct ctagaaataa ttttgtttaa ctttaagaag      60
gagtatataa tgagccatca tcatcatcat catcatcata tgtcccctat actaggttat     120
tggaaaatta agggccttgt gcaacccact cgacttcttt tggaatatct tgaagaaaaa     180
tatgaagagc atttgtatga gcgcgatgaa ggtgataaat ggcgaaacaa aaagtttgaa     240
```

```
ttgggtttgg agtttcccaa tcttccttat tatattgatg gtgatgttaa attaacacag    300
tctatggcca tcatacgtta tatagctgac aagcacaaca tgttgggtgg ttgtccaaaa    360
gagcgtgcag agatttcaat gcttgaagga gcggttttgg atattagata cggtgtttcg    420
agaattgcat atagtaaaga ctttgaaact ctcaaagttg attttcttag caagctacct    480
gaaatgctga aaatgttcga agatcgttta tgtcataaaa catatttaaa tggtgatcat    540
gtaacccatc ctgacttcat gttgtatgac gctcttgatg ttgttttata catggaccca    600
atgtgcctgg atgcgttccc aaaattagtt tgttttaaaa aacgtattga agctatccca    660
caaattgata agtacttgaa atccagcaag tatatagcat ggcctttgca gggctggcaa    720
gccacgtttg gtggtggcga ccatcctcca aaattggaag tgctgtttca gggtccagcc    780
atgtctggag agaagcagcc gtgggcgagg cctgaggaga tgagcgagga gaagtgtggc    840
ttcgttggcc atgaccagct ggctggcagt gacgacagcg aaatggagga tgaggctgag    900
cccccgggg cacccctgc accccgccc tcctatgggg ccacacacag cacatttcag       960
ccccccaggc ccccaccccc tgtccgggac tactgataac tcgagcacca ccaccaccac   1020
cactgagatc cggctgctaa caaagcccga aaggaagctg agttggctgc tgccaccgct   1080
gagcaataac tagcataacc ccttgggggcc tctaaacggg tcttgagggg ttttttgctg   1140
aaaggaggaa ctatatccgg attggcgaat gggacgcgcc ctgtagcggc gcattaagcg   1200
cggcgggtgt ggtggttacg cgcagcgtga ccgctacact tgccagcgcc ctagcgcccg   1260
ctcctttcgc tttcttccct tcctttctcg ccacgttcgc cggctttccc cgtcaagctc   1320
taaatcgggg gctcccttta gggttccgat ttagtgcttt acggcacctc gaccccaaaa   1380
aacttgatta gggtgatggt tcacgtagtg ggccatcgcc ctgatagacg gttttttcgcc   1440
ctttgacgtt ggagtccacg ttctttaata gtggactctt gttccaaact ggaacaacac   1500
tcaaccctat ctcggtctat tcttttgatt tataagggat tttgccgatt tcggcctatt   1560
ggttaaaaaa tgagctgatt taacaaaaat ttaacgcgaa ttttaacaaa atattaacgt   1620
ttacaatttc aggtggcact tttcggggaa atgtgcgcgg aacccctatt tgtttatttt   1680
tctaaataca ttcaaatatg tatccgctca tgaattaatt cttagaaaaa ctcatcgagc   1740
atcaaatgaa actgcaattt attcatatca ggattatcaa taccatattt ttgaaaaagc   1800
cgttctgta atgaaggaga aaactcaccg aggcagttcc ataggatggc aagatcctgg   1860
tatcggtctg cgattccgac tcgtccaaca tcaatacaac ctattaattt ccccctcgtca   1920
aaaataaggt tatcaagtga gaaatcacca tgagtgacga ctgaatccgg tgagaatggc   1980
aaaagtttat gcatttcttt ccagacttgt tcaacaggcc agccattacg ctcgtcatca   2040
aaatcactcg catcaaccaa accgttattc attcgtgatt gcgcctgagc gagacgaaat   2100
acgcgatcgc tgttaaaagg acaattacaa acaggaatcg aatgcaaccg gcgcaggaac   2160
actgccagcg catcaacaat attttcacct gaatcaggat attcttctaa tacctggaat   2220
gctgttttcc cggggatcgc agtggtgagt aaccatgcat catcaggagt acggataaaa   2280
tgcttgatgg tcggaagagg cataaattcc gtcagccagt ttagtctgac catctcatct   2340
gtaacatcat tggcaacgct acctttgcca tgtttcagaa acaactctgg cgcatcgggc   2400
ttcccataca atcgatagat tgtcgcacct gattgcccga cattatcgcg agcccattta   2460
tacccatata aatcagcatc catgttggaa tttaatcgcg gcctagagca agacgtttcc   2520
cgttgaatat ggctcataac accccttgta ttactgttta tgtaagcaga cagttttatt   2580
gttcatgacc aaaatccctt aacgtgagtt ttcgttccac tgagcgtcag accccgtaga   2640
```

```
aaagatcaaa ggatcttctt gagatccttt ttttctgcgc gtaatctgct gcttgcaaac    2700
aaaaaaacca ccgctaccag cggtggtttg tttgccggat caagagctac caactctttt    2760
tccgaaggta actggcttca gcagagcgca gataccaaat actgtccttc tagtgtagcc    2820
gtagttaggc caccacttca agaactctgt agcaccgcct acatacctcg ctctgctaat    2880
cctgttacca gtggctgctg ccagtggcga taagtcgtgt cttaccgggt tggactcaag    2940
acgatagtta ccgataagg cgcagcggtc gggctgaacg gggggttcgt gcacacagcc    3000
cagcttggag cgaacgacct acaccgaact gagataccta cagcgtgagc tatgagaaag    3060
cgccacgctt cccgaaggga gaaggcgga caggtatccg gtaagcggca gggtcggaac    3120
aggagagcgc acgagggagc ttccagggggg aaacgcctgg tatctttata gtcctgtcgg    3180
gtttcgccac ctctgacttg agcgtcgatt tttgtgatgc tcgtcagggg ggcggagcct    3240
atggaaaaac gccagcaacg cggccttttt acggttcctg gccttttgct ggccttttgc    3300
tcacatgttc tttcctgcgt tatccctga ttctgtggat aaccgtatta ccgcctttga    3360
gtgagctgat accgctcgcc gcagccgaac gaccgagcgc agcgagtcag tgagcgagga    3420
agcggaagag cgcctgatgc ggtattttct ccttacgcat ctgtgcggta tttcacaccg    3480
catatatggt gcactctcag tacaatctgc tctgatgccg catagttaag ccagtataca    3540
ctccgctatc gctacgtgac tgggtcatgg ctgcgcccg acaccgcca cacccgctg     3600 acgcgccctg acgggcttgt ctgctcccgg catccgctta cagacaagct gtgaccgtct    3660
ccgggagctg catgtgtcag aggttttcac cgtcatcacc gaaacgcgcg aggcagctgc    3720
ggtaaagctc atcagcgtgg tcgtgaagcg attcacagat gtctgcctgt tcatccgcgt    3780
ccagctcgtt gagtttctcc agaagcgtta atgtctggct tctgataaag cgggccatgt    3840
taagggcggt tttttcctgt ttggtcactg atgcctccgt gtaaggggga tttctgttca    3900
tgggggtaat gataccgatg aaacgagaga ggatgctcac gatacgggtt actgatgatg    3960
aacatgcccg gttactggaa cgttgtgagg gtaaacaact ggcggtatgg atgcggcggg    4020
accagagaaa aatcactcag ggtcaatgcc agcgcttcgt taatacagat gtaggtgttc    4080
cacagggtag ccagcagcat cctgcgatgc agatccggaa cataatggtg cagggcgctg    4140
acttccgcgt ttccagactt tacgaaacac ggaaaccgaa gaccattcat gttgttgctc    4200
aggtcgcaga cgttttgcag cagcagtcgc ttcacgttcg ctcgcgtatc ggtgattcat    4260
tctgctaacc agtaaggcaa ccccgccagc ctagccgggt cctcaacgac aggagcacga    4320
tcatgcgcac ccgtggggcc gccatgccgg cgataatggc ctgcttctcg ccgaaacgtt    4380
tggtggcggg accagtgacg aaggcttgag cgagggcgtg caagattccg aataccgcaa    4440
gcgacaggcc gatcatcgtc gcgctccagc gaaagcggtc ctcgccgaaa atgacccaga    4500
gcgctgccgg cacctgtcct acgagttgca tgataaagaa gacagtcata agtgcggcga    4560
cgatagtcat gccccgcgcc caccggaagg agctgactgg gttgaaggct ctcaagggca    4620
tcggtcgaga tcccggtgcc taatgagtga gctaacttac attaattgcg ttgcgctcac    4680
tgcccgcttt ccagtcggga aacctgtcgt gccagctgca ttaatgaatc ggccaacgcg    4740
cggggagagg cggtttgcgt attgggcgcc agggtggttt ttcttttcac cagtgagacg    4800
ggcaacagct gattgccctt caccgcctgg ccctgagaga gttgcagcaa gcggtccacg    4860
ctggtttgcc ccagcaggcg aaaatcctgt ttgatggtgg ttaacggcgg gatataacat    4920
gagctgtctt cggtatcgtc gtatcccact accgagatat ccgcaccaac gcgcagcccg    4980
```

```
gactcggtaa tggcgcgcat tgcgcccagc gccatctgat cgttggcaac cagcatcgca   5040
gtgggaacga tgccctcatt cagcatttgc atggtttgtt gaaaaccgga catggcactc   5100
cagtcgcctt cccgttccgc tatcggctga atttgattgc gagtgagata tttatgccag   5160
ccagccagac gcagacgcgc cgagacagaa cttaatgggc ccgctaacag cgcgatttgc   5220
tggtgaccca atgcgaccag atgctccacg cccagtcgcg taccgtcttc atgggagaaa   5280
ataatactgt tgatgggtgt ctggtcagag acatcaagaa ataacgccgg aacattagtg   5340
caggcagctt ccacagcaat ggcatcctgg tcatccagcg atagttaat gatcagccca    5400 ctgacgcgtt gcgcgagaag attgtgcacc gccgctttac aggcttcgac gccgcttcgt   5460
tctaccatcg acaccaccac gctggcaccc agttgatcgg cgcgagattt aatcgccgcg   5520
acaatttgcg acggcgcgtg cagggccaga ctggaggtgg caacgccaat cagcaacgac   5580
tgtttgcccg ccagttgttg tgccacgcgg ttgggaatgt aattcagctc cgccatcgcc   5640
gcttccactt tttcccgcgt tttcgcagaa acgtggctgg cctggttcac cacgcgggaa   5700
acggtctgat aagagacacc ggcatactct gcgacatcgt ataacgttac tggtttcaca   5760
ttcaccaccc tgaattgact ctcttccggg cgctatcatg ccataccgcg aaaggttttg   5820
cgccattcga tggtgtccgg gatctcgacg ctctccctta tgcgactcct gcattaggaa   5880
gcagcccagt agtaggttga ggccgttgag caccgccgcc gcaaggaatg gtgcatgcaa   5940
ggagatggcg cccaacagtc ccccggccac ggggcctgcc accatacccca cgccgaaaca    6000 agcgctcatg agcccgaagt ggcgagcccg atcttcccca tcggtgatgt cggcgatata   6060
ggcgccagca accgcacctg tggcgccggt gatgccggcc acgatgcgtc cggcgtagag   6120
gatcgagatc tcgatcccgc gaaattaata cgactcacta ta                      6162

<210> SEQ ID NO 99
<211> LENGTH: 6213
<212> TYPE: DNA
<213> ORGANISM: Artificial Sequence
<220> FEATURE:
<223> OTHER INFORMATION: pET24d-N-GST-(PSc)-VGLUT3[human](aa503-589)

<400> SEQUENCE: 99
ggggaattgt gagcggataa caattcccct ctagaaataa ttttgtttaa ctttaagaag     60
gagtatataa tgagccatca tcatcatcat catcatcata tgtcccctat actaggttat    120
tggaaaatta agggccttgt gcaacccact cgacttcttt tggaatatct tgaagaaaaa    180
tatgaagagc atttgtatga gcgcgatgaa ggtgataaat ggcgaaacaa aaagtttgaa    240 ttgggttttgg agtttcccaa tcttccttat tatattgatg gtgatgttaa attaacacag    300
tctatggcca tcatacgtta tatagctgac aagcacaaca tgttgggtgg ttgtccaaaa    360
gagcgtgcag agatttcaat gcttgaagga gcggttttgg atattagata cggtgtttcg    420
agaattgcat atagtaaaga ctttgaaact ctcaaagttg atttcttag caagctacct     480 gaaatgctga aaatgttcga agatcgttta tgtcataaaa catatttaaa tggtgatcat    540
gtaacccatc ctgacttcat gttgtatgac gctcttgatg ttgttttata catggaccca    600
atgtgcctgg atgcgttccc aaaattagtt tgttttaaaa aacgtattga agctatccca    660
caaattgata agtacttgaa atccagcaag tatatagcat ggcctttgca gggctggcaa    720
gccacgtttg gtggtggcga ccatcctcca aaattggaag tgctgtttca gggtccagcc    780
atgtctgggg agaaacagga gtgggctgac ccagagaatc tctctgagga gaatgtggaa    840
atcattgacc aggacgaatt agctgaggag atagaactca accatgagag ttttgcgagt    900
```

```
cccaaaaaga agatgtctta tggagccacc tcccagaatt gtgaagtcca gaagaaggaa      960
tggaaaggac agagaggagc gacccttgat gaggaagagc tgacatccta ccagaatgaa     1020
gagagaaact tctcaactat atcctaatga ctcgagcacc accaccacca ccactgagat     1080
ccggctgcta acaaagcccg aaaggaagct gagttggctg ctgccaccgc tgagcaataa     1140
ctagcataac cccttggggc ctctaaacgg gtcttgaggg gttttttgct gaaaggagga     1200
actatatccg gattggcgaa tgggacgcgc cctgtagcgg cgcattaagc gcggcgggtg     1260
tggtggttac gcgcagcgtg accgctacac ttgccagcgc cctagcgccc gctcctttcg     1320
ctttcttccc ttcctttctc gccacgttcg ccggctttcc ccgtcaagct ctaaatcggg     1380
ggctcccttt agggttccga tttagtgctt tacggcacct cgaccccaaa aaacttgatt     1440
agggtgatgg ttcacgtagt gggccatcgc cctgatagac ggtttttcgc cctttgacgt     1500
tggagtccac gttctttaat agtggactct tgttccaaac tggaacaaca ctcaaccta     1560 tctcggtcta ttcttttgat ttataaggga ttttgccgat ttcggcctat tggttaaaaa     1620
atgagctgat ttaacaaaaa tttaacgcga attttaacaa aatattaacg tttacaattt     1680
caggtggcac ttttcgggga aatgtgcgcg gaacccctat ttgtttattt ttctaaatac     1740
attcaaatat gtatccgctc atgaattaat tcttagaaaa actcatcgag catcaaatga     1800
aactgcaatt tattcatatc aggattatca ataccatatt tttgaaaaag ccgtttctgt     1860
aatgaaggag aaaactcacc gaggcagttc cataggatgg caagatcctg gtatcggtct     1920
gcgattccga ctcgtccaac atcaatacaa cctattaatt tcccctcgtc aaaaataagg     1980
ttatcaagtg agaaatcacc atgagtgacg actgaatccg gtgagaatgg caaaagttta     2040
tgcatttctt tccagacttg ttcaacaggc cagccattac gctcgtcatc aaaatcactc     2100
gcatcaacca aaccgttatt cattcgtgat tgcgcctgag cgagacgaaa tacgcgatcg     2160
ctgttaaaag gacaattaca aacaggaatc gaatgcaacc ggcgcaggaa cactgccagc     2220
gcatcaacaa tattttcacc tgaatcagga tattcttcta atacctggaa tgctgttttc     2280
ccggggatcg cagtggtgag taaccatgca tcatcaggag tacgataaa atgcttgatg     2340 gtcggaagag gcataaattc cgtcagccag tttagtctga ccatctcatc tgtaacatca     2400
ttggcaacgc tacctttgcc atgtttcaga acaactctg gcgcatcggg cttcccatac     2460
aatcgataga ttgtcgcacc tgattgcccg acattatcgc gagcccattt atacccatat     2520
aaatcagcat ccatgttgga atttaatcgc ggcctagagc aagacgtttc ccgttgaata     2580
tggctcataa caccccttgt attactgttt atgtaagcag acagttttat tgttcatgac     2640
caaaatccct taacgtgagt tttcgttcca ctgagcgtca gacccgtag aaaagatcaa     2700 aggatcttct tgagatcctt ttttctgcg cgtaatctgc tgcttgcaaa caaaaaaacc     2760
accgctacca gcggtggttt gtttgccgga tcaagagcta ccaactcttt tccgaaggt     2820 aactggcttc agcagagcgc agataccaaa tactgtcctt ctagtgtagc cgtagttagg     2880
ccaccacttc aagaactctg tagcaccgcc tacatacctc gctctgctaa tcctgttacc     2940
agtggctgct gccagtggcg ataagtcgtg tcttaccggg ttggactcaa gacgatagtt     3000
accggataag gcgcagcggt cgggctgaac ggggggttcg tgcacacagc ccagcttgga     3060
gcgaacgacc tacaccgaac tgagatacct acagcgtgag ctatgagaaa gcgccacgct     3120
tcccgaaggg agaaaggcgg acaggtatcc ggtaagcggc agggtcggaa caggagagcg     3180
cacgagggag cttccagggg gaaacgcctg gtatctttat agtcctgtcg ggtttcgcca     3240
```

```
cctctgactt gagcgtcgat ttttgtgatg ctcgtcaggg gggcggagcc tatggaaaaa    3300
cgccagcaac gcggccttttt tacggttcct ggccttttgc tggccttttg ctcacatgtt    3360
ctttcctgcg ttatcccctg attctgtgga taaccgtatt accgcctttg agtgagctga    3420
taccgctcgc cgcagccgaa cgaccgagcg cagcgagtca gtgagcgagg aagcggaaga    3480
gcgcctgatg cggtatttttc tccttacgca tctgtgcggt atttcacacc gcatatatgg    3540
tgcactctca gtacaatctg ctctgatgcc gcatagttaa gccagtatac actccgctat    3600
cgctacgtga ctgggtcatg gctgcgcccc gacacccgcc aacacccgct gacgcgccct    3660
gacgggcttg tctgctcccg gcatccgctt acagacaagc tgtgaccgtc tccgggagct    3720
gcatgtgtca gaggttttca ccgtcatcac cgaaacgcgc gaggcagctg cggtaaagct    3780
catcagcgtg gtcgtgaagc gattcacaga tgtctgcctg ttcatccgcg tccagctcgt    3840
tgagtttctc cagaagcgtt aatgtctggc ttctgataaa gcgggccatg ttaagggcgg    3900
ttttttcctg tttggtcact gatgcctccg tgtaaggggg atttctgttc atgggggtaa    3960
tgataccgat gaaacgagag aggatgctca cgatacgggt tactgatgat gaacatgccc    4020
ggttactgga acgttgtgag ggtaaacaac tggcggtatg gatgcggcgg gaccagagaa    4080
aaatcactca gggtcaatgc cagcgcttcg ttaatacaga tgtaggtgtt ccacagggta    4140
gccagcagca tcctgcgatg cagatccgga acataatggt gcagggcgct gacttccgcg    4200
tttccagact ttacgaaaca cggaaaccga agaccattca tgttgttgct caggtcgcag    4260
acgttttgca gcagcagtcg cttcacgttc gctcgcgtat cggtgattca ttctgctaac    4320
cagtaaggca accccgccag cctagccggg tcctcaacga caggagcacg atcatgcgca    4380
cccgtggggc cgccatgccg cgataatgg cctgcttctc gccgaaacgt tggtggcgg     4440
gaccagtgac gaaggcttga gcgagggcgt gcaagattcc gaataccgca agcgacaggc    4500
cgatcatcgt cgcgctccag cgaaagcggt cctcgccgaa aatgacccag agcgctgccg    4560
gcacctgtcc tacgagttgc atgataaaga agacagtcat aagtgcggcg acgatagtca    4620
tgccccgcgc ccaccggaag gagctgactg ggttgaaggc tctcaagggc atcggtcgag    4680
atcccggtgc ctaatgagtg agctaactta cattaattgc gttgcgctca ctgcccgctt    4740
tccagtcggg aaacctgtcg tgccagctgc attaatgaat cggccaacgc gcggggagag    4800
gcggtttgcg tattgggcgc cagggtggtt tttcttttca ccagtgagac gggcaacagc    4860
tgattgccct tcaccgcctg gccctgagag agttgcagca agcggtccac gctggtttgc    4920
cccagcaggc gaaaatcctg tttgatggtg gttaacggcg ggatataaca tgagctgtct    4980
tcggtatcgt cgtatcccac taccgagata tccgcaccaa cgcgcagccc ggactcggta    5040
atggcgcgca ttgcgcccag cgccatctga tcgttggcaa ccagcatcgc agtgggaacg    5100
atgccctcat tcagcatttg catggtttgt tgaaaaccgg acatggcact ccagtcgcct    5160
tcccgttccg ctatcggctg aatttgattg cgagtgagat atttatgcca gccagccaga    5220
cgcagacgcg ccgagacaga acttaatggg cccgctaaca gcgcgatttg ctggtgaccc    5280
aatgcgacca gatgctccac gcccagtcgc gtaccgtctt catgggagaa aataatactg    5340
ttgatgggtg tctggtcaga gacatcaaga ataacgccg gaacattagt gcaggcagct    5400
tccacagcaa tggcatcctg gtcatccagc ggatagttaa tgatcagccc actgacgcgt    5460
tgcgcgagaa gattgtgcac cgccgcttta caggcttcga cgccgcttcg ttctaccatc    5520
gacaccacca cgctgcacc cagttgatcg gcgcgagatt taatcgccgc gacaatttgc    5580
gacggcgcgt gcagggccag actggaggtg caacgccaa tcagcaacga ctgtttgccc    5640
```

```
gccagttgtt gtgccacgcg gttgggaatg taattcagct ccgccatcgc cgcttccact    5700 tttttcccgcg ttttcgcaga aacgtggctg gcctggttca ccacgcggga aacggtctga    5760
taagagacac cggcatactc tgcgacatcg tataacgtta ctggtttcac attcaccacc    5820
ctgaattgac tctcttccgg gcgctatcat gccataccgc gaaaggtttt gcgccattcg    5880
atggtgtccg ggatctcgac gctctccctt atgcgactcc tgcattagga agcagcccag    5940
tagtaggttg aggccgttga gcaccgccgc cgcaaggaat ggtgcatgca aggagatggc    6000
gcccaacagt cccccggcca cggggcctgc caccatacccc acgccgaaac aagcgctcat    6060
gagcccgaag tggcgagccc gatcttcccc atcggtgatg tcggcgatat aggcgccagc    6120
aaccgcacct gtggcgccgg tgatgccggc cacgatgcgt ccggcgtaga ggatcgagat    6180
ctcgatcccg cgaaattaat acgactcact ata                                 6213
```

<210> SEQ ID NO 100
<211> LENGTH: 308
<212> TYPE: PRT
<213> ORGANISM: Artificial Sequence
<220> FEATURE:
<223> OTHER INFORMATION: H8-GST-(PSc)-VGLUT1-aa491-560

<400> SEQUENCE: 100

```
Met Ser His His His His His His His Met Ser Pro Ile Leu Gly
1               5                   10                  15

Tyr Trp Lys Ile Lys Gly Leu Val Gln Pro Thr Arg Leu Leu Leu Glu
                20                  25                  30

Tyr Leu Glu Glu Lys Tyr Glu Glu His Leu Tyr Glu Arg Asp Glu Gly
            35                  40                  45

Asp Lys Trp Arg Asn Lys Lys Phe Glu Leu Gly Leu Glu Phe Pro Asn
50                  55                  60

Leu Pro Tyr Tyr Ile Asp Gly Asp Val Lys Leu Thr Gln Ser Met Ala
65                  70                  75                  80

Ile Ile Arg Tyr Ile Ala Asp Lys His Asn Met Leu Gly Gly Cys Pro
                85                  90                  95

Lys Glu Arg Ala Glu Ile Ser Met Leu Glu Gly Ala Val Leu Asp Ile
            100                 105                 110

Arg Tyr Gly Val Ser Arg Ile Ala Tyr Ser Lys Asp Phe Glu Thr Leu
        115                 120                 125

Lys Val Asp Phe Leu Ser Lys Leu Pro Glu Met Leu Lys Met Phe Glu
130                 135                 140

Asp Arg Leu Cys His Lys Thr Tyr Leu Asn Gly Asp His Val Thr His
145                 150                 155                 160

Pro Asp Phe Met Leu Tyr Asp Ala Leu Asp Val Val Leu Tyr Met Asp
                165                 170                 175

Pro Met Cys Leu Asp Ala Phe Pro Lys Leu Val Cys Phe Lys Lys Arg
            180                 185                 190

Ile Glu Ala Ile Pro Gln Ile Asp Lys Tyr Leu Lys Ser Ser Lys Tyr
        195                 200                 205

Ile Ala Trp Pro Leu Gln Gly Trp Gln Ala Thr Phe Gly Gly Gly Asp
210                 215                 220

His Pro Pro Lys Leu Glu Val Leu Phe Gln Gly Pro Ala Met Ser Gly
225                 230                 235                 240

Glu Lys Gln Pro Trp Ala Glu Pro Glu Glu Met Ser Glu Glu Lys Cys
                245                 250                 255
```

Gly Phe Val Gly His Asp Gln Leu Ala Gly Ser Asp Asp Ser Glu Met
                260                 265                 270

Glu Asp Glu Ala Glu Pro Pro Gly Ala Pro Ala Pro Pro Ser
        275                 280                 285

Tyr Gly Ala Thr His Ser Thr Phe Gln Pro Pro Arg Pro Pro Pro
    290                 295                 300

Val Arg Asp Tyr
305

<210> SEQ ID NO 101
<211> LENGTH: 28
<212> TYPE: PRT
<213> ORGANISM: Artificial Sequence
<220> FEATURE:
<223> OTHER INFORMATION: VGLUT2 Epitop

<400> SEQUENCE: 101

Ile Thr Gln Asn Tyr Ile Asn Tyr Gly Thr Thr Lys Ser Tyr Gly Ala
1               5                   10                  15

Thr Thr Gln Ala Asn Gly Gly Trp Pro Ser Gly Trp
            20                  25

<210> SEQ ID NO 102
<211> LENGTH: 46
<212> TYPE: PRT
<213> ORGANISM: Artificial Sequence
<220> FEATURE:
<223> OTHER INFORMATION: VGLUT2 Epitop, amino acids 520-564

<400> SEQUENCE: 102

His Glu Asp Glu Leu Asp Glu Glu Thr Gly Asp Ile Thr Gln Asn Tyr
1               5                   10                  15

Ile Asn Tyr Gly Thr Thr Lys Ser Tyr Gly Ala Thr Thr Gln Ala Asn
            20                  25                  30

Gly Gly Trp Pro Ser Gly Trp Glu Lys Lys Glu Glu Phe Val
        35                  40                  45

<210> SEQ ID NO 103
<211> LENGTH: 28
<212> TYPE: PRT
<213> ORGANISM: Artificial Sequence
<220> FEATURE:
<223> OTHER INFORMATION: VGLUT1 Epitop, amino acids 523-550

<400> SEQUENCE: 103

Glu Met Glu Asp Glu Ala Glu Pro Pro Gly Ala Pro Ala Pro Pro
1               5                   10                  15

Pro Ser Tyr Gly Ala Thr His Ser Thr Phe Gln Pro
            20                  25

METHOD AND REAGENTS FOR THE DETECTION OF AN AUTOANTIBODY

CROSS-REFERENCE TO RELATED APPLICATIONS

This application claims priority to European Application No. 21165448.2, filed on Mar. 29, 2021, the content of which is hereby incorporated by reference in its entirety.

REFERENCE TO A SEQUENCE LISTING

The present application is accompanied by an ASCII text file as a computer readable form containing the sequence listing entitled, "003942US_SL_ST25.txt", created on Mar. 17, 2022, with a file size of 327,613 bytes, the content or which is hereby incorporated by reference in its entirety.

BACKGROUND OF THE INVENTION

Field of the Invention

The present invention relates to a method comprising the step detecting in a sample an autoantibody binding specifically to a mammalian VGLUT, an autoantibody binding specifically to a mammalian VGLUT, a diagnostically useful carrier with a solid phase with an immobilized polypeptide comprising a mammalian VGLUT or a variant thereof, a kit and a use of the autoantibody for diagnosing a neurological autoimmune disease or a cancer.

Description of Related Art

Neurological autoimmune diseases are rare, but are potentially treatable. Their hallmark it the occurrence of neurological symptoms and an autoimmune response, usually the emergence of an autoantibody binding specifically to structures in the brain such as polypeptides having important functions for neurotransmission. They can affect any area of the nervous system. Including the central, peripheral and autonomic nervous system. Although the system involvement is often multifocal, like encephalomyelitis, it can involve a single system, e.g. cerebellar degeneration.

The neurological autoimmune disease may be associated with cancer. If that is the case, it is referred to as PNS (paraneoplastic syndrome). The neurological symptoms precede or follow the cancer diagnosis, although. In some cases, the primary cancer is not found even at autopsy. Most of the PNS reflect a nervous system-specific autoimmune attack initiated by onconeural antigens released to the peripheral lymphoid tissue from an unsuspected primary or recurrent neoplasm. Frequently, a cerebrospinal fluid (CSF) study in these patients reveals lymphocytic pleocytosis, elevated protein, increased IgG synthesis and oligoclonal bands, supporting the immunological pathology. Antibodies targeted against an accessible membrane target are directly responsible for the disease, as in the case of acetyl choline receptor antibodies in myasthenia gravis and P/Q type of voltage-gated calcium channels in Lambert Eaton Myasthenic syndrome. Often, the cancer is asymptomatic at the time of presentation with neurological syndrome. Some of the paraneoplastic antibodies are specifically associated with cancer and some are not.

Autoimmune encephalitis is another major neurological autoimmune disease, in particular anti-NMDA receptor autoimmune encephalitis which affects 1.5 patient per million per year. Symptoms such as paranoia, psychosis and violent behavior usually appear psychiatric in nature at first, but as the disease progresses, this may be accompanied seizures, impaired cognition, memory deficit and speech problems. At a later stage treatment in an intensive care unit may be required if patients suffer from medically urgent symptoms including cerebellar ataxia, autonomic dysfunction and catatonia. An autoantibody to the NR1 subunit of the NMDA receptor was discovered as the cause (Dalmau et al., Anti-NMDA-receptor encephalitis: case series and analysis of the effects of antibodies. Lancet Neurology, Volume 7. Issue 12, 2008).

Early diagnosis and treatment of neurological autoimmune diseases is important because any delay can result in rapid progression and irreversible neurological damage. By contrast, early and appropriate treatment, usually by some form of immunosuppressive therapy, may reverse some of the damages. In some cases a complete recovery is possible. For example, 80% of patients suffering from NMDA receptor encephalitis have a good outcome with treatment, although long-term mental problems or a recurrence are possible.

Diagnosing neurological autoimmune diseases is often difficult, though. One of the reasons is the absence of a particular clinical pattern and absence of specific imaging and laboratory abnormalities. A combination of clinical and laboratory evaluations has to be deployed to reach diagnosis early. Treatment of underlying cancer, if present, is important in the treatment of the neurological condition.

Neurological autoantibodies are helpful for the diagnosis. Their presence, alone or in combination with other indicators, helps to establish the autoimmune nature of the disease, helping the clinician to differentiate the new neurological symptoms of a neurological autoimmune disease from a neurological condition which is the result of an infection, treatment-related-complications like toxic neuropathies drug abuse and psychiatric diseases. Moreover, they are of help in detecting the recurrence of the disease in already seropositive patients.

However, many patients suspected of suffering from a neurological autoimmune disease, 30 to 40% in the case of PNS, will not have any antibodies detectable by state of the art tests, not in the least because many diagnostically relevant antibodies are still unknown. There is the danger that these patients may be undiagnosed or even be misdiagnosed. In the past, some of them have been sent to psychiatric wards while, with appropriate immunosuppressive treatment, they could have led reasonably normal lives.

SUMMARY OF THE INVENTION

Therefore, the problem underlying the present invention is to provide reagents and methods for the diagnosis of a neurological autoimmune disease and/or cancer, preferably associated with the presence of an autoantibody binding specifically to a mammalian VGLUT.

Another problem underlying the present invention is to distinguish an autoimmune encephalitis and an encephalitis caused by an infection.

Another problem underlying the present invention is to provide an assay with an increased diagnostic reliability, in particular with regard to specificity and/or sensitivity, for the diagnosis for a neurological autoimmune disease or cancer, optionally in combination with state of the art assays.

The problem underlying the present invention is solved by the subject matter as described below.

In a first aspect, the problem underlying the present invention is solved by a method comprising the step detecting in a sample an autoantibody binding specifically to a mammalian VGLUT, preferably the presence or absence of such autoantibody.

In a second aspect, the problem underlying the present invention is solved by a method for isolating an antibody binding to a mammalian VGLUT, comprising the steps
   a) Immobilizing on a carrier a polypeptide comprising a mammalian VGLUT or a variant thereof,
   b) contacting a sample comprising antibodies with the polypeptide under conditions compatible with formation of a complex, wherein said antibody binds to said polypeptide,
   c) separating the complex formed in step a) from the sample, and
   d) separating the antibody from the polypeptide.

In a third aspect, the problem underlying the present invention is solved by a method comprising the steps
   a) Immobilizing a polypeptide comprising mammalian VGLUT or a variant thereof on a carrier,
   b) contacting the carrier with a liquid, wherein a candidate drug is present and/or the liquid does not comprise a sample from a subject to be diagnosed, comprising an antibody binding specifically to a mammalian VGLUT,
   c) contacting the carrier with a means for detecting an immobilized antibody, and
   d) detecting the presence, preferably in quantitative manner.
   e) Optionally determining whether the autoantibody binds to a mammalian VGLUT under non-physiological conditions or studying the interaction of the autoantibody with a mammalian VGLUT and/or its effects, preferably in the presence of a candidate drug.

In a fourth aspect, the problem is solved by an autoantibody binding specifically to a mammalian VGLUT, preferably in a solution comprising one or more, more preferably all from the group comprising an artificial buffer, a stabilizer, a preservative and an artificial anticoagulant.

In a fifth aspect, a diagnostically useful carrier with a solid phase with an immobilized polypeptide comprising a mammalian VGLUT or a variant thereof and a) a negative control and/or b) at least one additional diagnostically useful antigen, wherein the polypeptide and the negative control or additional antigen are spatially separate on the carrier, or a first diagnostically useful carrier with an solid phase with an immobilized polypeptide comprising a mammalian VGLUT or a variant thereof and a second diagnostically useful carrier comprising a solid phase with an immobilized a) negative control and/or b) at least one additional immobilized antigen or a variant thereof.

In a preferred embodiment, at least one additional antigen is at least one antigen, preferably all antigens from the group comprising NMDAR, Lgl1, AMPA1, AMPA2, CASPR2, GABA B, GABA A, DPPX, IGLON5, Hu, Yo, CV2/CRMP5, Ri, Ma2, Amphiphysin, Recoverin, RGS8, DAGLA, STX1B, AK5, AP3B2, Flotillin1+2, GRM1, GRM2, GRM5, GLURD2, ITPR1, KCNA2, NCDN, Septin 3+5+6+7+11 and Sez6L2.

In a sixth aspect, the problem is solved by a use of a) the autoantibody according to the described embodiment or b) of the combination of a mammalian VGLUT and a means for detecting or capturing an IgG antibody or c) the carrier according to the described embodiments for diagnosing a neurological autoimmune disease or a cancer.

In a 7th aspect, the problem is solved by a kit comprising a polypeptide comprising a mammalian VGLUT or a variant thereof and A) a diagnostically useful carrier, preferably according to the described embodiments, or B) a second polypeptide comprising a mammalian VGLUT or a variant thereof, wherein in the case of A)
   a) the polypeptide is immobilized on a diagnostically useful carrier, preferably according to the present invention, and the kit further comprises a means for detecting an antibody binding specifically to a mammalian VGLUT,
   b) the polypeptide and the carrier are configured for immobilizing the polypeptide on the surface of the carrier, preferably via an affinity tag and a ligand binding to the affinity tag, and the kit further comprises a means for detecting an immobilized antibody binding specifically to the mammalian VGLUT.
   c) the carrier comprises a means for capturing an antibody and the kit further comprises a means for detecting a captured antibody binding specifically to the transporter, which is preferably polypeptide comprising a detectable label,
   d) the carrier and a means for capturing an antibody are configured for immobilizing the means for capturing an antibody on the surface of the carrier, preferably via an affinity tag and a ligand binding to the affinity tag, and the kit further comprises a means for detecting a captured antibody binding specifically to the mammalian VGLUT, which is preferably the polypeptide comprising a detectable label,
      wherein in the case of B) the polypeptide comprising a mammalian VGLUT or a variant thereof comprises a first detectable label and the second polypeptide comprising a mammalian VGLUT or a variant thereof comprises a second detectable label or is configured from immobilization on a surface,
and preferably one or more, more preferably al from the group comprising a recombinant antibody binding to a mammalian VGLUT or a variant thereof, an isolated autoantibody binding to a mammalian VGLUT, a chemical solution reactive with a detectable label, a positive control, a negative control, a water-tight vessel for incubating a sample with a carrier or reagent, a wash buffer, and a calibrator, preferably a set of calibrators.

In an 8th aspect, the problem is solved by use of a polypeptide comprising a mammalian VGLUT or a variant thereof or an autoantibody binding specifically to a mammalian VGLUT or a recombinant antibody binding specifically to a mammalian VGLUT for the manufacture of a kit or medical device, preferably diagnostic device, for the diagnosis of a disease.

In a 9th aspect, the problem is solved by a use of an autoantibody binding specifically to a mammalian VGLUT or a recombinant antibody binding specifically to a mammalian VGLUT, which is preferably recognized by secondary antibodies to human IgG class immunoglobulins, as a positive control for the detection of an autoantibody binding specifically to a mammalian VGLUT in a sample.

In a 10th aspect, the problem is solved by an ex vivo method for removing an autoantibody binding specifically to a mammalian VGLUT from blood, preferably serum of a patient.

In a preferred embodiment, the polypeptide is a recombinant, Isolated and/or purified polypeptide.

In a preferred embodiment, the antibody or autoantibody is a mammalian, preferably human autoantibody or the sample is a mammalian, preferably human sample comprising a representative set of antibodies, preferably selected from the group comprising whole blood, plasma, serum, cerebrospinal fluid and saliva. In a preferred embodiment, the autoantibody or complex is detected using a detection method selected from the group comprising immunodiffusion, immunoelectrophoresis, light scattering immunoassays, agglutination, labeled immunoassays such as those from the group comprising radiolabeled immunoassay, enzyme immunoassays, more preferably ELISA, chemiluminescence immunoassays, preferably electrochemiluminescence immunoassay, and immunofluorescence, preferably indirect immunofluorescence.

In a preferred embodiment, the carrier is selected from the group comprising a glass slide, preferably for microscopy, a biochip, a microtiter plate, a lateral flow device, a test strip, a membrane, preferably a line blot, a chromatography column and a bead, preferably a magnetic or fluorescent bead.

The invention also includes the following embodiments:
1. A method comprising the step detecting in a sample an autoantibody binding specifically to a mammalian VGLUT.
2. A method for isolating an antibody binding to a mammalian VGLUT, comprising the steps
   a) immobilizing on a carrier a polypeptide comprising a mammalian VGLUT or a variant thereof.
   b) contacting a sample comprising antibodies with the polypeptide under conditions compatible with formation of a complex, wherein said antibody binds to said polypeptide,
   c) separating the complex formed in step a) from the sample, and
   d) separating the antibody from the polypeptide.
3. A method comprising the steps
   a) immobilizing a polypeptide comprising a mammalian VGLUT or a variant thereof on a carrier,
   b) contacting the carrier with a liquid, wherein a candidate drug is present and/or the liquid does not comprise a sample from a subject to be diagnosed, comprising an antibody binding specifically to a mammalian VGLUT,
   c) contacting the carrier with a means for detecting an immobilized antibody, and
   d) detecting the presence, preferably in quantitative manner.
4. An autoantibody binding specifically to a mammalian VGLUT, preferably in a solution comprising one or more, preferably all from the group comprising an artificial buffer, a stabilizer, a preservative and an artificial anticoagulant.
5. A diagnostically useful carrier with a sold phase with an immobilized polypeptide comprising a mammalian VGLUT or a variant thereof and a) a negative control and/or b) at least one additional diagnostically useful antigen, wherein the polypeptide and the negative control or additional antigen are spatially separate on the carrier,
or a first diagnostically useful carrier with a solid phase with an immobilized polypeptide comprising a mammalian VGLUT or a variant thereof and a second diagnostically useful carrier comprising a solid phase with an immobilized a) negative control and/or b) at least one additional polypeptide comprising an immobilized antigen or a variant thereof.
6. The carrier according to embodiment 5, wherein the at least one additional antigen is at least one antigen, preferably all antigens from the group comprising NMDAR, Lgl1, AMPA1, AMPA2, CASPR2, GABA B, GABA A, DPPX, IGLON5, Hu, Yo, CV2/CRMP5, Ri, Ma2, Amphiphysin, Recoverin, RGS8, DAGLA, STX1B, AK5, AP3B2, Flotillin1+2, GRM1, GRM2, GRM5, GLURD2, ITPR1, KCNA2, NCDN, Septin 3+5+6+7+11 and Sez6L2.
7. A use of a) the autoantibody according to embodiment 4 or b) of the combination of a polypeptide comprising a mammalian VGLUT and a means for detecting or capturing an IgG antibody or c) the carrier according to any of embodiments 5 to 6 for diagnosing a neurological autoimmune disease or a cancer.
8. A kit comprising a polypeptide comprising a mammalian VGLUT or a variant thereof and A) a diagnostically useful carrier, preferably according to any of embodiments 5 to 6, or B) a second polypeptide comprising a mammalian VGLUT or a variant thereof, wherein in the case of A)
   a) the polypeptide is immobilized on a diagnostically useful carrier, preferably according to any of embodiments 5 to 6, and the kit further comprises a means for detecting an antibody binding specifically to the mammalian VGLUT,
   b) the polypeptide and the carrier are configured for immobilizing the polypeptide on the surface of the carrier, preferably via an affinity tag and a ligand binding to the affinity tag, and the kit further comprises a means for detecting an immobilized antibody binding specifically to the mammalian VGLUT.
   c) the carrier comprises a means for capturing an antibody and the kit further comprises a means for detecting an antibody binding specifically to the mammalian VGLUT, preferably the polypeptide comprising a detectable label, or
   d) the carrier and a means for capturing an antibody are configured for immobilizing the means for capturing an antibody on the surface of the carrier, preferably via an affinity tag and a ligand binding to the affinity tag, and the kit further comprises a means for detecting an antibody binding specifically to the mammalian VGLUT, preferably the polypeptide comprising a mammalian VGLUT or a variant thereof comprising a detectable label,
   wherein in the case of B) the polypeptide comprising a mammalian VGLUT or a variant thereof comprises a detectable label and the second polypeptide comprising a mammalian VGLUT or a variant thereof comprises a detectable label or is configured for immobilization on a surface,
   and preferably one or more, more preferably all from the group comprising a recombinant antibody binding to a mammalian VGLUT or a variant thereof, an isolated autoantibody binding to a mammalian VGLUT, a chemical solution reactive with a detectable label, a positive control, a negative control, a water-tight vessel for incubating a sample with a carrier or reagent, a wash buffer, and a calibrator, preferably a set of calibrators.
9. A use of a polypeptide comprising a mammalian VGLUT or a variant thereof or an autoantibody binding specifically to a mammalian VGLUT or a recombinant antibody binding specifically to a mammalian VGLUT for the manufacture of a kit or medical device, preferably diagnostic device, for the diagnosis of a disease.
10. A use of an autoantibody binding specifically to a mammalian VGLUT or a recombinant antibody binding specifically to a mammalian VGLUT, which is preferably recognized by secondary antibodies to human IgG class immunoglobulins, as a positive control for the detection of an antibody binding specifically to a mammalian VGLUT in a sample.

11. An ex vivo method for removing an autoantibody binding specifically to a mammalian VGLUT from blood, preferably serum of a patient.

12. The method, carrier, use or kit according to any of the preceding embodiments, wherein the polypeptide is a recombinant, isolated and/or purified polypeptide.

13. The method, carrier, use or kit according to any of the preceding embodiments, wherein the antibody or autoantibody is a mammalian, preferably human autoantibody or the sample is a mammalian, preferably human sample comprising a representative set of antibodies, preferably selected from the group comprising whole blood, plasma, serum, cerebrospinal fluid and saliva.

14. The method, carrier, use or kit according to any of the preceding embodiments, wherein the autoantibody or complex is detected using a detection method selected from the group comprising immunodiffusion, electrophoresis, light scattering immunoassays, agglutination, labeled immunoassays such as those from the group comprising radiolabeled immunoassay, enzyme immunoassays, more preferably ELISA, chemiluminescence immunoassays, preferably electrochemiluminescence immunoassay, and immunofluorescence, preferably indirect immunofluorescence.

15. The method, carrier, use or kit according to any of the preceding embodiments, wherein the carrier is selected from the group comprising a glass slide, preferably for microscopy, a biochip, a microtiter plate, a lateral flow device, a test strip, a membrane, preferably a line blot, a chromatography column and a bead, preferably a magnetic or fluorescent bead.

BRIEF DESCRIPTION OF THE DRAWINGS

FIG. 11A shows sequences of His-GST-VGLUT2 aa 520-564 WT fragment (SEQ ID NO: 66), mutated His-GST-VGLUT2/1 fragments (Mut 1-3) (SEQ ID NOs: 71, 72, 73) and His-GST-VGLUT1 aa 491-580 WT fragment (SEQ ID NO: 100).

DETAILED DESCRIPTION OF THE INVENTION

Figure 1:
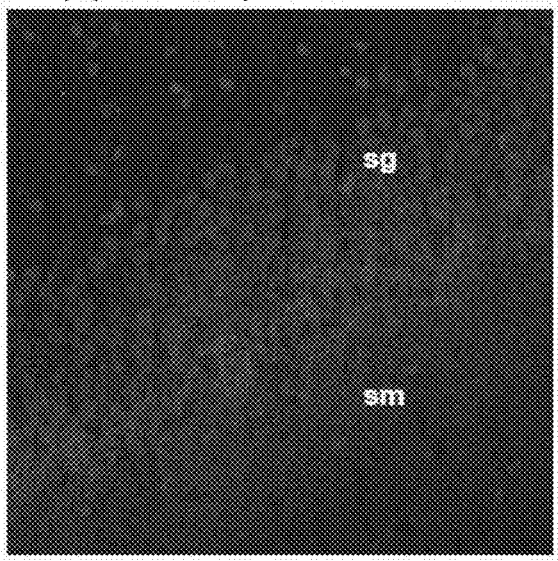
FIG. 1 shows the immunofluorescence staining of neuronal tissues.
Figure 1:
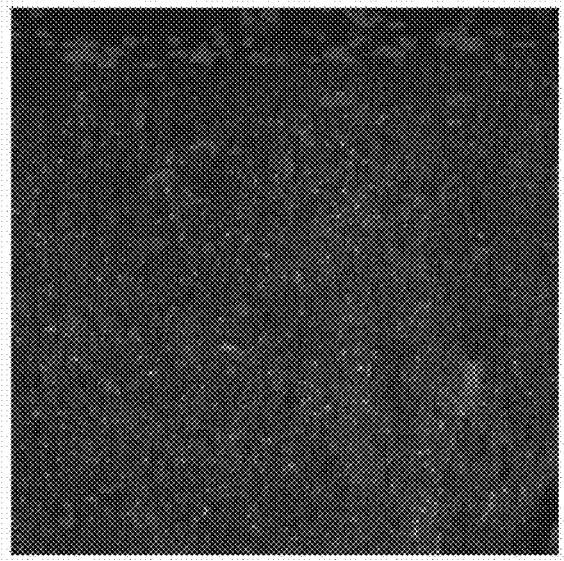
Figure 1:
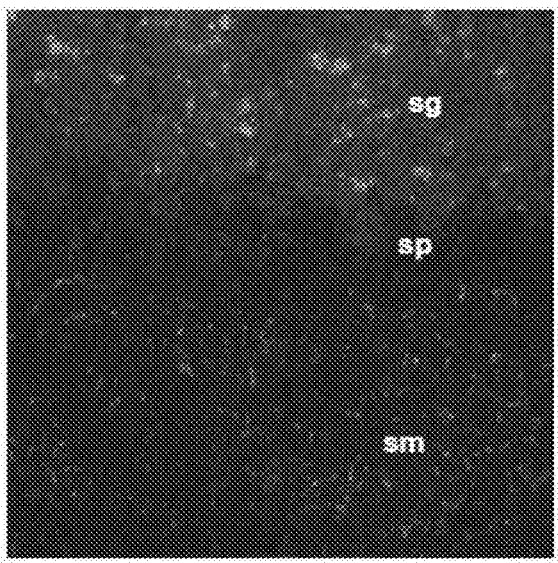
Figure 1:
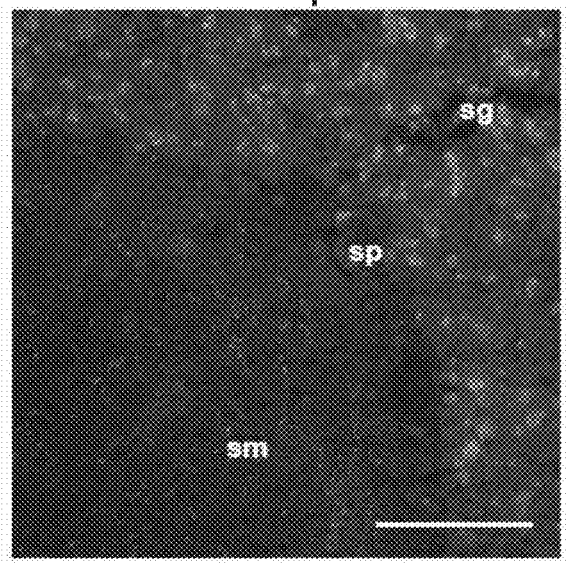

The present invention is based on the inventors' surprising finding that antibodies to mammalian VGLUTs exist and can be detected in samples from patients suffering from a neurological autoimmune disease and/or cancer, but not in samples from healthy subjects. Hence, they can be used for the diagnosis of or to aid in the diagnosis of diseases.

Mammalian VGLUTs (VGLUTs) are a group of membrane proteins which, in humans, comprises VGLUT1, VGLUT2 and VGLUT3.

SEQ ID NO: 1 represents the sequence of VGLUT2, also referred to as solute carrier family 17 member 6 [SLC17A6] or differentiation-associated BNPI [DNPI], an integral protein of the vesicular membrane. Its twelve transmembrane helices (TM1-12) form a positively charged central hole through which glutamate is transported into the vesicular lumen (Li F. et al. Science. 2020, 368:893-897). Upon vesicle fusion with the plasma membrane during glutamate exocytosis, VGLUT2 is translocated from the synaptic vesical to the presynaptic plasma membrane. The N- and C-terminal regions of VGLUT2 (aa1-71 [SEQ ID NO: 16] and aa499-582 [SEQ ID NO: 19], respectively) are facing the cytoplasm. Furthermore, Its structure contains two larger loops (>20 aa), one between TM1 and TM2 (aa 93-125 [SEQ ID NO: 17]) facing the vesicular lumen (or the extracellular space after exocytosis) and one between TM6 and TM7 (aa 268-310 [SEQ ID NO: 18]), which includes two intracellular helical domains (ICH1 and ICH2) facing the cytoplasm.

VGLUT2 facilitates the uptake of glutamate into synaptic vesicles at presynaptic nerve terminals of excitatory neurons (Fremeau R T et al. Neuron. 2001, 31:247-80 and Herzog E et al. J Neurosci. 2001, 21:RC181). VGLUT2 is broadly expressed in brain and spinal cord, predominantly in deeper brain regions including the thalamus and the brainstem but also in a subpopulation of neurons of the cerebellum and hippocampus and plays various roles in many different neuronal circuitries (Kaneko T et al. J. Comp. Neurol., 2002; 444, 39-62). A number of diseases have been linked to malfunctioning glutamate signaling, including schizophrenia, depression, Alzheimer's disease, and amyotrophic lateral sclerosis (Chen J et al. Biol Psychiatry. 2006, 59:1180-8; Nestler et al. Neuron. 2002, 34:13-25; Kashani A et al. Neurobiol Aging. 2008, 29:1619-30; Wootz H et al. Neurobiol Dis. 2010, 37:58-46).

In mice selectively depleted of Vglut2 in the cortex, hippocampus, and amygdala schizophrenia-like behavioral deficits were observed. (Wallen-Mackenzie A et al. J Neurosci. 2009, 29:2238-51). Vglut2+/− heterozygous knockout mice, which show a VGLUT2 expression of around 50%, exhibited altered neuropathic pain responses and enhanced sensitivity to clonic epileptic seizures (Leo S et al. Eur J Pain. 2009, 13:1008-17, Schallier A et al. Neurochem Int. 2009, 55:41-4)

Known Interaction partners of VGLUT2 are the clathrin adaptor proteins AP-1, AP-2 and AP-3 which regulate VGLUT2 recycling via endocytosis. (Haiyan L et al. Front Cell Neurosci. 2017, 11:324)

Human VGLUT2 shares 80% and 78% sequence identity to human VGLUT1 and VGLUT3, respectively. VGLUT1 and VGLUT3 also function as vesicular glutamate transporter in excitatory neurons lacking VGLUT2 (Bellocchio E et al. Science. 2000, 289:957-80: Takamori S et al. Nature. 2000, 407:189-94; Fremeau Jr R, et al., Proc. Natl. Acad. Sci. U.S.A., 2002, 99:14488-14493: Gras C. et al. J. Neurosci., 2002, 22:5442-5451). The structures of VGLUT1 and 3 are similar to VGLUT2, and contain also twelve transmembrane helices with the N- and C-terminal regions facing the cytoplasm.

In a preferred embodiment, the mammalian VGLUT is from a mammal selected from the group comprising a human, a non-human primate, a rodent, a cow, a horse, a dog, a cat, a bear, a donkey, a sheep, a goat, a camel and a dromedary, more preferably a human. In another preferred embodiment, the mammalian VGLUT comprises a polypeptide having SEQ ID NO: 15 or a variant thereof and has preferably a length of at least 200, 300, 400, 500, 520, 539, 540, 550 or 580 amino acids. In a preferred embodiment the mammalian VGLUT is a human transporter selected from the group comprising SEQ ID NO: 1, SEQ ID NO: 13 and SEQ ID NO: 14, preferably SEQ ID NO: 1. In a preferred embodiment the mammalian VGLUT is SEQ ID NO: 1. In a preferred embodiment the mammalian VGLUT is SEQ ID NO: 13. In a preferred embodiment the mammalian VGLUT is SEQ ID NO: 14. In another preferred embodiment, the mammalian VGLUT is a rat VGLUT selected from the group comprising SEQ ID NO: 20, SEQ ID NO: 21 and SEQ ID NO: 22. For practicing the invention, the mammalian VGLUT is preferably comprised by a recombinant polypeptide.

In a preferred embodiment, the method according to the present invention comprises the step providing the carrier according to the present invention. A polypeptide comprising a mammalian VGLUT or a variant thereof may be immobilized on a solid surface of the carrier or It may be configured for immobilization on the carrier, which may be done at a later stage, but before removing the sample and washing the carrier. The polypeptide comprising the mammalian VGLUT, immobilized on the carrier or not, may then be contacted with the sample suspected of comprising the antibody to the mammalian VGLUT under conditions allowing for binding of any antibodies. The sample may then be removed and the carrier may be washed to remove any remaining sample. A means for detecting the antibody such as a secondary antibody carrying a detectable label such as a fluorescent dye or enzymatically active label may then be contacted with the carrier under conditions allowing formation of a complex between any bound autoantibody and the means. The carrier may be washed again. Finally, the presence of the autoantibody is detected by checking whether the means such as a secondary antibody can be detected. Preferably an ELISA microtiter plate or an immunofluorescence assay using a mammalian cell or tissue expressing a polypeptide comprising a mammalian VGLUT or a variant thereof is used. In the case of immunofluorescence, a distinct pattern determined by the expression pattern of the transporter in the cell or the tissue indicates the presence of the antibody, as carried out or shown in the examples. In the case of an ELISA or another semi-quantitative or quantitative detection method a value above a cut off value determined as known in the art indicates the presence of the antibody.

A competitive assay, a capture bridge assay, an immunometric assay, a class-specific second antibody on the solid phase, a direct or indirect class capture assay may also be used. The principle of each of these formats is detailed in The Immunoassay Handbook, 3rd edition, edited by David Wild, Elsevier, 2005. Briefly, in a competitive format, the antibody to be detected may compete with a recombinant antibody for binding sites on the antigen, which is the mammalian VGLUT or a variant thereof. Alternatively, a sample comprising the antibody may be preincubated with the antigen, preferably a polypeptide comprising a mammalian VGLUT, followed by exposure to immobilized antigen or antigen configured for immobilization in one reaction and may be exposed to the antigen without pre-incubation with the antigen in another reaction to show specific binding. In a capture bridge assay, two antigen molecules bind to two antigen binding sites on one molecule of the (auto)antibody to be detected. One of the antigen molecules is labeled and the other one also labeled, preferably with a second label emitting a signal when interacting with the label of the other antigen molecule, immobilized or configured for immobilization, preferably via an affinity tag and a ligand binding specifically to said affinity tag. In an immunometric assay, the antibody to be detected binds to the antigen, which is Immobilized after or before the binding. The antibody is detected using a means for detecting an antibody such as a labeled secondary antibody. In a direct class capture assay, the antibody to be detected is immobilized using a means for capturing an antibody and detected using a labeled antigen. In an indirect class capture assay, the antibody to be detected is immobilized using a means for capturing an antibody such as a secondary antibody binding all antibodies from the class of the antibody to be detected. It is detected using at least one, preferably two molecules of the antigen which bind to the antibody to be detected, and a means for detecting the antigen such as a labeled secondary antibody.

In a preferred embodiment, the carrier and a means for capturing and/or a means for detecting an antibody are configured for immobilizing the means on the solid surface of the carrier. A particularly preferred way for the configuration or the immobilization is modifying the carrier and/or the means such that they comprise an affinity tag and a ligand to the affinity tag. Alternatively, the carrier or the means may comprise reactive chemical groups such as thiol, amino, epoxide, ester and anhydride groups. In a preferred embodiment, the term "immobilized", as used herein, refers to a molecule bound to a solid carrier insoluble in an aqueous solution, more preferably via a covalent or non-covalent bond, electrostatic interactions, encapsulation, unspecific absorption, printing or entrapment, for example by denaturing a globular polypeptide in a gel, or via hydrophobic interactions, most preferably via one or more covalent bonds. Various suitable carriers, for example paper, polystyrene, metal, silicon or glass surfaces, microfluidic channels, membranes, beads such as magnetic beads, column chromatography media, biochips, polyacrylamide gels and the like have been described in the literature, for example in Kim. D., and Herr, A. E. (2013), Protein immobilization techniques for microfluidic assays, Biomicrofluidics 7(4), 041501. This way, the immobilized molecule, together with the insoluble carrier, may be separated from an aqueous solution in a straightforward manner, for example by centrifugation or decanting. An immobilized molecule may be immobilized in a reversible or irreversible manner. For example, the immobilization is reversible if the molecule interacts with the carrier via ionic interactions that can be masked by addition of a high concentration of salt or if the molecule is bound via a cleavable covalent bond such as a disulfide bridge which may be cleaved by addition of thiol-containing reagents. By contrast, the immobilization is irreversible if the molecule is tethered to the carrier via a covalent bond that cannot be cleaved in aqueous solution, for example a bond formed by reaction of an epoxide group and an amine group as frequently used to couple lysine side chains to affinity columns. The protein may be indirectly immobilized, for example by immobilizing an antibody or other entity having affinity to the molecule, followed by formation of a complex to the effect that the molecule-antibody complex is immobilized. Various ways to immobilize molecules are described in the literature, for example in Kim, D., Herr, and A. E. (2013), Protein immobilization techniques for microfluidic assays. Biomicrofluidics 7(4). 041501. In addition, various reagents and kits for immobilization reactions are commercially available, for example from Pierce Biotechnology.

According to the present invention, a cell may be provided, which comprises an expression vector comprising a nucleotide sequence encoding a polypeptide comprising the mammalian VGLUT or a variant thereof under the control of a promotor, optionally a strong and/or inducible promotor. The vector may encode for an N-terminal or C-terminal affinity tag fused to the mammalian VGLUT in a polypeptide comprising the mammalian VGLUT, preferably via a linker sequence. The cell may be cultured under conditions allowing for the expression of the mammalian VGLUT. Any expressed VGLUT may then be purified, preferably using the affinity tag. However, a non-purified VGLUT may also be used in some embodiments. Subsequently it is immobilized on the carrier according to the present invention. In a preferred embodiment, the cell, nucleic acid or vector may be used for the manufacture of a kit for the diagnosis of a neurological autoimmune disease.

According to the present invention, a medical or diagnostic device such as the diagnostically useful carrier may be prepared by expressing a recombinant polypeptide comprising a variant of the mammalian VGLUT comprising an affinity tag, optionally with an artificial linker, which may include a protease cleavage site, in a cell such as a eukaryotic or prokaryotic cell. Contacting the polypeptide with a ligand binding specifically to the affinity tag, which ligand is immobilized on a solid phase, washing the solid phase such that non-specifically bound material from the cell is removed and eluting the expressed variant from the solid phase, preferably by adding an excess of non-immobilized ligand. The variant may then be immobilized on the device. Optionally, the affinity tag may be removed by contacting the variant with a protease, preferably a protease recognizing the protease cleavage site, before the immobilization.

The affinity tag may be selected from the group of tags comprising His, immobilized nickel, glutathione, chitin, 18A, ACP, Aldehyd, Avi, BCCP, Calmodulin, Chitin binding protein, E-Tag, ELK16, FLAG, flash, poly glutamate, poly aspartate, GST, GFP, HA, Isope, maltose binding protein, myc, nus, NE, ProtA, ProtC, Tho1d4, S-Tag, SnoopTag, SpyTag, SofTag, Streptavidin, Strep-tag II, T7 Epitope Tag, TAP, TC, Thioredoxin, Ty, V5, VSV, biotin, Xpress Tag and a recombinant antibody binding to the ligand to an affinity tag. Useful proteases include, but are not limited to TEV, Thrombin, Faktor Xa or Enteropeptidase. Suitable linkers are part of vectors, for example pET vector series (Novagen). SEQ ID NO: 12 is an example.

In a preferred embodiment, the absence or presence of two or more antibodies to two or more antigens is detected simultaneously, i.e. at the same time.

In another preferred embodiment, the presence or absence of at least one autoantibody other than an antibody binding specifically to a mammalian VGLUT is detected, preferably from the group comprising an autoantibody binding specifically to NMDAR, an autoantibody binding specifically to Lgl1, an autoantibody binding specifically to AMPA1, an autoantibody binding specifically to AMPA2, an autoantibody binding specifically to CASPR2, an autoantibody binding specifically to GABA B, an autoantibody binding specifically to GABA A, an autoantibody binding specifically to DPPX, an autoantibody binding specifically to IGLON5, an autoantibody binding specifically to Hu, an autoantibody binding specifically to Yo, an autoantibody binding specifically to CRMP5, an autoantibody binding specifically to Ri, an autoantibody binding specifically to Ma2, an autoantibody binding specifically to Amphiphysin, an autoantibody binding specifically to Recoverin, an autoantibody binding specifically to RGS8, an autoantibody binding specifically to DAGLA, an autoantibody binding specifically to NSF, an autoantibody binding specifically to STX1B, an autoantibody binding specifically to DNM1, an autoantibody binding specifically to VAMP2, an autoantibody binding specifically to Anna-3, an autoantibody binding specifically to Zic-4, an autoantibody binding specifically to SOX1 (U.S. Pat. No. 7,314,721), an autoantibody binding specifically to PCA2, an autoantibody binding specifically to Tr, an autoantibody binding specifically to glutamic acid decarboxylase, an autoantibody binding specifically to AK5, an autoantibody binding specifically to AP3B2, an autoantibody binding specifically to Flotillin1/2, an autoantibody binding specifically to GRM1, an autoantibody binding specifically to GRM2, an autoantibody binding specifically to GRM5, an autoantibody binding specifically to GLURD2, an autoantibody binding specifically to ITPR1, an autoantibody binding specifically to KCNA2, an autoantibody binding specifically to NCDN, an autoantibody binding specifically to Septin 3+5+6+7+11 and an autoantibody binding specifically to Sez6L2. In a preferred embodiment, the detection of the presence of any of these autoantibodies aid in the diagnosis or implies a diagnosis of a neurological autoimmune disease. In a preferred embodiment, two or more autoantibodies are detected in the same sample and preferably essentially simultaneously. The carrier according to the present invention may be configured for detecting two or more autoantibodies in the same sample, preferably essentially simultaneously.

In a preferred embodiment, the presence or absence of two or more antibodies is detected and can be distinguished. In other words, a signal indicating the presence of an antibody indicates which of the two antibodies is present. In a preferred embodiment, the absence or presence of two or more antibodies is detected in spatially separate reactions, more preferably in different reaction mixtures in separate vessels. In another preferred embodiment, a signal indicating the presence of one of the two autoantibodies may be distinguished from a signal indicating the presence of the other autoantibody. This may be achieved by using different detectable labels, more preferably distinguishable fluorophores. For example, a fluorophore emitting green light and another one emitting red light may be used.

In a preferred embodiment, the presence or absence of two or more antibodies is detected, but cannot be distinguished. In a preferred embodiment, their absence or presence is detected in a one pot reaction, preferably in two or more reactions in the same reaction vessel without spatial separation, and with no signal distinction. In other words, a signal indicates that at least one of the two antibodies is present, but not which one. In a preferred embodiment, two or more autoantigens may be present in a mixture.

In a preferred embodiment, the sample comprises a representative set of antibodies, more preferably IgG. IgA and IgM class antibodies, most preferably IgG class antibodies. It is preferably selected from the group comprising whole blood, plasma, serum, cerebrospinal fluid and saliva. The sample may be a liquid sample or a dried blood spot made using the sample, preferably whole blood, plasma, serum or capillary blood, preferably capillary blood.

In a preferred embodiment, the sample is from an organism having a brain and producing autoantibodies, preferably from the group comprising mammal and birds, more preferably a mammal from the group comprising a human, a non-human primate, a rodent, a cow, a horse, a dog, a cat, a bear, a donkey, a sheep, a goat, a camel and a dromedary, most preferably a human. In another preferred embodiment it is from a bird, more preferably from the group comprising a chicken, a parrot and a falcon. The animal may have gone through extensive training, for example for assisting people in need, for riding or for hunting.

The autoantibody to be detected or a means for detecting or capturing an antibody binds specifically to its interaction partner, which is an autoantigen in the case of an autoantibody or an antibody in the case of a means for detecting an antibody, preferably the autoantibody binding specifically to the mammalian VGLUT. In a preferred embodiment, the term "binding specifically", as used herein, preferably means that the binding reaction is stronger than a binding reaction characterized by a dissociation constant of $1\times10^{-5}$ M, more preferably $1\times10^{-7}$ M, more preferably $1\times10^{-8}$ M, more preferably $1\times10^{-9}$ M, more preferably $1\times10^{-10}$ M, more preferably $1\times10^{-11}$ M, more preferably $1\times10^{-12}$ M, as determined by surface plasmon resonance using Biacore equipment at 25° C. in PBS buffer at pH 7.

In a preferred embodiment, the term "autoantibody", as used herein, refers to an antibody which binds specifically to a structure, preferably an autoantigen, from the organism which produces said antibody. The organism is preferably a patient suspected of or actually suffering from a disease, preferably a mammalian, more preferably human patient. Such an autoantibody has a constant region, as have other antibodies of the same class from the same organism. Particularly preferably, the autoantibody is a mammalian (auto)antibody, even more preferably a human (auto)antibody, even more preferably a human (auto)antibody of class IgG, IgM or IgA, preferably IgG. The variable domain is capable of binding specifically against the autoantigen. The constant domain binds specifically to molecules recognizing the constant domain of IgG class antibodies such as secondary antibodies. It has sequence elements shared by other IgG class antibodies from the same organism, which may comprise SEQ ID NO: 23 or a variant thereof.

According to the present invention, an antibody binding specifically to the mammalian VGLUT is provided or isolated. The person skilled in the art is familiar with the isolation or purification of antibodies. Comprehensive Instructions are available in the prior art, for example in Affinity Chromatography Vol. 1 Antibody by GE Healthcare, www.gelifesciences.com. April 2016 and Thermo Scientific Pierce Antibody Production and Purification Technical Handbook, Version 2, www.thermoscientific.com. For example, specific purification steps may involve affinity chromatography using a polypeptide comprising the mammalian VGLUT or a variant thereof immobilized to beads by coupling using primary amines and/or Protein G.

The teachings of the present invention may not only be carried out using the polypeptides, in particular a polypeptide comprising the native sequence of a polypeptide referred to such as the mammalian VGLUT or nucleic acids having the exact sequences referred to in this application explicitly, for example by function, name, sequence or accession number, or implicitly, but also using variants of such polypeptides or nucleic acids.

In a preferred embodiment, the term 'variant', as used herein, may refer to at least one fragment of the full length sequence referred to, more specifically one or more amino acid or nucleic acid sequence which is, relative to the full-length sequence, truncated at one or both termini by one or more amino acids. Such a fragment comprises or encodes for a peptide having at least 6, 7, 8, 10, 12, 15, 20, 25, 50, 75, 100, 150, 200, 300, 400, 500, 600, 620, 640, or 680 successive amino acids of the original sequence or a variant thereof. The total length of the variant may be at least 6, 7, 8, 9, 10, 11, 12, 20, 25, 30, 40, 50, 60, 70, 80, 90, 100, 200, 300, 400, 450, 500, 520, 540, 580, 580, 600, 610, 620, 630, 640, 650, 680 or 670 or more amino acids.

The term "variant" relates not only to at least one fragment, but also to a polypeptide or a fragment thereof comprising amino acid sequences that are at least 40, 50, 60, 70, 75, 80, 85, 90, 92, 94, 95, 96, 97, 98, 99, 99.3, 99.4, 99.5, 99.6, 99.7, 99.8 or 99.9, preferably at least 99.3% identical to the reference amino acid sequence referred to or the fragment thereof, wherein amino acids other than those essential for the biological activity, for example the ability of an antigen to bind to an (auto)antibody, or the fold or structure of the polypeptide are deleted or substituted and/or one or more such essential amino acids are replaced in a conservative manner and/or amino acids are added such that the biological activity of the polypeptide is preserved. The state of the art comprises various methods that may be used to align two given nucleic acid or amino acid sequences and to calculate the degree of identity, see for example Arthur Lesk (2008), Introduction to bioinformatics, Oxford University Press, 2008, 3rd edition. In a preferred embodiment, the ClustalW software (Larkin, M. A., Blackshields, G., Brown, N. P., Chenna, R., McGettigan, P. A., McWilliam, H., Valentin, F., Wallace, I. M., Wilm, A., Lopez, R., Thompson, J. D., Gibson, T. J., Higgins, D. G. (2007). Clustal W and Clustal X version 2.0. Bioinformatics, 23, 2947-2948) is used using default setting.

In a preferred embodiment, the polypeptide and variants thereof may, in addition, comprise chemical modifications, for example isotopic labels or covalent modifications such as glycosylation, phosphorylation, acetylation, decarboxylation, citrullination, methylation, hydroxylation and the like. The person skilled in the art is familiar with methods to modify polypeptides. Any modification is designed such that it does not abolish the biological activity of the variant.

Moreover, variants may also be generated by N- or/and C-terminal fusion of polypeptides, fragments or variants thereof with other known polypeptides or variants thereof or artificial sequences such as linkers and comprise active portions or domains, preferably having a sequence identity of at least 70, 75, 80, 85, 90, 92, 94, 95, 96, 97, 98 or 99% when aligned with the active portion of the reference sequence, wherein the term "active portion", as used herein, refers to an amino acid sequence, which is less than the full length amino acid sequence or, in the case of a nucleic acid sequence, codes for less than the full length amino acid sequence, respectively, and/or is a variant of the natural sequence, but retains at least some of the biological activity. Preferably the active portion is an active portion of the mammalian VGLUT. The polypeptide may comprise additional sequences, preferably artificial sequences for example inkers or binding epitopes. Any fused sequences are chosen such that the ability of the VGLUT or a variant thereof to bind specifically to the antibody to be detected or the diagnostic reliability, in particular sensitivity and/or specificity, is not significantly altered, let alone abolished. Exemplary fragments to which an autoantibody according to the present invention binds or that may be used to detect such autoantibody include SEQ ID NO: 101, SEQ ID NO: 102 and SEQ ID NO: 103.

In a preferred embodiment, the term "variant" of a nucleic acid comprises nucleic acids the complementary strand of which hybridizes, preferably under stringent conditions, to the reference or wild type nucleic acid. Stringency of hybridization reactions is readily determinable by one of ordinary skilled in the art, and in generally is an empirical calculation dependent on probe length, washing temperature and salt concentration. In general longer probes require higher temperatures for proper annealing, while shorter probes less so. Hybridization generally depends on the ability of denatured DNA to reanneal to complementary strands present in an environment below their melting temperature: The higher the degree of desired homology between the probe and hybridizable sequence, the higher the relative temperature which may be used. As a result it follows that higher relative temperatures would tend to make the reaction conditions more stringent, while lower temperature less so. For additional details and explanation of stringency of hybridization reactions, see Ausubel, F. M. (1995), Current Protocols in Molecular Biology. John Wiley & Sons, Inc. Moreover, the person skilled in the art may follow the instructions given in the manual Boehringer Mannheim GmbH (1993) The DIG System Users Guide for Filter Hybridization, Boehringer Mannheim GmbH, Mannheim, Germany and in Liebl, W., Ehrmann, M., Ludwig, W., and Schleifer, K. H. (1991) International Journal of Systematic Bacteriology 41: 255-260 on how to identify DNA sequences by means of hybridization. In a preferred embodiment, stringent conditions are applied for any hybridization, i.e. hybridization occurs only if the probe is 70% or more identical to the target sequence. Probes having a lower degree of identity with respect to the target sequence may hybridize, but such hybrids are unstable and will be removed in a washing step under stringent conditions, for example lowering the concentration of salt to 2×SSC or, optionally and subsequently, to 0.5×SSC, while the temperature is, in order of increasing preference, approximately 50° C.-68° C., approximately 52° C.-68° C., approximately 54° C.-68° C., approximately 56° C.-68° C., approximately 58° C.-68° C., approximately 60° C.-68° C., approximately 62° C.-68° C., approximately 64° C.-68° C. approximately 66° C.-68° C. In a particularly preferred embodiment, the temperature is approximately 64° C.-68° C. or approximately 66° C.-68° C. It is possible to adjust the concentration of salt to 0.2×SSC or even 0.1×SSC. Nucleic acid sequences having a degree of identity with respect to the reference or wild type sequence of at least 70, 80, 90, 91, 92, 93, 94, 95, 96, 97, 98, 99% may be isolated. In a preferred embodiment, the term variant of a nucleic acid sequence, as used herein, refers to any nucleic acid sequence that encodes the same amino acid sequence, preferably a mammalian VGLUT and variants thereof, as the reference nucleic acid sequence, in line with the degeneracy of the genetic code.

In a preferred embodiment, the term "sensitivity" refers to the number of samples correctly determined as positive relative to the total number of samples examined. In a preferred embodiment, the term "specificity" refers to number of samples correctly determined as negative relative to the total number of samples examined.

The variant of the polypeptide, more specifically the mammalian VGLUT has biological activity. In a preferred embodiment, such biological activity is the ability to bind specifically to an autoantibody binding specifically to the mammalian VGLUT, as found in a patient suffering from a neurological autoimmune disease associated with the presence of such autoantibody in a sample, preferably selected from the group comprising PNS, cerebellar ataxia, gait ataxia, polyneuropathy, encephalitis, preferably limbic encephalitis, epilepsy, dementia, cerebellar syndrome and hypersensitive encephalopathy and cancers such as leukemia, graft versus host disease and non-Hodgkin lymphoma. For example, whether or not a variant of the polypeptide has such biological activity may be checked by determining whether or not it binds specifically to an autoantibody from a sample of such a patient comprising an autoantibody binding specifically to wild type autoantigen, preferably as determined by indirect immunofluorescence as described in the experimental section of this application. In a preferred embodiment, the person skilled in the art will, when designing variants consider that domains exposed to the cytoplasm or extracellular space, in particular SEQ ID NO: 16, SEQ ID NO: 17, SEQ ID NO: 18 and SEQ ID NO: 19, are likely to contain epitopes of the autoantibody to be detected.

According to the present invention, a cell is provided which overexpresses a polypeptide comprising the mammalian VGLUT or a variant thereof, preferably in combination with at least one additional cell which overexpresses another autoantigen from the group comprising Hu, Yo, Ri, CV2, PNMA1, PNMA2, DNER/Tr, ARHGAP28, ITPR1 (EP14003703.7), ATP1A3, NBC1 (EP14003958.7), Neurochrondrin (EP15001188), CARPVIII, Zic4, SOX1 (U.S. Pat. No. 7,314,721), Ma, MAG, MP0, MBP, GAD65, amphiphysin, recoverin, GABA A receptor, GABA B receptor, glycine receptor, gephyrin, IgLON5, DPPX, aquaporin-4, MOG, NMDA receptor, AMPA receptors, GRM1, GRM5, LGl1, VGCC, mGluR1, CASPR2, ATP1A3, also referred to as alpha 3 subunit of human neuronal Na(+)/K(+) ATPase (EP14171581.5) and Flotillin1/2 (EP3101424) a variant thereof comprised in a polypeptide.

In a preferred embodiment, the term "overexpressing", as used herein, means that the cell has been transfected with a nucleic acid that comprises a nucleic acid sequence encoding a polypeptide comprising the mammalian VGLUT or the other autoantigen or a variant thereof under the control of a promotor. Consequently, the transfected cell expresses more polypeptide recognized by the autoantibody binding specifically to be detected than the same type of cell normally would, probably at least 10, 20, 30, 50, 100, or 500% more as judged by quantitative Western Blot. The promotor may be an inducible promotor, which allows for the induction of expression by addition of an inducer. The person skilled in the art is familiar with protocols and vectors for transiently overexpressing a polypeptide in a eukaryotic cell, for example the pTriEx system from Novagen and with protocols and vectors for stably transfecting a eukaryotic cell, for example the pcDNA™4/TO vector system from Invitrogen.

In a preferred embodiment, a fixed mammalian cell may be used. In a preferred embodiment, the term "fixed" cell, as used herein, refers to a cell that has been treated with a reactive chemical compound to the effect that the cell is no longer metabolically active, but still presents its epitopes for immunostaining with antibodies and their subsequent detection, for example by fluorescence. More preferably, the reactive chemical compound is selected from the group comprising acetone, formalin, methanol and ethanol or mixtures thereof, preferably all of them. The person skilled in the art is familiar with protocols that may be used to prepare fixed cells.

According to the present invention, the cell is on a carrier for microscopic immunofluorescence analysis. Such a carrier may be a glass side. The cell on the glass slide may be covered with a mounting buffer. A mounting medium is a liquid which helps maintain a near physiological pH to maintain the molecular structure of any diagnostically relevant molecular and their epitopes, Is compatible with the emission of a fluorescence signal and prevents a premature loss of fluorescence due to bleaching of the fluorophore. It may be selected from the group comprising water, glycerol, natural oil or plastic or a mixture thereof, preferably water and glycerol. Various compositions are described in the state of the art, for example in "Mountants and Antifades", published by Wright Cell Imaging Facility, Toronto Western Research Institute University Health Network, (https://de.scribd.com/document/47879592/Mountants-Antifades), Krenek et al. (1989) J. Immunol. Meth 117, 91-97 and Naim et al. (1969) Clin. Exp. Immunol. 4, 697-705.

A cover glass may be placed on top of the composition comprising the sample and the mounting medium. Sides with cover glasses (FB 112d-1005-1 or ZZ 3000-0112) are available from EUROIMMUN Medizinische Labordiagnostika, AG. However, any carrier compatible with microscopic analysis of the fluorescence pattern may be used. The carrier may comprise a mock-transfected cell, which has been transfected with the same vector as the cell overexpressing a polypeptide comprising the mammalian VGLUT or a variant thereof, but without the nucleic acid encoding for the latter. Such mock-transfected cell may serve as a negative control. The carrier is configured for analysis using an immunofluorescence microscope.

In a preferred embodiment, the carrier may comprise a field comprising the cell according to the invention. In addition the carrier may comprise additional fields. The fields are preferably surrounded by a hydrophobic surface. Each of these fields may comprise a cell overexpressing another autoantigen or a variant thereof. A field may comprise a section of primate cerebellum, rat cerebellum or rat hippocampus and thalamus. In a preferred embodiment, the cell is a eukaryotic cell overexpressing the polypeptide, such as a cell selected from the group comprising HEK, Hela. CHO and Jurkat cells and derivatives thereof. In a preferred embodiment, the cell is a recombinant cell overexpressing the polypeptide, which is preferably under the control of a heterologous strong promoter.

In another preferred embodiment, the diagnostically useful carrier is a bead. Various beads for numerous applications are commercially available, mainly based on carbohydrate, for example sepharose or agarose, or plastic. They may contain active or activatable chemical groups such as a carboxyl or tosyl or ester group, which can be utilized for the immobilization of a means for specifically capturing an antibody. Preferably, the beads are beads having an average diameter of from 0.1 μm to 10 μm, from 0.5 μm to 8 μm, from 0.75 μm to 7 μm or from 1 μm to 6 μm. Preferably, the bead is provided in the form of an aqueous suspension having a bead content of from 10 to 90%, preferably from 20 to 80%, preferably from 30 to 70%, more preferably from 40 to 60% (w/w). The person skilled in the art is familiar with such beads (Diamindis, E. P., Chriopoulus, T. K., Immunoassays, 1996. Academic Press), which are commercially available, for example Bio-Plex COOH beads MC10026-01 or 171-506011 from Bio-Rad.

In another preferred embodiment, the carrier is a microtiter plate comprising at least 8 wells that may be used for ELISA. At least one of the wells is coated with the means for specifically capturing an antibody, either directly or indirectly, preferably a polypeptide comprising SEQ ID NO: 1 or a variant thereof. At least 3, preferably 4, more preferably 5 calibrators, at defined concentrations may be used to set up a calibration curve for semi-quantitative analysis. When the inventive method is carried out, the calibrators, which typically cover a range of concentrations covering the calibrating curve, may be processed and developed in parallel to the samples. A secondary antibody comprising a detectable label such as an enzymatically active label may be provided, for example a label having horse radish peroxidase activity or alkaline phosphatase activity or an enzyme capable of chemiluminescence.

In another preferred embodiment, the carrier is a microarray. In a preferred embodiment, the term "microarray", as used herein, refers to a chip spotted with a variety of spatially separate antigens, preferably at least 5, more preferably 10, 20, 30, 40, 50, 80 or 100. Preferably each antigen is a peptide comprising or consisting of 5 to 25, preferably 7 to 15 successive amino acids spanning a fragment or a mammalian. At least one antigen is a polypeptide comprising a mammalian VGLUT or a variant thereof. Preferably two or more antigens are a polypeptide comprising a mammalian VGLUT or a variant thereof, for example SEQ ID NO: 1, SEQ ID NO: 13 and SEQ ID NO: 14 or a variant thereof. A secondary antibody comprising a label, preferably a fluorescent label, may be used for the detection. Preferably at least one additional antigen or a variant thereof is spotted.

According to the present invention, a means for detecting an antibody or an antibody is used, which is a molecule binding specifically to the antibody and allowing detection, typically comprising a detectable label. In a preferred embodiment, a detectable label may be used to distinguish a population of molecules from others using biophysical detection methods. It is preferably selected from the group comprising a fluorescent, a radioactive, a chemiluminescent label, a heavy metal such as gold label, a nanoparticle, a bead or an enzymatically active label, preferably one catalyzing a colorimetric reaction. In a preferred embodiment, a fluorescent label is selected from the group comprising Alexa dyes, FITC, TRITC and green fluorescent protein (GFP). Iodine-125 may be used as radioactive label. In a preferred embodiment, an enzymatically active label is selected from the group comprising horseradish peroxidase, glucose oxidase, beta galactosidase, alkaline phosphatase and luciferase. In a preferred embodiment, a chemiluminescent label is selected from the group comprising luminol or a derivative, an acridinium ester and luciferase. The person skilled in the art is able to choose suitable labels and to attach them to proteins, nucleic acids and other molecules (Hassanzadeh L, Chen S, Veedu R N. Radiolabeling of Nucleic Acid Aptamers for Highly Sensitive Disease-Specific Molecular Imaging. Pharmaceuticals (Basel). 2018; 11(4):106. Published 2018 Oct. 15. doi: 10.3390/ph11040106 Hassanzadeh L, Chen S, Veedu R N. Radiolabeling of Nucleic Acid Aptamers for Highly Sensitive Disease-Specific Molecular Imaging. Pharmaceuticals (Basel). 2018; 11(4):106. Published 2018 Oct. 15. doi:10.3390/ph11040106, Bioconjugate Techniques, 3rd Edition (2013) by Greg T. Hermanson, Obermaier C, Griebel A, Westermeier R. Principles of protein labeling techniques. Methods Mol Biol. 2015; 1295: 153-65), and a wide range of labeled molecules are commercially available. According to the present invention, a means for capturing an antibody such as an IgG class antibody is a molecule binding specifically to the antibody to be immobilized and capable of immobilizing it, either because it is immobilized itself or configured for immobilization, preferably via an affinity tag. The means for detecting an immobilized antibody is a ligand binding specifically to mammalian VGLUT and may be selected from the group comprising a secondary antibody, a polypeptide comprising a mammalian VGLUT and a ligand binding specifically, Protein G or variant thereof or an aptamer or an antibody binding specifically to the immobilized antibody.

In accordance with the present invention, the term "secondary antibody" in its broadest sense is to be understood to refer to any kind of "binding moiety", preferably binding protein, capable of specific binding to an IgA, IgG and/or IgM class antibody or a fragment thereof such as a constant domain of a particular Ig class of a selected species, preferably human species. Non-linking examples of binding moieties include antibodies, for example antibodies immunologically or genetically derived from any species, for example human, chicken, camel, llama, lamprey, shark, goat, rodent, cow, dog, rabbit, etc., antibody fragments, domains or parts thereof, for example Fab, Fab', F(ab')2, scFab, Fv, scFv, VH, VHH, VL, VLRs, and the like, diabodies, monoclonal antibodies (mAbs), polyclonal antibodies (pAbs), mAbdAbs, phage display-derived binders, affibodies, heteroconjugate antibodies, bispecific antibodies, evibodies, lipocalins, anticalins, affibodies, avimers, maxibodies, heat shock proteins such as GroEL and GroES, trans-bodies, DARPins, aptamers, C-type lectin domains such as tetranectins; human γ-crystallin and human ubiquitin-derived binders such as affilins, PDZ domain-derived binders; scorpion toxin and/or Kunitz-type domain binders, fibronectin-derived binders such as adnectins, receptors, ligands, lectins, streptavidin, biotin, including derivatives and/or combinations thereof such as bi-/multi-specific formats formed from two or more of these binding molecules. Various antibody-derived and alternative (i.e. non-antibody) binding protein scaffolds including methods of generation thereof are known in the art (e.g. reviewed in Chiu M L et al., Antibodies (Basel), (2019); 8(4):55; Simeon R. & Chen Z., Protein Cell. (2018):9(1):3-14; and Chapter 7—Non-Antibody Scaffolds from Handbook of Therapeutic Antibodies (2007) edited by Stefan Dübel, U.S. Pat. No. 7,166, 697, Rothe C & Skerra A., BioDrugs. (2018); 32(3):233-243; Gebauer M & Skerra A, Curr Opin Biotechnol. (2019); 60:230-241; Feldwisch, J & Tolmachev, V. (2012) Methods Mol. Biol. 899:103-126; Wikman M et al., Protein Eng Des Sel. (2004); 17(5):455-62: Silverman J et al. (2005), Nat Biotechnol 23:1556-1561; Plückthun A., Annu Rev Pharmacol Toxicol. (2015); 55:489-511; Hosse R J et al. (2006). Protein Sci 15:14-27: Hackel B J, et al. (2008) J Mol Biol 381:1238-1252. In a preferred embodiment, a secondary antibody is an antibody binding to all antibodies from an antibody or immunoglobulin class, preferably a human antibody class, preferably IgA and/or IgG and/or IgM antibodies, preferably IgG. Secondary antibodies may recognize the constant domain of said class or one or more epitopes across the sequence or 3D structure shared by antibodies of the Ig class of interest. Secondary antibodies are typically from a mammal other than a human or from a bird, preferably from chicken, rabbit, mouse, rat, horse, pig, donkey, goat, cow, camel, llama, or non-human primate. A secondary antibody may be a monoclonal, preferably recombinant antibody or may be a polyclonal antibody. A wide range of them is commercially available.

In a preferred embodiment, a ligand to an affinity tag, as used herein, is an entity, optionally artificial, binding specifically to an affinity tag, typically a chemically synthesized modification or a recombinant protein or peptide attached to a molecule of interest. The ligand to an affinity tag depends on the type of affinity tag chosen and may be selected from the group comprising His, immobilized nickel, glutathione, chitin, 18A, ACP, Aldehyd, Avi, BCCP, Calmodulin, Chitin binding protein, E-Tag, ELK16, FLAG, flash, poly glutamate, poly aspartate, GST, GFP, HA, Isope, maltose binding protein, myc, nus, NE, ProtA, ProtC, Tho1d4, S-Tag, SnoopTag, SpyTag, SofTag, Streptavidin, Strep-tag II, T7 Epitope Tag, TAP, TC, Thioredoxin, Ty, V5, VSV, biotin, Xpress Tag and a recombinant antibody binding to the affinity tag.

According to the present invention, an autoantibody binding specifically to a mammalian VGLUT is provided, preferably in a solution comprising one or more, more preferably all from the group comprising an artificial buffer, a preservative and an artificial anticoagulant. An artificial buffer is a buffer which is synthetic and/or may not occur in the body of the patient or at least at concentrations well below the concentration used. The buffer may be selected from the group comprising Tris, phosphate, Tricine, acetate, MOPS, MES, carbonate, citrate and HEPES. In a preferred embodiment, the term "preservative" as used herein, refers to a substance inhibiting microbial growth and/or chemical degradation in a liquid solution and may preferably be selected from the group comprising azide, lactic acid, nitrate, nitrite, antibiotics, a protease inhibitor and ethanol. In a preferred embodiment, the term "stabilizer", as used herein, Is a reagent that stabilizes a proteinaceous molecule such as an antibody, for example by decreasing degradation, by decreasing unfolding or by decreasing loss of the molecule, for example as a result of non-specific absorption to a solid phase such as reaction vessel. Examples of stabilizers include bovine serum albumin, casein and soybean protein.

Various methods or uses according to the invention can be conducted with a sample from a subject as described herein. These methods or uses can also be characterized as "in vitro" methods or "In vitro" uses.

In a preferred embodiment, the term "chemical solution reactive with a detectable label" refers to a compound in a liquid which, upon exposure to the detectable label, emits a detectable signal. The solution may comprise a chromogenic substrate of an enzymatically active label. For example, 3,3',5,5' tetramethylbenzidine/H2O2 may be used if the label is a peroxidase. The solution may comprise a small inorganic or organic compound capable of reacting with a chemiluminescent label. In the case of an acridinium ester, a mixture of $H_2O_2$ and sodium hydroxide is frequently used as the chemical solution. Various other chemical solutions and detectable labels are known in the art (Weeks, I., Beheshti, I., McCapra, F., Campbell, A. K., Woodhead, J. S. (1983) Acridinium esters as high specific activity labels in immunoassay. Clin Chem 29: 1474-1479), Thermo Scientific Pierce Antibody Production and Purification Technical Handbook, Version 2, www.thermoscientific.com).

In a preferred embodiment, the term "diagnosis", as used herein, is to be used in its broadest possible sense and may to any kind of procedure aiming to obtain information instrumental in the assessment whether a patient, known or an anonymous subject from a cohort, suffers or is likely or more likely than the average or a comparative subject, the latter preferably having similar symptoms, to suffer from certain a disease or disorder in the past, at the time of the diagnosis or in the future, to find out how the disease is progressing or is likely to progress in the future or to evaluate the responsiveness of a patient or patients in general with regard to a certain treatment, for example the administration of immunosuppressive drugs, or to find out whether a sample is from such a patient. Such information may be used for a clinical diagnosis, but may also be obtained by an experimental and/or research laboratory for the purpose of general research, for example to determine the proportion of subjects suffering from the disease in a patient cohort or in a population. In other words, the term "diagnosis" comprises not only diagnosing, but also prognosticating and/or monitoring the course of a disease or disorder, including monitoring the response of one or more patients to the administration of a drug or candidate drug, for example to determine its efficacy. While the result may be assigned to a specific patient for clinical diagnostic applications and may be communicated to a medical doctor or institution treating said patient, this is not necessarily the case for other applications, for example in diagnostics for research purposes, where it may be sufficient to assign the results to a sample from an anonymized patient. In another preferred embodiment, the detection of an autoantibody binding specifically to a mammalian VGLUT is considered to imply a definitive diagnosis of a neurological autoimmune disease because of the presence of the autoantibody.

In a preferred embodiment, the methods and products according to the present invention may be used for interaction studies, including determining whether a drug candidate or other compound may interfere with the binding of an autoantibody binding specifically to a mammalian VGLUT or may affect any downstream process or the strength of its binding to its target. In preferred embodiment, they may be used for monitoring the immune response, more preferably the emergence and/or titer of antibodies to a mammalian VGLUT, following the administration of an immunogenic composition comprising a polypeptide comprising a mammalian VGLUT or an immunogenic variant thereof, for example to a mammal, which may be a mammal other than a human such as a laboratory animal.

In a preferred embodiment, the methods and products may be used for providing reagents such as an antibody to a mammalian VGLUT which may serve as a positive control or a calibrator for a diagnostic test or for developing and/or validating a diagnostic test. In a preferred embodiment, the term "validating", as used herein, refers to a procedure for establishing an assay in a specific environment based on a previously known principle and confirming that it yields useful results. For example, while this application discloses the usefulness of an antibody to a mammalian VGLUT as a marker for a diagnosis, a clinical or research laboratory may need to confirm the diagnostic value of the results before routinely using the test for their patients or a new group of patients, for example a group of animals, which may not have been known previously to suffer from a disease or condition.

In another preferred embodiment, the methods and products according to the present invention may be used for determining the concentration of an antibody binding specifically to a mammalian VGLUT. In a more preferred embodiment, said antibody is an autoantibody from a patient suffering from a neurological autoimmune disease. In another preferred embodiment, said antibody is a recombinant antibody which binds to a mammalian VGLUT, but is recognized by a secondary antibody binding specifically to human IgG class antibodies, preferably IgG1, IgG2, IgG3 and IgG4 isotypes. In a more preferred embodiment, such a concentration needs to be determined for the purposes of research, for the preparation or for monitoring the quality of reagents, animal models or devices that may or may not be used for the diagnosis of a neurological autoimmune disease.

In many cases the mere detection of the autoantibody, in other words determining whether or not detectable levels of the antibody are present in the sample, is sufficient for the diagnosis. In a more preferred embodiment, this may involve determining whether the concentration is at least 10%, preferably 20%, 50%, 100%, 200%, 500%, 1,000%, 2,000%, 2,500%, 5,000%, 1,0000%, 2,0000%, 5,0000%, 100,000%, 1,000,000% or 10,000,000% times higher than the concentration of the antibody of interest found in the average healthy subject. If the autoantibody can be detected, this will be information instrumental for the clinician's diagnosis. It may indicate an increased likelihood that the patient suffers from a disease.

The person skilled in the art will appreciate that a clinician does usually not arrive at the conclusion whether or not the patient suffers or is likely to suffer from a disease, condition or disorders solely on the basis of a single diagnostic parameter, but needs to take into account other aspects, for example the presence of other autoantibodies, markers, blood parameters, clinical assessment of the patient's symptoms or the results of medical imaging or other non-invasive methods such as polysomnography, to arrive at a conclusive diagnosis. See Baenkler H. W. (2012), General aspects of autoimmune diagnostics, in Renz, H., Autoimmune diagnostics, 2012, de Gruyter, page 3. The value of a diagnostic agent or method may also reside the possibility to rule out one disease, thus allowing for the indirect diagnosis of another. In a preferred embodiment, the meaning of any symptoms or diseases referred to throughout this application is in line with the person skilled in the art's understanding as of the filing date or, preferably, earliest priority date of this application as evidenced by text books and scientific publications. In a preferred embodiment, the inventive methods or uses or products are not used, taken alone, to arrive at a definite, final diagnosis. In a preferred embodiment, any information or data demonstrating the presence of absence of the autoantibody may be communicated to the patient or a medical doctor treating the patient orally, preferably by telephone, in a written form, preferably fax or letter, or in an electronic form via fax or via the Internet, for example as an email or text message.

The inventive teachings may also be used in a method for preventing or treating a disease, preferably after a diagnosis according to the present invention, comprising the steps a) reducing the concentration of autoantibodies binding to the inventive polypeptide in the subject's blood and/or b) administering one or more immunosuppressive pharmaceutical substances, preferably selected from the group comprising rituximab, prednisone, methylprednisolone, cyclophosphamide, mycophenolate mofetil, intravenous immunoglobulin, tacrolimus, cyclosporine, methotrexate and azathioprine.

According to the present invention, the presence of an antibody may be determined in a qualitative or a quantitative manner. In a preferred embodiment, the term "detecting in a quantitative manner", as used herein, means that not only the presence of an antibody is detected, but that a result is obtained that includes information regarding the absolute or relative amount of the antibody in the sample. In a more preferred embodiment, a value representing an absolute concentration is obtained. In another more preferred embodiment, a value representing a relative concentration or change of concentration is obtained. In another preferred embodiment, also referred to as "semi-quantitative" approach, the concentration of the antibody is placed in one of several groups, most preferably a concentration window meaning that it is virtually absent, a concentration window meaning that a borderline result is obtained and a concentration window meaning that the antibody is present. A further distinction into categories such as "weak positive" or "strong positive" signal is possible.

In a preferred embodiment, the term "autoantibody", as used herein, refers to an antibody binding specifically to an endogenous molecule of the animal, preferably mammal, more preferably human, which produces said autoantibody, wherein the level of such antibody is more preferably elevated compared to the average healthy subject. The autoantibody may have the sequence of an antibody's constant regions from the animal, preferably human, making it, but the variable region is able to bind specifically to the endogenous molecule of the animal, more specifically a mammalian VGLUT. In a preferred embodiment, the autoantibody is isolated and/or purified from a sample, preferably tissue, serum, plasma, blood or CSF from the animal, preferably human. The autoantibody can be isolated as a mixture of polyclonal, native antibodies from the animal or patient, it is not a synthetic, monoclonal or recombinant antibody. A recombinant antibody binding specifically to a mammalian VGLUT may be generated using standard methods. It may be useful as a positive control and for detection assays, for example sandwich assays or competitive assays.

The method according to the present invention is preferably an in vitro method.

According to the present invention, a polypeptide, preferably the polypeptide comprising a mammalian VGLUT or a variant thereof, may be a recombinant protein. In a preferred embodiment, the term "recombinant", as used herein, refers to a polypeptide produced using genetic engineering approaches at any stage of the production process, for example by fusing a nucleic acid encoding the polypeptide to a strong promoter for overexpression in cells or tissues or by engineering the sequence of the polypeptide itself. The person skilled in the art is familiar with methods for engineering nucleic acids and polypeptides encoded (for example, described in Sambrook, J., Fritsch, E. F. and Maniatis. T. (1989), Molecular Cloning, CSH or in Brown T. A. (1988), Gene Cloning—an introduction, Chapman & Hal) and for producing and purifying native or recombinant polypeptides (for example Handbooks "Strategies for Protein Purification", "Antibody Purification", published by GE Healthcare Life Sciences, and in Burgess, R. R., Deutscher, M. P. (2009): Guide to Protein Purification). In another preferred embodiment, a polypeptide provided or used according to the present invention such as a polypeptide comprising a mammalian VGLUT or a variant thereof or an antibody is an isolated polypeptide, wherein the term 'isolated' means that the polypeptide has been enriched compared to its state upon production using a biotechnological or synthetic approach and is preferably pure, i.e. at least 60, 70, 80, 90, 95 or 99 percent of the polypeptide in the respective liquid consists of said polypeptide as judged by SDS polyacrylamide gel electrophoresis followed by Coomassie blue staining and visual inspection. Preferably any polypeptide on a carrier used as a means to capture an antibody is pure.

Patients having autoantibodies to a mammalian VGLUT suffer from a variety of cancers comprising leukemia, graft versus host disease and non-Hodgkin lymphoma. In a preferred embodiment, the term "cancer", as used herein, refers to is a group of diseases involving abnormal cell growth with the potential to invade or spread to other parts of the body.

In a preferred embodiment, the term "non-Hodgkin lymphoma", as used herein, refers to a group of blood cancers that includes all types of lymphomas except Hodgkin lymphomas.

In a preferred embodiment, the term "Leukemia", as used herein, refers to a group of blood cancers that usually begin in the bone marrow and result in high numbers of abnormal blood cells. These blood cells are not fully developed and are called blasts or leukemia cells.] Symptoms may include bleeding and bruising, fatigue, fever, and an increased risk of infections. These symptoms occur due to a lack of normal blood cells.

In a preferred embodiment, the term "Graft-versus-host disease", as used herein, refers to a syndrome characterized by inflammation in different organs, with the specificity of epithelial cell apoptosis and crypt drop out. GvHD is commonly associated with bone marrow transplants and stem cell transplants.

Additional background and definitions related to cancers and their diagnoses or differential diagnoses including the detection of autoantibodies may be taken from neurology textbooks available at the earliest priority date or filing date of this publication such as Kaye. Textbook of Medical Oncology, 3rd edition, Taylor & Francis; Shoenfeld, Meroni and Gershwin, Autoantibodies 3rd edition, Elsevier, in particular Part 11 including Chapter 76; and Darnell and Posner, Paraneoplastic Syndromes, Oxford University Press, 2011. Patients having autoantibodies to a mammalian VGLUT suffer from a variety of neurological autoimmune diseases comprising PNS, cerebellar ataxia, gait ataxia, polyneuropathy, encephalitis, preferably limbic encephalitis, epilepsy, dementia, cerebellar syndrome and hypersensitive encephalopathy and cancers such as leukemia, graft versus host disease and non-Hodgkin lymphoma.

In a preferred embodiment, the term "ataxia", as used herein, refers to lack of voluntary coordination of muscle movements that can include gait abnormality, speech changes, and abnormalities in eye movements. Ataxia is a clinical manifestation indicating dysfunction of the parts of the nervous system that coordinate movement, such as the cerebellum.

In a preferred embodiment, the term "polyneuropathy", as used herein, refers to a disease affecting peripheral nerves (peripheral neuropathy) in roughly the same areas on both sides of the body, featuring weakness, numbness, and burning pain.

In a preferred embodiment, the term "encephalopathy", as used herein, refers to an altered mental state characterized by impairment of the cognition, attention, orientation, sleep-wake cycle and consciousness In a preferred embodiment, the term "Encephalitis", as used herein, refers to an inflammation of the brain, with symptoms including reduced or alteration in consciousness, personality changes, psychotic delusions, rigidity, headache, fever, confusion, a stiff neck, and vomiting. Complications may include seizures, hallucinations, trouble speaking, memory problems, and problems with hearing. The disease may be the result of an infection or may be an autoimmune disease, hence the detection of an autoantibody according to the invention may be used to distinguish these two types of encephalitis.

In a preferred embodiment, the term "cerebellar syndrome", as used herein, refers to an Impaired cerebellar function typically associated with ataxia, nystagmus and dysarthria.

In a preferred embodiment, the term "Paraneoplastic Neurological Syndrome" (PNS), as used herein, refers to neurological syndromes associated with the presence of a cancer associated with tumors which presents an antigen which Is normally exclusive to the nervous system. As a result, an autoantibody binding specifically to the neurological antigen is produced which may then damage the nervous system. Manifestations of PNS Include, but are not limited to encephalitis, typically associated with seizures, psychiatric manifestations such as hallucinations, anxiety and depression, cerebellar symptoms, such as ataxia, nystagmus and dysarthria, opsoclonus-myoclonus and sensory neuropathy; and Lambert-Eaton myasthenic syndrome. It should be mentioned that PNS-associated tumors are often small, grow slowly and may not yet be detectable when neurological syndromes surface. PNS may be associated with one or more antibodies, which may bind specifically to an autoantigen from the group comprising NMDAR, Lgl1, AMPA1, AMPA2, CASPR2, GABA B, GABA A, DPPX, IGLON5, Hu, Yo, CRMP5, Ri, Ma2, Amphiphysin, Recoverin, RGS8, DAGLA, NSF, STX1B, DNM1 and VAMP2, Hu, Ri, Ma, Anna-3, Zic-4, SOX1, Yo, PCA2, Tr and glutamic acid decarboxylase.

Additional background and definitions related to neurological syndromes and symptoms and their diagnoses or differential diagnoses including the detection of autoantibodies may be taken from neurology textbooks available at the earliest priority date or filing date of this publication such as Simon, Greenberg, Aminoff, Clinical Neurology, 7th edition, 2009, McGraw; Shoenfeld, Meroni and Gershwin. Autoantibodies 3rd edition, Elsevier. In particular Part 11 including Chapter 76; and Darnell and Posner, Paraneoplastic Syndromes, Oxford University Press, 2011.

As part of a diagnosis relating to the neurological syndromes associated with VGLUT-associated autoantibodies, the clinician will initially consider a range of tests and risk factors which may point them either to autoimmune disease or infectious disease for many of the conditions associated with the presence of an autoantibody binding specifically to SEQ ID NO: 1 (Lancaster, J Clin Neurol. 2016 January; 12(1) https://doi.org/10.3988/jcn.2016.12.1.1, Lee and Lee, The Laboratory Diagnosis of Autoimmune Encephalitis, Journal of Epilepsy Research 6 (2), 45), preferably encephalitis. Detection of an autoantibody binding specifically to SEQ ID NO: 1 will then confirm an autoimmune background, while the absence of an autoantibody will tempt the clinician to consider autoimmune disease associated with other autoantibodies. However, typically the presence or absence of a range of autoantibodies will then be detected, and a negative result will be a pointer to Infectious diseases.

According to the present invention, a kit is provided, comprising the cell or the carrier and further comprising one or more, preferably all reagents from the group comprising a secondary antibody, preferably labeled with a detectable label, a washing solution, a positive control, a negative control, a detergent, a cover glass, a mounting medium and a physiological salt solution, preferably PBS, or salt required to prepare it. In a preferred embodiment, the positive control is a diluted sample, preferably serum or CSF, from a patient suffering from a neurological autoimmune disease or a monoclonal antibody binding specifically to a mammalian VGLUT. The negative control may be a diluted sample from a healthy subject, for example a blood donor. The kit may comprise instructions how to carry out the assay. Preferably, the secondary antibody is a secondary antibody binding specifically to IgG class antibodies, preferably human IgG class antibodies.

In a preferred embodiment, the present Invention provides a use of the cell, the polypeptide, the carrier for the manufacture of kit a composition for the diagnosis of a disease.

In a preferred embodiment, any method or use according to the present Invention may be intended for a non-diagnostic use, i.e. determining the presence of an autoantibody binding specifically to binding to a mammalian VGLUT, for a use other than diagnosing a patient. For example, the method or use may be for testing in vitro the efficiency of a medical device designed to remove an autoantibody from a patient's blood, wherein the testing is performed on a liquid other than patient's blood. After the use of the medical device with a patient, its capacity to remove autoantibody may be checked by running a solution comprising antibody binding specifically to a mammalian VGLUT through the device, followed by use of the method according to the present invention to confirm that less or no antibody is in the solution that has been passed through the device, i.e. showing that the device has still the capacity to remove antibody from the solution. According to the present invention, the method may be used for testing the efficacy or a drug candidate which may be used to treat patients suffering from or likely to suffer from a neurological autoimmune disease. Such a drug candidate may be any molecule capable of Interfering with the interaction between the mammalian VGLUT and the autoantibody.

In another preferred embodiment, the method may be for confirming the reliability of a diagnostic assay and may involve detecting an antibody binding specifically to a mammalian VGLUT in a solution, which is not a sample from a patient who requires a diagnosis, but is known to comprise an antibody binding specifically to a mammalian VGLUT, preferably at a known concentration. For example, it may be a recombinant antibody or a sample diluted in a dilution buffer such as PBS from an anonymous patient whose identity cannot be traced back. Alternatively, the solution may be a negative control not comprising the antibody binding specifically to check the background. Such method may be run in parallel with, after or before a diagnostic method. In a preferred embodiment, any method or use according to the present invention may be intended for generating an autoantibody profile, preferably for detecting a disease in a mammal, preferably a human.

In a preferred embodiment, any method or use according to the present invention may be for identifying a subject at risk of suffering from or developing a disease and/or a tumor.

In a preferred embodiment, the method may be for detecting an antibody, preferably autoantibody binding specifically to a mammalian VGLUT in a solution which is not a sample from a mammal to be diagnosed or for the purpose of providing a diagnosis. In a preferred embodiment, the problem underlying the present invention is solved by a method comprising the step contacting a device comprising a solid phase on which a polypeptide comprising a mammalian VGLUT or a variant thereof is immobilized with a buffered solution comprising an antibody binding specifically to a mammalian VGLUT, which solution is preferably not a sample from a patient in need of a diagnosis, wherein preferably
  a) the concentration of the antibody in the solution is known, and/or
  b) the antibody is a recombinant antibody and/or
  c) the medical or diagnostic device Is contacted with two or more solutions comprising the antibody, wherein the two or more solutions have a different concentration of the antibody, and/or
  d) the antibody Is recognized by secondary antibodies binding specifically to IgG antibodies,
followed by detection of a signal which indicates whether or not the antibody has bound to the polypeptide, optionally a signal relating to the concentration of the antibody in the solution or solutions.

In a preferred embodiment, the present Invention provides an apparatus for analyzing a sample from a patient to detect an autoantibody against a mammalian VGLUT, Indicating an increased likelihood of a neurological autoimmune disease or of developing it, comprising:
  a) a carrier, which contains a means for capturing the autoantibody from the sample when the sample Is contacted with the carrier, wherein the means is the cell and the carrier Is the carrier according to the present Invention,
  b) a detectable means capable of binding to the antibody captured by the carrier when the detectable means is contacted with the carrier, wherein the detectable means Is preferably a labeled secondary antibody capable of binding to the autoantibody captured on the carrier,
  c) optionally a means for removing any sample from the carrier and the detectable means, preferably by washing;
  d) a detecting device for detecting the presence of the detectable means and converting the results into an electrical signal, for example a fluorescence reader or a fluorescence microscope connected with a software capable of recognizing a pattern characteristic of a stained cell overexpressing a polypeptide comprising a mammalian VGLUT or a variant thereof in an image of the cell taken by the fluorescence reader or camera, and
optionally a means for receiving the electronical signal from the detecting device and determining if the level of the signal is indicative of an increased likelihood of having or developing a disease, by comparing with the patterns characteristic of wild type or non-stained cells, preferably by a mock-transfected cell or cells not positively stained by an autoantibody binding specifically to a mammalian VGLUT on the same carrier, or an input reference value obtained with samples from healthy subjects or by comparing the level of signal obtained with one sample with the level of signal obtained with a second sample obtained at a later time point, preferably at least one month later.

According to the present invention, a device for removing an autoantibody binding specifically to a mammalian VGLUT from blood, preferably serum or a patient suffering from a neurological autoimmune disease, wherein the device comprises a carrier with a solid phase on which a polypeptide comprising a mammalian VGLUT or a variant thereof is immobilized Is provided as Is an ex vivo method for removing an autoantibody binding specifically to a mammalian VGLUT from a patient. A device on which a polypeptide comprising a mammalian VGLUT or a variant thereof or a secondary antibody or protein capturing all IgG class antibodies, among them IgG class autoantibodies to a mammalian VGLUT, may be used. Suitable methods are described in Eisei Noiri and Noria Hanafusa, The Concise Manual of Apharesis Therapy, Springer Tokyo, 2014. Hamilton, P., Kanigicherla, D., Hanumapura, P., Walz, L., Kramer, D., Fischer, M., Brenchley, P., and Mitra, S. (2018) J. Clin. Aph. 33(3), 283-290. Another method is disclosed in EP3477300.

The present Invention comprises a range or polypeptide sequences, more specifically (human VGLUT2, identical with Uniprot Q9P2U8)

SEQ ID NO: 1

MESVKQRILAPGKEGLKNFAGKSLGQIYRVLEKKQDTGETIELTEDGKPLEVPERKAPLCDCTCFGLPRR

YIIAIMSGLGFCISFGRCNLGVAIVDMVNNSTIHRGGKVIKEKAKFNWDPETVGMIHGSFFWGYIITQIPGG

YIASRLAANRVFGAAILLTSTLNMLIPSAARVHYGCVIFVRILQGLVEGVTYPACHGIWSKWAPPLERSRLA

TTSFCGSYAGAVIAMPLAGILVQYTGWSSVFYVYGSFGMVWYMFWLLVSYESPAKHPTITDEERRYIEES

IGESANLLGAMEKFKTPWRKFFTSMPVYAIIVANFCRSWTFYLLLISQPAYFEEVFGFEISKVGMLSAVPHL

VMTIIVPIGGQIADFLRSKQILSTTTVRKIMNCGGFGMEATLLLVVGYSHTRGVAISFLVLAVGFSGFAISGF

NVNHLDIAPRYASILMGISNGVGTLSGMVCPIIVGAMTKNKSREEWQYVFLIAALVHYGGVIFYAIFASGEK

QPWADPEETSEEKCGFIHEDELDEETGDITQNYINYGTTKSYGATTQANGGWPSGWEKKEEFVQGEVQ

DSHSYKDRVDYS (VGLUT2, gene synthesis fragment 1, coding aa1-293)

SEQ ID NO: 2

GGTCTCGCATGGAATCCGTAAAACAAAGGATTTTGGCACCTGGCAAAGAAGGGCTGAAGAACTTTGC

CGGTAAGTCACTCGGCCAGATTTACCGAGTGCTGGAGAAGAAGCAGGACACTGGAGAAACCATCGA

GCTTACAGAGGATGGGAAACCGTTGGAGGTGCCCGAAAGGAAGGCCCCACTGTGTGATTGCACCTG

TTTCGGTCTGCCTCGGCGGTATATTATAGCGATCATGTCTGGACTGGGCTTTTGCATATCCTTTGGG

ATCAGATGCAATCTCGGGGTTGCCATAGTGGACATGGTGAACAACTCCACCATCCACAGAGGAGGC

AAAGTCATAAAAGAGAAAGCTAAGTTCAACTGGGATCCTGAAACAGTGGGCATGATCCACGGTTCTT

TCTTCTGGGGATACATCATCACCCAGATACCCGGCGGCTACATCGCTAGTCGCTTGGCCGCAAATC

GGGTTTTCGGGGCTGCCATCCTGCTTACTAGCACCCTCAATATGCTCATTCCTAGCGCTGCCAGAGT

CCACTATGGCTGCGTCATTTTCGTCAGGATACTGCAGGGCTTGGTGGAGGGTGTGACGTATCCCGC

ATGTCATGGCATTTGGAGCAAATGGGCTCCACCTTTGGAGAGGAGCAGGCTGGCCACAACCAGCTT

CTGTGGATCCTATGCAGGCGCCGTGATTGCTATGCCCCTGGCTGGTATTCTCGTCCAGTACACTGG

GTGGTCCTCTGTCTTTTACGTGTATGGCAGCTTTGGGATGGTCTGGTACATGTTCTGGCTGCTTGTG

AGCTACGAAAGTCCAGCCAAGCATCCGACCATTACGGATGAAGAGCGTCGGTACATTGAGGAGTCT

ATTGGCGAATCTGCCAATCTGTTGGCGAGACC (VGLUT2, gene synthesis fragment 2, coding aa294-582)

SEQ ID NO: 3

GGTCTCCTTGGGAGCTATGGAGAAGTTTAAGACTCCATGGCGCAAATTCTTCACAAGCATGCCCGTA

TATGCAATCATCGTTGCCAATTTCTGCAGATCCTGGACCTTTTATCTGCTGTTGATTTCTCAACCCGC

GTATTTTGAGGAGGTGTTTGGGTTCGAAATCAGCAAGGTGGGAATGCTTTCAGCAGTTCCACACCTG

GTGATGACAATCATCGTACCCATAGGAGGGCAAATTGCTGACTTTCTGCGCAGTAAACAGATCCTGA

GTACCACAACTGTCCGAAAGATTATGAACTGTGGAGGATTCGGCATGGAAGCCACCCTCCTGCTTGT

GGTTGGCTATAGCCATACCAGAGGTGTCGCCATCTCATTTCTGGTTCTGGCGGTAGGTTTCAGTGGA

TTTGCCATCTCCGGTTTCAATGTTAACCACCTCGACATCGCACCCCGTTATGCTAGCATTCTGATGG

GCATCAGCAATGGCGTGGGCACACTCAGCGGAATGGTATGCCCAATTATCGTAGGCGCCATGACTA

AGAACAAATCACGCGAAGAGTGGCAGTACGTGTTTCTGATTGCAGCACTGGTGCATTATGGTGGGG

TCATTTTCTACGCGATCTTTGCTTCAGGGGAAAAGCAACCGTGGGCAGATCCTGAAGAGACTAGTGA

GGAGAAGTGCGGTTTCATCCATGAGGACGAACTGGACGAGGAAACAGGAGACATAACACAGAACTA

CATCAACTATGGAACGACGAAATCCTACGGGCCACCACTCAGGCCAATGGAGGCTGGCCTTCTGG

GTGGGAAAAGAAGGAGGAATTTGTGCAAGGGGAGGTGCAGGATTCCCACTCCTATAAGGACCGAGT

TGATTATTCATAATCGACGAGACC (VGLUT2, gene synthesis fragment 1, BsaI)

SEQ ID NO: 4

CATGGAATCCGTAAAACAAAGGATTTTGGCACCTGGCAAAGAAGGGCTGAAGAACTTTGCCGGTAAG

TCACTCGGCCAGATTTACCGAGTGCTGGAGAAGAAGCAGGACACTGGAGAAACCATCGAGCTTACA

GAGGATGGGAAACCGTTGGAGGTGCCCGAAAGGAAGGCCCCACTGTGTGATTGCACCTGTTTCGGT

CTGCCTCGGCGGTATATTATAGCGATCATGTCTGGACTGGGCTTTTGCATATCCTTTGGGATCAGAT

GCAATCTCGGGGTTGCCATAGTGGACATGGTGAACAACTCCACCATCCACAGAGGAGGCAAAGTCA

TAAAAGAGAAAGCTAAGTTCAACTGGGATCCTGAAACAGTGGGCATGATCCACGGTTCTTTCTTCTG

GGGATACATCATCACCCAGATACCCGGCGGCTACATCGCTAGTCGCTTGGCCGCAAATCGGGTTTT

```
CGGGGCTGCCATCCTGCTTACTAGCACCCTCAATATGCTCATTCCTAGCGCTGCCAGAGTCCACTAT

GGCTGCGTCATTTTCGTCAGGATACTGCAGGGCTTGGTGGAGGGTGTGACGTATCCCGCATGTCAT

GGCATTTGGAGCAAATGGGCTCCACCTTTGGAGAGGAGCAGGCTGGCCACAACCAGCTTCTGTGGA

TCCTATGCAGGCGCCGTGATTGCTATGCCCCTGGCTGGTATTCTCGTCCAGTACACTGGGTGGTCCT

CTGTCTTTTACGTGTATGGCAGCTTTGGGATGGTCTGGTACATGTTCTGGCTGCTTGTGAGCTACGA

AAGTCCAGCCAAGCATCCGACCATTACGGATGAAGAGCGTCGGTACATTGAGGAGTCTATTGGCGA

ATCTGCCAATCTGTTGG
```

(VGLUT2, gene synthesis fragment 2, BsaI)
SEQ ID NO: 5

```
TTGGGAGCTATGGAGAAGTTTAAGACTCCATGGCGCAAATTCTTCACAAGCATGCCCGTATATGCAA

TCATCGTTGCCAATTTCTGCAGATCCTGGACCTTTTATCTGCTGTTGATTTCTCAACCCGCGTATTTTG

AGGAGGTGTTTGGGTTCGAAATCAGCAAGGTGGGAATGCTTTCAGCAGTTCCACACCTGGTGATGA

CAATCATCGTACCCATAGGAGGGCAAATTGCTGACTTTCTGCGCAGTAAACAGATCCTGAGTACCAC

AACTGTCCGAAAGATTATGAACTGTGGAGGATTCGGCATGGAAGCCACCCTCCTGCTTGTGGTTGG

CTATAGCCATACCAGAGGTGTCGCCATCTCATTTCTGGTTCTGGCGGTAGGTTTCAGTGGATTTGCC

ATCTCCGGTTTCAATGTTAACCACCTCGACATCGCACCCCGTTATGCTAGCATTCTGATGGGCATCA

GCAATGGCGTGGGCACACTCAGCGGAATGGTATGCCCAATTATCGTAGGCGCCATGACTAAGAACA

AATCACGCGAAGAGTGGCAGTACGTGTTTCTGATTGCAGCACTGGTGCATTATGGTGGGTCATTTT

CTACGCGATCTTTGCTTCAGGGGAAAAGCAACCGTGGGCAGATCCTGAAGAGACTAGTGAGGAGAA

GTGCGGTTTCATCCATGAGGACGAACTGGACGAGGAAACAGGAGACATAACACAGAACTACATCAA

CTATGGAACGACGAAATCCTACGGGCCACCACTCAGGCCAATGGAGGCTGGCCTTCTGGGTGGG

AAAAGAAGGAGGAATTTGTGCAAGGGGAGGTGCAGGATTCCCACTCCTATAAGGACCGAGTTGATT

ATTCATAATCGA
```

(sense VGLUT2)
SEQ ID NO: 6
```
ATAGGTCTCCTTGGGAGCTATGGAGAAG
```

(asense VGLUT2)
SEQ ID NO: 7
```
TATGGTCTCGTCGAGTGAATAATCAACTCGGTCCTTATAGCT
```

(VGLUT2-PCR-fragment without Stop-Codon)
SEQ ID NO: 8
```
ATAGGTCTCCTTGGGAGCTATGGAGAAGTTTAAGACTCCATGGCGCAAATTCTTCACAAGCATGCCC

GTATATGCAATCATCGTTGCCAATTTCTGCAGATCCTGGACCTTTTATCTGCTGTTGATTTCTCAACCC

GCGTATTTTGAGGAGGTGTTTGGGTTCGAAATCAGCAAGGTGGGAATGCTTTCAGCAGTTCCACACC

TGGTGATGACAATCATCGTACCCATAGGAGGGCAAATTGCTGACTTTCTGCGCAGTAAACAGATCCT

GAGTACCACAACTGTCCGAAAGATTATGAACTGTGGAGGATTCGGCATGGAAGCCACCCTCCTGCTT

GTGGTTGGCTATAGCCATACCAGAGGTGTCGCCATCTCATTTCTGGTTCTGGCGGTAGGTTTCAGTG

GATTTGCCATCTCCGGTTTCAATGTTAACCACCTCGACATCGCACCCCGTTATGCTAGCATTCTGATG

GGCATCAGCAATGGCGTGGGCACACTCAGCGGAATGGTATGCCCAATTATCGTAGGCGCCATGACT

AAGAACAAATCACGCGAAGAGTGGCAGTACGTGTTTCTGATTGCAGCACTGGTGCATTATGGTGGG

GTCATTTTCTACGCGATCTTTGCTTCAGGGGAAAAGCAACCGTGGGCAGATCCTGAAGAGACTAGTG

AGGAGAAGTGCGGTTTCATCCATGAGGACGAACTGGACGAGGAAACAGGAGACATAACACAGAACT

ACATCAACTATGGAACGACGAAATCCTACGGGCCACCACTCAGGCCAATGGAGGCTGGCCTTCTG

GGTGGGAAAAGAAGGAGGAATTTGTGCAAGGGGAGGTGCAGGATTCCCACAGCTATAAGGACCGA

GTTGATTATTCACTCGACGAGACCATA
```

-continued (pTriEx-1-VGLUT2 [human])

SEQ ID NO: 9

GGAGTCGCTGCGACGCTGCCTTCGCCCCGTGCCCCGCTCCGCCGCCGCCTCGCGCCGCCCGCCC

CGGCTCTGACTGACCGCGTTACTCCCACAGGTGAGCGGGCGGGACGGCCCTTCTCCTTCGGGCTG

TAATTAGCGCTTGGTTTAATGACGGCTTGTTTCTTTTCTGTGGCTGCGTGAAAGCCTTGAGGGGCTC

CGGGAGGGCCCTTTGTGCGGGGGGAGCGGCTCGGGGCTGTCCGCGGGGGGACGGCTGCCTTCG

GGGGGGACGGGGCAGGGCGGGGTTCGGCTTCTGGCGTGTGACCGGCGGCTCTAGAGCCTCTGCT

AACCATGTTCATGCCTTCTTCTTTTTCCTACAGCTCCTGGGCAACGTGCTGGTTATTGTGCTGTCTCA

TCATTTTGGCAAAGAATTGGATCGGACCGAAATTAATACGACTCACTATAGGGGAATTGTGAGCGGA

TAACAATTCCCCGGAGTTAATCCGGGACCTTTAATTCAACCCAACACAATATATTATAGTTAAATAAGA

ATTATTATCAAATCATTTGTATATTAATTAAAATACTATACTGTAAATTACATTTTATTTACAATCAAAGG

AGATATACCATGGAATCCGTAAAACAAAGGATTTTGGCACCTGGCAAAGAAGGGCTGAAGAACTTTG

CCGGTAAGTCACTCGGCCAGATTTACCGAGTGCTGGAGAAGAAGCAGGACACTGGAGAAACCATCG

AGCTTACAGAGGATGGGAAACCGTTGGAGGTGCCCGAAAGGAAGGCCCCACTGTGTGATTGCACCT

GTTTCGGTCTGCCTCGGCGGTATATTATAGCGATCATGTCTGGACTGGGCTTTTGCATATCCTTTGG

GATCAGATGCAATCTCGGGGTTGCCATAGTGGACATGGTGAACAACTCCACCATCCACAGAGGAGG

CAAAGTCATAAAAGAGAAAGCTAAGTTCAACTGGGATCCTGAAACAGTGGGCATGATCCACGGTTCT

TTCTTCTGGGGATACATCATCACCCAGATACCCGGCGGCTACATCGCTAGTCGCTTGGCCGCAAATC

GGGTTTTCGGGGCTGCCATCCTGCTTACTAGCACCCTCAATATGCTCATTCCTAGCGCTGCCAGAGT

CCACTATGGCTGCGTCATTTTCGTCAGGATACTGCAGGGCTTGGTGGAGGGTGTGACGTATCCCGC

ATGTCATGGCATTTGGAGCAAATGGGCTCCACCTTTGGAGAGGAGCAGGCTGGCCACAACCAGCTT

CTGTGGATCCTATGCAGGCGCCGTGATTGCTATGCCCCTGGCTGGTATTCTCGTCCAGTACACTGG

GTGGTCCTCTGTCTTTTACGTGTATGGCAGCTTTGGGATGGTCTGGTACATGTTCTGGCTGCTTGTG

AGCTACGAAAGTCCAGCCAAGCATCCGACCATTACGGATGAAGAGCGTCGGTACATTGAGGAGTCT

ATTGGCGAATCTGCCAATCTGTTGGGAGCTATGGAGAAGTTTAAGACTCCATGGCGCAAATTCTTCA

CAAGCATGCCCGTATATGCAATCATCGTTGCCAATTTCTGCAGATCCTGGACCTTTTATCTGCTGTTG

ATTTCTCAACCCGCGTATTTTGAGGAGGTGTTTGGGTTCGAAATCAGCAAGGTGGGAATGCTTTCAG

CAGTTCCACACCTGGTGATGACAATCATCGTACCCATAGGAGGGCAAATTGCTGACTTTCTGCGCAG

TAAACAGATCCTGAGTACCACAACTGTCCGAAAGATTATGAACTGTGGAGGATTCGGCATGGAAGCC

ACCCTCCTGCTTGTGGTTGGCTATAGCCATACCAGAGGTGTCGCCATCTCATTTCTGGTTCTGGCGG

TAGGTTTCAGTGGATTTGCCATCTCCGGTTTCAATGTTAACCACCTCGACATCGCACCCCGTTATGCT

AGCATTCTGATGGGCATCAGCAATGGCGTGGGCACACTCAGCGGAATGGTATGCCCAATTATCGTA

GGCGCCATGACTAAGAACAAATCACGCGAAGAGTGGCAGTACGTGTTTCTGATTGCAGCACTGGTG

CATTATGGTGGGGTCATTTTCTACGCGATCTTTGCTTCAGGGGAAAAGCAACCGTGGGCAGATCCTG

AAGAGACTAGTGAGGAGAAGTGCGGTTTCATCCATGAGGACGAACTGGACGAGGAAACAGGAGACA

TAACACAGAACTACATCAACTATGGAACGACGAAATCCTACGGGCCACCACTCAGGCCAATGGAG

GCTGGCCTTCTGGGTGGGAAAAGAAGGAGGAATTTGTGCAAGGGGAGGTGCAGGATTCCCACTCCT

ATAAGGACCGAGTTGATTATTCATAATCGAGCACCACCATCACCATCACCATCACTAAGTGATTAACC

TCAGGTGCAGGCTGCCTATCAGAAGGTGGTGGCTGGTGTGGCCAATGCCCTGGCTCACAAATACCA

CTGAGATCGATCTTTTTCCCTCTGCCAAAAATTATGGGGACATCATGAAGCCCCTTGAGCATCTGACT

TCTGGCTAATAAAGGAAATTTATTTTCATTGCAATAGTGTGTTGGAATTTTTTGTGTCTCTCACTCGGA

-continued

```
AGGACATATGGGAGGGCAAATCATTTAAAACATCAGAATGAGTATTTGGTTTAGAGTTTGGCAACATA
TGCCCATATGTAACTAGCATAACCCCTTGGGGCCTCTAAACGGGTCTTGAGGGGTTTTTTGCTGAAA
GCATGCGGAGGAAATTCTCCTTGAAGTTTCCCTGGTGTTCAAAGTAAAGGAGTTTGCACCAGACGCA
CCTCTGTTCACTGGTCCGGCGTATTAAAACACGATACATTGTTATTAGTACATTTATTAAGCGCTAGA
TTCTGTGCGTTGTTGATTTACAGACAATTGTTGTACGTATTTTAATAATTCATTAAATTTATAATCTTTA
GGGTGGTATGTTAGAGCGAAAATCAAATGATTTTCAGCGTCTTTATATCTGAATTTAAATATTAAATCC
TCAATAGATTTGTAAAATAGGTTTCGATTAGTTTCAAACAAGGGTTGTTTTTCCGAACCGATGGCTGG
ACTATCTAATGGATTTTCGCTCAACGCCACAAAACTTGCCAAATCTTGTAGCAGCAATCTAGCTTTGT
CGATATTCGTTTGTGTTTTGTTTTGTAATAAAGGTTCGACGTCGTTCAAAATATTATGCGCTTTTGTAT
TTCTTTCATCACTGTCGTTAGTGTACAATTGACTCGACGTAAACACGTTAAATAGAGCTTGGACATATT
TAACATCGGGCGTGTTAGCTTTATTAGGCCGATTATCGTCGTCGTCCCAACCCTCGTCGTTAGAAGT
TGCTTCCGAAGACGATTTTGCCATAGCCACACGACGCCTATTAATTGTGTCGGCTAACACGTCCGCG
ATCAAATTTGTAGTTGAGCTTTTTGGAATTATTTCTGATTGCGGGCGTTTTTGGGCGGGTTTCAATCTA
ACTGTGCCCGATTTFAATTCAGACAACACGTTAGAAAGCGATGGTGCAGGCGGTGGTAACATTTCAG
ACGGCAAATCTACTAATGGCGGCGGTGGTGGAGCTGATGATAAATCTACCATCGGTGGAGGCGCAG
GCGGGGCTGGCGGCGGAGGCGGAGGCGGAGGTGGTGGCGGTGATGCAGACGGCGGTTTAGGCT
CAAATGTCTCTTTAGGCAACACAGTCGGCACCTCAACTATTGTACTGGTTTCGGGCGCCGTTTTTGG
TTTGACCGGTCTGAGACGAGTGCGATTTTTTTCGTTTCTAATAGCTTCCAACAATTGTTGTCTGTCGT
CTAAAGGTGCAGCGGGTTGAGGTTCCGTCGGCATTGGTGGAGCGGGCGGCAATTCAGACATCGAT
GGTGGTGGTGGTGGAGGCGCTGGAATGTTAGGCACGGGAGAAGGTGGTGGCGGCGGTGCCG
CCGGTATAATTTGTTCTGGTTTAGTTTGTTCGCGCACGATTGTGGGCACCGGCGCAGGCGCCGCTG
GCTGCACAACGGAAGGTCGTCTGCTTCGAGGCAGCGCTTGGGGTGGTGGCAATTCAATATTATAATT
GGAATACAAATCGTAAAAATCTGCTATAAGCATTGTAATTTCGCTATCGTTTACCGTGCCGATATTTAA
CAACCGCTCAATGTAAGCAATTGTATTGTAAAGAGATTGTCTCAAGCTCGGAACGCTGCGCTCGGTC
GTTCGGCTGCGGCGAGCGGTATCAGCTCACTCAAAGGCGGTAATACGGTTATCCACAGAATCAGGG
GATAACGCAGGAAAGAACATGTGAGCAAAAGGCCAGCAAAAGGCCAGGAACCGTAAAAAGGCCGC
GTTGCTGGCGTTTTTCCATAGGCTCCGCCCCCCTGACGAGCATCACAAAAATCGACGCTCAAGTCAG
AGGTGGCGAAACCCGACAGGACTATAAAGATACCAGGCGTTTCCCCCTGGAAGCTCCCTCGTGCGC
TCTCCTGTTCCGACCCTGCCGCTTACCGGATACCTGTCCGCCTTTCTCCCTTCGGGAAGCGTGGCG
CTTTCTCAATGCTCACGCTGTAGGTATCTCAGTTCGGTGTAGGTCGTTCGCTCCAAGCTGGGCTGTG
TGCACGAACCCCCCGTTCAGCCCGACCGCTGCGCCTTATCCGGTAACTATCGTCTTGAGTCCAACC
CGGTAAGACACGACTTATCGCCACTGGCAGCAGCCACTGGTAACAGGATTAGCAGAGCGAGGTATG
TAGGCGGTGCTACAGAGTTCTTGAAGTGGTGGCCTAACTACGGCTACACTAGAAGGACAGTATTTGG
TATCTGCGCTCTGCTGAAGCCAGTTACCTTCGGAAAAAGAGTTGGTAGCTCTTGATCCGGCAAACAA
ACCACCGCTGGTAGCGGTGGTTTTTTTGTTTGCAAGCAGCAGATTACGCGCAGAAAAAAAGGATCTC
AAGAAGATCCTTTGTTACCAATGCTTAATCAGTGAGGCACCTATCTCAGCGATCTGTCTATTTCGTTC
ATCCATAGTTGCCTGACTCCCCGTCGTGTAGATAACTACGATACGGGAGGGCTTACCATCTGGCCCC
AGTGCTGCAATGATACCGCGAGACCCACGCTCACCGGCTCCAGATTTATCAGCAATAAACCAGCCA
GCCGGAAGGGCCGAGCGCAGAAGTGGTCCTGCAACTTTATCCGCCTCCATCCAGTCTATTAATTGTT
GCCGGGAAGCTAGAGTAAGTAGTTCGCCAGTTAATAGTTTGCGCAACGTTGTTGCCATTGCTACAGG
CATCGTGGTGTCACGCTCGTCGTTTGGTATGGCTTCATTCAGCTCCGGTTCCCAACGATCAAGGCGA
```

-continued

```
GTTACATGATCCCCCATGTTGTGCAAAAAAGCGGTTAGCTCCTTCGGTCCTCCGATCGTTGTCAGAA

GTAAGTTGGCCGCAGTGTTATCACTCATGGTTATGGCAGCACTGCATAATTCTCTTACTGTCATGCCA

TCCGTAAGATGCTTTTCTGTGACTGGTGAGTACTCAACCAAGTCATTCTGAGAATAGTGTATGCGGC

GACCGAGTTGCTCTTGCCCGGCGTCAATACGGGATAATACCGCGCCACATAGCAGAACTTTAAAAGT

GCTCATCATTGGAAAACGTTCTTCGGGGCGAAAACTCTCAAGGATCTTACCGCTGTTGAGATCCAGT

TCGATGTAACCCACTCGTGCACCCAACTGATCTTCAGCATCTTTTACTTTCACCAGCGTTTCTGGGTG

AGCAAAAACAGGAAGGCAAAATGCCGCAAAAAAGGGAATAAGGGCGACACGGAAATGTTGAATACT

CATACTCTTCCTTTTTCAATATTATTGAAGCATTTATCAGGGTTATTGTCTCATGTCCGCGCGTTTCCT

GCATCTTTTAATCAAATCCCAAGATGTGTATAAACCACCAAACTGCCAAAAAATGAAAACTGTCGACA

AGCTCTGTCCGTTTGCTGGCAACTGCAAGGGTCTCAATCCTATTTGTAATTATTGAATAATAAAACAA

TTATAAATGTCAAATTTGTTTTTTATTAACGATACAAACCAAACGCAACAAGAACATTTGTAGTATTATC

TATAATTGAAAACGCGTAGTTATAATCGCTGAGGTAATATTTAAAATCATTTTCAAATGATTCACAGTT

AATTTGCGACAATATAATTTTATTTTCACATAAACTAGACGCCTTGTCGTCTTCTTCTTCGTATTCCTTC

TCTTTTTCATTTTTCTCTTCATAAAAATTAACATAGTTATTATCGTATCCATATATGTATCTATCGTATAG

AGTAAATTTTTGTTGTCATAAATATATATGTCTTTTTAATGGGGTGTATAGTACCGCTGCGCATAGT

TTTTCTGTAATTTACAACAGTGCTATTTTCTGGTAGTTCTTCGGAGTGTGTTGCTTTAATTATTAAATTT

ATATAATCAATGAATTTGGGATCGTCGGTTTTGTACAATATGTTGCCGGCATAGTACGCAGCTTCTTC

TAGTTCAATTACACCATTTTTTAGCAGCACCGGATTAACATAACTTTCCAAAATGTTGTACGAACCGTT

AAACAAAAACAGTTCACCTCCCTTTTCTATACTATTGTCTGCGAGCAGTTGTTTGTTGTTAAAAATAAC

AGCCATTGTAATGAGACGCACAAACTAATATCACAAACTGGAAATGTCTATCAATATATAGTTGCTCT

AGTTATTAATAGTAATCAATTACGGGGTCATTAGTTCATAGCCCATATATGGAGTTCCGCGTTACATA

ACTTACGGTAAATGGCCCGCCTGGCTGACCGCCCAACGACCCCCGCCCATTGACGTCAATAATGAC

GTATGTTCCCATAGTAACGCCAATAGGGACTTTCCATTGACGTCAATGGGTGGACTATTTACGGTAAA

CTGCCCACTTGGCAGTACATCAAGTGTATCATATGCCAAGTACGCCCCCTATTGACGTCAATGACGG

TAAATGGCCCGCCTGGCATTATGCCCAGTACATGACCTTATGGGACTTTCCTACTTGGCAGTACATC

TACGTATTAGTCATCGCTATTACCATGCATGGTCGAGGTGAGCCCCACGTTCTGCTTCACTCTCCCC

ATCTCCCCCCCCCTCCCCACCCCCAATTTTGTATTTATTTATTTTTTAATTATTTTGTGCAGCGATGGGG

GCGGGGGGGGGGGGGGCGCGCGCCAGGCGGGGCGGGGCGGGGCGAGGGGCGGGGCGGGG

CGAGGCGGAGAGGTGCGGCGGCAGCCAATCAGAGCGGCGCGCTCCGAAAGTTTCCTTTTATGGCG

AGGCGGCGGCGGCGGCCCTATAAAAAGCGAAGCGCGCGGCGGGCG
```

(VGLUT2 [human])

SEQ ID NO: 10

```
MESVKQRILAPGKEGLKNFAGKSLGQIYRVLEKKQDTGETIELTEDGKPLEVPERKAPLCDCTCFGLPRR

YIIAIMSGLGFCISFGIRCNLGVAIVDMVNNSTIHRGGKVIKEKAKFNWDPETVGMIHGSFFWGYIITQIPGG

YIASRLAANRVFGAAILLTSTLNMLIPSAARVHYGCVIFVRILQGLVEGVTYPACHGIWSKWAPPLERSRLA

TTSFCGSYAGAVIAMPLAGILVQYTGWSSVFYVYGSFGMVWYWFWLLVSYESPAKHPTITDEERRYIEES

IGESANLLGAMEKFKTPWRKFFTSMPVYAIIVANFCRSWTFYLLLISQPAYFEEVFGFEISKVGMLSAVPHL

VMTIIVPIGGQIADFLRSKQILSTTTVRKIMNCGGFGMEATLLLVVGYSHTRGVAISFLVLAVGFSGFAISGF

NVNHLDIAPRYASILMGISNGVGTLSGMVCPIIVGAMTKNKSREEWQYVFLIAALVHYGGVIFYAIFASGEK

QPWADPEETSEEKCGFIHEDELDEETGDITQNYINYGTTKSYGATTQANGGWPSGWEFEKKEEFVQGEVQ

DSHSYKDRVDYS
```

(pTriEx-1-VGLUT2 [human]-His)

SEQ ID NO: 11

GGAGTCGCTGCGACGCTGCCTTCGCCCCGTGCCCCGCTCCGCCGCCGCCTCGCGCCGCCCGCCC

CGGCTCTGACTGACCGCGTTACTCCCACAGGTGAGCGGGCGGGACGGCCCTTCTCCTTCGGGCTG

TAATTAGCGCTTGGTTTAATGACGGCTTGTTTCTTTTCTGTGGCTGCGTGAAAGCCTTGAGGGGCTC

CGGGAGGGCCCTTTGTGCGGGGGGAGCGGCTCGGGGCTGTCCGCGGGGGACGGCTGCCTTCG

GGGGGGACGGGCAGGGCGGGGTTCGGCTTCTGGCGTGTGACCGGCGGCTCTAGAGCCTCTGCT

AACCATGTTCATGCCTTCTTCTTTTTCCTACAGCTCCTGGGCAACGTGCTGGTTATTGTGCTGTCTCA

TCATTTTGGCAAAGAATTGGATCGGACCGAAATTAATACGACTCACTATAGGGGAATTGTGAGCGGA

TAACAATTCCCCGGAGTTAATCCGGGACCTTTAATTCAACCCAACACAATATATTATAGTTAAATAAGA

ATTATTATCAAATCATTTGTATATTAATTAAAATACTATACTGTAAATTACATTTTATTTACAATCAAAGG

AGATATACCATGGAATCCGTAAAACAAAGGATTTTGGCACCTGGCAAAGAAGGGCTGAAGAACTTTG

CCGGTAAGTCACTCGGCCAGATTTACCGAGTGCTGGAGAAGAAGCAGGACACTGGAGAAACCATCG

AGCTTACAGAGGATGGGAAACCGTTGGAGGTGCCCGAAAGGAAGGCCCCACTGTGTGATTGCACCT

GTTTCGGTCTGCCTCGGCGGTATATTATAGCGATCATGTCTGGACTGGGCTTTTGCATATCCTTTGG

GATCAGATGCAATCTCGGGGTTGCCATAGTGGACATGGTGAACAACTCCACCATCCACAGAGGAGG

CAAAGTCATAAAAGAGAAAGCTAAGTTCAACTGGGATCCTGAAACAGTGGGCATGATCCACGGTTCT

TTCTTCTGGGGATACATCATCACCCAGATACCCGGCGGCTACATCGCTAGTCGCTTGGCCGCAAATC

GGGTTTTCGGGGCTGCCATCCTGCTTACTAGCACCCTCAATATGCTCATTCCTAGCGCTGCCAGAGT

CCACTATGGCTGCGTCATTTTCGTCAGGATACTGCAGGGCTTGGTGGAGGGTGTGACGTATCCCGC

ATGTCATGGCATTTGGAGCAAATGGGCTCCACCTTTGGAGAGGAGCAGGCTGGCCACAACCAGCTT

CTGTGGATCCTATGCAGGCGCCGTGATTGCTATGCCCCTGGCTGGTATTCTCGTCCAGTACACTGG

GTGGTCCTCTGTCTTTTACGTGTATGGCAGCTTTGGGATGGTCTGGTACATGTTCTGGCTGCTTGTG

AGCTACGAAAGTCCAGCCAAGCATCCGACCATTACGGATGAAGAGCGTCGGTACATTGAGGAGTCT

ATTGGCGAATCTGCCAATCTGTTGGGAGCTATGGAGAAGTTTAAGACTCCATGGCGCAAATTCTTCA

CAAGCATGCCCGTATATGCAATCATCGTTGCCAATTTCTGCAGATCCTGGACCTTTTATCTGCTGTTG

ATTTCTCAACCCGCGTATTTTGAGGAGGTGTTTGGGTTCGAAATCAGCAAGGTGGGAATGCTTTCAG

CAGTTCCACACCTGGTGATGACAATCATCGTACCCATAGGAGGGCAAATTGCTGACTTTCTGCGCAG

TAAACAGATCCTGAGTACCACAACTGTCCGAAAGATTATGAACTGTGGAGGATTCGGCATGGAAGCC

ACCCTCCTGCTTGTGGTTGGCTATAGCCATACCAGAGGTGTCGCCATCTCATTTCTGGTTCTGGCGG

TAGGTTTCAGTGGATTTGCCATCTCCGGTTTCAATGTTAACCACCTCGACATCGCACCCCGTTATGCT

AGCATTCTGATGGGCATCAGCAATGGCGTGGGCACACTCAGCGGAATGGTATGCCCAATTATCGTA

GGCGCCATGACTAAGAACAAATCACGCGAAGAGTGGCAGTACGTGTTTCTGATTGCAGCACTGGTG

CATTATGGTGGGGTCATTTTCTACGCGATCTTTGCTTCAGGGGAAAAGCAACCGTGGGCAGATCCTG

AAGAGACTAGTGAGGAGAAGTGCGGTTTCATCCATGAGGACGAACTGGACGAGGAAACAGGAGACA

TAACACAGAACTACATCAACTATGGAACGACGAAATCCTACGGGGCCACCACTCAGGCCAATGGAG

GCTGGCCTTCTGGGTGGGAAAAGAAGGAGGAATTTGTGCAAGGGGAGGTGCAGGATTCCCACAGC

TATAAGGACCGAGTTGATTATTCACTCGAGCACCACCATCACCATCACCATCACTAAGTGATTAACCT

CAGGTGCAGGCTGCCTATCAGAAGGTGGTGGCTGGTGTGGCCAATGCCCTGGCTCACAAATACCAC

TGAGATCGATCTTTTTCCCTCTGCCAAAAATTATGGGGACATCATGAAGCCCCTTGAGCATCTGACTT

CTGGCTAATAAAGGAAATTTATTTTCATTGCAATAGTGTGTTGGAATTTTTTGTGTCTCTCACTCGGAA

GGACATATGGGAGGGCAAATCATTTAAAACATCAGAATGAGTATTTGGTTTAGAGTTTGGCAACATAT

-continued

```
GCCCATATGTAACTAGCATAACCCCTTGGGGCCTCTAAACGGGTCTTGAGGGGTTTTTTGCTGAAAG
CATGCGGAGGAAATTCTCCTTGAAGTTTCCCTGGTGTTCAAAGTAAAGGAGTTTGCACCAGACGCAC
CTCTGTTCACTGGTCCGGCGTATTAAAACACGATACATTGTTATTAGTACATTTATTAAGCGCTAGATT
CTGTGCGTTGTTGATTTACAGACAATTGTTGTACGTATTTTAATAATTCATTAAATTTATAATCTTTAGG
GTGGTATGTTAGAGCGAAAATCAAATGATTTTCAGCGTCTTTATATCTGAATTTAAATATTAAATCCTC
AATAGATTTGTAAAATAGGTTTCGATTAGTTTCAAACAAGGGTTGTTTTTCCGAACCGATGGCTGGAC
TATCTAATGGATTTTCGCTCAACGCCACAAAACTTGCCAAATCTTGTAGCAGCAATCTAGCTTTGTCG
ATATTCGTTTGTGTTTTGTTTTGTAATAAAGGTTCGACGTCGTTCAAAATATTATGCGCTTTTGTATTTC
TTTCATCACTGTCGTTAGTGTACAATTGACTCGACGTAAACACGTTAAATAGAGCTTGGACATATTTAA
CATCGGGCGTGTTAGCTTTATTAGGCCGATTATCGTCGTCGTCCCAACCCTCGTCGTTAGAAGTTGC
TTCCGAAGACGATTTTGCCATAGCCACACGACGCCTATTAATTGTGTCGGCTAACACGTCCGCGATC
AAATTTGTAGTTGAGCTTTTTGGAATTATTTCTGATTGCGGGCGTTTTTGGGCGGGTTTCAATCTAACT
GTGCCCGATTTTAATTCAGACAACACGTTAGAAAGCGATGGTGCAGGCGGTGGTAACATTTCAGACG
GCAAATCTACTAATGGCGGCGGTGGTGGAGCTGATGATAAATCTACCATCGGTGGAGGCGCAGGCG
GGGCTGGCGGCGGAGGCGGAGGCGGAGGTGGTGGCGGTGATGCAGACGGCGGTTTAGGCTCAAA
TGTCTCTTTAGGCAACACAGTCGGCACCTCAACTATTGTACTGGTTTCGGGCGCCGTTTTTGGTTTGA
CCGGTCTGAGACGAGTGCGATTTTTTTCGTTTCTAATAGCTTCCAACAATTGTTGTCTGTCGTCTAAA
GGTGCAGCGGGTTGAGGTTCCGTCGGCATTGGTGGAGCGGGCGGCAATTCAGACATCGATGGTGG
TGGTGGTGGTGGAGGCGCTGGAATGTTAGGCACGGGAGAAGGTGGTGGCGGCGGTGCCGCCGGT
ATAATTTGTTCTGGTTTAGTTTGTTCGCGCACGATTGTGGGCACCGGCGCAGGCGCCGCTGGCTGC
ACAACGGAAGGTCGTCTGCTTCGAGGCAGCGCTTGGGGTGGTGGCAATTCAATATTATAATTGGAAT
ACAAATCGTAAAAATCGCTATAAGCATTGTAATTTCGCTATCGTTTACCGTGCCGATATTTAACAACC
GCTCAATGTAAGCAATTGTATTGTAAAGAGATTGTCTCAAGCTCGGAACGCTGCGCTCGGTCGTTCG
GCTGCGGCGAGCGGTATCAGCTCACTCAAAGGCGGTAATACGGTTATCCACAGAATCAGGGGATAA
CGCAGGAAAGAACATGTGAGCAAAAGGCCAGCAAAAGGCCAGGAACCGTAAAAAGGCCGCGTTGCT
GGCGTTTTTCCATAGGCTCCGCCCCCCTGACGAGCATCACAAAAATCGACGCTCAAGTCAGAGGTG
GCGAAACCCGACAGGACTATAAAGATACCAGGCGTTTCCCCCTGGAAGCTCCCTCGTGCGCTCTCC
TGTTCCGACCCTGCCGCTTACCGGATACCTGTCCGCCTTTCTCCCTTCGGGAAGCGTGGCGCTTTCT
CAATGCTCACGCTGTAGGTATCTCAGTTCGGTGTAGGTCGTTCGCTCCAAGCTGGGCTGTGTGCAC
GAACCCCCCGTTCAGCCCGACCGCTGCGCCTTATCCGGTAACTATCGTCTTGAGTCCAACCCGGTA
AGACACGACTTATCGCCACTGGCAGCAGCCACTGGTAACAGGATTAGCAGAGCGAGGTATGTAGGC
GGTGCTACAGAGTTCTTGAAGTGGTGGCCTAACTACGGCTACACTAGAAGGACAGTATTTGGTATCT
GCGCTCTGCTGAAGCCAGTTACCTTCGGAAAAAGAGTTGGTAGCTCTTGATCCGGCAAACAAACCAC
CGCTGGTAGCGGTGGTTTTTTTGTTTGCAAGCAGCAGATTACGCGCAGAAAAAAAGGATCTCAAGAA
GATCCTTTGTTACCAATGCTTAATCAGTGAGGCACCTATCTCAGCGATCTGTCTATTTCGTTCATCCA
TAGTTGCCTGACTCCCCGTCGTGTAGATAACTACGATACGGGAGGGCTTACCATCTGGCCCCAGTG
CTGCAATGATACCGCGAGACCCACGCTCACCGGCTCCAGATTTATCAGCAATAAACCAGCCAGCCG
GAAGGGCCGAGCGCAGAAGTGGTCCTGCAACTTTATCCGCCTCCATCCAGTCTATTAATTGTTGCCG
GGAAGCTAGAGTAAGTAGTTCGCCAGTTAATAGTTTGCGCAACGTTGTTGCCATTGCTACAGGCATC
GTGGTGTCACGCTCGTCGTTTGGTATGGCTTCATTCAGCTCCGGTTCCCAACGATCAAGGCGAGTTA
```

-continued

```
CATGATCCCCCATGTTGTGCAAAAAAGCGGTTAGCTCCTTCGGTCCTCCGATCGTTGTCAGAAGTAA
GTTGGCCGCAGTGTTATCACTCATGGTTATGGCAGCACTGCATAATTCTCTTACTGTCATGCCATCC
GTAAGATGCTTTTCTGTGACTGGTGAGTACTCAACCAAGTCATTCTGAGAATAGTGTATGCGGCGAC
CGAGTTGCTCTTGCCCGGCGTCAATACGGGATAATACCGCGCCACATAGCAGAACTTTAAAAGTGCT
CATCATTGGAAAACGTTCTTCGGGGCGAAAACTCTCAAGGATCTTACCGCTGTTGAGATCCAGTTCG
ATGTAACCCACTCGTGCACCCAACTGATCTTCAGCATCTTTTACTTTCACCAGCGTTTCTGGGTGAGC
AAAAACAGGAAGGCAAAATGCCGCAAAAAAGGGAATAAGGGCGACACGGAAATGTTGAATACTCATA
CTCTTCCTTTTTCAATATTATTGAAGCATTTATCAGGGTTATTGTCTCATGTCCGCGCGTTTCCTGCAT
CTTTTAATCAAATCCCAAGATGTGTATAAACCACCAAACTGCCAAAAAATGAAAACTGTCGACAAGCT
CTGTCCGTTTGCTGGCAACTGCAAGGGTCTCAATCCTATTTGTAATTATTGAATAATAAAACAATTATA
AATGTCAAATTTGTTTTTTATTAACGATACAAACCAAACGCAACAAGAACATTTGTAGTATTATCTATAA
TTGAAAACGCGTAGTTATAATCGCTGAGGTAATATTTAAAATCATTTTCAAATGATTCACAGTTAATTT
GCGACAATATAATTTTATTTTCACATAAACTAGACGCCTTGTCGTCTTCTTCTTCGTATTCCTTCTCTTT
TTCATTTTTCTCTTCATAAAAATTAACATAGTTATTATCGTATCCATATATGTATCTATCGTATAGAGTA
AATTTTTTGTTGTCATAAATATATATGTCTTTTTTAATGGGGTGTATAGTACCGCTGCGCATAGTTTTTC
TGTAATTTACAACAGTGCTATTTTCTGGTAGTTCTTCGGAGTGTGTTGCTTTAATTATTAAATTTATATA
ATCAATGAATTTGGGATCGTCGGTTTTGTACAATATGTTGCCGGCATAGTACGCAGCTTCTTCTAGTT
CAATTACACCATTTTTTAGCAGCACCGGATTAACATAACTTTCCAAAATGTTGTACGAACCGTTAAACA
AAAACAGTTCACCTCCCTTTTCTATACTATTGTCTGCGAGCAGTTGTTTGTTGTTAAAAATAACAGCCA
TTGTAATGAGACGCACAAACTAATATCACAAACTGGAAATGTCTATCAATATATAGTTGCTCTAGTTAT
TAATAGTAATCAATTACGGGGTCATTAGTTCATAGCCCATATATGGAGTTCCGCGTTACATAACTTAC
GGTAAATGGCCCGCCTGGCTGACCGCCCAACGACCCCCGCCCATTGACGTCAATAATGACGTATGT
TCCCATAGTAACGCCAATAGGGACTTTCCATTGACGTCAATGGGTGGACTATTTACGGTAAACTGCC
CACTTGGCAGTACATCAAGTGTATCATATGCCAAGTACGCCCCCTATTGACGTCAATGACGGTAAAT
GGCCCGCCTGGCATTATGCCCAGTACATGACCTTATGGGACTTTCCTACTTGGCAGTACATCTACGT
ATTAGTCATCGCTATTACCATGCATGGTCGAGGTGAGCCCCACGTTCTGCTTCACTCTCCCCATCTC
CCCCCCCTCCCCACCCCCAATTTTGTATTTATTTATTTTTTAATTATTTTGTGCAGCGATGGGGCGG
GGGGGGGGGGGGGCGCGCGCCAGGCGGGGCGGGGCGGGGCGAGGGGCGGGGCGGGGCGAG
GCGGAGAGGTGCGGCGGCAGCCAATCAGAGCGGCGCGCTCCGAAAGTTTCCTTTTATGGCGAGGC
GGCGGCGGCGGCCCTATAAAAAGCGAAGCGCGCGGCGGGCG
```

(VGLUT2 [human]-H8)

SEQ ID NO: 12

```
MESVKQRILAPGKEGLKNFAGKSLGQIYRVLEKKQDTGETIELTEDGKPLEVPERKAPLCDCTCFGLPRR
YIIAIMSGLGFCISFGIRCNLGVAIVDMVNNSTIHRGGKVIKEKAKFNWDPETVGMIHGSFFWGYIITQIPGG
YIASRLAANRVFGAAILLTSTLNMLIPSAARVHYGCVIFVRILQGLVEGVTYPACHGRAISKWAPPLERSRLA
TTSFCGSYAGAVIAMPLAGILVQYTGWSSVFYVYGSFGMVWYMANLLVSYESPAKHPTITDEERRYIEES
IGESANLLGAMEKFKTPWRKFFTSMPVYAIIVANFCRSWTFYLLLISQPAYFEEVFGFEISKVGMLSAVPHL
VMTIIVPIGGQIADFLRSKDILSTTTVRKIMNCGGFGMEATLLLVVGYSHTRGVAISFLVLAVGFSGFAISGF
NVNHLDIAPRYASILMGISNGVGTLSGMVCPIIVGAMTKNKSREEWQYVFLIAALVHYGGVIFYAIFASGEK
QPWADPEETSEEKCGFIHEDELDEETGDITQNYINYGTTKSYGATTQANGGWPSGWEKKEEFVQGEVQ
DSHSYKDRVDYSLEHHHHHHHH
```

(human VGLUT1, identical with Uniprot Q9P2U7)

SEQ ID NO: 13

MEFRQEEFRKLAGRALGKLHRLLEKRQEGAETLELSADGRPVTTQTRDPPVVDCTCFGLPRRYIIAIMSG

LGFCISFGIRCNLGVAIVSMVNNSTTHRGGHVVVQKAQFSWDPETVGLIHGSFFWGYIVTQIPGGFICQKF

AANRVFGFAIVATSTLNMLIPSAARVHYGCVIFVRILQGLVEGVTYPACHGIWSKWAPPLERSRLATTAFC

GSYAGAVVAMPLAGVLVQYSGWSSVFYWGSFGIFWYLFWLLVSYESPALHPSISEEERKYIEDAIGESA

KLMNPLTKFSTPWRRFFTSMPVYAIIVANFCRSWTFYLLLISQPAYFEEVFGFEISKVGLVSALPHLVMTIIV

PIGGQIADFLRSRRIMSTTNVRKLMNCGGFGMEATLLLVVGYSHSKGVAISFLVLAVGFSGFAISGFNVNH

LDIAPRYASILMGISNGVGTLSGMVCPIIVGAMTKHKTREEWQYVFLIASLVHYGGVIFYGVFASGEKQPW

AEPEEMSEEKCGFVGHDQLAGSDDSEMEDEAEPPGAPPAPPPSYGATHSTFQPPRPPPPVRDY (human VGLUT3, identical with Uniprot Q8NDX2)

SEQ ID NO: 14

MPFKAFDTFKEKILKPGKEGVKNAVGDSLGILQRKIDGTTEEEDNIELNEEGRPVQTSRPSPPLCDCHCC

GLPKRYIIAIMSGLGFCISFGIRCNLGVAIVEMVNNSTVYVDGKPEIQTAQFNWDPETVGLIHGSFFWGYIM

TQIPGGFISNKFAANRVFGAAIFLTSTLNMFIPSAARVHYGCVMCVRILQGLVEGVTYPACHGMWSKWAP

PLERSRLATTSFCGSYAGAVVAMPLAGVLVQYIGWSSVFYIYGMFGIIWYMFWLLQAYECPAAHPTISNE

EKTYIETSIGEGANVVSLSKFSTPWKRFFTSLPVYAIIVANFCRSWTFYLLLISQPAYFEEVFGFAISKVGLL

SAVPHMVMTIVVPIGGQLADYLRSRQILTTTAVRKIMNCGGFGMEATLLLVVGFSHTKGVAISFLVLAVGF

SGFAISGFNVNHLDIAPRYASILMGISNGVGTLSGMVCPLIVGAMTRHKTREEWQNVFLIAALVHYSGVIFY

GVFASGEKQEWADPENLSEEKCGIIDQDELAEEIELNHESFASPKKKMSYGATSQNCEVQKKEWKGQR

GATLDEEELTSYQNEERNFSTIS (consensus sequence from human VGLUT1, VGLUT2, VGLUT3)

SEQ ID NO: 15

XXXXXXXXXXXXXXXXXXXXXXXEXXXXXXXGXXLGXXXRXXXXXXXXXXXXELXXXGXPXXXXXXXXXPXXDCXC

XGLPXRYIIAIMSGLGFCISFGIRCNLGVAIVXMVNNSTXXXXGXXXXXXXAXFXWDPETVGXIHGSFFWGYI

XTQIPGGXIXXXXAANRVFGXAIXXTSTLNMXIPSAARVHYGCVXXVRILQGLVEGVTYPACHIGXWSKWA

PPLERSRLATTXFCGSYAGAVVAMPLAGXLVQYXGWSSVFYXYGXFGXXWYXFWLLXXYEXPAXHPXIX

XEEXXXYIEXXIGEXAXXXXXXXXKFXTPWXXFFTSXPVYAIIVANFCRSWTFYLLLISQPAYFEEVFGFXISKV

GXXSAXPHXVMTIXVPIGGQXADXLRSXXIXXTTXVRKXMNCGGEGMEATLLLVVGXSHXXGVAISFLVLA

VGFSGFAISGFNVNHLDIAPRYASILMGISNGVGTLSGMVCPXIVGAMTXXKXREEWQXVFLIAXLVHYXG

VIFYXXFASGEKQXWAXPEXXSEEKCGXXXXDXLXXXXXXXXXXXXXXXXXXXXXSYGATXXXXXXX

XXXXXXXXXXXXXXXXXXXXXXXXXXXXX;

wherein X is one or no amino acid, preferably one amino acid.

(VGLUT2 human aa1-71)

SEQ ID NO: 16

MESVKQRILAPGKEGLKNFAGKSLGQIYRVLEKKQDTGETIELTEDGKPLEVPERKAPLCDCTCFGLPRRY (VGLUT2 human aa93-125)

SEQ ID NO: 17

VAIVDMVNNSTIHRGGKVIKEKAKFNWDPETVG (VGLUT2 human aa266-310)

SEQ ID NO: 18

ESPAKHPTITDEERRYIEESIGESANLLGAMEKFKTPWRKFFTSM (VGLUT2 human aa499-582)

SEQ ID NO: 19

SGEKQPWADPEETSEEKCGFIHEDELDEETGDITQNYINYGTTKSYGATTQANGGWPSGWEKKEEFVQ

GEVQDSHSYKDRVDYS (VGLUT1 rat, Uniprot Q62634)

SEQ ID NO: 20

MEFRQEEFRKLAGRALGRLHRLLEKRQEGAETLELSADGRPVTTHTRDPPVVDCTCFGLPRRYIIAIMSG
LGFCISEGIRCNLGVAIVSMVNNSTTHRGGHVVVQKAQFNWDPETVGLIHGSFFWGYIVTQIPGGFICQKF
AANRVFGFAIVATSTLNMLIPSAARVHYGCVIFVRILQGLVEGVTYPACHGIWSKWAPPLERSRLATTAFC
GSYAGAVVAMPLAGVLVQYSGWSSVFYVYGSFGIFWYLFWLLVSYESPALHPSISEEERKYIEDAIGESA
KLMNPVTKFNTPWRRFFTSMPVYAIIVANFCRSWTFYLLLISQPAYFEEVFGFEISKVGLVSALPHLVMTIIV
PIGGQIADFLRSRHIMSTTNVRKLMNCGGFGMEATLLLVVGYSHSKGVAISFLVLAVGFSGFAISGENVNH
LDIAPRYASILMGISNGVGTLSGMVCRIVGAMTKHKTREEWQYVFLIASLVHYGGVIFYGVFASGEKQPW
AEPEEMSEEKCGFVGHDQLAGSDESEMEDEVEPPGAPPAPPPSYGATHSTVQPPRPPPPVRDY (VGLUT2 rat, Uniprot Q9JI12)

SEQ ID NO: 21

MESVKQRILAPGKEGIKNFAGKSLGQIYRVLEKKQDNRETIELTEDGKPLEVPEKKAPLCDCTCFGLPRRY
IIAIMSGLGFCISFGIRCNLGVAIVDMVNNSTIHRGGKVIKEKAKFNWDPETVGMIHGSFFWGYIITQIPGGYI
ASRLAANRVFGAAILLTSTLNMLIPSAARVHYGCVIEVRILQGLVEGVTYPACHGIWSKWAPPLERSRLATT
SFCGSYAGAVIAMPLAGILVQYTGWSSVFYVYGSFGMVWYMFWLLVSYESPAKFIPTITDEERRYIEESIG
ESANLLGAMEKFKTPWRKFFTSMPVYAIIVANFCRSWTFYLLLISQPAYFEEVFGFEISKVGMLSAVPHLV
MTIIVPIGGQIADFLRSKQILSTTTVRKIMNCGGFGMEATLLLVVGYSHIRGVAISFLVLAVGFSGFAISGFN
VNHLDIAPRYASILMGISNGVGTLSGMVCPIIVGAMTKNKSREEWQYVFLIAALVHYGGVIFYALFASGEKQ
PWADPEETSEEKCGFIHEDELDEETGDITQNYINYGTIKSYGATSQENGGWPNGWEKKEEFVQESAQD
AYSYKDRDDYS (VGLUT3 rat, Uniprot Q7TSF2)

SEQ ID NO: 22

MPFNAFDTFKEKILKPGKEGVKNAVGDSLGILQRKLDGTNEEGDAIELSEEGRPVQTSRARAPVCDCSCC
GIPKRYIIAVMSGLGFCISFGIRCNLGVAIVEMVNNSTVYVDGKPEIQTAQFNWDPETVGLIHGSFFWGYIV
TQIPGGFISNKFAANRVFGAAIFLTSTLNMFIPSAARVHYGCVMCVRILQGLVEGVTYPACHGMWSKWAP
PLERSRLATTSFCGSYAGAVVAMPLAGVLVGYIGWASVFYIYGMFGIIWYMFWLLQAYECPAVHPTISNE
ERTYIETSIGEGANLASLSKFNTPWRRFFTSLPVYAIIVANFCRSWTFYLLLISQPAYFEEVFGFAISKVGLL
SAVPHMVMTIVVPIGGQLADYLRSRKILTTTAVRKIMNCGGFGMEATLLLVVGFSHTKGVAISFLVLAVGFS
GFAISGFNVNHLDIAPRYASILMGISNGVGTLSGMVCPLIVGAMTKHKTREEWQNVFLIAALVHYSGVIFYG
VFASGEKQDWADPENLSEEKCGIIDQDELAEETELNHEAFVSPRKKMSYGATTQNCEVQKTDRRQQRE
SAFEGEEPLSYQNEEDFSETS (consensus sequence from immunoglobulin heavy constant gamma 1, 2, 3, 4)

SEQ ID NO: 23

ASTKGPSVFPLAPXSXSTSXXTAALGCLVKDYFPEPVTVSWNSGALTSGVHTFPAVLQSSGLYSLSSVVT
VPSSXXGTXTYXCNVXHKPSNTKVDKXVEXXXXXXXXXXXXXXXXXXXXXXXXXXXXXXXXXXXXXX
XXXXXXXXXXXXXXXXXCPXCPAPXXXXGPSVFLFPPKPKDTLMISRTPEVTCVVVDVSXEDPEVXFXWYV
DGVEVHNAKTKPREEQXNSTXRVVSVLTVXHQDWLNGKEYKCKVSNKXLPXXIEKTISKXKGQPREPQV
YTLPPSXXEXTKNQVSLTCLVKGFYPSDIXVEWESXGQPENNYXTTPPXLDSDGSFFLYSXLTVDKSRW
QXGNXFSCSVMHEALHNXXTQKSLSLSXGK wherein X is one or no amino acid, preferably one amino acid (H8-GST-(PSc)-VGLUT2-aa1-71)

SEQ ID NO: 61

MSHHHHHHHHMSPILGYWKIKGLVQPTRLLLEYLEEKYEEHLYERDEGDKWRNKKFELGLEFPNLPYYID
GDVKLTQSMAIIRYIADKHNMLGGCPKERAEISMLEGAVLDIRYGVSRIAYSKDFETLKVDFLSKLPEMLKM
FEDRLCHKTYLNGDHVTHPDFMLYDALDVVLYMDPMCLDAFPKLVCFKKRIEAIPQIDKYLKSSKYIAWPL

-continued

QGWQATFGGGDHPPKLEVLFQGPAMESVKQRILAPGKEGLKNFAGKSLGQIYRVLEKKQDTGETIELTE

DGKPLEVPERKAPLCDCTCFGLPRRY (H8-GST-(PSc)-VGLUT2-aa93-125)
SEQ ID NO: 62

MSHHHHHHHHMSPILGYWKIKGLVQPPTRLLLEYLEEKYEEHLYERDEGDKWRNKKFELGLEFPNLPYYID

GDVKLTQSMAIIRYIADKHNMLGGCPKERAESMLEGAVLDIRYGVSRIAYSKDFETLKVDFLSKLPEMLKM

FEDRLCHKTYLNGDHVTHPDFMLYDALDVVLYMDPMCLDAFPKLVCFKKRIEAIPQIDKYLKSSKYIAWFL

QGWQATFGGGDHPPKLEVLFQGPAMVAIVDMVNNSTIHRGGKVIKEKAKFNWDPETVG (H8-GST-(PSc)-VGLUT2-aa266-310)
SEQ ID NO: 63

MSHHHHHHHHMSPILGYWKIKGLVQPTRLLLEYLEEKYEEHLYERDEGDKWRNKKFELGLEFPNLPYYID

GDVKLTQSMAIIRYIADKHNMLGGCPKERAEISMLEGAVLDIRYGVSRIAYSKDFETLKVDFLSKLPEMLKM

FEDRLCHKTYLNGDHVTHPDFMLYDALDVVLYMDPMCLDAFPKLVCFKKRIEAIPQIDKYLKSSKYIAWFL

QGWQATFGGGDHPFKLEVLFQGPAMESPAKHPTITDEERRYIEESIGESANLLGAMEKFKTPWRKFFTSM (H8-GST-(PSc)-VGLUT2-aa499-582)
SEQ ID NO: 64

MSHHHHHHHHIHMSPILGYWKIKGLVQPTRLLLEYLEEKYEEHLYERDEGDKWRNKKFELGLEFPNLPYYID

GDVKLTQSMAIIRYIADKHNMLGGCPKERAEISMLEGAVLDIRYGVSRIAYSKDFETLKVDFLSKLPEMLKM

FEDRLCHKTYLNGDHVTHPDFMLYDALDVVLYMDPMCLDAFPKLVCFKKRIEAIPQIDKYLKSSKYIAWPL

QGWQATFGGGDHPPKLEVLFQGPAMSGEKQPWADPEETSEEKCGFIHEDELDEETGDITQNYINYGTT

KSYGATTQANGGWPSGWEKKEEFVQGEVQDSHSYKDRVDYS (H8-GST-(PSc)-VGLUT2-aa520-582)
SEQ ID NO: 65

MSHHHHHHHHMSPILGYWKIKGLVQPTRLLLEYLEEKYEEHLYERDEGDKWRNKKFELGLEFPNLPYYID

GDVKLTQSMAIIRYIADKHNMLGGCPKERAEISMLEGAVLDIRYGVSRIAYSKDFETLKVDFLSKLPEMLKM

FEDRLCHKTYLNGDHVTHPDFMLYDALDVVLYMDPMCLDAFFKLVCFKKRIEAIPQIDKYLKSSKYIAWPL

QGINQATFGGGIDHPPKLEVLFQGPAMHEDELDEETGDITQNVINYGTTKSYGATTQANGGINPSGINEKK

EEFVQGEVQDSHSYKDRVDYS (H8-GST-(PSc)-VGLUT2-aa520-564)
SEQ ID NO: 66

MSHHHHHHHHMSPILGYWKIKGLVQPTRLLLEYLEEKYEEHLYERDEGDKWRNKKFELGLEFPNLPYYID

GDVKLTQSMAIIRYIADKHNMLGGCPKERAEISMLEGAVLDIRYGVSRIAYSKDFETLKVDFLSKLPEMLKM

FEDRLCHKTYLNGDHVTHPDFMLYDALDVVLYMDPMCLDAFPKLVCFKKRIEAIPQOIDKYLKSSKYIAWPL

QGWQATFGGGDHPFKLEVLFQGPAMHEDELDEETGDITQNYINYGUKSYGATTOANGGVVPSGWEKK

EEF (H8-GST-(PSc)-VGLUT2-aa543-582)
SEQ ID NO: 67

MSHHHHHHHHMSPILGYWKIKGLVQPTRLLLEYLEEKYEEHLYERDEGDKWRNKKFELGLEFPNLPYYID

GDVKLTQSMAIIRYIADKHNMLGGCPKERAEISMLEGAVLDIRYGVSRIAYSKDFETLKVDFLSKLPEMLKM

FEDRLCHKTYLNGDHVTHPDFMLYDALDVVLYMDPMCLDAFPKLVCFKKRIEAIPQIDKYLKSSKYIAWPL

QGWQATFGGGDHPPKLEVLFQGPAMSYGATTQANGGWPSGWEKKEEFVQGEVQDSHSYKDRVDYS (H8-GST-(PSc)-VGLUT2-aa565-582)
SEQ ID NO: 68

MSHHHHHHHHIMSPILGYWKIKGLVQPTRLILEYLEEKYEEHLYERDEGDKWRNKKFELGLEFPNLPYYID

GDVKLTQSMAIIRYIADKHNMLGGCPKERAEISMLEGAVLDIRYGVSRIAYSKDFETLKVDFLSKLPEMLKM

FEDRLCHKTYLNGDFIVTHPDFMLYDALDVVLYMDPMCLDAFPKLVCFKKRIEAIPQIDKYLKSSKYIAWPL

QGWQATFGGGDHPFKLEVLFQGPAMVQGEVQDSFISYKDRVDYS

-continued (H8-GST-(PSc)-VGLUT2-aa499-542)

SEQ ID NO: 69

MSHHHHHHHHMSPILGYWKKGLVQPTRLLLEYLEEKYEEHLYERDEGDKWRNKKFELGLEFPNLPYYID

GDVKLTQSMAIIRYIADKHNMLGGCPKERAISMLEGAVLDIRYGVSRIAYSKDFETLKVDFLSKLPEMLKM

FEDRLCHKTYLNGDHVTHPDFMLYDALDVVLYMDPMCLDAFPKLVCFKKRIEAIPQIDKYLKSSKYIAWPL

QGWQATFGGGDHPPKLEVLFQGPAMSGEKQPWADPEETSEEKCGFIHEDELDEETGDITQNYINYGTTK (H8-GST-(PSc)-VGLUT2-aa499-564)

SEQ ID NO: 70

MSHHHHHHHHMSPILGYWKIKGLVQPTRLLLEYLEEKYEEHLYERDEGDKWRNKKFELGLEFPNLPYYID

GDVKLTQSMAIIRYIADKHNMLGGCPKERAEISMLEGAVLDIRYGVSRIAYSKDFETLKVDFLSKLPEMLKM

FEDRLCHKTYLNGDHVTHPDFMLYDALDVVLYMDPMCLDAFPKLVCFKKRIEAIPQIDKYLKSSKYIAWPL

QGWQATFGGGDHPPKLEVLFQGPAMSGEKQPWADPEETSEEKCGFIHEDELDEETGDITQNYINYGTT

KSYGATTQANGGWPSGWEKKEEF (H8-GST-(PSc)-VGLUT2-mutant-1)

SEQ ID NO: 71

MSHHHHHHHHMSPILGYWKIKGLVQPTRLLLEYLEEKYEEHLYERDEGDKWRNKKFELGLEFPNLPYYID

GDVKLTQSMAIIRYIADKHNMLGGCPKERAEISMLEGAVLDIRYGVSRIAYSKDFETLKVDFLSKLPEMLKM

FEDRLCHKTYLNGDHVTHPDFMLYDALDVVLYMDPMCLDAFPKLVCFKKRIEAIPQIDKYLKSSKYIAWPL

QGWQATFGGGDHPPKLEVLFQGPAMFIGHDQLAGSDDSITQNYINYGTTKSYGATTQANGGWPSGWE

KKEEF (H8-GST-(PSc)-VGLUT2-mutant-2)

SEQ ID NO: 72

MSHHHHHHHHMSPILGYWKIKGLVQPTRLLLEYLEEKYEEHLYERDEGDKWRNKKFELGLEFPNLPYYID

GDVKLIQSMAIIRYIADKHNMLGGCPKERAEISMLEGAVLDIRYGVSRIAYSKDFETLKVDFLSKLPEMLKM

FEDRLCHKTYLNGDHVTHPDFMLYDALDVVLYMDPMCLDAFPKLVCFKKRIEAIPQIDKYLKSSKYIAWPL

QGWQATFGGGDHPPKLEVLFQGPAMHEDELDEETGDITQNYINYGTTKSYGATTQANGGWPSGWPRP

PPPVRDYVQ (H8-GST-(PSc)-VGLUT2-mutant-3)

SEQ ID NO: 73

MSHHHHHHHHMSPILGYWKIKGLVQPTRLLLEYLEEKYEEHLYERDEGDKWRNKKFELGLEFPNLPYYID

GDVKLTQSMAIIRYIADKHNMLGGCPKERAEISMLEGAVLDIRYGVSRIAYSKDFETLKVDFLSKLPEMLKM

FEDRLCHKTYLNGDHVTHPDFMLYDALDVVLYMDPMCLDAFPKLVCFKKRIEAIPQIDKYLKSSKYIAWPL

QGWQATFGGGDHPPKLEVLFQGPAMHEDELDEETGDEMEDEAEPPGAPPAPPPSYGATHSTFQPEKK

EEF (H8-GST-(PSc)-VGLUT2-mutant-4)

SEQ ID NO: 74

MSHHHHHHHHMSPILGYWKIKGLVQPTRLLLEYLEEKYEEHLYERDEGDKWRNKKFELGLEFPNLPYYID

GDVKLTQSMAIIRYIADKHNMLGGCPKERAEISMLEGAVLDIRYGVSRIAYSKDFETLKVDFLSKLPEMLKM

FEDRLCHKTYLNGDHVTHPDFMLYDALDVVLYMDPMCLDAFPKLVCFKKRIEAIPQIDKYLKSSKYIAWPL

QGWQATFGGGDHPPKLEVLFQGPAMHDEEAEEIEGDITQNYINYGTTKSYGATTQANGGWPSGWEKKE

EF (VGLUT1-isoform1-H8)

SEQ ID NO: 75

MEFRQEEFRKLAGRALGKLHRLLEKRQEGAETLELSADGRPVTTQTRDPPVVDCTCFGLPRRYIIAIMSG

LGFCISEGIRCNLGVAIVSMVNNSTTHRGGHVVVQKAQFSWDPETVGLIFIGSFFWGYIVTQIPGGFICQKF

AANRVEGFAIVATSTLNMLIPSAARVHYGCVIEVRILQGLVEGVTYPACHGIWSKWAPPLERSRLATTAFC

GSYAGAVVAMPLAGVLVQYSGVVSSVEYWGSFGIFWYLRNLLVSYESPALHPSISEEERKYIEDAIGESA

KLMNPLTKESTPWRREFTSMPVYAIIVANFCRSWTFYLLLISQPAYFEEVEGFEISKVGLVSALPHLVMTIIV

```
PIGGQIADFLRSRRIMSTTNVRKLMNCGGFGMEATLLLVVGYSHSKGVAISFLVLAVGFSGFAISGFNVNH

LDIARRYASILMGISNGVGTLSGMVCPIIVGAMTKHKTREEWQYVFLIASLVHYGGVIFYGVFASGEKQPW

AEPEEMSEEKCGFVGHDQLAGSDDSEMEDEAEPPGAPPAPPPSYGATHSTFQPPRPPPPVRDYLEHHH

HHHHH
```

(VGLUT1-isoform1)
SEQ ID NO: 76

```
MEFRQEEFRKLAGRALGKLHRLLEKRQEGAETLELSADGRPVTTQTRDPPVVDCTCFGLPRRYIIAIMSG

LGFCISFGIRCNLGVAIVSMVNNSTTHRGGHVVVQKAQFSWDPETVGLIHGSFFWGYIVTQIPGGFICQKF

AANRVFGFAIVATSTLNMLIPSAARVHYGCVIFVRILQGLVEGVTYPACHGIWSKWAPPLERSRLATTAFC

GSYAGAVVAMPLAGVLVQYSGVVSSVFYWGSEGIFWYLRNLLVSYESPALHPSISEEERKYIEDAIGESA

KLMNPLTKESTPVVRRFFTSMPVYAIIVANFCRSWTFYLLLISQPAYFEEVEGFEISKVGLVSALPHLVMTIIV

PIGGQIADFLRSRRIMSTINVRKLMNCGGFGMEATILLVVGYSHSKGVAISFLVLAVGFSGFAISGFNVNH

LDIARRYASILMGISNGVGILSGMVCPIIVGAMTKHKTREEVVQYVFLIASLVHYGGVIFYGVFASGEKQPW

AEPEEMSEEKCGFVGHDQLAGSDOSEMEDEAEPPGAPPAPPPSYGATHSTFQPPRPPPPVRDY
```

(VGLUT3-isoform1-H8)
SEQ ID NO: 77

```
MPFKAFDTFKEKILKPGKEGVKNAVGDSLGILQRKIDGTTEEEDNIELNEEGRPVQTSRPSPPLCDCHCC

GLPKRYIIAIMSGLGFCISFGIRCNLGVAIVEMVNNSTVYVDGKPEIQTAQFNWDPETVGLIHGSFFWGYIM

TQIPGGFISNKFAANRVFGAAIFLTSTLNMFIPSAARVHYGCVMCVRILQGLVEGVTYPACHGMWSKVVAP

PLERSRLATTSFCGSYAGAVVAMPLAGVLVQYIGWSSVFYIYGMFGIIMYFWLLQAYECPAAHPTISNE

EKTYIETSIGEGANVVSLSKFSTPWKRFFTSLPVYAIIVANFCRSWTFYLLLISQPAYFEEVFGFAISKVGLL

SAVPHMVMTIVVPIGGQLADYLRSRQILTTTAVRKIMNCGGEGMEATLLLVVGFSHTKGVAISFLVLAVGF

SGFAISGFNVNHLDIAPRYASILMGISNGVGTLSGMVCPLIVGAMTRHKTREENQNVFLIAALVHYSGVIFY

GVFASGEKQEWADPENLSEEKCGIIDQDELAEEIELNHESFASPKKKMSYGATSQNCEVQKKEWKGQR

GATLDEEELTSYQNEERNFSTISLEHHHHHHHH
```

(VGLUT3-isoform1)
SEQ ID NO: 78

```
MPFKAFDTFKEKILKPGKEGVKNAVGDSLGILQRKIDGTTEEEDNIELNEEGRPVQTSRPSPPLCDCHCC

GLPKRYIIAIMSGLGFCISFGIRCNLGVAIVEMVNNSTVYVDGKPEIQTAQFNWDPETVGLIHGSFFWGYIM

TQIPGGFISNKFAANRVFGAAIFLTSTLNMFIPSAARVHYGCVMCVRILQGLVEGVTYPACHGMWSKWAP

PLERSRLATTSFCGSYAGAVVAMPLAGVLVQYIGWSSVFYIYGMFGIIWYMFWLLQAYECPAAHPTISNE

EKTYIETSIGEGANVVSLSKFSTPWKRFFTSLPVYAIIVANFCRSWTFYLLLISQPAYFEEVFGFAISKVGLL

SAVPHMVMTIVVPIGGQLADYLRSRQILTTTAVRKIMNCGGFGMEATLLLVVGFSHIKGVAISFLVLAVGF

SGFAISGFNVNHLDIAPRYASILMGISNGVGTLSGMVCPLIVGAMTRHKTREEWQNVFLIAALVHYSGVIFY

GVFASGEKQEWADPENLSEEKCGIIDQDELAEEIELNHESFASPKKKMSYGATSQNCEVQKKEWKGQR

GATLDEEELTSYQNEERNFSTIS
```

(H8-GST-(PSc)-VGLUT3-aa503-589)
SEQ ID NO: 79

```
MSHHHHHHHHMSPILGYWKIKGLVQPTRLLLEYLEEKYEEHLYERDEGDKWRNKKFELGLEFPNLPYYID

GDVKLTQSMAIIRYIADKHNMLGGCPKERAEISMLEGAVLDIRYGVSRIAYSKDFETLKVDFLSKLPEMLKM

FEDRLCHKTYLNGDHVTHPDFMLYDALDVVLYMDPMCLDAFPKLVCFKKRIEAIPQIDKYLKSSKYIAWPL

QGWQATFGGGDHPPKLEVLFQGPAMSGEKQEWADPENLSEEKCGIIDQDELAEEIELNHESFASPKKK

MSYGATSQNCEVQKKEWKGQRGATLDEEELTSYQNEERNFSTIS
```

```
(H8-GST-(PSc)-VGLUT1-aa491-560)
                                                                                   SEQ ID NO: 100
MSHHHHHHHHMSPILGYWKIKGLVQPTRLLLEYLEEKYEEHLYERDEGDKWRNKKFELGLEFPNLPYYID

GDVKLIQSMAIIRYIADKHNMLGGCPKERAEISMLEGAVLDIRYGVSRIAYSKDFETLKVDELSKLPEMLKM

FEDRLCHKTYLNGDHVTHPDFMLYDALDVVLYMDPMCLDAFPKLVCFKKRIEAIPQIDKYLKSSKYIAWPL

QGWQATFGGGDHPPKLEVLFQGPAMSGEKQPWAEPEEMSEEKCGFVGHDQLAGSDDSEMEDEAEPP

GAPPAPPPSYGATHSTFQPPRPPPPVRDY (VGLUT2 Epitop)
                                                                                   SEQ ID NO: 101
ITQNYINYGTTKSYGATTQANGGWPSGW (VGLUT2 Epitop, amino acids 520-564)
                                                                                   SEQ ID NO: 102
HEDELDEETGDITQNYINYGTTKSYGATTQANGGWPSGWEKKEEFV (VGLUT1 Epitop, amino adds 523-550)
                                                                                   SEQ ID NO: 103
EMEDEAEPPGAPPAPPPSYGATHSTFQP
```

The present invention is further illustrated by the following non-limiting examples from which further features, embodiments, aspects and advantages of the present invention may be taken.

FIG. 1 shows the immunofluorescence staining of neuronal tissues. Cryosections of rat hippocampus, thalamus and cerebellum as well as primate cerebellum were incubated with patient serum 1 (1:100, green) in the first step, and with Alexa488-labelled goat anti-human IgG in the second step. Nuclei were counterstained by incubation with TO-PRO-3 iodide (blue). A spotty staining of the granular layer and interrupted striped structures in the molecular layer were observed. Hippocampal tissue sections showed a weak fine granular fluorescence of the inner molecular layer as well as a speckled reactivity of the adjacent thalamus. (sm: stratum molecular, sg: stratum granulosum, sp: stratum purkinjense, scale bar 100 μm).

Figure 2A:
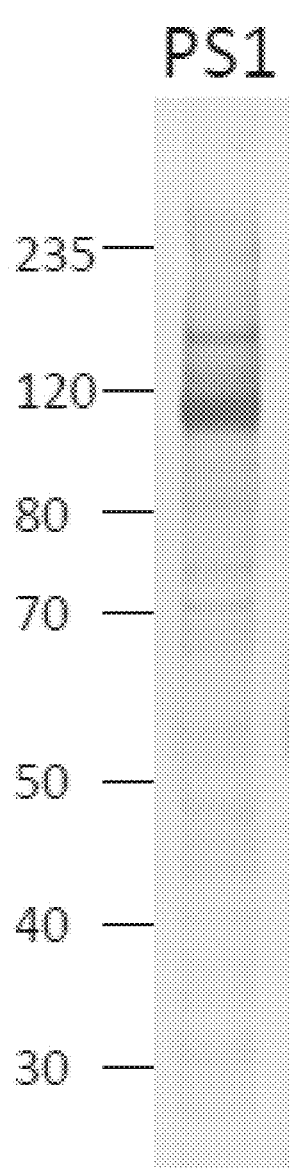
FIG. 2A shows an immunoblot with cerebellar lysate incubated with patient serum 1 (1:200).
Figure 2B:
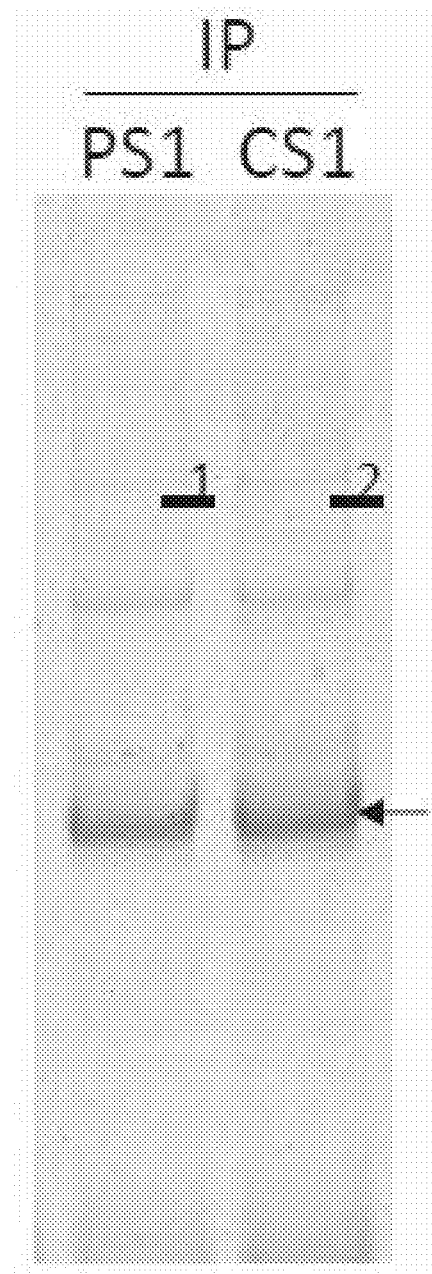
FIG. 2B shows lysates of rat cerebellum were incubated with patient (PS1) or control serum (CS1).

FIGS. 2A & 2B show an immunoprecipitation leading to the identification or VGLUT2 as an autoantigen. 2A: Immunoblot with cerebellar lysate incubated with patient serum 1 (1:200). 2B: Lysates of rat cerebellum were incubated with patient (PS1) or control serum (CS1). Immunocomplexes were isolated with protein-G-coated magnetic beads, eluted by SDS and subjected to SDS-PAGE analysis followed by staining with colloidal coomassie. Arrow indicates position of IgGs.

Figure 3A:
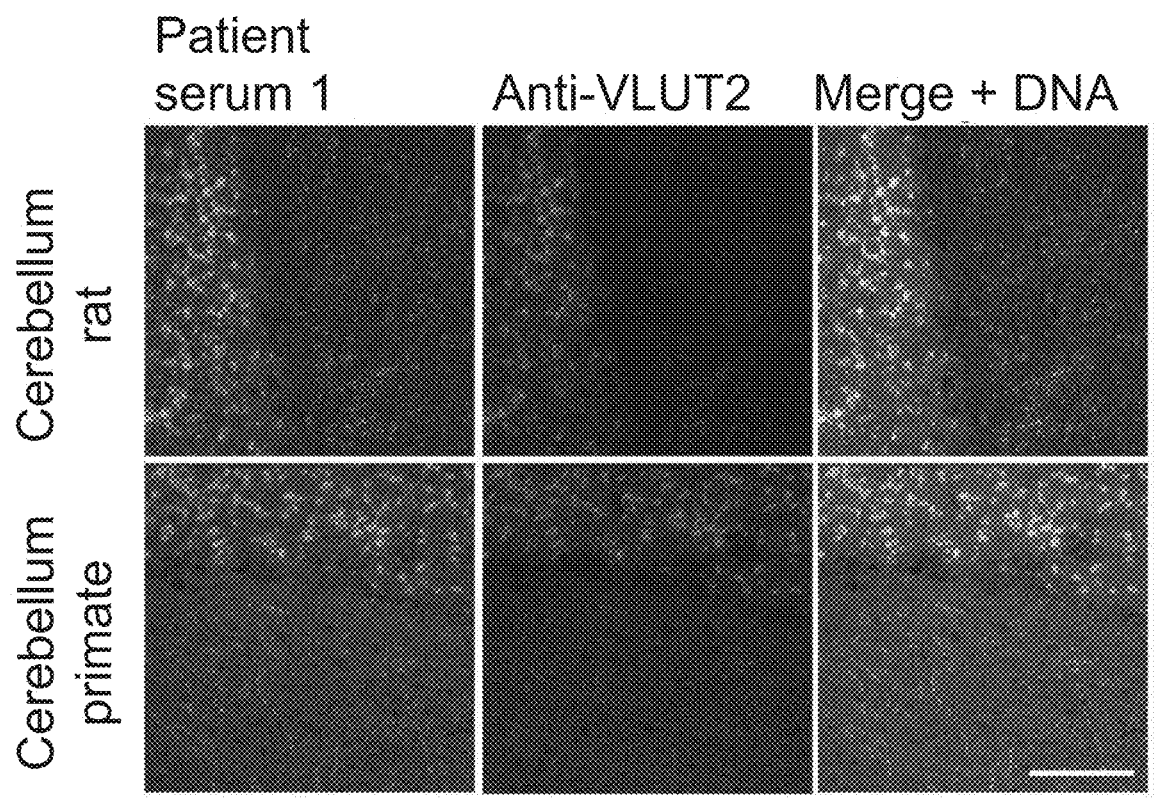
FIG. 3A shows the colocalization of patient sera and anti-VGLUT2 antibody on cerebellum, observing a colocalization of the blotchy staining of the cerebellar granular layer.
Figure 3B:
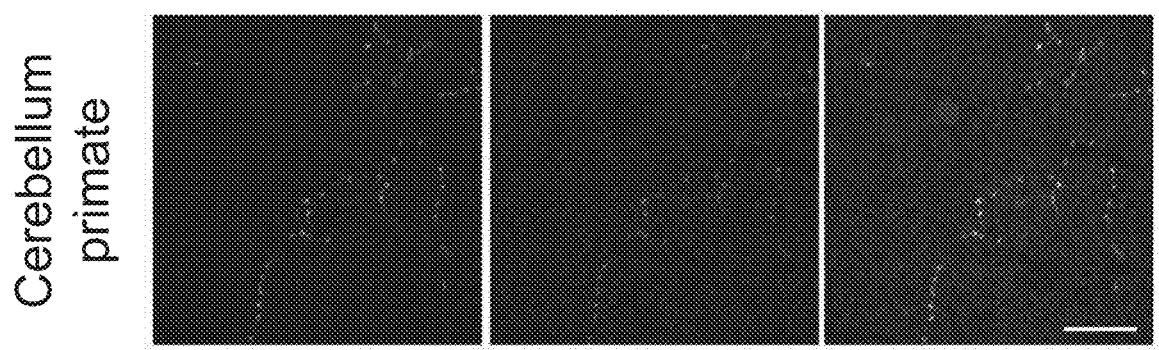
FIG. 3B shows the colocalization of patient sera and anti-VGLUT2 antibody on cerebellum, observing a colocalization of the dotted and striped like structures in the molecular layer.

FIGS. 3A & 3B show the colocalization of patient sera and anti-VGLUT2 antibody on cerebellum. Patient serum 1 (1:100, green) and anti-VGLUT2 mouse monoclonal antibody (1:200, red) were incubated on rat and primate cerebellum followed by an anti-human-Alexa488 (1:500) and anti-mouse-Cy3 (1:200) incubation. Nuclei were counterstained with TO-PRO-3 iodide (blue). A colocalization of the blotchy staining of the cerebellar granular layer (3A) and of the dotted and striped like structures in the molecular layer (3B) was observed. Scale bar 3A: 100 μm, 3B: 20 μm.

Figure 4:
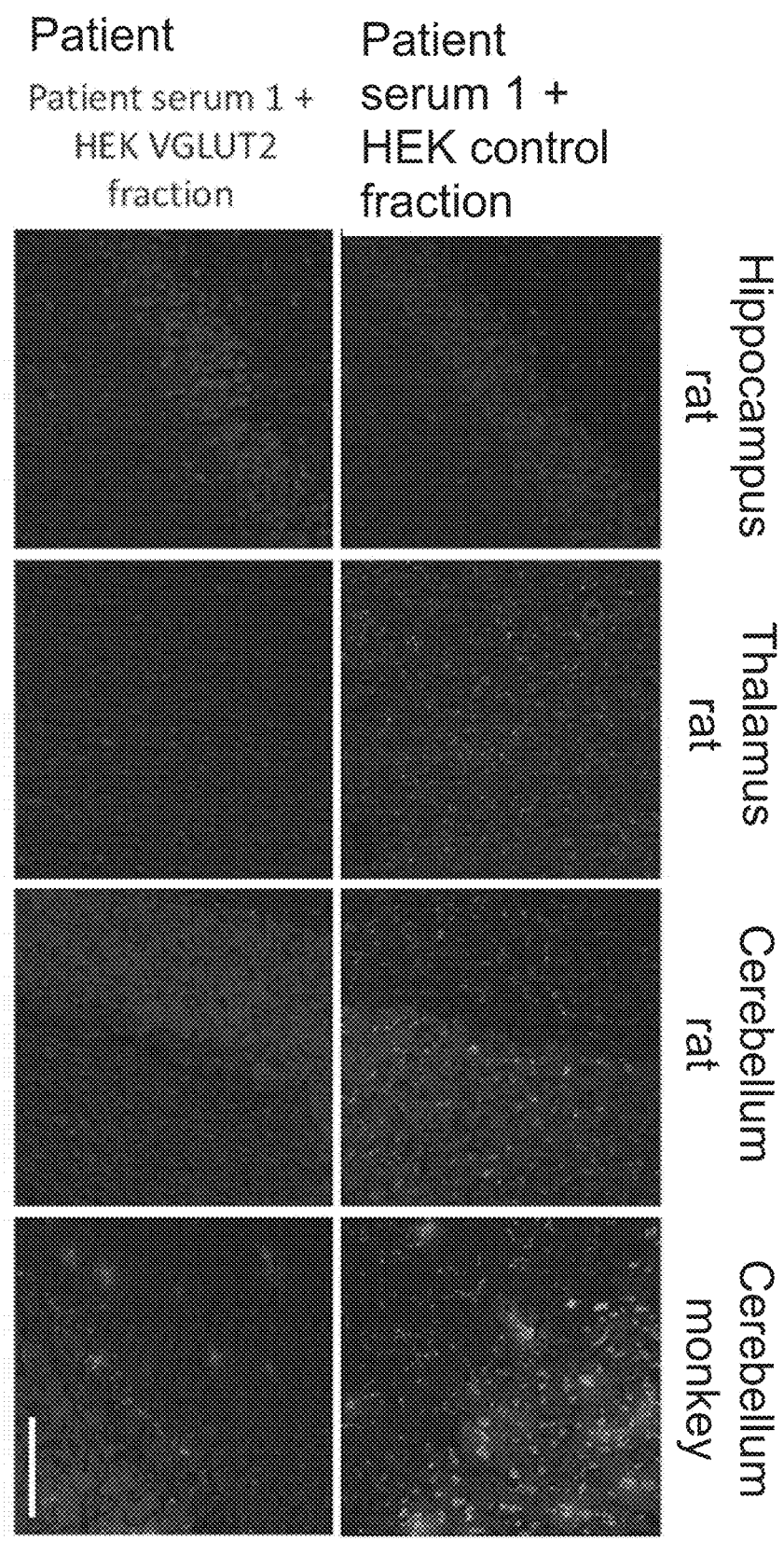
FIG. 4 shows the neutralization of antibody reaction on neuronal tissues.

FIG. 4 shows the neutralization of antibody reaction on neuronal tissues. Patient serum 1 (1:320, green) was pre-incubated with extracts (1:10) of HEK293 cells transfected with empty control vector or with plasmids harboring VGLUT2 cDNA in the first step, and with Alexa488-labeled goat anti-human IgG in the second step. The extract containing VGLUT2 greatly abolished the immune reaction of the serum on rat and monkey neuronal tissues. Nuclei were counterstained by incubation with TO-PRO-3 iodide (blue). Scale bar 100 μm.

Figure 5B:
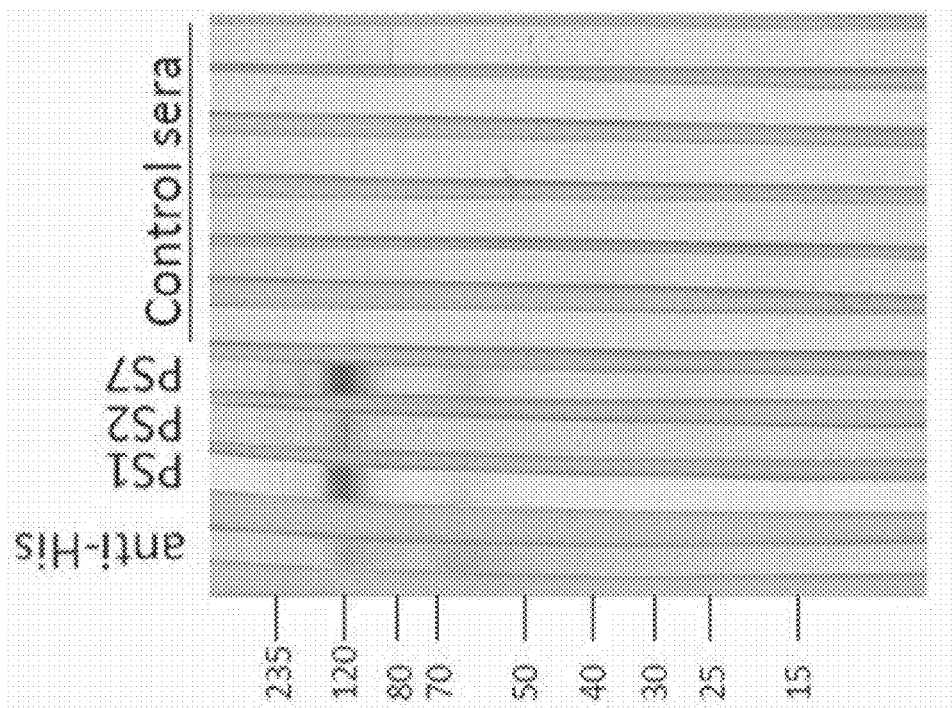
FIG. 5B shows immunoblot with lysates of VGLUT2-His transfected HEK293 cells incubated with anti-His antibody, patient (PS1, 2, 7) or control sera (1:200).
Figure 5A:
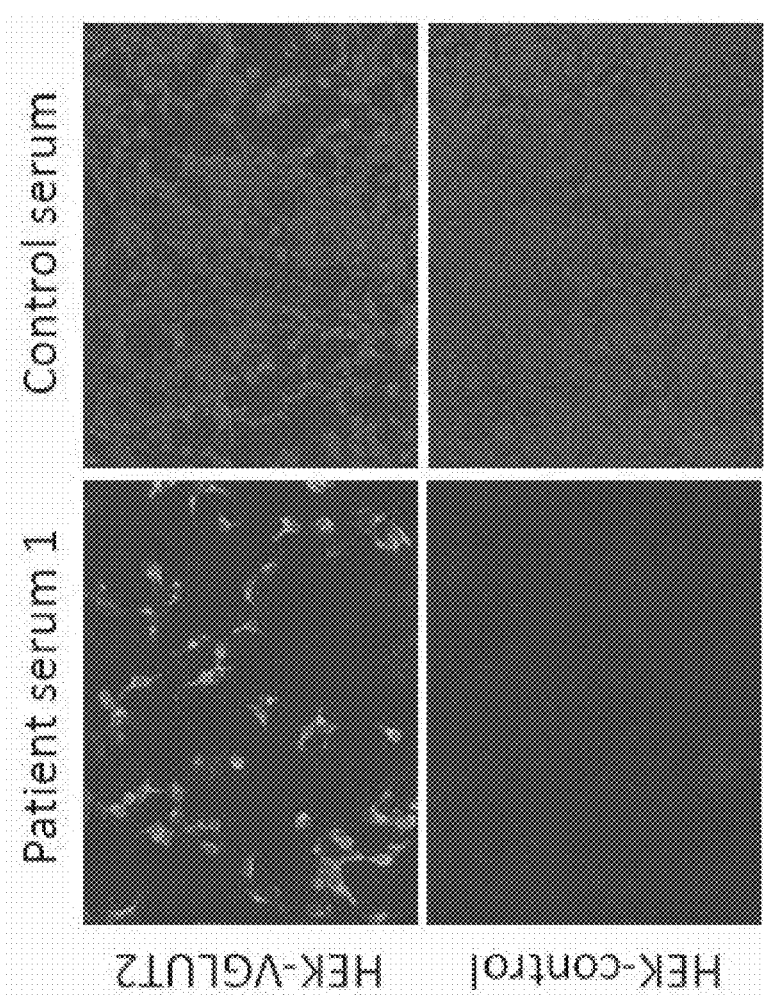
FIG. 5A shows indirect immunofluorescence using acetone-fixed VGLUT2 dHis or mock-transfected HEK293 cells incubated with patient serum 1 (1:100) or a healthy control (1:10) and anti-human IgG-FITC.

FIGS. 5A & 5B show the verification of VGLUT2 as the novel autoantigen by indirect immunofluorescence with the recombinant antigen. 5A: Indirect immunofluorescence using acetone-fixed VGLUT2 dHis or mock-transfected HEK293 cells incubated with patient serum 1 (1:100) or a healthy control (1:10) and anti-human IgG-FITC. 5B: Immunoblot with lysates of VGLUT2-His transfected HEK293 cells incubated with anti-His antibody, patient (PS1, 2, 7) or control sera (1:200).

Figure 6A:
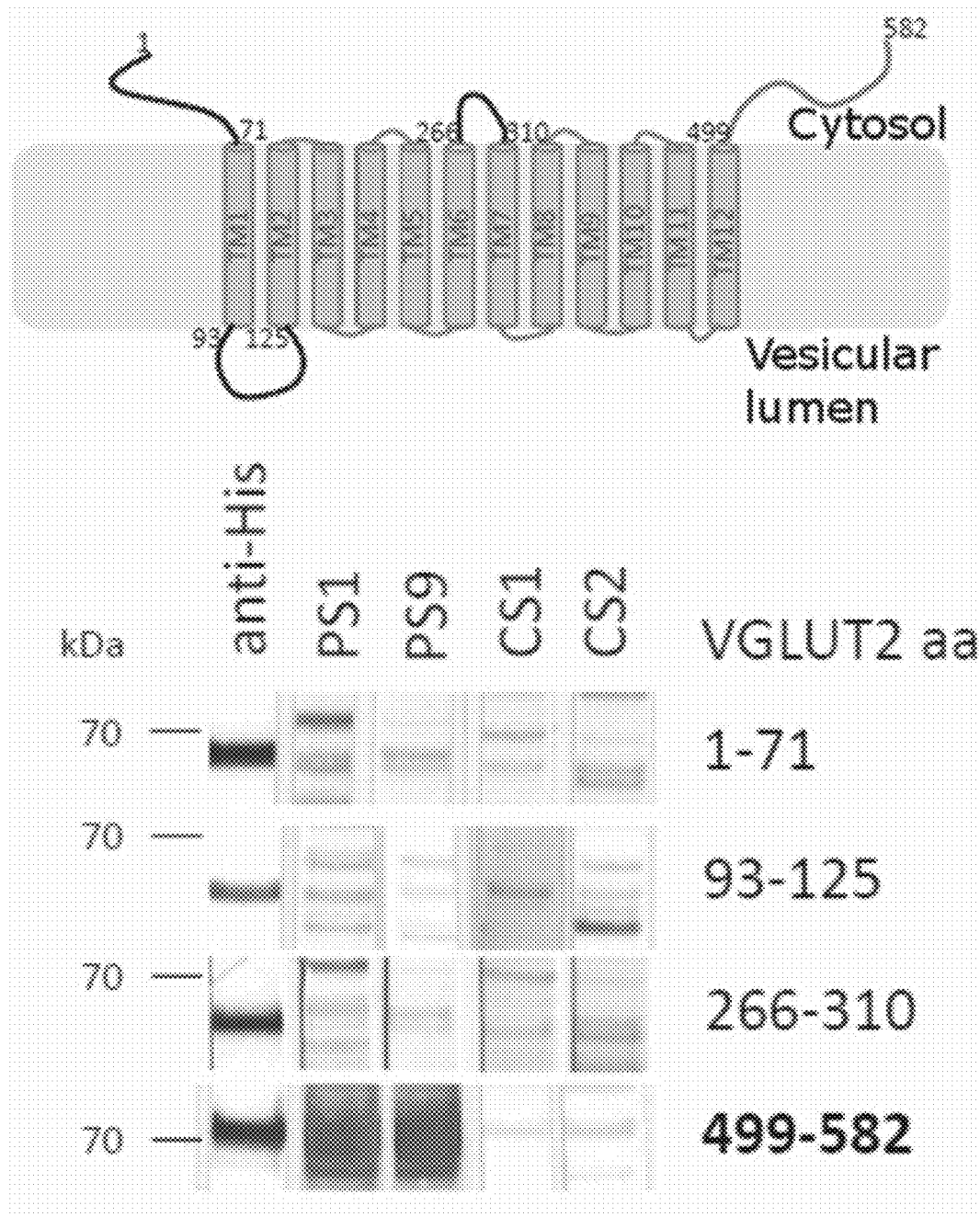
FIG. 6A shows a scheme of VGLUT2 with the four cytoplasmic or vesicular located fragments aa 1-71 (SEQ ID NO: 61), aa 93-125 (SEQ ID NO: 62), aa 266-310 (SEQ ID NO: 63), aa 499-582 (SEQ ID NO: 64); and the immunoblots with E. coli lysates expressing the four His-GST-VGLUT2 fragments incubated with anti. His antibody, patient (PS1, 9) or control sera (CS1, CS2) (1:200).
Figure 6B:
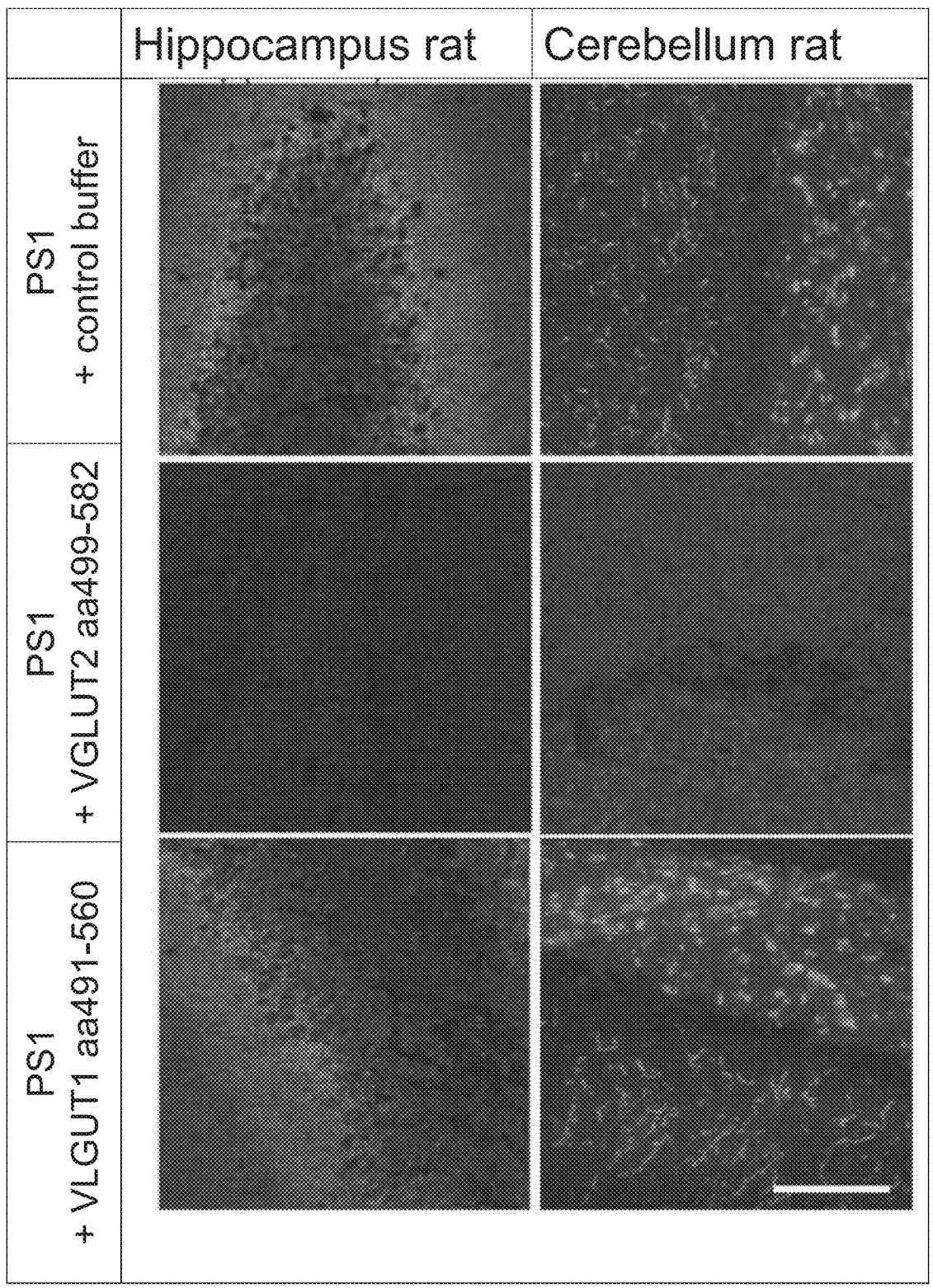
FIG. 6B shows IIFA competitive inhibition experiments with patient serum 1 (1:100, green) pre-incubated with purified His-GST-VGLUT2 aa 499-582 (1 µg) (SEQ ID NO: 64), E. coli expressed His-GST-VGLUT1 aa 491-560 (SEQ ID NO: 100) fraction or control buffer and Alexa488-labelled goat anti-human IgG as secondary antibody.

FIGS. 6A & 6B show the VGLUT2 epitope is located on the C-terminal His-GST-VGLUT2 aa 499-582 fragment (SEQ ID NO: 64). 6A, Upper panel: Scheme of VGLUT2 with the four cytoplasmic or vesicular located fragments aa 1-71 (SEQ ID NO: 61), aa 93-125 (SEQ ID NO: 62), aa 266-310 (SEQ ID NO: 63), aa 499-582 (SEQ ID NO: 64). Lower panel: Immunoblots with E. coli lysates expressing the four His-GST-VGLUT2 fragments incubated with anti-His antibody, patient (PS1, 9) or control sera (CS1, CS2) (1:200). 6B: IIFA competitive inhibition experiments with patient serum 1 (1:100, green) pre-incubated with purified His-GST-VGLUT2 as 499-582 (1 μg). E. coli expressed His-GST-VGLUT1 as 491-560 (SEQ ID NO: 100) fraction or control buffer and Alexa488-labelled goat anti-human IgG as secondary antibody. His-GST-VGLUT2 as 499-582 but not His-GST-VGLUT1 as 491-560 abolished the immune reaction or patient serum on rat hippocampus and cerebellum. Nuclei were counterstained by incubation with TO-PRO-3 iodide (blue). Scale bar 100 μm.

Figure 7A:
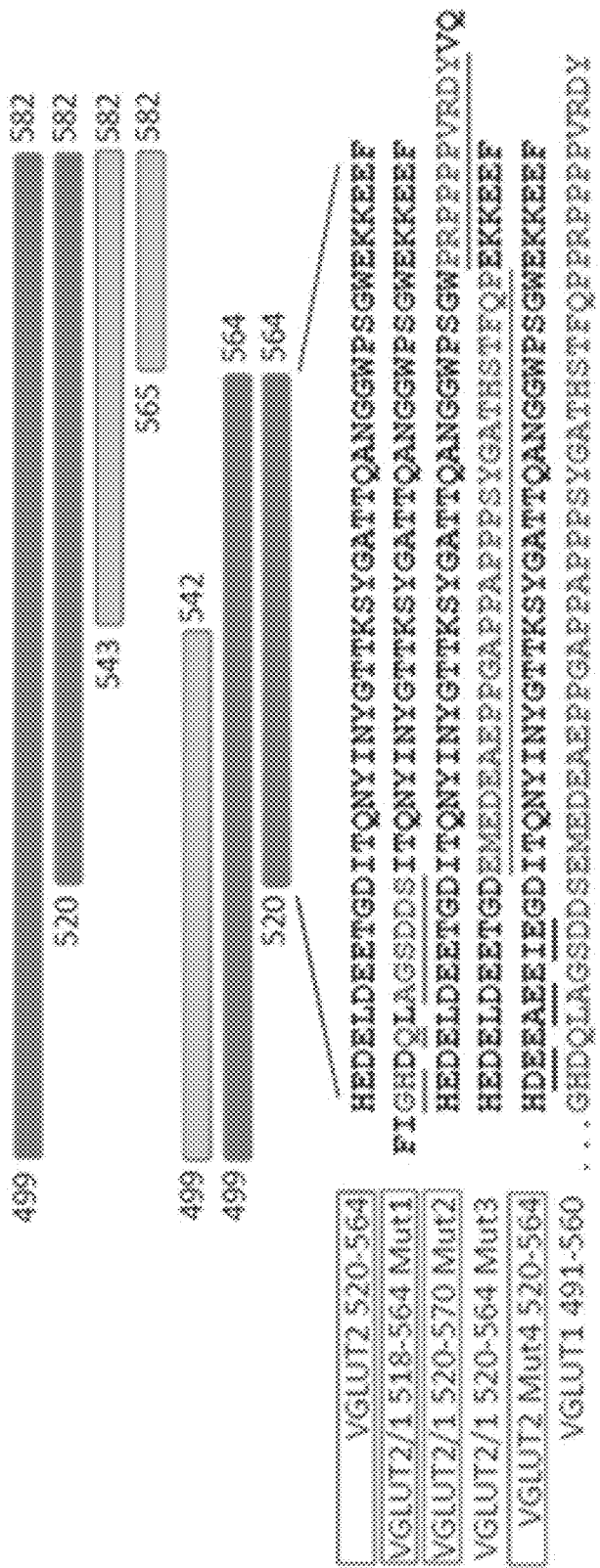
FIG. 7A shows a scheme of His-GST-VGLUT2 aa 499-582 (SEQ ID NO: 64), aa 520-582 (SEQ ID NO: 65), aa 543-582 (SEQ ID NO: 67), aa 565-582 (SEQ ID NO: 68), aa 499-542 (SEQ ID NO: 69), aa 499-564 (SEQ ID NO: 70), aa 520-564 fragments (SEQ ID NO: 66); and the sequences of His-GST-VGLUT2 aa 520-564 WT fragment, mutated His-GST-VGLUT2/1 (Mut 1-4) fragments (SEQ ID NOs: 71, 72, 73, 74) and His-GST-VGLUT1 aa 491-560 WT fragment (SEQ ID NO: 100).
Figure 7B:
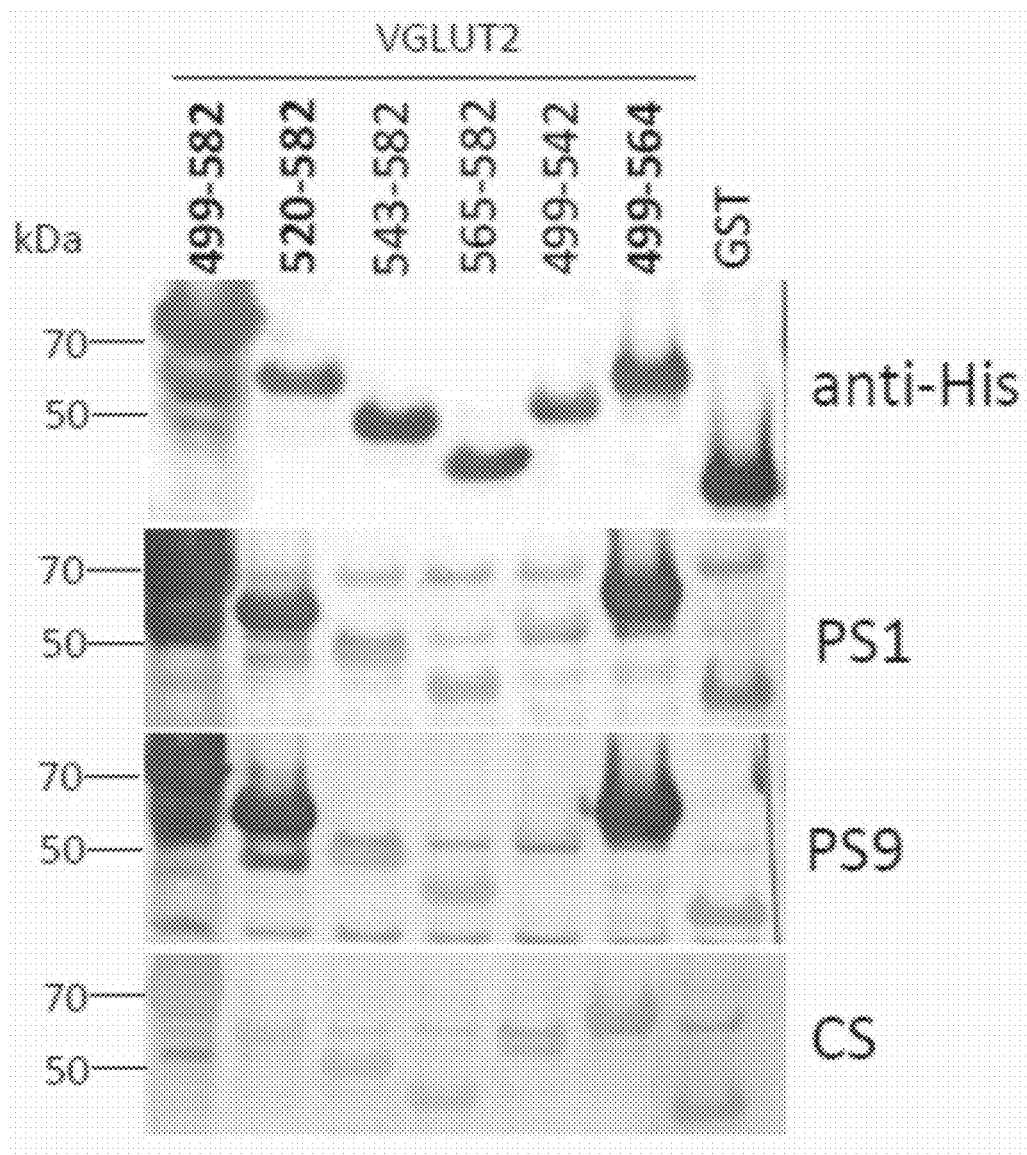
FIG. 7B shows immunoblots with E. coli lysates expressing His-GST-VGLUT2 fragments incubated with anti. His antibody, patient (PS1, 9) or control serum (CS) (1:200).
Figure 7C:
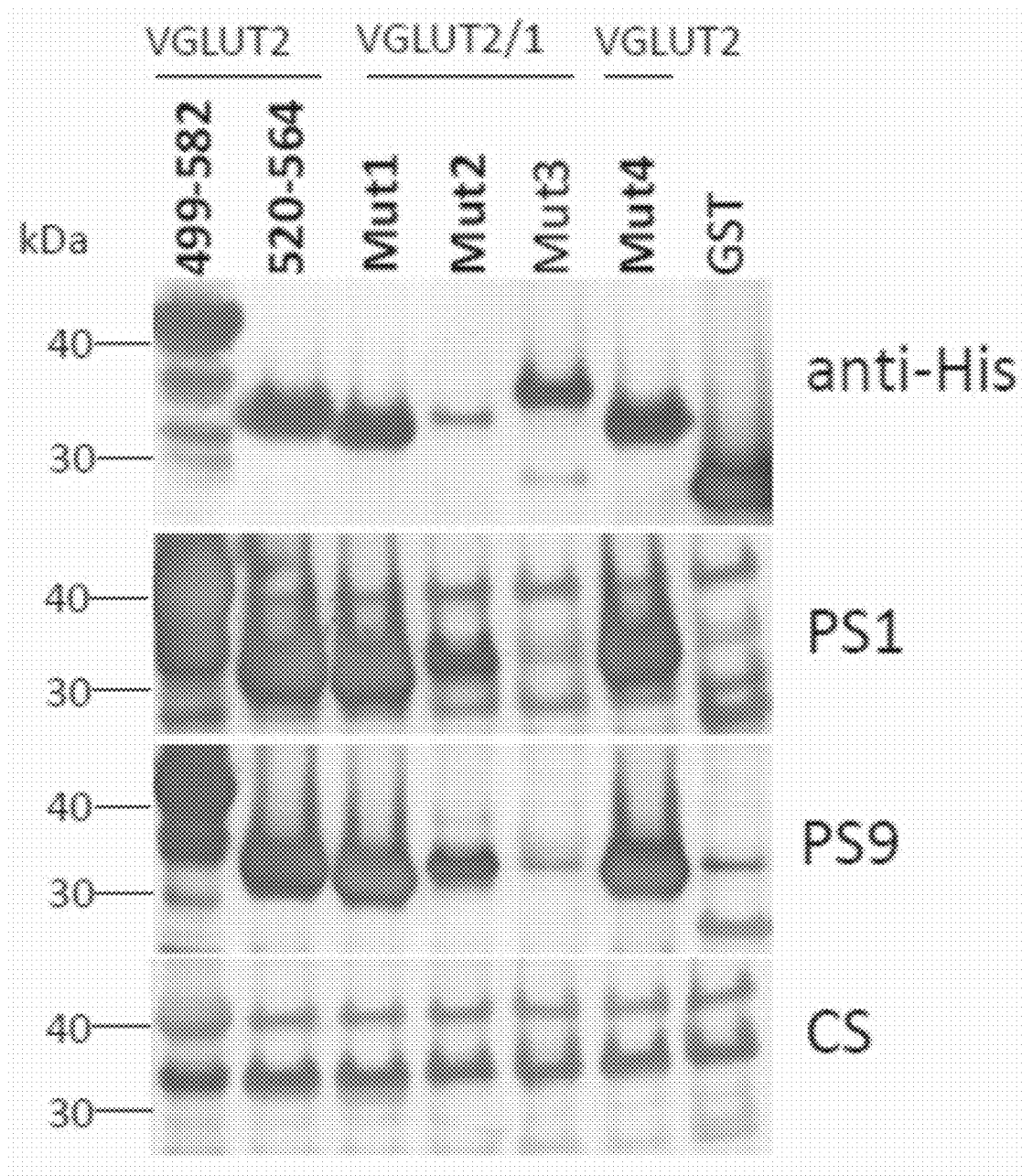
FIG. 7C shows immunoblots with E. coli lysates expressing His-GST-VGLUT2 mutants incubated with anti-His antibody, patient (PS1, 9) or control serum (CS) (1:200).

FIGS. 7A, 7B, & 7C show the VGLUT2 epitope is located between VGLUT2 as 531-558. 7A: Upper panel: Scheme of His-GST-VGLUT2 as 499-582 (SEQ ID NO: 64), as 520-582 (SEQ ID NO: 65), as 543-582 (SEQ ID NO: 67), as 565-582 (SEQ ID NO: 68), as 499-542 (SEQ ID NO: 69), as 499-564 (SEQ ID NO: 70), as 520-564 (SEQ ID NO: 66) fragments. Lower panel: Sequences of His-GST-VGLUT2 as 520-564 WT fragment, mutated His-GST-VGLUT2/1 (Mut 1-4) fragments (SEQ ID NOs: 71, 72, 73, 74) and His-GST-VGLUT1 as 491-560 WT fragment (SEQ ID NO: 100). Fragments or mutants showing positive reactions with anti-VGLUT2 patient sera in immunoblot assays are marked in green. Mutated amino acids are underlined. VGLUT1 sequences are displayed red. 7B/7C: Immunoblots with E. coli lysates expressing His-GST-VGLUT2 fragments (7B) or mutants (7C) incubated with anti-His antibody, patient (PS1, 9) or control serum (CS) (1:200).

Figure 8:
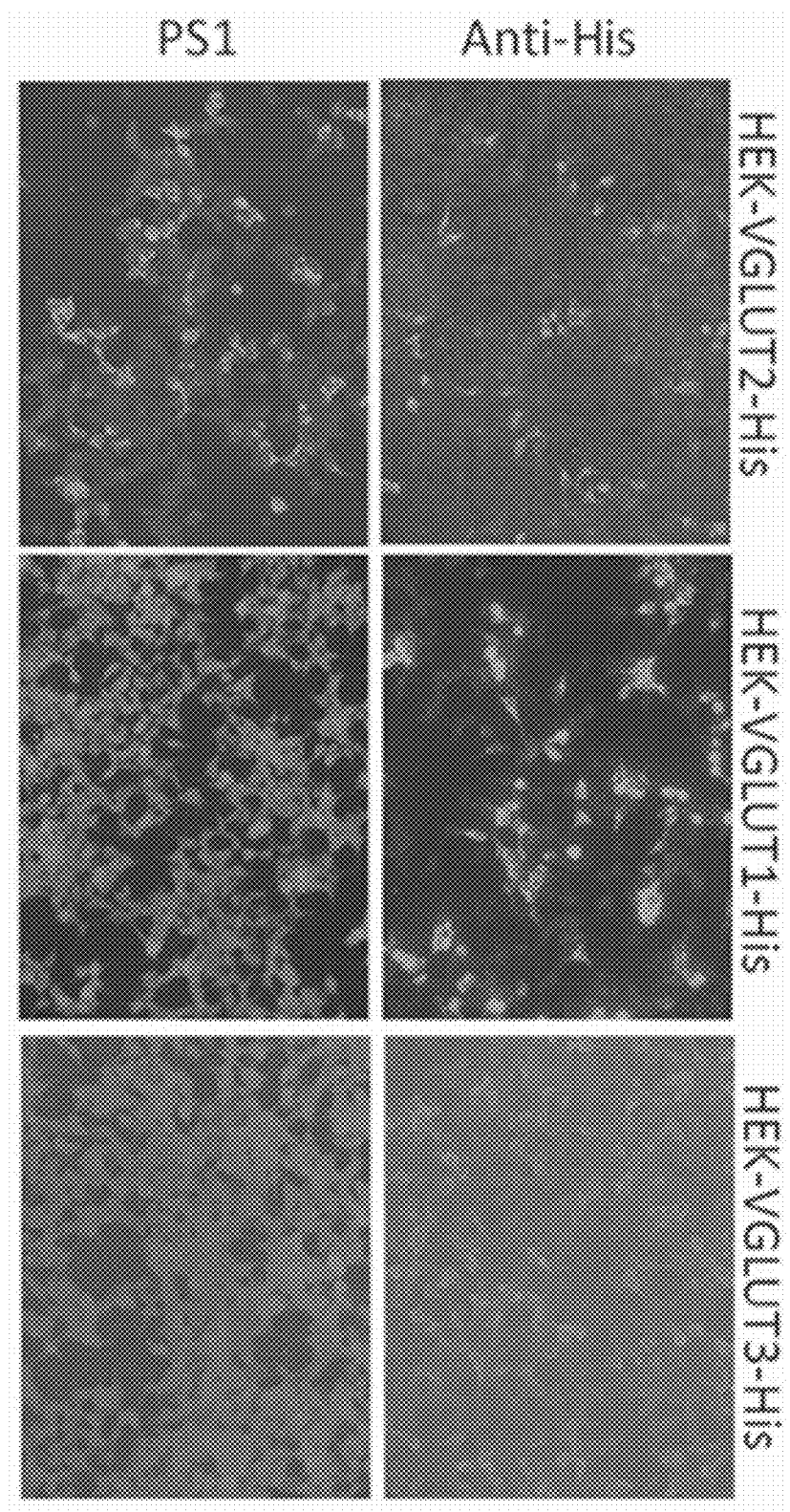
FIG. 8 shows anti-VGLUT2 patient serum recognizing VGLUT2 but not VGLUT1 and VGLUT3.

FIG. 8 shows anti-VGLUT2 patient serum recognizes VGLUT2 but not VGLUT1 and VGLUT3. IIFA using acetone-fixed VGLUT2-His, VGLUT1-His or VGLUT3-His transfected HEK293 cells incubated with anti-His or patient serum 1 and anti-mouse-Alexa488 or anti-human IgG-FITC.

Figure 9A:
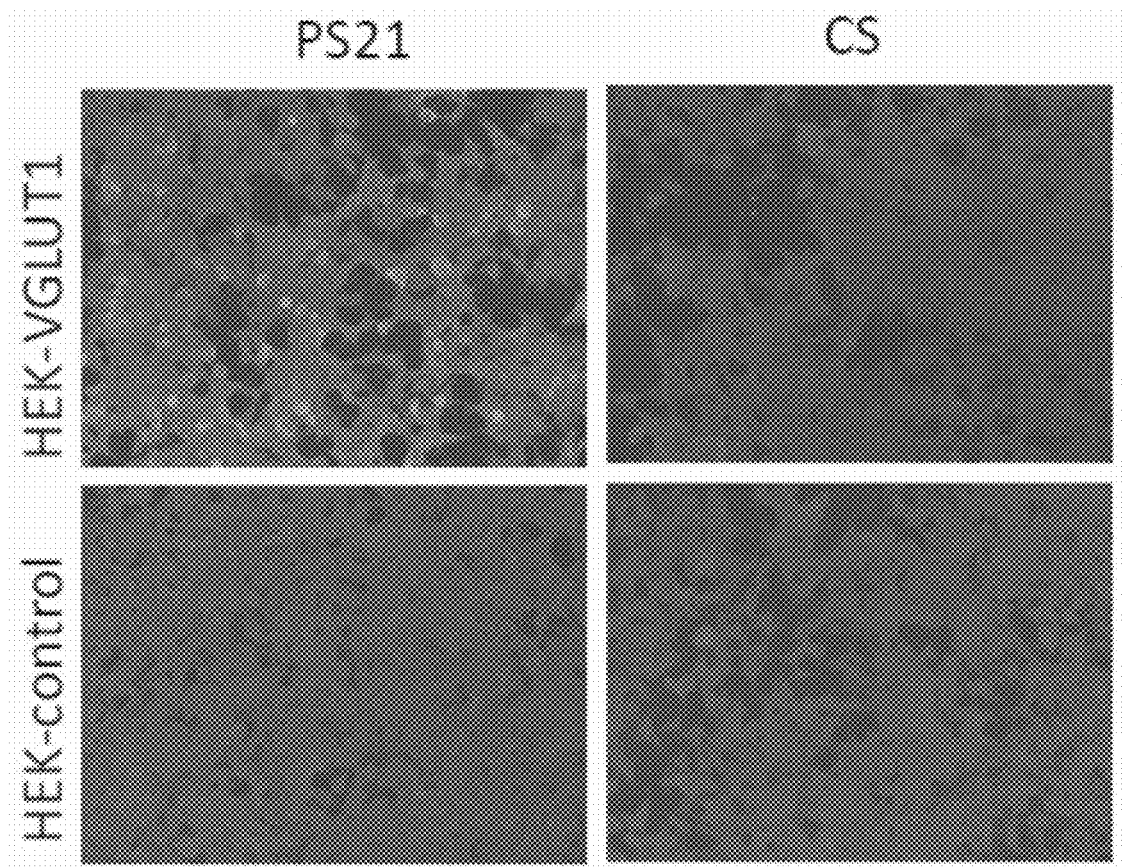
FIG. 9A shows IIFA using acetone-fixed VGLUT1 dHis or mock-transfected HEK293 cells incubated with patient serum 21 (PS21) or a control serum (1:10) and anti-human IgG-FITC.
Figure 9B:
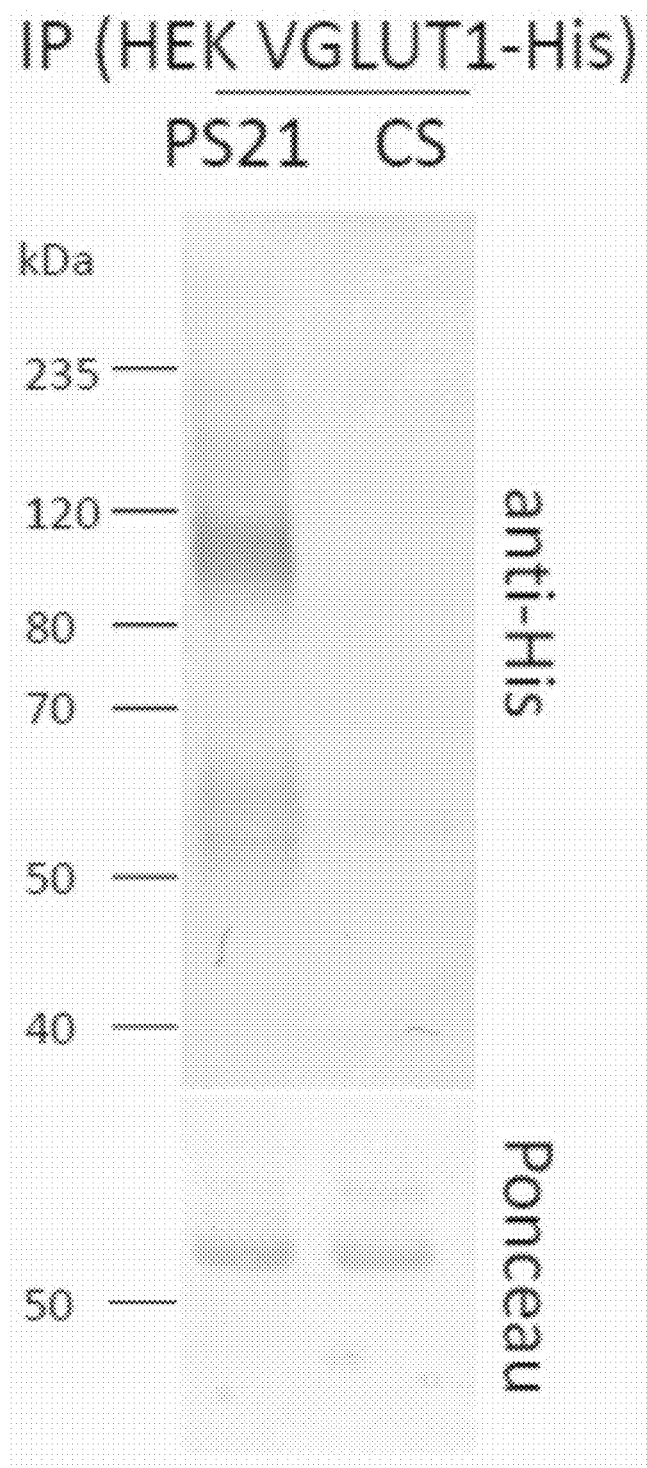
FIG. 9B shows immunoprecipitation (IP) with lysates of VGLUT1-His transfected HEK cells and patient (PS21) or control serum (CS).
Figure 9C:
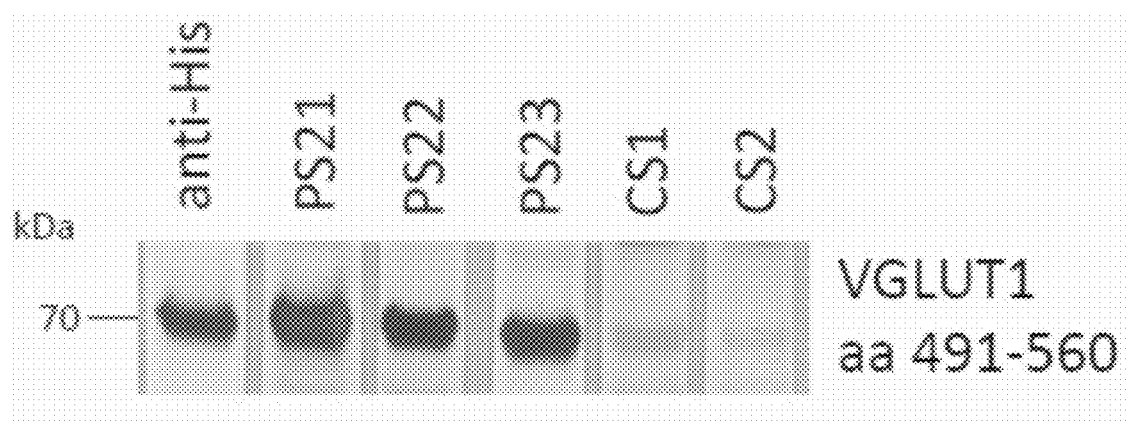

FIGS. 9A, 9B, & 9C show the verification of VGLUT1 as novel autoantigen by different immunoassays with the recombinant antigen. 9A: IIFA using acetone-fixed VGLUT1 dHis or mock-transfected HEK293 cells incubated with patient serum 21 (PS21) or a control serum (1:10) and anti-human IgG-FITC. 96: Immunoprecipitation (IP) with lysates of VGLUT1-His transfected HEK cells and patient (PS21) or control serum (CS). Isolated immunocomplexes were subjected to SDS-PAGE analysis followed by immunoblot with anti-His. Ponceau staining of immunoblot is shown as control. 9C: Immunoblot with lysates of His-VGLUT1 aa 491-560 (SEQ ID NO: 100) transfected E. coli cells incubated with anti-His antibody, patient (PS21, 22, 23) or control sera (1:200).

Figure 10:
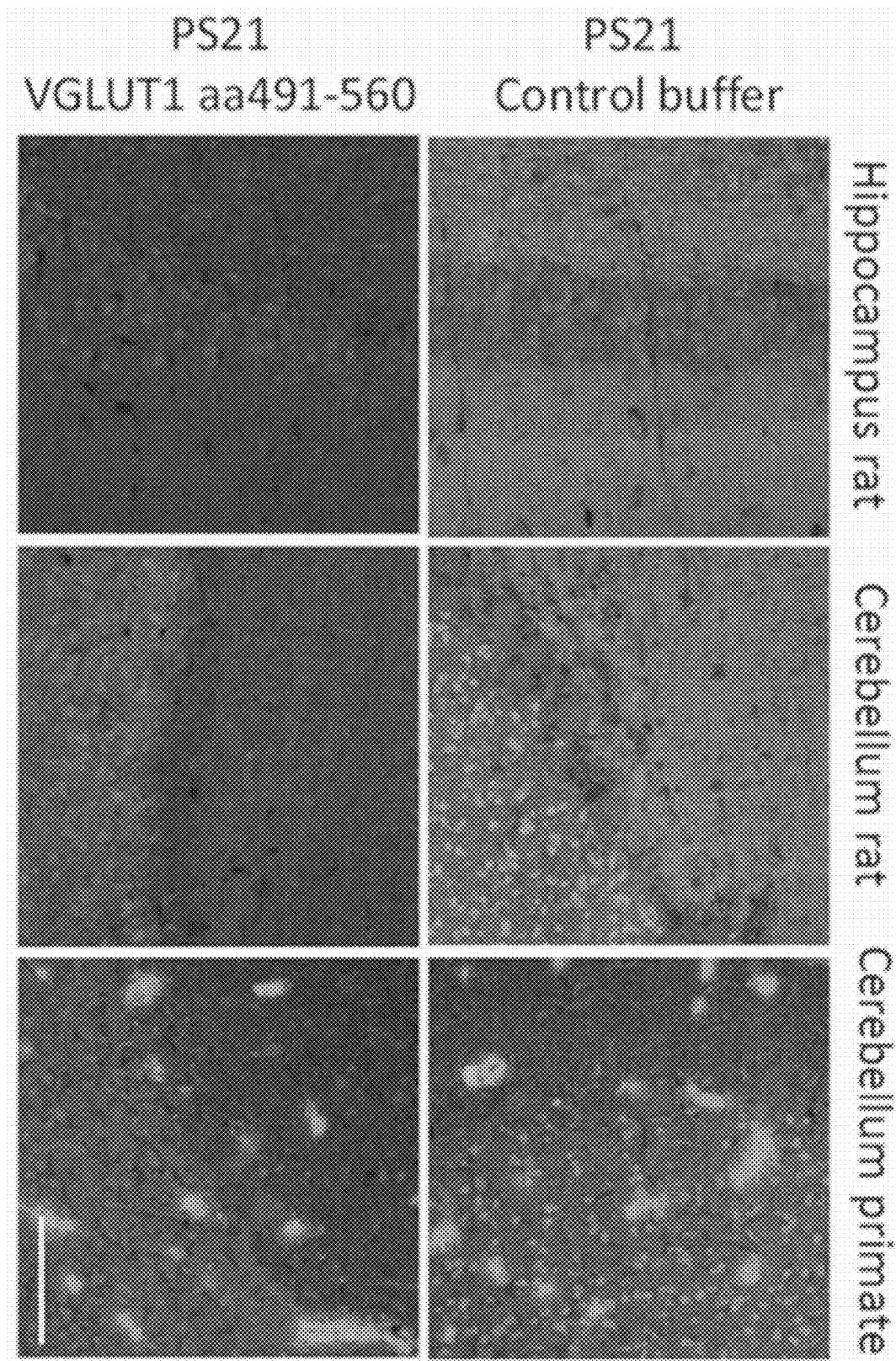
FIG. 10 shows the neutralization of anti-VGLUT1 antibody reaction on neuronal tissues.

FIG. 10 shows the neutralization of anti-VGLUT1 antibody reaction on neuronal tissues. IIFA was performed with PS21 (green) pre-incubated with extracts (1:5) of E. coli cells transfected with His-GST-VGLUT1 as 491-560 (SEQ ID NO: 100) or control buffer. Alexa488-labelled goat anti-human IgG was used as secondary antibody. The extract containing His-GST-VGLUT1 as 491-560 abolished the immune reaction of the serum on rat and primate neuronal tissues. Nuclei were counterstained by incubation with TO-PRO-iodide (blue). Scale bar 100 μm.

Figure 11B:
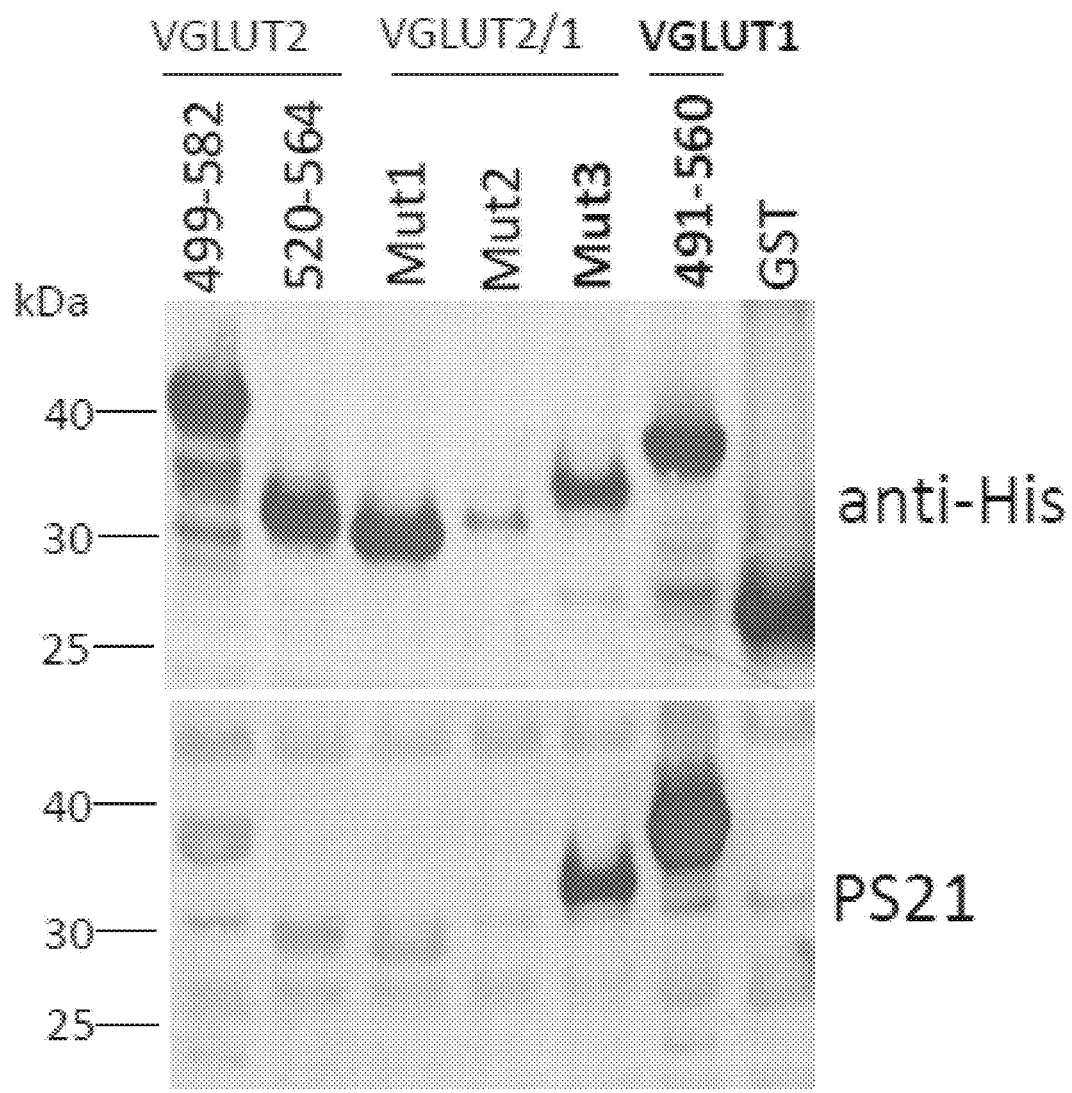
FIG. 11B shows immunoblots with E. coli lysates expressing His-GST-VGLUT1 or 2 fragments or mutants incubated with anti-His antibody, patient (PS21) or control serum (1200).

FIGS. 11A & 11B show the VGLUT1 epitope of patient serum 21 is located between VGLUT1 as 523-550 11A: Sequences of His-GST-VGLUT2 aa 520-564 WT fragment (SEQ ID NO: 66), mutated His-GST-VGLUT2/1 fragments (Mut 1-3) (SEQ ID NOs: 71, 72, 73) and His-GST-VGLUT1 as 491-560 WT fragment (SEQ ID NO: 100). Fragments or mutants showing positive reactions with anti-VGLUT1 patient serum 21 in immunoblot assays are marked in green. VGLUT1 sequences are displayed red. 11B: Immunoblots with E. coli lysates expressing His-GST-VGLUT1 or 2 fragments or mutants incubated with anti-His antibody, patient (PS21) or control serum (1:200).

Figure 12A:
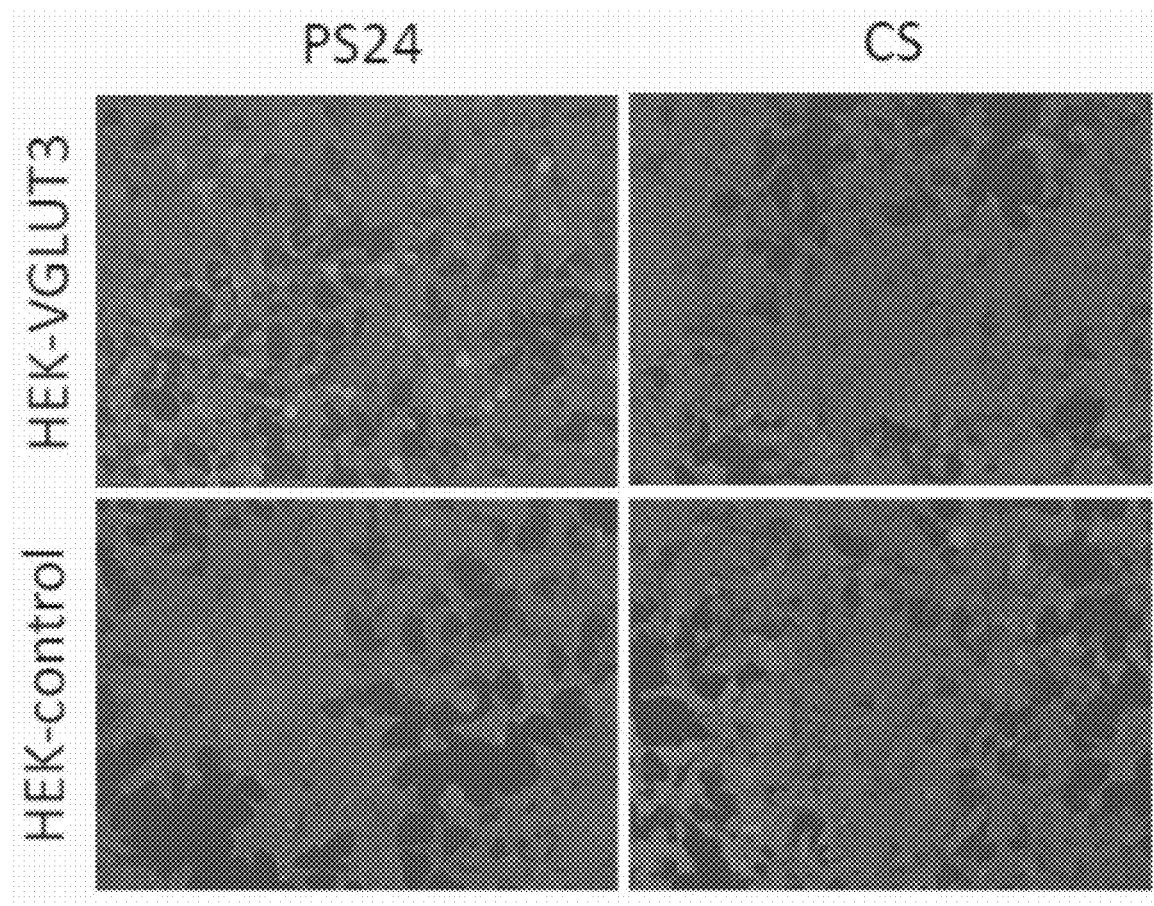
FIG. 12A shows IIFA using acetone-fixed VGLUT3 dHis or mock-transfected HEK293 cells incubated with PS24 or a healthy control (1:10) and anti-human IgG-FITC.
Figure 12B:
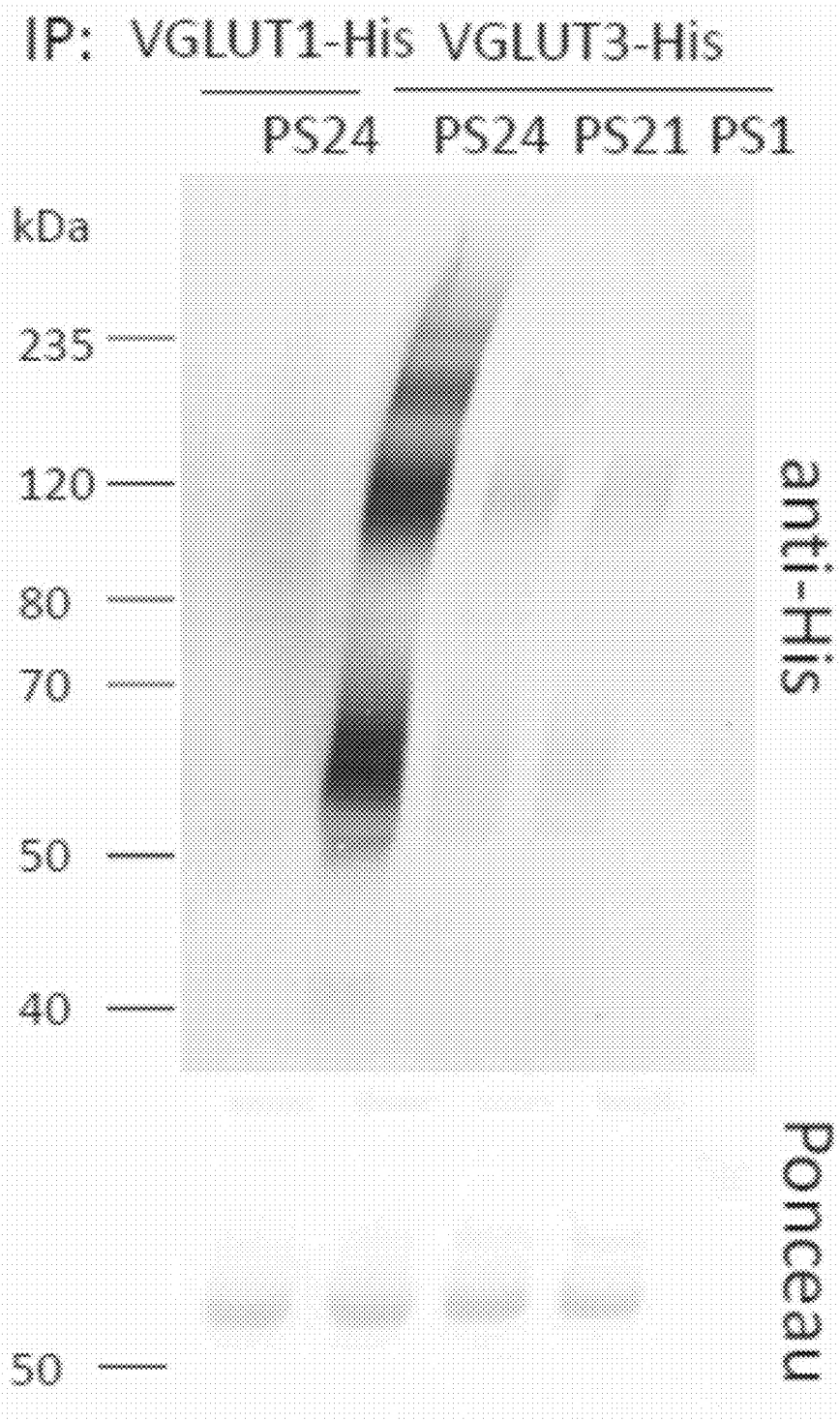
FIG. 12B shows immunoprecipitation (IP) with lysates of VGLUT3-His or VGLUT1-His transfected HEK cells and patient sera (PS24, PS21, PS1).

FIGS. 12A & 12B show the verification of VGLUT3 as the novel autoantigen by different immunoassays with the recombinant antigen. 12A: IIFA using acetone-fixed VGLUT3 dHis or mock-transfected HEK293 cells incubated with PS24 or a healthy control (1:10) and anti-human IgG-FITC. 126: Immunoprecipitation (IP) with lysates of VGLUT3-His or VGLUT1-His transfected HEK cells and patient sera (PS24, PS21, PS1). Isolated immunocomplexes were subjected to SDS-PAGE analysis followed by immunoblot with anti-His. Ponceau staining of immunoblot is shown as control.

Example 1

Summary

Methods: One patient (P1) suffering from neurological conditions underwent serological Investigation. For this purpose serum of P1 (PS1) was subjected to comprehensive autoantibody screening by indirect immunofluorescence assay (IFA) with neuronal tissue sections or HEK cells expressing recombinant neuronal antigens.

Immunoprecipitation of patient or control serum with lysates of cerebellum followed by mass spectrometry (MS) was used to identify the autoantigen, which was verified by colocalization experiments with anti-VGLUT2 mouse monoclonal antibody as well as by recombinant expression of the target antigen in HEK293 cells and use of the recombinant protein in immunoassays. Furthermore, sera or CSF of patients (n=65) with neurological symptoms and a similar reactivity on neuronal tissue sections compared to PS1 as well as healthy control sera (n=50) were analyzed in a recombinant immunofluorescence assay with HEK cells expressing VGLUT2.

Results: IFA screening of PS1 revealed IgG reactivity with the molecular layer and the granular layer in rodent and monkey cerebellum, as well as rat hippocampus and thalamus. Furthermore, no IgG reactivity was found with a panel of 30 recombinantly expressed established neural autoantigens. PS1 immunoprecipitated VGLUT 2 (VGLUT2), as detected by ESI mass spectrometry. The anti-VGLUT2 mouse monoclonal antibody showed an identical reactivity on cerebellar tissue sections as PS1. In addition to this, all the analyzed sera of 65 patients with similar fluorescence reactivity on neuronal tissue sections compared to PS1 were anti-VGLUT2 positive. Of the 50 control sera only two showed a weak reactivity with HEK-VGLUT2 cells but no comparable tissue reactivity. A positive reaction of patient sera but not control sera was also observed in immunoblot with recombinant VGLUT2-His.

Clinical data from a total of seven anti-VGLUT2 positive patients were available. They suffered from encephalitis (P2, P3, P6, P8), cerebellar syndrome (P4, P7), dementia (P2) or epilepsy (P5). For two patients (P3, P8) a paraneoplastic neurological syndrome was concluded, as their neurological symptoms were accompanied by cancer (P3: acute myeloid leukemia, P8: non-Hodgkin lymphoma).

Methods

Indirect Immunofluorescence Assay (IFA)

IFA was performed using slides with a biochip mosaic of brain tissue cryosections (cerebellum of rat and monkey, hippocampus, thalamus of rat) in addition to recombinant HEK293 cells separately expressing 30 different neuronal antigens: Hu, Yo, Ri, CV2, PNMA2, ITPR1, Homer 3, CARP VIII, ARHGAP26, ZIC4, DNER/Tr, GAD65, GAD67, amphiphysin, recoverin, GABAB receptor, glycine receptor, DPPX, IgLON5, glutamate receptors (types NMDA, AMPA, mGluR1, mGluR5, GLURD2), LGI1, CASPR2, AQP4 (M1 and M23), MOG, ATP1A3, NCDN (EUROIMMUN, FA 111a-1003-51, FA 1112-1003-50, FA-1128-1003-50, FA112d-1003-1, FA 112m-1003-50, FA 1151-1003-50; Miske R, Hahn S, Rosenkranz T, Müller M, Dettmann I M, Mindorf S, Denno Y, Brakopp S, Scharf M, Teegen B, Probst C, Melzer N, Meinck H M, Terborg C, Stöcker W, Komorowski L., 2016, Autoantibodies against glutamate receptor δ2 after allogenic stem cell transplantation. Neurol Neuroimmunol Neuroinflamm., 3(4): e255; Scharf M, Miske R, Heidenreich F. Gloss R, Landwehr P, Blöcker I M, Begemann N, Denno Y, Tiede S, Dähnrich C, Schlumberger W, Unger M, Teegen B, Stöcker W, Probst C, Komorowski L, 2015, Neuronal Na+/K+ ATPase is an autoantibody target in paraneoplastic neurologic syndrome, Neurology; 84(16):1673-9; Miske R, Gross C C, Scharf M. Golombeck K S, Hartwig M, Bhatia U, Schulte-Mecklenbeck A, Bönte K. Strippel C, Schöls L, Synofzik M, Lohmann H, Dettmann I M, Deppe M, Mindorf S, Wamecke T, Denno Y, Teegen B, Probst C. Brakopp S, Wandinger K P, Wiendl H, Stöcker W, Meuth S G, Komorowski L, Melzer N, 2016, Neurochondrin is a neuronal target antigen in autoimmune cerebellar degeneration, Neurol Neuroimmunol Neuroinflamm.; 4(1): e307)).

Each biochip array was Incubated with serum or CSF diluted in PBS for 30 min, washed with PBS-Tween and Immersed in PBS-Tween for 5 min. Subsequently, either fluorescein isothiocyanate (FITC)-labelled goat anti-human IgG (EUROIMMUN Medizinische Labordiagnostika AG, Luebeck Germany) or Alexa488-labelled goat anti-human IgG (1:500, Jackson Research, Suffolk, United Kingdom) were applied for 30 min. After another washing step with PBS-Tween, and embedding the slides in PBS-buffered DABCO-containing glycerol, they were analyzed by fluorescence microscopy. Based on the fluorescence Intensity of the transfected cells in direct comparison with non-transfected cells and control samples, reactivities were classified as positive or negative. Endpoint titers refer to the last dilution showing visible fluorescence.

For colocalization experiments biochips were Incubated with anti-VGLUT2 mouse monoclonal antibody (1:200, Merck, AMAB91081) and anti-mouse-Cy3 (1:200, Jackson ImmunoResearch).

In competitive inhibition experiments, sera diluted 1:320 in PBS-Tween were pre-incubated for 1 h with lysate of recombinant HEK293 cells comprising the vector represented by SEQ ID NO: 9 and expressing VGLUT2 represented by SEQ ID NO: 1 or as control empty vector transfected HEK293 cell lysate diluted 1:10 in PBS-Tween, before they were incubated in an IFA on neuronal tissue sections. Cell nuclei were visualized by DNA staining with TO-PRO-3 iodide (1:2000, ThermoFisher Scientific, Dreieich, Germany). Results were evaluated by two Independent observers using laser scanning microscopes (LSM700, Zeiss, Jena, Germany). All incubation steps were carried out at room temperature.

Immunoprecipitation

The immunoprecipitation was performed with 200 µl tissue homogenate of rat brain. Homogenates were centrifuged at 16000×g for 10 min. The sediment together with 30 µl patient or control sera was resuspended in 500 µl solubilization buffer (100 mmol/L tris-HCl pH 7.4, 150 mmol/L sodium chloride, 2.5 mmol/L EDTA, 0.5% (w/v) deoxycholate, 1% (w/v) Triton X-100 containing protease inhibitors) and rotated 1 h. The suspension was spun down at 16000×g for 10 min. The supernatants were then Incubated with Protein G Dynabeads (ThermoFisher Scientific, Schwerte, Germany) for 3 h to capture immunocomplexes. Beads were washed 3 times with PBS, and eluted with NuPage LDS sample buffer (ThermoFisher Scientific, Schwerte, Germany) containing 25 mmol/L dithiothreitol at 70° C. for 10 min. Prior to SDS-PAGE (NuPAGE, ThermoFisher Scientific, Schwerte, Germany), carbamidomethylation with 59 mM Iodoacetamide (Bio-Rad. Hamburg. Germany) was performed at RT. Separated proteins were visualized with Coomassie Brilliant Blue (G-250) (Merck) gel staining, and identified by mass spectrometric analysis as described below. All Incubation steps were carried out at 4° C., If not indicated otherwise.

Mass Spectrometry

Protein bands were excised from Coomassie Brilliant Blue G-250 stained gels. After destaining and tryptic digestion peptides were extracted, dried in SpeedVac and dissolved in water prior to nano-LC-MS/MS analysis.

Nano-LC-MS/MS measurements were performed with a Dionex Ultimate 3000 RSLC nanoLC coupled to a Bruker maXis II ETD QTOF via CaptiveSpray Ionization source using otofControl 5.2 and Bruker Compass HyStar 5.1 (Bruker Daltonik GmbH. Bremen, Germany). Peptides were trapped on an Acclaim PepMap 100 C18 trap column and separated on an Acclaim PepMap 100 C18 analytical column (Thermo Scientific, Waltham, MA) using gradient elution.

Spectra were recorded in positive mode with a scan speed of 4 Hz for precursor Ions and a dynamic acquisition of 4 to 16 Hz for MS/MS spectra, in a mass range from 150 to 2200 m/z. Ions were fragmented by collision Induced dissociation (CID) with nitrogen gas using a dynamic CID energy ranging from 23 to eV depending on mass and charge state.

Spectra were recalibrated and processed with Bruker Compass DataAnalysis software 5.2. Database search against SwissProt limited to Mammalia was performed by Bruker BioPharma Compass software 3.1 using the Mascot search engine version 2.3 (Matrix Science, London, U.K.). To evaluate the protein hits, a significance threshold or $p<0.05$ was chosen. Peptides and proteins were accepted if their Mascot score exceeded 15.

Recombinant Expression of Full Length VGLUT2 and VGLUT2-His in HEK293

A cDNA clone coding for full length of human VGLUT2 (SEQ ID NO: 1) was not available. Therefore two synthetic gene fragments coding for amino acids 1-293 and 294-582 of human VGLUT2 (SEQ ID NO: 2 and SEQ ID NO: 3) were obtained from Eurofins Genomics Germany GmbH (Ebersberg) digested with Bsal (New England Biolabs, R3733) resulting in 877 bp fragment-1 and 873 bp fragment-2 (SEQ ID NO: 4 and SEQ ID NO: 5) that were both Gel-purified. By PCR a third fragment of VGLUT2 was amplified using the gene synthesis product (SEQ ID NO: 3) as template and the DNA oligonucleotide primers sense VGLUT2 (SEQ ID NO: 6) and a sense VGLUT2 (SEQ ID NO: 7), resulting in SEQ ID NO: 8 without the Stop-codon. The amplification product was digested with Bsal (New England Biolabs. R3733). The fragments SEQ ID NO: 4 and SEQ ID NO: 5 were ligated with Ncol and Xhol linearized pTriEx-1 vector (Merck, Darmstadt, Germany) resulting in SEQ ID NO: 9, coding for VGLUT2 [human] (SEQ ID NO: 10). The fragments SEQ ID NO: 4 and the Bsal-digested fragment SEQ ID NO: 8 were also ligated with Ncol and Xhol linearized pTriEx-1 vector (Merck, Darmstadt, Germany) resulting in SEQ ID NO: 11, coding for VGLUT2 [human] fused to a C-terminal octa Histidin-tag (H8) (SEQ ID NO: 12).

VGLUT2-His or dHis were expressed in human HEK293 cells after ExGen500-mediated transfection (ThermoFisher Scientific, Schwerte, Germany) according to the manufacturer's instructions with vectors represented by SEQ ID NO: 11 and SEQ ID NO: 9, respectively. In order to prepare substrates for IFA, HEK293 cells were seeded on sterile cover glasses, transfected, and allowed to express VGLUT2 for 48 h. Cover glasses were washed with PBS, fixed with acetone for 10 min at room temperature, air-dried, cut Into millimeter-sized biochips and used as substrates in IFA as described. Alternatively, cells were transfected in standard T-flasks and harvested after 5 days. The cell sediment was extracted with solubilization buffer. The extracts were stored in aliquots at −80° C. until further use.

Immunoblot

Cerebellar lysates or HEK293-VGLUT2-His fractions were separated by SDS-PAGE (NuPAGE, ThermoFisher Scientific, Schwerte, Germany) and subsequently electrotransferred onto a nitrocellulose membrane by tank blotting with transfer buffer (ThermoFisher Scientific, Schwerte, Germany) according to the manufacturer's instructions. The membranes were blocked with 1:5 diluted sample buffer (EUROIMMUN. Germany) for 15 min and incubated with the patient or control sera (dilution 1:200) in Universal Blot Buffer plus for 3 h.

Results
Characterization of the Patients' Autoantibodies

Indirect Immunofluorescence assays (IFA) using permeabilized cerebellar cryosections and the serum of P1 (PS1) showed a spotty staining of the granular layer and interrupted striped structures in the molecular layer. On hippocampal tissue sections a weak fine granular fluorescence near the granular layer was detected as well as a speckled reactivity of the adjacent thalamus (FIG. 1, Table 1). Further monospecific analyses with recombinant HEK293 cells expressing 30 neural autoantigens: Hu, Yo, Ri, CV2, PNMA2, SOX1, ITPR1, Homer 3, CARP VIII, ARHGAP26, ZIC4, DNER/Tr, GAD65, GAD67, amphiphysin, recoverin, GABAB receptor, glycine receptor, DPPX, IgLON5, glutamate receptors (types NMDA, AMPA, mGluR1, mGluR5, GLURD2), LGl1, CASPR2, AQP4 (M1 and M23), MOG, ATP1A3, and NCDN revealed no positive reactions.

Identification of VGLUT2 as the Target Neuronal Auto-Antigen

PS1 reacted with a 120 kDa band in immunoblot with cerebellar lysate. However, immunoprecipitates from homogenized rat cerebellum obtained with PS1 or a control serum (CS) presented no visible band at this size after coomassie staining of the gel (FIGS. 2A & 2B). However, bands at the position of the 120 kDa immunoblot reaction were subjected to ESI mass spectrometry analysis (PS1: band 1, CS: band 2). VGLUT (VGLUT2) from *Rattus norvegicus* (UNIPROT acc. #Q9JI12) was Identified in the eluate of PS1 but it was absent in the control serum immunoprecipitate as judged by mass spectrometry.

Correct antigen identification was confirmed with colocalization experiments in which an anti-VGLUT2 mouse monoclonal antibody showed an identical staining pattern on cerebellar tissue sections as PS1 (FIGS. 3A & 3B).

In addition to this, the reaction of the patients' autoantibodies on tissue could be abolished by pre-incubation with HEK293 lysate containing VGLUT2 (SEQ ID NO: 10) (FIG. 4).

Detection of Anti-VGLUT2 Autoantibodies in Immunofluorescence Assays (IFTs) with Recombinant VGLUT2

In recombinant IFA with VGLUT2 (SEQ ID NO: 10)-expressing HEK293 cells (FIG. 5A), PS1 reacted with VGLUT2 (titer 1:3200) but not with mock-transfected HEK293 cells. Furthermore, 74 sera and 7 CSF samples from 65 patients, which displayed a similar reactivity in IFA with neuronal tissue sections as PS1, revealed positive reactions in IFA with HEK293-VGLUT2 cells (titers of P2-7 shown in table 1), whereas only two of 50 sera from healthy donors showed a week reactivity with HEK293-VGLUT2 cells (titer 1:32) but were negative in IFA with neuronal tissue sections. PS1, P2 and P7 but no control sera also recognized recombinant VGLUT2-His at around 120 kDa in immunoblot using HEK293-VGLUT2 lysate (FIG. 5B).

Clinical data were available of patient 1-7 and are summarized in Table 1:

| Patient | Material | Titer cerebellum rat IFA | titer HEK-VGLUT2 IFA | Diagnosis/ Neurological symptoms | Cancer |
|---|---|---|---|---|---|
| 1 | Serum | 1:1000 | 1:3200 | | |
| 2 | Serum | 1:1000 | 1:3200 | encephalitis, dementia | |
| 3 | Serum | 1:1000 | 1:3200 | ? | acute myeloid leukemia (Graft versus Host disease after stem cell transplantation) |
| 3 | CSF | 1:1 | borderline | | |
| 4 | Serum | 1:100 | 1:3200-1:10.000 | rapidly progressive cerebellar ataxia, gait ataxia, polyneuropathy | |
| 4 | CSF | 1:1 | 1:10 | | |
| 5 | Serum | 1:320 | 1:1000 | epilepsy, weakness | |
| 6 | Serum | 1:100 | 1:1000 | autoimmune encephalitis | |
| 7 | Serum | 1:320 | 1:1000 | cerebellar syndrome | |
| 8 | Serum | 1:32 | 1:100 | encephalitis | non-Hodgkin lymphoma |

Summary:

The experimental data in example 1 show that:
- An autoantibody binding specifically to human VGLUT could be identified on account of its characteristic staining pattern, in addition to immunoprecipitation and mass spec
- It is present in sera and CSF samples from patients suffering from various neurological autoimmune diseases and cancers, while other autoantibodies are absent
- It can be detected by recognizing its characteristic staining pattern on a tissue, where it Is present together with many other neurological proteins or based on a signal which can be assigned to recombinant antigen
- The autoantibody is also essentially absent in sera from healthy subjects, showing that the assay is specific
- Several variants (wildtype non-human primate and rodent: recombinant human with and without His tag) of the human VGLUT are reactive with the autoantibody
- Several assay formats (immunofluorescence with tissue and recombinant protein, immunoprecipitation, competitive assays with Immobilized and soluble autoantigen, immunoblot) can be used Example 2

Methods:
Recombinant Expression of his-VGLUT2 Fragments and Mutants in *E. coli*

For epitope characterisation different fragments of human VGLUT2 were amplified by PCR using SEQ ID NO: 9 as template. The following table gives an overview over the generated VGLUT2 epitopes and the used DNA oligonucleotide primers.

| Sense DNA oligo | Asense DNA oilgo | VGLUT2 epitope |
|---|---|---|
| SEQ ID NO: 24 | SEQ ID NO: 25 | VGLUT2-aa1-71 |
| SEQ ID NO: 26 | SEQ ID NO: 27 | VGLUT2-aa93-125 |
| SEQ ID NO: 28 | SEQ ID NO: 29 | VGLUT2-aa266-310 |
| SEQ ID NO: 30 | SEQ ID NO: 31 | VGLUT2-aa499-582 |
| SEQ ID NO: 32 | SEQ ID NO: 31 | VGLUT2-aa520-582 |
| SEQ ID NO: 32 | SEQ ID NO: 33 | VGLUT2-aa520-564 |
| SEQ ID NO: 34 | SEQ ID NO: 31 | VGLUT2-aa543-582 |
| SEQ ID NO: 35 | SEQ ID NO: 31 | VGLUT2-aa565-582 |
| SEQ ID NO: 30 | SEQ ID NO: 36 | VGLUT2-aa499-542 |
| SEQ ID NO: 30 | SEQ ID NO: 33 | VGLUT2-aa499-564 |

The amplification products were digested with Esp3I (New England Biolabs, Frankfurt am Main, Germany, R0734) and ligated with Ncol and Xhol linearized and modified pET24d vector (Merck, Darmstadt, Germany). The pET24d vector includes the sequence of an N-terminal octa Histidin-tag (H8), a GST-tag and the cleavage site of the HRV-3C protease cleavage enzyme (PreScission Protease—PSc). The following expression plasmids were generated:

| VGLUT2 epitope | Amino acid sequences of VGLUT2-fragments (SEQ ID) | Sequences of the expression plasmids (SEQ ID) |
|---|---|---|
| H8-GST-(PSc)-VGLUT2-aa1-71 | SEQ ID NO: 61 | SEQ ID NO: 80 |
| H8-GST-(PSc)-VGLUT2-aa93-125 | SEQ ID NO: 62 | SEQ ID NO: 81 |
| H8-GST-(PSc)-VGLUT2-aa266-310 | SEQ ID NO: 63 | SEQ ID NO: 82 |
| H8-GST-(PSc)-VGLUT2-aa499-582 | SEQ ID NO: 64 | SEQ ID NO: 83 |
| H8-GST-(PSc)-VGLUT2-aa520-582 | SEQ ID NO: 65 | SEQ ID NO: 84 |
| H8-GST-(PSc)-VGLUT2-aa520-564 | SEQ ID NO: 66 | SEQ ID NO: 85 |
| H8-GST-(PSc)-VGLUT2-aa543-582 | SEQ ID NO: 67 | SEQ ID NO: 86 |
| H8-GST-(PSc)-VGLUT2-aa565-582 | SEQ ID NO: 68 | SEQ ID NO: 87 |
| H8-GST-(PSc)-VGLUT2-aa499-542 | SEQ ID NO: 69 | SEQ ID NO: 88 |
| H8-GST-(PSc)-VGLUT2-aa499-564 | SEQ ID NO: 70 | SEQ ID NO: 89 |

Furthermore four different mutated C-terminal VGLUT2 fragments (Mut 1-4) were generated. For each fragment three different DNA oligonucleotide primers were used to insert the mutations by PCR. The following table gives an overview over the used DNA oligonucleotide primers and the used template to generate the four mutants.

| Mutant | DNA oligo 1 | DNA oligo 2 | DNA oligo 3 | template |
|---|---|---|---|---|
| 1 | SEQ ID NO: 37 sense | SEQ ID NO: 38 | SEQ ID NO: 33 | SEQ ID NO: 89 |
| 2 | SEQ ID NO: 32 sense | SEQ ID NO: 39 | SEQ ID NO: 40 | SEQ ID NO: 84 |
| 3 | SEQ ID NO: 32 sense | SEQ ID NO: 41 | SEQ ID NO: 42 | SEQ ID NO: 98 |
| 4 | SEQ ID NO: 43 sense | SEQ ID NO: 44 | SEQ ID NO: 33 | SEQ ID NO: 89 |

All amplification products were digested with Esp3I (New England Biolabs, Frankfurt am Main, Germany, R0734) and ligated with Ncol and Xhol linearized and modified pET24d vector (Merck, Darmstadt, Germany). The following expression plasmids were generated:

| Mutant | Amino acid sequences of mutants (SEQ ID) | Sequences of the expression plasmids (SEQ ID) |
|---|---|---|
| 1 | SEQ ID NO: 71 | SEQ ID NO: 90 |
| 2 | SEQ ID NO: 72 | SEQ ID NO: 91 |
| 3 | SEQ ID NO: 73 | SEQ ID NO: 92 |
| 4 | SEQ ID NO: 74 | SEQ ID NO: 93 |

Recombinant Expression of Full Length VGLUT1, VGLUT1-his, VGLUT3 and VGLUT3-his in HEK293

The cDNA done IRATp970D1166D encoding human VGLUT-isoform1 (Acc. BC059379) was obtained from Source BioScience UK Limited. For expression of human VGLUT1-isoform1 (Uniprot Q9P2U7, SEQ ID NO: 13) two fragments were amplified by PCR using the cDNA done as template. Fragment VGLUT1 was amplified by using DNA oligonucleotide primers sense VGLUT1-IF1 (SEQ ID NO: 45) and a sense VGLUT1-IF1 (SEQ ID NO: 46). Fragment VGLUT1-Stop was amplified by using DNA oligonucleotide primers sense VGLUT1-IF1 (SEQ ID NO: 45) and a sense VGLUT1-IF1-Stop (SEQ ID NO: 47). Both fragments were digested with Bsal (New England Biolabs, Frankfurt am Main, Germany, R3733) and ligated with Ncol and Xhol linearized pTriEx-1 vector (Merck, Darmstadt, Germany) resulting in SEQ ID NO: 94, coding for human VGLUT1-isoform1 fused to a C-terminal octa Histidin-tag (H8) (SEQ ID NO: 75) and resulting in SEQ ID NO: 95, coding for human VGLUT1-isoform1 without fusion-tags (SEQ ID NO: 76).

The cDNA clone IRCMp5012F0513D encoding human VGLUT3-isoform2 (Acc. BC117229) was obtained from Source BioScience UK Limited (Nottingham, UK). For expression of human VGLUT3-isoform1 (Uniprot Q8NDX2, SEQ ID NO: 14) a PCR-fragment was generated coding for the missing amino acids 302-351 of VGLUT3-isoform1. Therefore, six overlapping DNA oligonucleotide primers were ordered (sense VGLUT3-IF1-F1-1 (SEQ ID NO: 48), sense VGLUT3-IF1-F1-2 (SEQ ID NO: 49), sense VGLUT3-IF1-F1-3 (SEQ ID NO: 50), a sense VGLUT3-IF1-F1-4 (SEQ ID NO: 51), a sense VGLUT3-IF1-F1-5 (SEQ ID NO: 52) and a sense VGLUT3-IF1-F1-8 (SEQ ID NO: 53)). In addition to this, three further fragments were amplified by PCR using the cDNA clone IRCMp5012F0513D as template. Fragment VGLUT3-IF1-F2 was amplified by using DNA oligonucleotide primers sense VGLUT3-IF1-F2 (SEQ ID NO: 54) and a sense VGLUT3-IF1-ZF2 (SEQ ID NO: 55). Fragment VGLUT3-IF1-F3 was amplified by using DNA oligonucleotide primers sense VGLUT3-IF1-F3 (SEQ ID NO: 58) and a sense VGLUT3-IF1-ZF3 (SEQ ID NO: 57) and fragment VGLUT3-IF1-F3-Stop was amplified by using DNA oligonucleotide primers sense VGLUT3-IF1-F3 (SEQ ID NO: 58) and a sense VGLUT3-IF1-ZF3-Stop (SEQ ID NO: 58). AN VGLUT3-fragments were digested with Esp3l (New England Biolabs, Frankfurt am Main, Germany, R0734) and ligated with Ncol and Xhol linearized pTriEx-1 vector (Merck, Darmstadt, Germany) resulting in SEQ ID NO: 96, coding for human VGLUT3-isoform1 fused to a C-terminal octa Histidin-tag (H8) (SEQ ID NO: 77) and resulting in SEQ ID NO: 97, coding for human VGLUT3-isoform1 without fusion-tags (SEQ ID NO: 78).

VGLUT1-His or dHis (SEQ ID NO: 75 and SEQ ID NO: 76) or VGLUT3-His or dHis (SEQ ID NO: 77 and SEQ ID NO: 78) were expressed in human HEK293 cells after ExGen500-mediated transfection (ThermoFisher Scientific, Schwerte, Germany) according to the manufacturer's instructions with vectors represented by SEQ ID NO: 94, SEQ ID NO: 95, SEQ ID NO: 96 and SEQ ID NO: 97, respectively. In order to prepare substrates for IFA, HEK293 cells were seeded on sterile cover glasses, transfected, and allowed to express VGLUT1 or VGLUT3 for 48 h. Cover glasses and were prepared as described above. For immunoprecipitation experiments cells were transfected in standard T-flasks and harvested after 5 d. The cell sediment was stored in sucrose buffer (20 mM TRIS-HCl pH 7.4, 10% sucrose, 5 mM EDTA, 1 mM PMSF) (50 Mio cells/ml) at −80° C. until further use.

Recombinant Expression of his-GST-VGLUT1 and his-GST-VGLUT3 Fragments in E. coli A fragment of human VGLUT1 spanning amino acid residues 491 to 560 was amplified by PCR using SEQ ID NO: 95 as template and the DNA oligonucleotide primers sense VGLUT1-491-560 (SEQ ID NO: 59) and a sense VGLUT1-IF1-Stop (SEQ ID NO: 47). The amplification product was digested with BsaI (New England Biolabs, Frankfurt am Main, Germany, R3733).

A fragment of human VGLUT3 spanning amino acid residues 503 to 589 was amplified by PCR using SEQ ID NO: 97 as template and the DNA oligonucleotide primers sense VGLUT3-503-589 (SEQ ID NO: 60) and a sense VGLUT3-IF1-F3-Stop (SEQ ID NO: 58). The amplification product was digested with Esp3I (New England Biolabs, Frankfurt am Main, Germany, R0734).

Both fragments were separately ligated with NcoI and XhoI linearized and modified pET24d vector (Merck, Darmstadt, Germany). The pET24d vector includes the sequence of an N-terminal octa Histidin-tag (H8), a GST-tag and the cleavage site of the HRV-3C protease cleavage enzyme (PreScission Protease—PSc) resulting in SEQ ID NO: 98 coding for H8-GST-PSc-VGLUT1 aa 491-560 (SEQ ID NO: 100) and resulting in SEQ ID NO: 99 coding for H8-GST-PSc-VGLUT3 aa 503-589 (SEQ ID NO: 79).

Bacterial expression was essentially performed as described in the pET system manual (Merck, Darmstadt. Germany) employing E. coli strain RosettaBlue(DE3)pLacl (Merck, Darmstadt, Germany). Protein expression was induced by the addition of 2 mM Isopropyl β-D-thiogalactoside (IPTG) for 3 hours at 37° C. For competitive inhibition experiments bacterial sediments were resuspended in solubilization buffer and disrupted by ultrasonic treatment. His-GST-VGLUT2 aa 499-582 Purification His-GST-VGLUT2 aa 499-582 SEQ ID NO: 64 was expressed in E. coli RosettaBlue (DE3)pLacl (Merck, Germany). For protein purification, bacterial sediments were resuspended in 50 mM TRIS-HCl pH 8.0, 0.3 M NaCl, 1 mM PMSF, 25 mM DTT and lysed with high pressure homogenizer (GEA, Germany). Lysed bacteria were centrifuged at 21,200×g for 30 min at 4° C. His-GST-VGLUT2 aa 499-582 was sedimented from the supernatant by 45% ammonium sulfate precipitation, solubilized in 5 mM TRIS-HCl pH 8.0, 300 mM NaCl, 10 mM imidazole and applied to immobilized metal chelate affinity chromatography using Nickel Rapid Run resin (ABT, Spain, Elution 300 mM imidazole) and ion-exchange chromatography (SP Sepharose Fast Flow, GE-Healthcare, US, Elution 20 mM TRIS-HCl pH 8.5, 500 mM NaCl) Protein analysis was performed by SDS-PAGE using the NuPAGE system according to the manufacturer's manual (Invitrogen) and by mass spectrometry.

VGLUT2 and VGLUT1 Epitope Mapping

E. coli expressing His-GST-VGLUT2 fragments aa 1-71, 93-125, 268-310, 499-582, 520-582, 543-582, 565-582, 499-542, 499-584, 520-564 (SEQ IDs NO 61, 62, 63, 64, 65, 67, 88, 69, 70, 66), His-GST-VGLUT1 aa 491-580 fragment (SEQ IDs NO 100) and His-GST-VGLUT2/1 mutants Mut 1, 2, 3, 4 (SEQ IDs NO 71, 72, 73, 74) were incubated with NuPage LDS sample buffer (ThermoFisher Scientific, Germany) containing 25 mmol/L dithiothreitol at 70° C. for 10 min. Lysates were immunoblotted as described above. Briefly, membranes were incubated with anti-His mouse monoclonal antibody (Merck. Germany. 1-2000), patient or control sera (1:200) in Sample buffer (EUROIMMUN, Germany, 1:5) for 3 h, and for 30 min with anti-mouse-IgG-AP (Jackson ImmunoResearch, UK, 1:2000) or anti-human-IgG-AP (1:10) in Sample buffer (1:5).

Indirect Immunofluorescence Assay (IIFA) for Anti-VGLUT1 and Anti-VGLUT3 Autoantibody Detection Standard IIFA with HEK-VGLUT1-His. HEK-VGLUT1 dHis. HEK-VGLUT3-His and HEK-VGLUT3 dHis cells was performed as described above.

In competitive inhibition experiments, sera diluted 1:100 in PBS-Tween were pre-incubated for 1 h with lysates of recombinant E. coli cells expressing His-GST-VGLUT1aa 491-560 represented by SEQ ID NO: 100, purified His-GST-VGLUT2 aa 499-582 SEQ ID NO: 64 or control buffer, before they were Incubated on neuronal tissue sections.

Immunoprecipitation with HEK-VGLUT1 and HEK-VGLUT3 Extracts

The immunoprecipitation was performed with 100 µl HEK-VGLUT1 or HEK-VGLUT3 homogenate (50 Mio cells/ml) with 30 µl patient or control sera as described above. SDS-PAGE separated eluates were immunoblotted and incubated with anti-His mouse monoclonal antibody (Merck, Germany, 1:2000) in Sample buffer (EUROIMMUN, Germany, 1:5) for 3 h and for 30 min with anti-mouse-IgG-AP (Jackson ImmunoResearch, UK, 1:2000) or anti-human-IgG-AP (1:10) in 1:5 diluted Sample buffer.

Results:

Characterization of VGLUT2 Epitope Recognized by Patents' Autoantibodies

Immunoblot assays with four VGLUT2 fragments (aa 1-71, 93-125, 268-310, 499-582) show that patient sera (PS1 and PS9 exemplary) but not control sera (CS1 and CS2 exemplary) recognize the C-terminal cytosolic VGLUT2 aa 499-582 fragment (FIG. 6A). In competitive inhibition experiments the reaction of PS1 on neuronal tissue sections could be abolished by preincubation with purified VGLUT2 aa 499-582 but not by preincubation with the C-terminal VGLUT1 aa491-560 fragment (FIG. 6B). This indicates that anti-VGLUT2 autoantibodies recognize VGLUT2 specific sequences on the C-terminal part of the VGLUT2 protein.

The epitope was narrowed down further by the analysis of shorter C-terminal VGLUT2 fragments (aa 520-582, 543-582, 565-582, 499-542, 499-584, 520-584), VGLUT2 as 520-564 was the shortest VGLUT2 fragment which was recognized by anti-VGLUT2 positive patient sera (PS1, PS9) but not control serum (CS) in immunoblot experiments (FIGS. 7B, 7C). In addition to this, patient sera (PS1, PS9) but not control serum (CS) still bound to N- or C-terminal mutants of VGLUT2 aa 520-564 (FIG. 7A Mut 1, 2, 4) sharing 81-87% sequence identity to the VGLUT2 WT sequence SEQ ID NO: 1 (FIG. 7C). However, mutating VGLUT2 aa 531-558 into the VGLUT1 aa 523-550 sequence (FIG. 7A Mut 3) produced a fragment which was not recognized by anti-VGLUT2 positive patient sera (PS1, PS9), indicating that the VGLUT2 epitope is located between aa 531-558 SEQ ID NO: 101 (FIG. 7C). SEQ ID NO: 101 is not present in VGLUT1 or VGLUT3, which are not recognized by anti-VGLUT2 positive patient sera (PS1 exemplary) in IIFA with VGLUT1 or VGLUT3 expressing HEK cells (FIG. 8).

Detection of Anti-VGLUT1 Autoantibodies in Different Immunoassays with Recombinant VGLUT1 and Epitope Characterization Patient sera (n=189) which displayed an anti-VGLUT1 like pattern (hhttps://www.proteinatlas.om/ENSG00000104888-SLC17A7/tissue) in IIFA with cerebellar and hippocampal cryosections but did not recognize any of 30 known neuronal autoantigens (Hu, Yo, Ri, CV2, PNMA2, SOX1, ITPR1, Homer 3, CARP VIII, ARHGAP26, ZIC4, DNER/Tr, GAD65, GAD67, amphiphysin, recoverin, GABAB receptor, glycine receptor, DPPX, IgLON5, glutamate receptors (types NMDA, AMPA, mGluR1, mGluR5, GLURD2), LGl1, CASPR2, AQP4 (M1 and M23), MOG, ATP1A3, or NCDN) were analyzed in recombinant IIFA with VGLUT1 (SEQ ID NO: 76)-expressing HEK293 cells. Three patient sera (PS21, 22, 23) but none of the control sera (n=48) reacted with VGLUT1-expressing HEK293 cells (FIG. 9A).

In immunoprecipitation experiments with recombinant VGLUT1-His (SEQ ID NO: 75) containing HEK cell lysates, patient serum (PS21 exemplary) but not control serum (CS) precipitated VGLUT1-His (FIG. 9B). Furthermore, patient sera (PS21, 22, 23) but not control sera (CS1, 2 exemplary) reacted strongly with the C-terminal VGLUT1 aa 491-560 (SEQ ID NO: 100) fragment in immunoblot experiments (FIG. 9C).

The reactivity of patient serum (PS21 exemplary) on neuronal tissue section, which is characterized by a fine granular staining of the cerebellar and hippocampal molecular layer and a spotty staining of the cerebellar granular layer, could be abolished by preincubation of the patient serum (PS21 exemplary) with the C-terminal VGLUT1 aa 491-560 fragment (SEQ ID NO: 100) (FIG. 10).

The anti-VGLUT1 positive patient serum PS21 did not bind to the C-terminal VGLUT2 aa 499-582 or aa 520-584 fragment, neither to the N- or C-terminal mutants of VGLUT2/1 520-564 (FIG. 11A, 11B Mut 1, 2). However, PS21 showed a strong reactivity against the VGLUT 2/1 Mut 3 which contains aa 523-550 of VGLUT1 (FIG. 11A). Indicating that PS21 recognizes a VGLUT1 epitope located between aa 523-550 SEQ ID NO_ (FIG. 11B).

Detection of Anti-VGLUT3 Autoantibodies in Different Immunoassays with Recombinant VGLUT3

Patient sera (n=57) which displayed an anti-VGLUT3 like pattern (https://www.proteinatlas.om/ENSG00000179520-SLC17A8) in IIFA with hippocampal cryosections but did not recognize any of 30 known neuronal autoantigens (Hu, Yo, Ri, CV2, PNMA2, SOX1, ITPR1, Homer 3, CARP VIII, ARHGAP26, ZIC4, DNER/Tr, GAD65, GAD67, amphiphysin, recoverin, GABAB receptor, glycine receptor, DPPX, IgLON5, glutamate receptors (types NMDA, AMPA, mGluR1, mGluR5, GLURD2), LGl1, CASPR2, AQP4 (M1 and M23), MOG. ATP1A3, or NCDN) were analyzed in recombinant IIFA with VGLUT3 (SEQ ID NO: 78)-expressing HEK293 cells. One patient serum (PS24) but none of the control sera (n=48) reacted with VGLUT3-expressing HEK293 cells (FIG. 12A).

The presence of anti-VGLUT3 specific autoantibodies in PS24 was confirmed by immunoprecipitation experiments with recombinant VGLUT3-His (SEQ ID NO: 77). The anti-VGLUT3 positive PS24 but not the anti-VGLUT1 positive PS21 or the anti-VGLUT2 positive PS1 precipitated VGLUT3 from VGLUT3 or containing HEK cell lysates (FIG. 12B). However, the anti-VGLUT3 positive PS24 could not precipitate VGLUT1 from VGLUT1 containing HEK cell lysates (FIG. 12B), showing that PS24 recognizes a VGLUT3 specific epitope.

Clinical data were available of patient 1-7 and patient 10-24 and are summarized in Table 1:

| Patient | Material | Titer cerebellum rat IIFA | Autoantibodies against | Titer RC-IIFA | Diagnosis/ Neurological symptoms | Cancer |
|---|---|---|---|---|---|---|
| 1 | Serum | 1:1000 | VGLUT2 | 1:3200 | — | — |
| 2 | Serum | 1:1000 | VGLUT2 | 1:3200 | encephalitis, dementia | |
| 3 | Serum | 1:1000 | VGLUT2 | 1:3200 | psychotic delusions | acute myeloid leukemia |
| 3 | CSF | 1:1 | VGLUT2 | borderline | | |
| 4 | Serum | 1:100 | VGLUT2 | 1:3200-1:10.000 | rapidly progressive cerebellar ataxia, gait | |
| 4 | CSF | 1:1 | VGLUT2 | 1:10 | ataxia, polyneuropathy | |
| 5 | Serum | 1:320 | VGLUT2 | 1:1000 | epilepsy, weakness | |
| 6 | Serum | 1:100 | VGLUT2 | 1:1000 | autoimmune encephalitis, HSV-encephalitis | |
| 7 | Serum | 1:320 | VGLUT2 | 1:1000 | cerebellar syndrome | |
| 8 | Serum | 1:32 | VGLUT2 | 1:100 | encephalitis | non-Hodgkin lymphoma |
| 9 | Serum | 1:1000 | VGLUT2 | 1:3200 | — | — |
| 10 | Serum | 1:1.000 | VGLUT2 | 1:1000 | ? | |
| 11 | Serum | 1:320 | VGLUT2 | 1:1000 | epileptic seizures, dementia | |
| 12 | Serum | 1:1000 | VGLUT2 | 1:10.000 | autoimmune encephalitis, behavioral changes | |
| 12 | CSF | 1:3.2 | VGLUT2 | 1:3.2 | | |
| 13 | Serum | 1:100 | VGLUT2 | 1:1000 | limbic encephalitis | |
| 14 | Serum | 1:320 | VGLUT2 | 1:1000 | autoimmune encephalitis | |
| 15 | Serum | 1:320 | VGLUT2 | 1:1000 | ? | lung carcinoma |
| 15 | CSF | 1:3.2 | VGLUT2 | 1:10 | | |
| 16 | Serum | 1:100 | VGLUT2 | 1:320 | polyneuropathy | T-cell lymphoma |
| 17 | Serum | 1:1000 | VGLUT2 | 1:3200 | epileptic seizures | |
| 17 | Serum | 1:100 | VGLUT2 | 1:1000 | ? | lung carcinoma |

-continued

| Patient | Material | Titer cerebellum rat IIFA | Autoantibodies against | Titer RC-IIFA | Diagnosis/ Neurological symptoms | Cancer |
|---|---|---|---|---|---|---|
| 18 | Serum | 1:100 | VGLUT2 | 1:1000 | peripheral polyneuropathy | |
| 19 | Serum | 1:100 | VGLUT2 | 1:320 | epileptic seizures | |
| 20 | Serum | 1:32 | VGLUT2 | 1:320 | dementia | |
| 21 | Serum | 1:320 | VGLUT1 | 1:3200 | ? | |
| 22 | Serum | 1:100 | VGLUT1 | 1:320 | neuronal autoimmune disease | |
| 23 | Serum | 1:320 | VGLUT1 | 1:320 | ? | |
| 24 | Serum | 1:320 | VGLUT3 | 1:1000 | neuronal autoimmune disease | |
| 24 | CSF | 1:100 | VGLUT3 | 1:32 | | |

SUMMARY

The experimental data in example 2 show that:

An autoantibody to VGLUT1 and an autoantibody to VGLUT2 could be detected in addition to an autoantibody to VGLU3 In the samples from patients.

Various variants were used for the detection of these autoantibodies, and reactive epitopes could be Identified.

---

The invention claimed is:

1. A method, comprising:
   detecting, in a sample, an autoantibody binding specifically to a mammalian vesicular glutamate transporter (VGLUT).

2. The method according to claim 1, further comprising:
   contacting a carrier with a liquid of the sample comprising the autoantibody binding specifically to the mammalian vesicular glutamate transporter (VGLUT), and
   contacting the carrier with a means for detecting the autoantibody binding specifically to the mammalian vesicular glutamate transporter (VGLUT), to detect the autoantibody.

3. The method according to claim 2, further comprising:
   immobilizing a polypeptide comprising the mammalian vesicular glutamate transporter (VGLUT) on the carrier.

4. The method according to claim 2, wherein the carrier is selected from the group consisting of a glass slide, a biochip, a microtiter plate, a lateral flow device, a test strip, a membrane, a chromatography column, and a bead.

5. The method according to claim 1, wherein the autoantibody is detected using a detection method selected from the group consisting of immunodiffusion, electrophoresis, light scattering immunoassays, agglutination, labeled immunoassays, enzyme immunoassays, chemiluminescence immunoassays, and immunofluorescence.

6. The method according to claim 1, wherein the autoantibody is detected using a detection method selected from the group consisting of radiolabeled immunoassay, ELISA, electrochemiluminescence, and indirect immunofluorescence.

7. The method according to claim 1, wherein the sample is a human sample comprising a representative set of antibodies, wherein the human sample is selected from the group consisting of whole blood, plasma, serum, cerebrospinal fluid, and saliva.

8. The method according to claim 1, wherein the sample is from a patient having or suspected of having a neurological autoimmune disease or a cancer.

* * * * *